(12) United States Patent
Merten et al.

(10) Patent No.: US 9,862,934 B2
(45) Date of Patent: *Jan. 9, 2018

(54) BACULOVIRUS-BASED PRODUCTION OF BIOPHARMACEUTICALS FREE OF CONTAMINATING BACULOVIRAL VIRIONS

(71) Applicant: GENETHON, Evry (FR)

(72) Inventors: Otto-Wilhelm Merten, Crespieres (FR); Martin Marek, Malec (CZ); Monique Van Oers, Renkum (NL)

(73) Assignee: GENETHON, Evry (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/670,459

(22) Filed: Mar. 27, 2015

(65) Prior Publication Data

US 2015/0252335 A1    Sep. 10, 2015

Related U.S. Application Data

(63) Continuation of application No. 13/390,806, filed as application No. PCT/EP2010/061456 on Aug. 5, 2010, now Pat. No. 8,993,317.

(30) Foreign Application Priority Data

Aug. 17, 2009 (EP) ..................... 09305761

(51) Int. Cl.
  *C12N 15/866* (2006.01)
  *C12N 15/86* (2006.01)
  *C12N 7/00* (2006.01)

(52) U.S. Cl.
  CPC .............. *C12N 7/00* (2013.01); *C12N 15/86* (2013.01); *C12N 2710/14143* (2013.01); *C12N 2710/14152* (2013.01); *C12N 2750/14143* (2013.01); *C12N 2800/50* (2013.01)

(58) Field of Classification Search
  CPC ..................... C12N 15/74; C12N 2800/50
  See application file for complete search history.

(56) References Cited

U.S. PATENT DOCUMENTS

| 6,387,670 B1 | 5/2002 | Leblois-Prehaud et al. |
| 2006/0166363 A1 | 7/2006 | Zolotukhin et al. |

FOREIGN PATENT DOCUMENTS

| WO | WO 01/12829 | 2/2001 |
| WO | WO 2004/009768 | 1/2004 |

OTHER PUBLICATIONS

Olszewski et al. Journal of Virology, 1997, vol. 71 No. 7, pp. 5040-5050.*
Olszewski, J., et al., "Identification and Characterization of a Baculovirus Structural Protein, VP1054, Required for Nucleocapsid Formation," *Journal of Virology*, Jul. 1997, vol. 71, No. 7, pp. 5040-5050.
Wang, Y., et al., "Genomic analysis of Oryctes rhinoceros virus reveals genetic relatedness to Heliothis zea virus 1," *Archives of Virology*, 2007, vol. 152, pp. 519-531.
Tang, X.-D. et al. "Characterization of a *Bombyx mori* nucleopolyhedrovirus with Bmvp80 disruption" *Virus Research*, 2008, pp. 81-88, vol. 138.
Possee, R. D. et al. "Generation of Baculovirus Vectors for the High-Throughput Production of Proteins in Insect Cells" *Biotechnology and Bioengineering*, Dec. 15, 2008, pp. 1115-1122, vol. 101, No. 6.
Written Opinion in International Application No. PCT/EP2010/061456, Mar. 14, 2011, pp. 1-6.
Wang, X. et al. "High-Level Production of a Functional Recombinant Hepatitis B Virus Polymerase in Insect Cells with a Baculovirus Expression System" *Journal of Huazhong University of Science and Technology*, pp. 269-273, vol. 27, No. 3.
Todd, J. W. et al. "Eighteen Baculovirus Genes, Including lef-11, p35, 39K, and p47, Support Late Gene Expression" *Journal of Virology*, Feb. 1995, pp. 968-974, vol. 69, No. 2.
Wang, M. et al. "Specificity of Baculovirus P6.9 Basic DNA-Binding Proteins and Critical Role of the C Terminus in Virion Formation" *Journal of Virology*, Sep. 2010, pp. 8821-8828, vol. 84, No. 17.
Urabe, M. et al. "Scalable Generation of High-Titer Recombinant Adeno-Associated Virus Type 5 in Insect Cells" *Journal of Virology*, Feb. 2006, pp. 1874-1885, vol. 80, No. 4.
Palombo, F. et al. "Site-Specific Integration in Mammalian Cells Mediated by a New Hybrid Baculovirus-Adeno-Associated Virus Vector" *Journal of Virology*, Jun. 1998, pp. 5025-5034, vol. 72, No. 6.

* cited by examiner

*Primary Examiner* — Bao Li
(74) *Attorney, Agent, or Firm* — Saliwanchik, Lloyd & Eisenschenk

(57) ABSTRACT

The present invention relates to methods for the production of biopharmaceuticals implementing a baculovirus-based system. These methods advantageously allow the production of biopharmaceuticals with a reduced number of or without contaminating baculoviral virions.

Figure 1A:
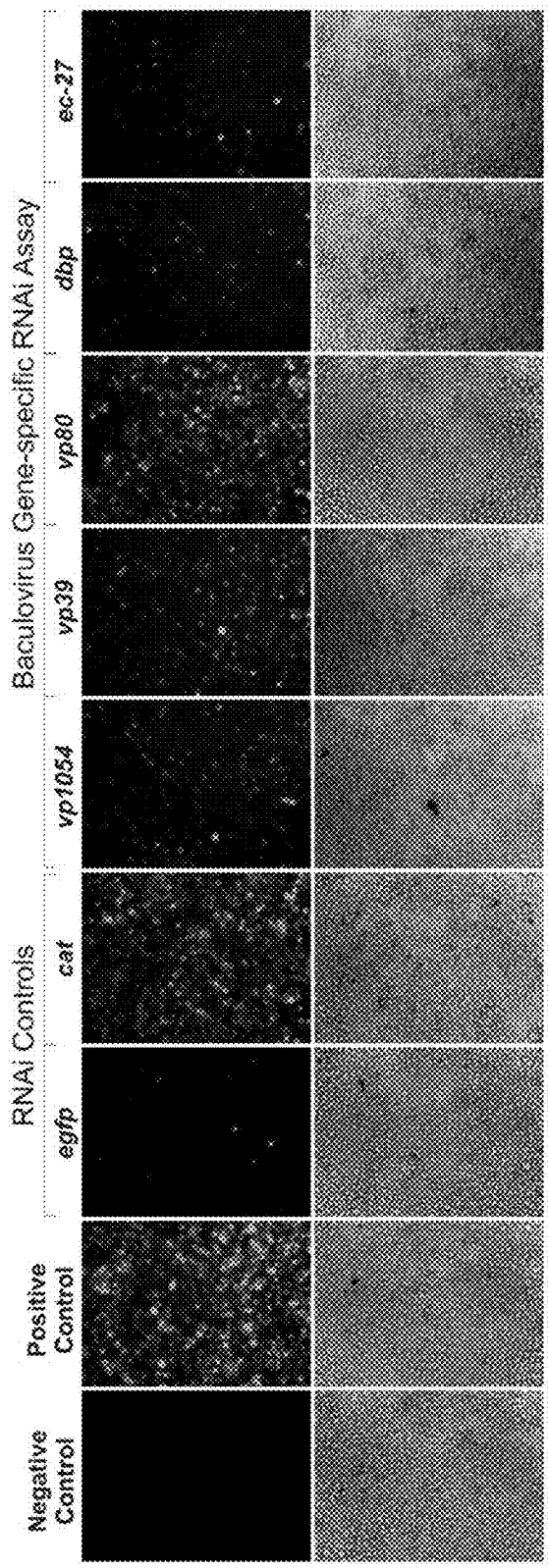

8 Claims, 36 Drawing Sheets
(10 of 36 Drawing Sheet(s) Filed in Color)

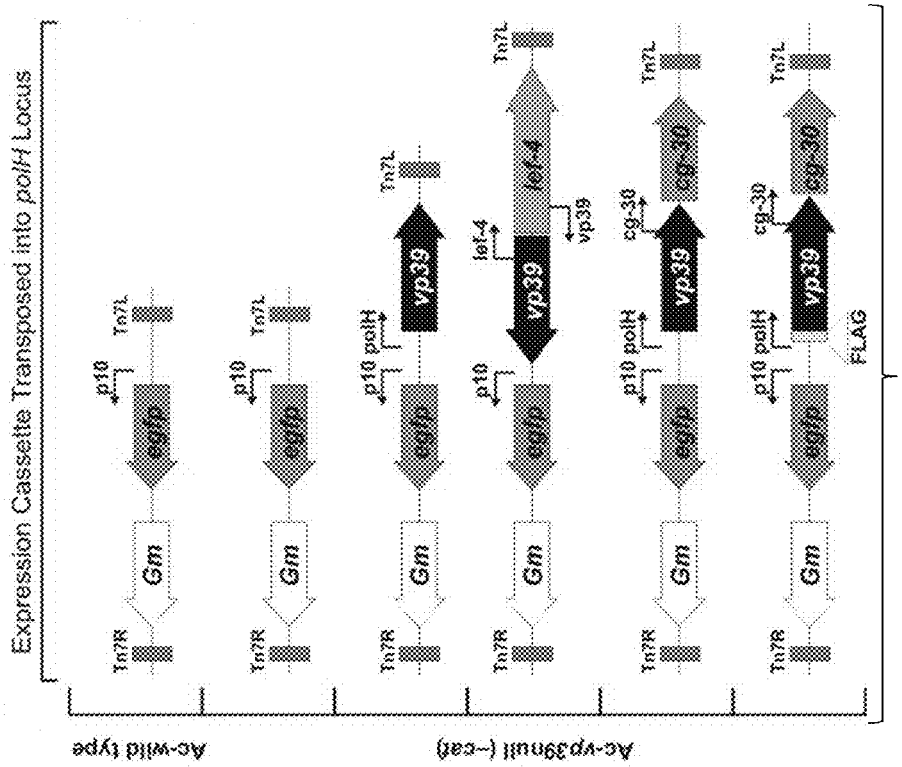
FIG 9C
FIG 9B
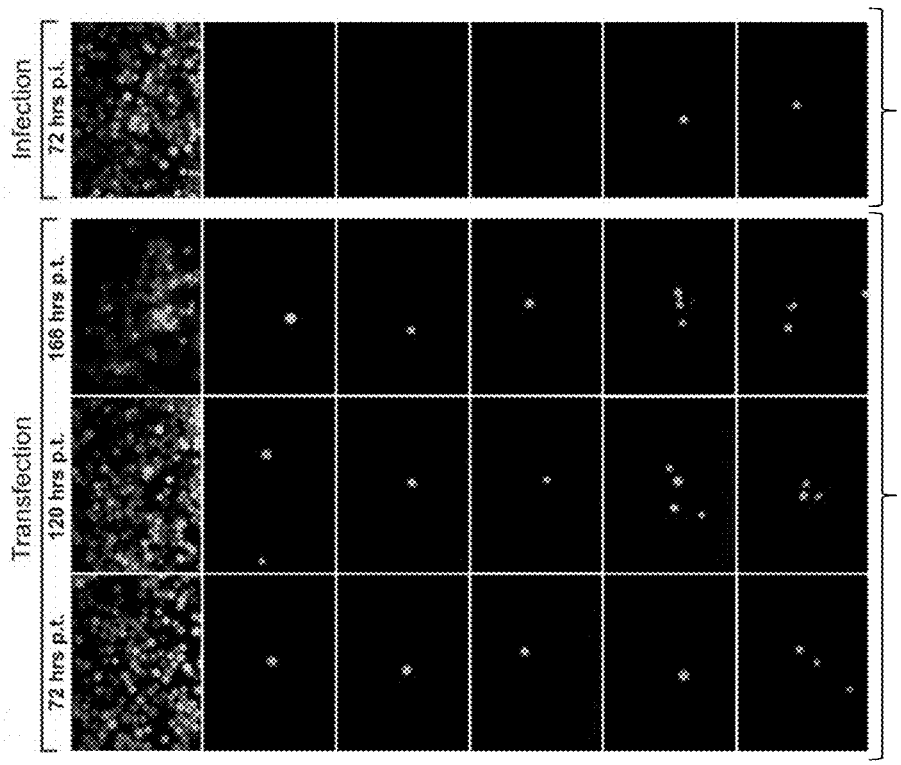
FIG 9A

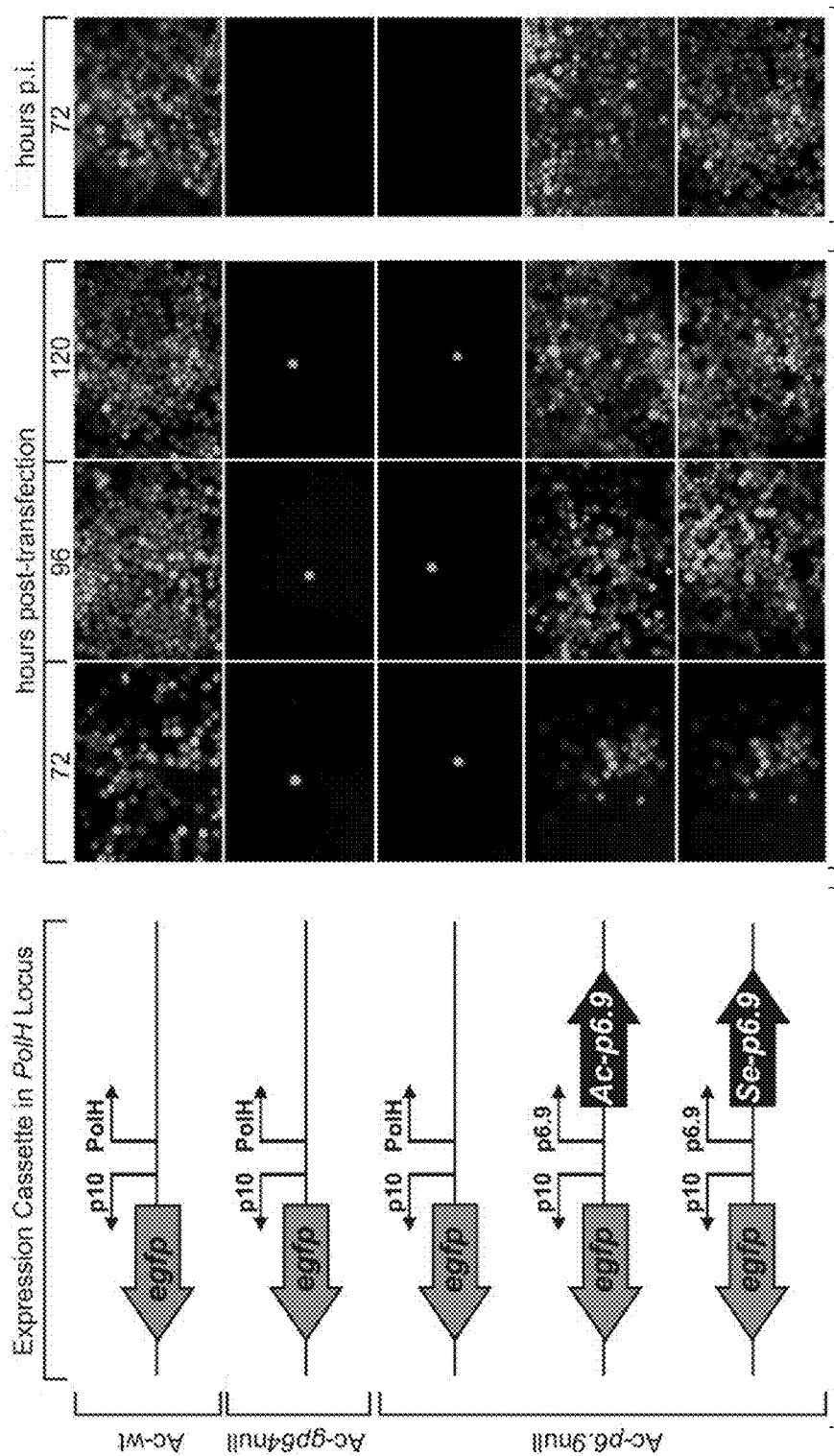

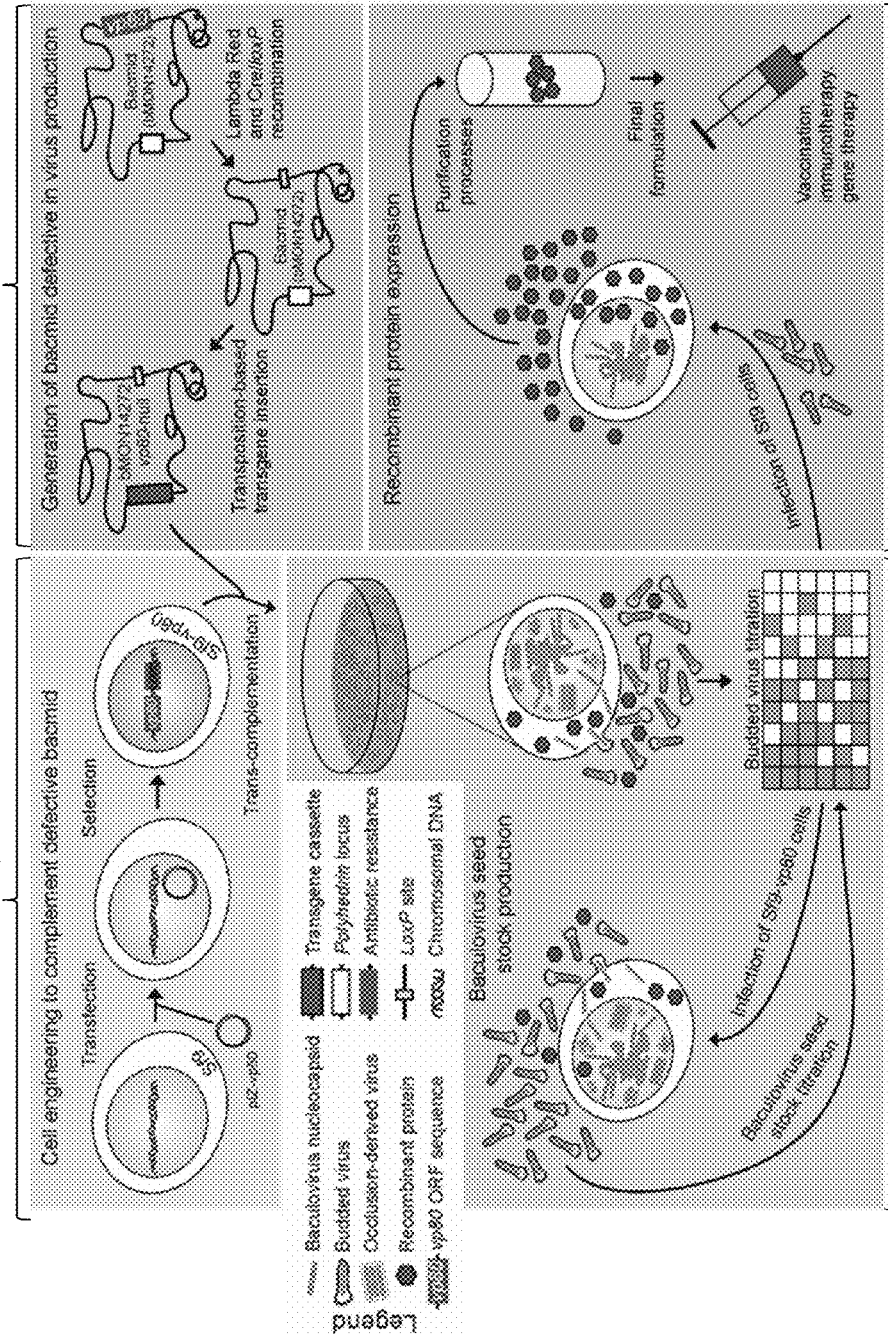

SEQUENCE LISTING

```
<160> NUMBER OF SEQ ID NOS: 56

<210> SEQ ID NO 1
<211> LENGTH: 133894
<212> TYPE: DNA
<213> ORGANISM: Autographa californica nucleopolyhedrovirus
```

<400> SEQUENCE: 1

```
gaattctacc cgtaaagcga gtttagtttt gaaaaacaaa tgacatcatt tgtataatga      60
catcatcccc tgattgtgtt ttacaagtag aattctatcc gtaaagcgag ttcagttttg     120
aaaacaaatg agtcatacct aaacacgtta ataatcttct gatatcagct tatgactcaa     180
gttatgagcc gtgtgcaaaa catgagataa gtttatgaca tcatccactg atcgtgcgtt     240
acaagtagaa ttctactcgt aaagccagtt cggttatgag ccgtgtgcaa acatgacat     300 cagcttatga ctcatacttg attgtgtttt acgcgtagaa ttctactcgt aaagcgagtt     360
cggttatgag ccgtgtgcaa acatgacat cagcttatga gtcataatta atcgtgcgtt     420
acaagtagaa ttctactcgt aaagcgagtt gaaggatcat atttagttgc gtttatgaga     480
taagattgaa agcacgtgta aaatgtttcc cgcgcgttgg cacaactatt tacaatgcgg     540
ccaagttata aagattcta atctgatatg ttttaaaaca cctttgcggc ccgagttgtt     600
tgcgtacgtg actagcgaag aagatgtgtg accgcagaa cagatagtaa aacaaaaccc     660
tagtattgga gcaataatcg atttaaccaa cacgtctaaa tattatgatg gtgtgcattt     720
tttgcgggcg ggcctgttat acaaaaaaat tcaagtacct ggccagactt tgccgcctga     780
aagcatagtt caagaattta ttgacacggt aaaagaattt acagaaaagt gtcccggcat     840
gttggtgggc gtgcactgca cacacggtat taatcgcacc ggttacatgg tgtgcagata     900
tttaatgcac accctgggta ttgcgccgca ggaagccata gatagattcg aaaaagccag     960
aggtcacaaa attgaaagac aaaattacgt tcaagattta ttaatttaat taatattatt    1020
tgcattcttt aacaaatact ttatcctatt ttcaaattgt tgcgcttctt ccagcgaacc    1080
aaaactatgc ttcgcttgct ccgtttagct tgtagccgat cagtggcgtt gttccaatcg    1140
acggtaggat taggccggat attctccacc acaatgttgg caacgttgat gttacgttta    1200
tgcttttggt tttccacgta cgtcttttgg ccggtaatag ccgtaaacgt agtgccgtcg    1260
cgcgtcacgc acaacaccgg atgtttgcgc ttgtccgcgg ggtattgaac cgcgcgatcc    1320
gacaaatcca ccactttggc aactaaatcg gtgacctgcg cgtctttttt ctgcattatt    1380
tcgtctttct tttgcatggt ttcctggaag ccggtgtaca tgcggtttag atcagtcatg    1440
acgcgcgtga cctgcaaatc tttggcctcg atctgcttgt ccttgatggc aacgatgcgt    1500
tcaataaact cttgtttttt aacaagttcc tcggttttt gcgccaccac cgcttgcagc    1560
gcgtttgtgt gctcggtgaa tgtcgcaatc agcttagtca ccaactgttt gctctcctcc    1620
tcccgttgtt tgatcgcggg atcgtacttg ccggtgcaga gcacttgagg aattacttct    1680
tctaaaagcc attcttgtaa ttctatggcg taaggcaatt tggacttcat aatcagctga    1740
atcacgccgg atttagtaat gagcactgta tgcggctgca aatacagcgg gtcgcccctt    1800
ttcacgacgc tgttagaggt agggccccca ttttggatgg tctgctcaaa taacgatttg    1860
tatttattgt ctacatgaac acgtatagct ttatcacaaa ctgtatattt taaactgtta    1920
gcgacgtcct tggccacgaa ccggacctgt tggtcgcgct ctagcacgta ccgcaggttg    1980
aacgtatctt ctccaaattt aaattctcca attttaacgc gagccatttt gatacacgtg    2040
tgtcgatttt gcaacaacta ttgttttta acgcaaacta aacttattgt ggtaagcaat    2100
aattaaatat gggggaacat gcgccgctac aacactcgtc gttatgaacg cagacggcgc    2160
cggtctcggc gcaagcggct aaaacgtgtt gcgcgttcaa cgcggcaaac atcgcaaaag    2220
ccaatagtac agttttgatt tgcatattaa cggcgatttt ttaaattatc ttatttaata    2280
```

```
aatagttatg acgcctacaa ctccccgccc gcgttgactc gctgcacctc gagcagttcg    2340
ttgacgcctt cctccgtgtg gccgaacacg tcgagcgggt ggtcgatgac cagcggcgtg    2400
ccgcacgcga cgcacaagta tctgtacacc gaatgatcgt cgggcgaagg cacgtcggcc    2460
tccaagtggc aatattggca aattcgaaaa tatatacagt tgggttgttt gcgcatatct    2520
atcgtggcgt tgggcatgta cgtccgaacg ttgatttgca tgcaagccga aattaaatca    2580
ttgcgattag tgcgattaaa acgttgtaca tcctcgcttt taatcatgcc gtcgattaaa    2640
tcgcgcaatc gagtcaagtg atcaaagtgt ggaataatgt tttctttgta ttcccgagtc    2700
aagcgcagcg cgtattttaa caaactagcc atcttgtaag ttagtttcat ttaatgcaac    2760
tttatccaat aatatattat gtatcgcacg tcaagaatta acaatgcgcc cgttgtcgca    2820
tctcaacacg actatgatag agatcaaata aagcgcgaat taaatagctt gcgacgcaac    2880
gtgcacgatc tgtgcacgcg ttccggcacg agctttgatt gtaataagtt tttacgaagc    2940
gatgacatga cccccgtagt gacaacgatc acgcccaaaa gaactgccga ctacaaaatt    3000
accgagtatg tcggtgacgt taaaactatt aagccatcca atcgaccgtt agtcgaatca    3060
ggaccgctgg tgcgagaagc cgcgaagtat ggcgaatgca tcgtataacg tgtggagtcc    3120
gctcattaga gcgtcatgtt tagacaagaa agctacatat ttaattgatc ccgatgattt    3180
tattgataaa ttgaccctaa ctccatacac ggtattctac aatggcgggg ttttggtcaa    3240
aatttccgga ctgcgattgt acatgctgtt aacggctccg cccactatta atgaaattaa    3300
aaattccaat tttaaaaaac gcagcaagag aaacatttgt atgaaagaat gcgtagaagg    3360
aaagaaaaat gtcgtcgaca tgctgaacaa caagattaat atgcctccgt gtataaaaaa    3420
aatattgaac gatttgaaag aaaacaatgt accgcgcggc ggtatgtaca ggaagaggtt    3480
tatactaaac tgttacattg caaacgtggt tcgtgtgcc aagtgtgaaa accgatgttt    3540
aatcaaggct ctgacgcatt tctacaacca cgactccaag tgtgtgggtg aagtcatgca    3600
tcttttaatc aaatcccaag atgtgtataa accaccaaac tgccaaaaaa tgaaaactgt    3660
cgacaagctc tgtccgtttg ctggcaactg caagggtctc aatcctattt gtaattattg    3720
aataataaaa caattataaa tgctaaattt gttttttatt aacgatacaa accaaacgca    3780
acaagaacat ttgtagtatt atctataatt gaaaacgcgt agttataatc gctgaggtaa    3840
tatttaaaat cattttcaaa tgattcacag ttaatttgcg acaatataat tttattttca    3900
cataaactag acgccttgtc gtcttcttct tcgtattcct tctctttttc attttctcc    3960 tcataaaaat taacatagtt attatcgtat ccatatatgt atctatcgta tagagtaaat    4020 ttttgttgt cataaatata tatgtctttt ttaatggggt gtatagtacc gctgcgcata    4080
gtttttctgt aatttacaac agtgctattt tctggtagtt cttcggagtg tgttgctttt a    4140 attattaaat ttatataatc aatgaatttg ggatcgtcgg ttttgtacaa tatgttgccg    4200
gcatagtacg cagcttcttc tagttcaatt acaccatttt ttagcagcac cggattaaca    4260
taactttcca aaatgttgta cgaaccgtta aacaaaaaca gttcacctcc cttttctata    4320
ctattgtctg cgagcagttg tttgttgtta aaaataacag ccattgtaat gagacgcaca    4380
aactaatatc acaaactgga aatgtctatc aatatatagt tgctgatatc atggagataa    4440
ttaaaatgat aaccatctcg caaataaata agtattttac tgttttcgta acagttttgt    4500
aataaaaaaa cctataaata tgccggatta ttcataccgt cccaccatcg ggcgtaccta    4560
cgtgtacgac aacaagtact acaaaaattt aggtgccgtt atcaagaacg ctaagcgcaa    4620
gaagcacttc gccgaacatg agatcgaaga ggctacccctc gaccccctag acaactacct    4680
```

```
agtggctgag gatcctttcc tgggacccgg caagaaccaa aaactcactc tcttcaagga    4740
aatccgtaat gttaaacccg acacgatgaa gcttgtcgtt ggatggaaag gaaaagagtt    4800
ctacagggaa acttggaccc gcttcatgga agacagcttc cccattgtta acgaccaaga    4860
agtgatggat gttttccttg ttgtcaacat gcgtcccact agacccaacc gttgttacaa    4920
attcctggcc caacacgctc tgcgttgcga ccccgactat gtacctcatg acgtgattag    4980
gatcgtcgag ccttcatggg tgggcagcaa caacgagtac cgcatcagcc tggctaagaa    5040
gggcggcggc tgcccaataa tgaaccttca ctctgagtac accaactcgt tcgaacagtt    5100
catcgatcgt gtcatctggg agaacttcta caagcccatc gtttacatcg gtaccgactc    5160
tgctgaagag gaggaaattc tccttgaagt ttccctggtg ttcaaagtaa aggagtttgc    5220
accagacgca cctctgttca ctggtccggc gtattaaaac acgatacatt gttattagta    5280
catttattaa gcgctagatt ctgtgcgttg ttgatttaca dacaattgtt gtacgtattt    5340
taataattca ttaaatttat aatctttagg gtggtatgtt agagcgaaaa tcaaatgatt    5400
ttcagcgtct ttatatctga atttaaatat taaatcctca atagatttgt aaaataggtt    5460
tcgattagtt tcaaacaagg gttgttttc cgaaccgatg gctggactat ctaatggatt    5520
ttcgctcaac gccacaaaac ttgccaaatc ttgtagcagc aatctagctt tgtcgatatt    5580 cgttgtgtt tgttttgta ataaaggttc gacgtcgttc aaaatattat gcgcttttgt    5640
atttctttca tcactgtcgt tagtgtacaa ttgactcgac gtaaacacgt taaataaagc    5700
ttggacatat ttaacatcgg gcgtgttagc tttattaggc cgattatcgt cgtcgtccca    5760
accctcgtcg ttagaagttg cttccgaaga cgattttgcc atagccacac gacgcctatt    5820
aattgtgtcg gctaacacgt ccgcgatcaa atttgtagtt gagcttttg gaattatttc    5880 tgattgcggg cgttttggg cgggtttcaa tctaactgtg cccgatttta attcagacaa    5940
cacgttagaa agcgatggtg caggcggtgg taacatttca gacggcaaat ctactaatgg    6000
cggcggtggt ggagctgatg ataaatctac catcggtgga ggcgcaggcg gggctggcgg    6060
cggaggcgga ggcggaggtg gtgcggtga tgcagacggc ggtttaggct caaatgtctc    6120
tttaggcaac acagtcggca cctcaactat tgtactggtt tcgggcgccg ttttggttt    6180 gaccggtctg agacgagtgc gattttttc gtttctaata gcttccaaca attgttgtct    6240
gtcgtctaaa ggtgcagcgg gttgaggttc cgtcggcatt ggtggagcgg gcggcaattc    6300
agacatcgat ggtggtggtg gtggtggagg cgctggaatg ttaggcacgg gagaaggtgg    6360
tggcggcggt gccgccggta taatttgttc tggtttagtt tgttcgcgca cgattgtggg    6420
caccggcgca ggcgccgctg gctgcacaac ggaaggtcgt ctgcttcgag gcagcgcttg    6480
gggtggtggc aattcaatat tataattgga atacaaatcg taaaaatctg ctataagcat    6540
tgtaatttcg ctatcgttta ccgtgccgat atttaacaac cgctcaatgt aagcaattgt    6600
attgtaaaga gattgtctca agctcggatc ccgcacgccg ataacaagcc ttttcatttt    6660
tactacagca ttgtagtggc gagacacttc gctgtcgtcg acgtacatgt atgctttgtt    6720
gtcaaaaacg tcgttggcaa gctttaaaat atttaaaaga acatctctgt tcagcaccac    6780
tgtgttgtcg taaatgttgt ttttgataat ttgcgcttcc gcagtatcga cacgttcaaa    6840
aaattgatgc gcatcaattt tgttgttcct attattgaat aaataagatt gtacagattc    6900
atatctacga ttcgtcatgg ccaccacaaa tgctacgctg caaacgctgg tacaatttta    6960
cgaaaactgc aaaaacgtca aaactcggta taaaataatc aacgggcgct ttggcaaaat    7020
```

```
atctatttta tcgcacaagc ccactagcaa attgtatttg cagaaaacaa tttcggcgca    7080 caatttaac gctgacgaaa taaaagttca ccagttaatg agcgaccacc caaattttat     7140
aaaaatctat tttaatcacg gttccatcaa caaccaagtg atcgtgatgg actacattga    7200
ctgtcccgat ttatttgaaa cactacaaat taaaggcgag ctttcgtacc aacttgttag    7260
caatattatt agacagctgt gtgaagcgct caacgatttg cacaagcaca atttcataca    7320
caacgacata aaactcgaaa atgtcttata tttcgaagca cttgatcgcg tgtatgtttg    7380
cgattacgga ttgtgcaaac acgaaaactc acttagcgtg cacgacggca cgttggagta    7440
ttttagtccg gaaaaaattc gacacacaac tatgcacgtt tcgtttgact ggtacgccgt    7500
cggcgtgtta acatacaagt tgctaaccgg cggccgacac ccatttgaaa aaagcgaaga    7560
cgaaatgttg gacttgaata gcatgaagcg tcgtcagcaa tacaatgaca ttggcgtttt    7620
aaaacacgtt cgtaacgtta acgctcgtga ctttgtgtac tgcctaacaa gatacaacat    7680
agattgtaga ctcacaaatt acaaacaaat tataaaacat gagttttgt cgtaaaaatg      7740 ccacttgttt tacgagtaga attctacgtg taacacacga tctaaaagat gatgtcattt    7800
tttatcaatg actcatttgt tttaaaacag acttgtttta cgagtagaat tctacgtgta    7860
aagcatgatc gtgagtggtg ttaataaaat cataaaaatt attgtaaatg tttattattt    7920
aaaaacgatt caaatatata ataaaaacaa tctacatcta tttcttcaca atccataaca    7980
cacaacaggt ccatcaatga gttttgtct ttatccgaca tactatgtgc atgtaacaaa     8040
tcaaatacat cttttaaatt tttatacaca tctttacatt gtctaccaaa atctttaata    8100
accctataac aaggaaaaga cttttcttct tgcgtggttt tgccgcgcag atattgaaat    8160
aaaatgtgca tgcacgacaa cttgtgttta ctaaaatgct ccttgcctat accgcaaaac    8220
cggccataca tttcggcgat tacacgcgga caattgtacg attcgtctac gtgtaaacga    8280
tcatcataat cactcttgcg caaacgaata aattttttca ccgcttccga caaacgaggc    8340
accaattcgg cgggcacgct tcgatacatt attctgtgca cataagttac cacacaaaat    8400
ttattgtacc accatccgac aacgtcgtta ttagggttga acacgttggc gatgcgcagc    8460
agtttcccgt ttctcatgaa atattcaaag cggcccaaaa taatttgcaa gcaatccaac    8520
atgtcttgag aaatttctcg ttcaaaattg ttcaaagaga atatctgcca tccgttttga    8580
acgcgcacgc tgacgggaac caccgcatcg atttgctcca acacttcacg gacgttatcg    8640
tcgatgccca tcgtttcgct ggtgctgaac caatgggaaa ggctcttgat ggaatcgccc    8700
gcgtctatca tcttgaccgc ttcgtcaaag gtgcaactgc cgctcttcaa acgccgcata    8760
gcggtcacgt cccgctctat gcacgacata ccgtttacgt acgattctga taggtattcc    8820
tgaactatac ggtaatggtg atacgactcg ccatacacgt cgtgcacctc attgtattta    8880
gcataataat tgtaaattat taactttgca gcgagagaca tgttgtcagt aaagcggtgc    8940
taggctcaat aatactgatg tacaggcacg cgtgctattt atatataatt tcgcaaggag    9000
gggagctgtt atcggttgct attattaaag aatggccgtc tgttttatc acaagcttgg     9060 cagcctcaac catgaagcgt cgtcattgta aattaaattc tctgcctcaa gaattatttg    9120
acaagattgt cgagtattta tctttatctg attactgcaa tttggtgctt gtctgtaaaa    9180
gaccttctag taaatataac gtgatatttg atagtactaa tcaccaacat ttgaaaggcg    9240
tgtacaaaaa gacagacgtg caaataacaa gctacaacga atacatcaac tgtatttgca    9300
acgaactgag acaagacgaa ttctatgcca aatcatcatg gattgcgagt atttgcggtc    9360
accagagagc gacaattttt agtgtaacaa ataaacaagt agaaatgaaa tatcatttgt    9420
```

```
ataatatagc aattgtggaa agtgaagatt gcaacggatt ttacccattt gagccaacgc    9480
gcgattgttt aatatgcaaa caaaaaaacc aatgtcctcg taattcattt attgtttcgt    9540
tgtgtaaata tttagaaaaa caaaatgtac aatcaaactt tatatattat ttatacgaaa    9600
taaatacata ataataacta ttatacatgt ttttatttta caatacttcc tgtataacct    9660
ctctaactac attaggagta caatccacgt caattacacg tttagctatt tttctaattt    9720
tgtaatgttt atcgtagagt ttttcgttaa tacattgaat agccaacaag ggatttgggt    9780
gcacaccgtc atagagtact tccatgtcgt cttcaaagcg catttttcgc ttgcgaaaat    9840
gccgctcttg gcccaaaaca aaagcgagtt tgatgcggtc gtcgatgcgt tccgaaaata    9900
cggccaaatg ctggtgtttg gtgatgtcgc gcggaaacgt caccgtgcca tttttgcttt    9960
ccgccacgac ggcggttttc aattttttcgg ccgactgcag catgttaagt ttggcgtcga   10020
gttcgtgcaa acgcaattca aactgctcaa acctgttgcc cacctcgttc ttgaacgtct   10080
cgtgggtgac cataaatttt tcgctgtttg cattcagttt ctttacatgt tttaaaacag   10140
attcaatctt gtcgcgcaaa tcatcacgct cgccttcagt ttgaatgtgc agcaacgcgt   10200
tgcttttgtt ggcaaaattt aaccgcatca aaatttccaa caacccgtgc ttggtcgcga   10260
acaatgcgcc caacgagttg agatcgcgtt tggatctctg tttgtgaaaa acaatttcgt   10320
ttaaatggta aacttgatcg ccgtcccaat tgcaatcaag tatgtcgtcg tgcgcaattt   10380
caagaccttt gcaaaaatct atcacattgt agcatttttgc gttcgtgtcg ctgtgcacgt   10440
atctgtactt gaaactgtgc gtgttgcatt tgaatgagtc ccatttaacg atgtgcgacc   10500
attgttgggc gtttatgtgg tacttttttgt agtcgtctgc attgaaccga tcttcggcgg   10560
cgatggcgtc gttgtcgttg tcaccggacc acatccacca gttccataac caggatagca   10620
ttgctttagc ttgtctagca attcctttgt tatacaacga gaaaatttcg ttcccttata   10680
attatagctg tacggtgcgc gtatttgttt gttaacgtta caaaaaatat ccctgtccac   10740
gtccggccaa tactgcaacg tgagcgcgtc caagtttgaa tcttgcatat gcggaacgta   10800
caaacgtacg gcctctctca cacaatgcgc aaaactgccc ggctgaatgt aatcactgtc   10860
caactttgca ggtttctcga aagccttgta ccgatgcacg cgaacatttt gagcggacgt   10920
gattttaaac ttgtcggtga attttaacca caaatgaaat ccacggttgc cggtatacat   10980
gactcttgac acgttctctt ccgtgtaaaa caacagaaac gccgtggcgc caatgtaaat   11040
tttcagcatt aaatcgtgtt cgtcaacata attttttgtaa tcggcgtcta cgacccattc   11100
cctgccgccg ccgtcgtcca acggtttgac gtgcacgtcg dacactttgt tttgcacaat   11160
ataactatac aattgtgcgg aggtatcaaa atatctgtcg gcgtgaatcc agcgcgcgtt   11220
gaccgtcatg aacgcgtact tgcggctgtc gttgtacgca atggcgtccc acatcatgtc   11280
gacgcgcttc tgcgtataat tgcacactaa catgttgccc tttgaacttg acctcgattg   11340
tgttaatttt tggctataaa aaggtcaccc tttaaaattt gttacataat caaattacca   11400
gtacagttat tcggtttgaa gcaaaatgac tattctctgc tggcttgcac tgctgtctac   11460
gcttactgct gtaaatgcgg ccaatatatt ggccgtgttt cctacgccag cttacagcca   11520
ccatatagtg tacaaagtgt atattgaagc ccttgccgaa aaatgtcaca acgttacggt   11580
cgtcaagccc aaactgtttg cgtattcaac taaaacttat tgcggtaata tcacggaaat   11640
taatgccgac atgtctgttg agcaatacaa aaaactagtg gcgaattcgg caatgtttag   11700
aaagcgcgga gtggtgtccg atacagacac ggtaaccgcc gctaactacc taggcttgat   11760
```

```
tgaaatgttc aaagaccagt tgacaatat caacgtgcgc aatctcattg ccaacaacca    11820
gacgtttgat ttagtcgtcg tggaagcgtt tgccgattat gcgttggtgt ttggtcactt    11880
gtacgatccg gcgcccgtaa ttcaaatcgc gcctggctac ggtttggcgg aaaactttga    11940
cacggtcggc gccgtggcgc ggcaccccgt ccaccatcct aacatttggc gcagcaattt    12000
cgacgacacg gaggcaaacg tgatgacgga aatgcgtttg tataaagaat ttaaaatttt    12060
ggccaacatg tccaacgcgt tgctcaaaca acagtttgga cccaacacac cgacaattga    12120
aaaactacgc aacaaggtgc aattgctttt gctaaacctg catcccatat ttgacaacaa    12180
ccgacccgtg ccgcccagcg tgcagtatct tggcggagga atccatcttg taaagagcgc    12240
gccgttgacc aaattaagtc cggtcatcaa cgcgcaaatg aacaagtcaa aaagcggaac    12300
gatttacgta agtttttgggt cgagcattga caccaaatcg tttgcaaacg agtttcttta    12360
catgttaatc aatacgttca aaacgttgga taattacacc atattatgga aaattgacga    12420
cgaagtagta aaaaacataa cgttgcccgc caacgtaatc acgcaaaatt ggtttaatca    12480
acgcgccgtg ctgcgtcata aaaaatggc ggcgtttatt acgcaaggcg gactacaatc    12540
gagcgacgag gccttggaag ccgggatacc catggtgtgt ctgcccatga tgggcgacca    12600
gttttaccat gcgcacaaat tacagcaact cggcgtagcc cgcgccttgg acactgttac    12660
cgtttccagc gatcaactac tagtggcgat aaacgacgtg ttgtttaacg cgcctaccta    12720
caaaaaacac atggccgagt tatatgcgct catcaatcat gataaagcaa cgtttccgcc    12780
tctagataaa gccatcaaat tcacagaacg cgtaattcga tatagacatg acatcagtcg    12840
tcaattgtat tcattaaaaa caacagctgc caatgtaccg tattcaaatt actacatgta    12900
taaatctgtg ttttctattg taatgaatca cttaacacac ttttaattac gtcaataaat    12960
gttattcacc attatttacc tggttttttt gagaggggct ttgtgcgact gcgcacttcc    13020
agcctttata aacgctcacc aaccaaagca ggtcattatt gtgccaggac gttcaaaggc    13080
gaaacatcga aatggagtct gttcaaacgc gcttatgtgc cagtagcaat caatttgctc    13140
cgttcaaaaa gcgccagctt gccgtgccgg tcggttctgt gaacagtttg acacacacca    13200
tcacctccac caccgtcacc agcgtgattc caaaaaatta tcaagaaaaa cgtcagaaaa    13260
tatgccacat aatatcttcg ttgcgtaaca cgcacttgaa tttcaataag atacagtctg    13320
tacataaaaa gaaactgcgg catttgcaaa atttgctaag aaaaaagaac gaattattg    13380 ccgagttggt tagaaaactt gaaagtgcac agaagaagac aacgcacaga atattagta    13440 aaccagctca ttggaaatac tttggagtag tcagatgtga caacacaatt cgcacaatta    13500
ttggcaacga aaagtttgta aggagacgtt tggccgagct gtgcacattg tacaacgccg    13560
agtacgtgtt ttgccaagca cgcgccgatg gagacaaaga tcgacaggca ctagcgagtc    13620
tgctgacggc ggcgtttggt tcgcgagtca tagtttatga aaatagtcgc cggttcgagt    13680
ttataaatcc ggacgagatt gctagtggta aacgtttaat aattaaacat tgcaagatg    13740 aatctcaaag tgatattaac gcctattaat ttgaaaggtg aggaagagcc caattgcgtt    13800
gagcgcatta ccataatgcc atgtatttta atagatactg agatctgttt aaatgtcaga    13860
tgccgttctc cttttgccaa attcaaagta ttgattattg tagatggctt tgatagcgct    13920
tatattcagg ctacctttttg tagcattagc gatagtgtaa caattgttaa caaatctaac    13980
gaaaagcatg taacgtttga cgggtttgta aggccggacg atgaaggtac aacaatgcct    14040
tatgtcattg gaccattata ttctgtcgac gctgctgtcg ccgaccgtaa agtgaaggac    14100
gtggtggatt caattcaaaa ccaacagaca atgttaaaag tatttattaa cgaggctaat    14160
```

```
gtgtataaca aatggaatat gcttaaaggt ttaatttata ataataacaa tgaatctgtt   14220
ttagtaaaat aatgtagtaa aatttataaa ggtagataaa aattataata ttaataaaaa   14280
aaataatgtt actaaatggg ttcctgcgtt aaattatttt acgggtagac agctattaac   14340
tattttattt attttaaat ttaaataaat gtattgttag aaaattgtgt tgttttatta   14400
gtataacgaa aaaatacatg acataaaccg cttccaattt tggtcacaca aactcttgtg   14460
tggatagttt acgtaatgag ttaaataggc gggcagttgt ccgctaaacg tgtcggtggt   14520
caagtagatg tgcattaatt tacgacaacc aaagcggggg ccgcttatgt caagtatttt   14580
tttcacaaaa ttggtaatgg tttcgttttg ttccttgtac aaacacatgt cggtgtgatc   14640
gttgacgcac gagttgtacg attccgccgg caggttggca acaagcgct tgagatgctt    14700 gagtctgcgt tcaattttat aatcaaactt gttggtgaaa atgtctttca gcaagcacat   14760
taactggtcg ttcaaaacgc gctgcaacga cgacaccaac acatgatatt cgtttccaaa   14820
aagcgaaaaa ttttttgatgc agcggtccgc gttgaagggt cgtttcataa tgcgcacgtt   14880
gacaaaaaac acgttgaaag acagcggggc tgtggttatt ttaacgccgt tgtcggtata   14940
ctcgtcgacg ccgtctgcgc ttgttatgtc aatttgtagc gcaaatctaa ccaaatcaaa   15000
ctcatcgttg tactgtgtct ttatgcattt tatatggcgg tttaagtgca agttgatttg   15060
gccgtttaat ctataggctc cgttttgata acatttcagc actaccaacg gatccgacat   15120
gtaaacttga cgcgttagca cgtccaattc agcgtaatgt tggtcgacgc attttttgtaa  15180 attagtttgc aggttgcaaa acattttttgc gcaaaagccg taatagtcaa aatctatgca   15240
ttttaatgcg cttctgtcgt cgtcaatatg gcatgtcacg gctgcgcctc cagttaacac   15300
gaataaaccg ccgttttcgc aaactacggc ttcgaaacaa tctttgataa atgccaactt   15360
tgctttagcc acaattttat cgcgcaggcg atcttcaata tcctttgtcg taatataagg   15420
taggacgcca agatttagtt gattcaacaa acgttccata atgaatagcg gcgacgcaac   15480
acgactacac tgttcaaatg cgcacgcaaa acaaacccctt gcaactttat ttgccaatcg   15540
taatcacagt agtttttacg agtacgccat cgcgtttgta agcacattgc ttttttaaaaa  15600 taatttaaat ttaatgaccg cgtgcaattt gatcaactcg ttgatcaact ttgaactcaa   15660
catgtttggt aaaagtttat tgctaaatgg atttgttaat ttctgcattg ctaacagcga   15720
cggggttacg attcaacata aaatgttaac caacgtgtta agttttttgt tggaaaaata   15780
ttattaaaaa taaataaata aacttgttca gttctaatta ttgttttatt ttttataaaa   15840
taatacaatt ttatttatac attaatactt tggtatttat taatacaatt atttacaata   15900
ctttatttac actataatac tttatttaca ttagtactaa attaatacta aattacgcta   15960
atactaaatt aatactttat ataatcaaaa ataatacttt atataatact ttctaatcat   16020
cataaacggg taatagtttt ttctcttgaa atttacgctg caactcttcg ctaaaacaca   16080
tgggcggtgg agtgggagcg ggtggagtag gagtccttac gggtttgatg ggcgacagtt   16140
ctctggactt gcggaacagc ttgggcgaaa acgtcggcgt gcgccgacta atgatttctt   16200
catcgcacga ggcgtcgcac attgtgcacg cgtccggtga ggtacacaaa actttcttgg   16260
gcacgctgta caccggcttg ggcacgctat atgtgttgcc aaaactagaa ctcgttgtgg   16320
ttgccgaacg gagacgatgg gtgtgaagac ggcgatggct gtgaagacaa gtccgaaggc   16380
gcgataaaag atgaaagtgt ttctgaaacc gaagtggtgg tagaagtggt agaaggcggg   16440
tgcgttacgg caaccacgct gctgctatt ctgccttcgg agaccacttc cagcaatcta   16500
```

```
gagttactct ctcgttcttc gcggcgatag tcaatgtcgc aataatgttc ataagatgcc    16560 tttcggctt cggcgcgcct tttcatgtat atgttgtgac gcatctcctt taactgcacg     16620
tacaaattcc agcattgcac agccagtatc gtaagcacgc ccattatgat tacgggataa    16680
ttttgattaa acacggtcgg ctcgtgatcg cttacaatcg ctcggcacat gatgcatttt    16740
ttgtaaatgt tcacatacac acagttttgg ctcaaggttt cggtatttgc gtagtcaatt    16800
tccagataca cgatagagtt ccagcacatt gattccaaat cgtagtgacg atataaaaca    16860
tctagcgccg gtagatgacc atttttgaac acgtagattt gaaacgcggc aaacagcatc    16920
caacacagcc cagtgatcac gtttaccata atacacgtga tagcgacgta aaagttttct    16980
ttcgcattga aatttacatt tgtgtttgaa gagctgctgc gattttcgt ccacacgata      17040 atcttccata taaataaaaa catgtaaaat aatatccaca tgccgaacgc cagcattatc    17100
ggtatagata gattgataac cgattgcttt ccttcaattt ccagcaaaaa cgcgtatctg    17160
ctgtctatca ctcccattat agataacaca aacactatca gatatgctaa taataatgag    17220
gcattaagcc cgaattgtaa aactgcagtg attttattta acattttgaa tatttaattc    17280
aacaactaag taatggcaat atgtatcgag tactgatcgt gttttttcctg ttcgtgtttc    17340 tttatatagt gtaccagccc ttttatcagg catacttgca tatcggacat gcccaacaag    17400
attacaatga cacgttggac gataggatgg attacattga atccgtaatg cgtagaaggc    17460
actacgtgcc gattgaagcg ttgcccgcaa tcaggtttga tactaatctc ggcacgttgg    17520
ccggtgacac gattaaatgc atgtcggtgc ctttgtttgt tagtgacatt gacctgccga    17580
tgtttgattg tagtcagata tgcgataacc cgtctgcggc gtatttcttt gtcaacgaaa    17640
cggatgtgtt tgtggtcaac ggccacagac tgacggtggg cggatactgc tccactaata    17700
gtttgccccg caactgtaat cgcgagacga gcgtcatttt aatgagtctc aatcagtgga    17760
cgtgcatagc cgaggacccg cgttactatg cgggcacaga taacatgacg caactcgcag    17820
gcagacaaca ctttgaccgc attatgcccg gacagagtga taggaacgtc ctgtttgacc    17880
gattactagg ccgagaggtg aacgtgacca ctaacacgtt tcgccgcagc tgggacgagt    17940
tgctggagga cggcactagg cggttcgaaa tgcgctgcaa cgcccgagat aacaacaata    18000
atctcatgtt tgttaatccg cttaatcccc tcgagtgtct cccgaacgtg tgcactaacg    18060
ttagcaacgt gcacaccagt gttagacccg tatttgaaac gggagagtgt gactgcggcg    18120
acgaagcggt cacgcgtgtt acgcacattg tgccggggga caggacctct atgtgtgcca    18180
gcattataga tggcctggat aaaagtacgg catcatatag atatcgcgta gagtgcgtta    18240
atctgtacac ctctattcta aattattcta ataacaaatt gttatgtccc agtgacactt    18300
ttgatagtaa cacggacgca gcttttgcct ttgaagtgcc cggctcctac cctttatcgc    18360
gcaacggcat caacgagcca acttatcgct tttatcttga taccagatct cgagttaatt    18420
acaatgacgt cagagggcag ttatcttaat tgtgataaca caaacaataa gtcatttaaa    18480
tgttacgtca gtagttagta tataagccgt acatgttggc ttgcaaattc agtcaatatc    18540
aggcttttat catggacggt gtaaagctgc tagggacgtg cgcgctaata attttgttat    18600
cgacgacgag tacagttgtc gggcgtgacc gtatcacgtt tacgccgata gaagatagcg    18660
caggcctcat gtttgaacgc atgtacggct tgcgacatca tacagacgac agatttgtgt    18720
ttgtgaaaaa attcaatttt gtttcggtgc tgcaagagct caataatatc aaatctaaaa    18780
ttgaattata tgaagcgcaa gtttcaactt gcacaaacgt cagacaaata aaacagaaca    18840
gatcgagtat catcaaagct cgcattgaaa atcagctgca gtttttgacg caactaaaca    18900
```

```
aaaatctcat cacatactct gtggaaagca gcattttaag caacgacgtg ctggacaaca   18960
tcgatctgga atatgacgac agcggtgagt ttgacgttta cgacgaatac gaacagcctt   19020
cgcattggag caacatgact gtatccgacg cgcaagcttt gctccgaaac ccgcccaaag   19080
acagagtaat gttttggac acggttacca ccagcgacgt gagcagcaaa tacgaagaat    19140
acataaactg cattgtgagc aaccgtaccg ttgaaaacga gtgcatgttt ttagccaaca   19200
tgatgaacgt gctcaacgac aaattggacg acgcagcagc tttggccaag atgctggagc   19260
gaatagtaaa acaaacgcga aagaacaaac tcaacatctc caacacggtt atagacgacg   19320
acacgctgct aacggaaatg aaaaaattaa cacaaacttt atacaaccaa aaccgcgtgt   19380
gggtagtgga ttttaacaag gacatgaata gttatttcga tttgtcgcaa gcgtataaat   19440
tgcatttata tgttgattta aacacggtca ttatgtttat taccatgcca ttgttaaaat   19500
ccaccgccgt ttcgtttaat ttgtatcgcg tcatgacggt gccttttgc aggggcaaaa    19560 tgtgtctgct tatcatttcg ggcaatgaat actttgggat tacagacagc aaaaactatt   19620
atgtgcccgt atctgataac tttagacaag attgccaaga gtttacgggc tacaatgagt   19680
ttttgtgtcc cgaaactgag ccgattgcca ctatgaactc gaaagtgtgc gagattgaaa   19740
tgtttatggg tcgatatagc gacgacgtgg acaacatgtg cgacattagg gtggccaatt   19800
ataatcccaa aaaagcttac gtgaacactt aatagacta ccgaaaatgg ttgtacattt     19860
ttccaaacac gaccgtgtcc gtccactatt attgtcacga cgcgcttgta aagttgata     19920 caaaagtttc gcccggcgtt ggtgttatgt tttcgactat ggcgcaaacg tgttcgatta   19980
gaataacgta tgatgtgacc ataactgtag attcgcgatt ttatgtcagc cattcaacta   20040
catactggcc taaaagaaa tttaatttta caactacat cgaccaaatg ttgcttgaaa     20100
aagcgaccac cagttttata ccgactgttg acaattttac ccggcccgtt ttattgcaac   20160
ttcctcataa atttcacatt aaagattaca catcgacgcc ccatcatttt ttccatcagt   20220
ctaaaattta caccaacagc gcggcgcccg acgaagactc gcaagacgac agtaatacca   20280
ccgtggttat tatcgctatt gtcgctgcaa tgatcctatt ctgtggatta ttgttatttt   20340
tgttttgctg tataaaaaaa cggtgtcatc aatcaaataa cgtggttgtg caatacaaaa   20400
ataacaatga atttgtcaca atttgcaata atttagaaga caatcgagca tacattaatt   20460
tacctaatga atacgatagc gatgatatgc caaaaccatt gtacccttta cttggcttta   20520
atgatgattt gttaaaagat gataaacctg tgttgtaccc tatgattata gaaagaataa   20580
aataaaacat gtataattga aataaatata ttatttaata aaatgttttt tatttatata   20640
ctattttcta ttacatattc caatgcacac aaatgtttaa tggctatcag ttttaatttt   20700
actaattcgt ctaaacaaaa attattcact tgctgttttt catccatttg acatatggcg   20760
tttataaata attcgctgtg ttttatgaac gaatcgtaaa ccgctgcctg ggccttcagc   20820
acggtcggcg cattgtattt ttgggtaaag tacgcaatat ttttagtcaa acacagagat   20880
tttaaatctt tttcatttat atccaagtcg gaacaatcgt atacaaaatc tagcttttca   20940
ctttcgggcg cgcccagata ctggtttacg agttcgagct gctccacttg gcctttgata   21000
tcggccgcta tgcacaacat tttgtcgatt gcagtttcat tgttttaac ataataattt    21060 ttaactttt tattttgcaa tttaatcaaa ctatttaaat tcgcttgacc tttcttacaa    21120
agcgcagtta atatgcaaga cattttgact tataataaaa aacaaaactt ttatatattc   21180
atttattgtt caataataac aaatattcca ggcttaaaag ctaacgaata gggcttttcg   21240
```

| | |
|---|---|
| gtaattttct tattattcat gtccgtcatc tgcatctctt tgccgtactt gacgccgtca | 21300 |
| atggtgccca tcatgtacat tttaatctcc tccgaaggtc cgtctatttt gtccatttcg | 21360 |
| aacaatctat caaaatcttc aacgctcatt ctctgcatat caagaggaac gtttctgatc | 21420 |
| tttccggtgg cgtaaattga tccgttgttg tcacggttga ttatgtaaaa ccgacgaatc | 21480 |
| aacatgtcgc gctcgctagt tttgttctta tccggcaaat gaatgcacac gtttggttcc | 21540 |
| atcttcaaag gaaaatcgct tgcaagtgt ttttgcaaaa tgttgccaaa tatattgttg | 21600 |
| tgtttgtgaa tgtctccgta ttgaatgcta aaaaactggc caaagttgct tttggcacgt | 21660 |
| tttatggttc caaagtcgga aaaccaaaat ccgcagggct tgccctgcac tcttggaccg | 21720 |
| atggtgtacg tagtcttgcc gttggccggc tccaacacca cgatattttt atcgggctcg | 21780 |
| ggatacaact tgtcttccca ttcgtgcaaa ctgttcaaat tagacagtcg acaaaattcg | 21840 |
| tttttcaaaa atctgccttc gaaacaacta caattcagta ttgaaaagtt gcctcgtttc | 21900 |
| acattaatcg ccatctgctc ctgccacaac atcttcgtca actcgtgtgg ctccaattga | 21960 |
| atggacgacg gcgtaaaata gcacattacg cccgtttcgt cgtgtttcac gttaaaagcg | 22020 |
| ccgctgttgt acggcaccag ctgctggtcc tcaccacctt ccgatctttc ccgcttcggc | 22080 |
| tggttgtcgt cgctgctcga atatccatcg ccaatcttgc gtttagttgc catgctaccg | 22140 |
| acgtgcgctg tctgctgtgg ttcaagtcta attgaagtgt tcacagaat ataagatata | 22200 |
| taataaatat ggacgactct gttgccagca tgtgcgtaga caacgcgttt gcgtacacta | 22260 |
| ctgacgattt attgaaaaat attcctttta gtcattccaa atgcgcccct ttcaagctac | 22320 |
| aaaattacac cgttttgaag cggttgagca acgggtttat cgacaagtat gtggacgtgt | 22380 |
| gctctatcag cgagttgcaa agtttaatt ttaagataga tcggctaacc aactacatat | 22440 |
| caaacatttt cgagtacgag tttgtagttt tagaacacga tttgtccaca gtgcacgtca | 22500 |
| ttaacgccga aacaaaaacc aaactgggcc atataaacgt gtcgctaaac caaaacgacg | 22560 |
| caaacgtgct cattttgacc gtaactttaa cgagctaaaa tgaacgagga cacgcccccg | 22620 |
| ttttatttta tcagcgtgtg tgacaacttt cgcgacaaca ccgccgaaca cgtattcgac | 22680 |
| atgttaatag aaagacatag ttcgtttgaa aattatccca ttgaaaacac ggcgtttatt | 22740 |
| aacagcttga tcgttaacgg gtttaaatac aatcaagttg acgatcacgt tgtgtgcgag | 22800 |
| tattgcgaag cagaaataaa aaattggtcc gaagacgagt gtattgaata tgcacacgta | 22860 |
| accttgtcgc cgtattgcgc gtatgctaac aagatcgccg agcgtgaatc gtttggcgac | 22920 |
| aacattacca tcaacgctgt actagtgaaa gaaggcaaac ccaagtgtgt gtacagatgc | 22980 |
| atgtccaatt tacagtcgcg tatggatacg tttgttaact tttggcctgc cgcattgcgt | 23040 |
| gacatgatta caaacattgc ggaagcggga cttttttaca cgggtcgcgg agacgaaact | 23100 |
| gtgtgtttct tttgcgactg ttgcgtacgt gattggcata ctaatgaaga cacctggcag | 23160 |
| cgacacgccg ccgaaaaccc gcaatgttat tttgtattgt cggtgaaagg taaagaattt | 23220 |
| tgtcaaaact caattactgt cactcacgtt gataaacgtg acgacgacaa tttaaacgaa | 23280 |
| aacgccgacg acattgagga aaaatatgaa tgcaaagtct gtctcgaacg ccaacgcgac | 23340 |
| gccgtgctta tgccgtgtcg gcattttgtc gtttgcgttc agtgttattt tggattagat | 23400 |
| caaaagtgtc cgacgtgtcg tcaggacgtc accgatttta taaaaatatt tgtggtgtaa | 23460 |
| taaaatggtg ttcaacgtgt actacaacgg ctattatgtg gaaaaaaaat tctccaagga | 23520 |
| gttttttaatt catattgcgc ctgatttgaa aaacagcgtc gactgaaacg gcagcacgcg | 23580 |
| caaacagctg cgcgttctag acaagcgcgc ctacaggcag gtgttgcact gcaacggcag | 23640 |

```
atactactgg cccgatggca caaagtttgt ctctcatccg tacaacaaat ctattcgcac    23700
gcacagcgca acagtcaaac ggaccgacag ctcgcatcga ttaaaaagcc acgtggtcga    23760
caaacgaccg cgccgctctt tagattctcc tcgcttggac ggatatgttt tggcatcgtc    23820
gcccatacca cacagcgact ggaatgaaga actaaagctg tacgcccaga gccacggcta    23880
cgacgactac gacgacaatt tagaagatgg cgaaatcgac gaacgtgact ctttaaaaag    23940
tttaaataat catctagacg acttgaatgt attagaaaaa caataaaaca tgtattaaaa    24000
ataataataa taaaactata ttttgtaata tataatgtat tttatttaaa aattgtctat    24060
tccgtagttg agaaagtttt gtcttgactt cataactctc ttctccatat tctgcagctc    24120
gtttacgttt tttgtgacgc ttttaatttt ctcaaaatgc tggctgtcaa tagttatttt    24180
ttgcttttgt ctattaattt cttccaattg agattttaaa tctcgctgag attgagatgc    24240
gttgtaattc cttgagaaca tcttgagaaa acatacagat gaggtaaaac agcatctttt    24300
atccaaatta ggagttaatt attattcatt tgtatcgcga ccatttgctc gtacacatct    24360
tccataaaat ggttattttt attgcgataa gtgttggcat tgacattttg caaatgtcgt    24420
aggttaaagg ggcaaatggg ctgcgtggcc gataaaagat tccagttcaa caatccctct    24480
tcgcccccgt ttaacttgaa aatggcgcta cacgtttcta cgctatcgtg ttcctgttga    24540
gtggcgcacg gttcgaccag tatcatcttg tgatatgcgg ttttgacatt catgtgcaac    24600
ggataacttt gcgggtcatc gcattcgtcg gaattaagct ttaaatggcg tccgtatgct    24660
ttccaaagtt tttcgtcgtc gaaccgcggc actgcttgca agtcgacgcg gggaaacggc    24720
gctctgtaca aaacgcctaa attcaaaaac tgattgcatt gttgcagctc tgtccaatcg    24780
acgcgatttt tgtaattttg aaacagcatc aggttgaacg ccgcgctggc gcgcacgttt    24840
gtaatcactg tgtaattgat cagcttgtgc caatactggg cattgaaatt tcttcaaac    24900 tcatttctaa actctggatg cgcaaacatg tgtctaatgt agtacgcggg cggggcgttg    24960
aacgcagtcc atttgtcaat acacttccag tctgaatgta acgtgttcac caaaccggga    25020
tattcgtcaa acacgagcat gtgatccgac cacggtatgc tgtgggcgat caattttagt    25080
tcttgcacgc ggccttcgcg taagcaatac aaaatgagcg cgtcgctgat cttgacacag    25140
tcttgcatgt acgcggacaa attaacgttt tccatacagc tcacattgtt tattagcgcc    25200
gtgttcaagt gtttgtattt ggacacataa tcgtagttga tgtactgttt aatgggttct    25260
tgaaaccatt cttttagtag tatgtgactg gccactatgc gtttccaatt taatttgtgt    25320
gcgtattttt gctgcaccga caacgagagg ttattgtaat ttttggatat ttcttccatg    25380
tccaacaagt ccccaaacgc gagtataaaa tcttgcgtca aaattttttg ctcagacacc    25440
aacgaccaga tcaaatgtga tttaaacctg ttggcgattg ttatcgacaa cggcgaaatt    25500
gaaataattt tccaatccaa cttgttgcga aacacgtgaa taaaatcgac gcgtccgtaa    25560
cattcgcgcg atatgcgctt ccaaaacgtg tcatcttgca aattaagcaa atagacacga    25620
ttgttgggag atttgacggc caattcaatt atttttatat attcttttg ctttaaagcg    25680 cgttgtagca cttgggttgg agccatgtcg actgaagctc cacgctgttt gaagcaaggt    25740
gaccgttttg gtcggcatgt tcaaacgtcg attacatgtt tgctttgcat caaatggcg    25800 taattaatta agaaacaaca tgaaagccat ctgcatcatt agcggcgatg ttcatggaaa    25860
aatttatttt caacaagaat cagcgaatca accgcttaaa attagcggct attgttaaa    25920 tttgcctcga ggtttgcacg ctttcacgt gcacgaatat ggcgacacga gcaacggttg    25980
```

```
cacgtcggcc ggtgagcact ttaatcccac caatgaggac cacggcgctc ccgatgctga    26040
aattaggcat gttggcgact tgggcaacat aaaatcggct ggctacaatt cactgaccga    26100
agtaaacatg atggacaacg ttatgtctct atatggcccg cataatatta tcggaagaag    26160
tttggtcgtg cacacggaca aagacgattt gggccttacc gatcatccgt tgagcaaaac    26220
aaccggcaat tctggcggcc gtttgggatg cggaataatt gccatatgta aatgatgtca    26280
tcgttctaac tcgctttacg agtagaattc tacgtgtaaa acataatcaa gagatgatgt    26340
catttgtttt tcaaaactga actcaagaaa tgatgtcatt tgttttcaa aactgaactg     26400 gctttacgag tagaattcta cttgtaacgc atgatcaagg gatgatgtca tttgtttttc    26460
aaaaccgaac tcgctttacg agtagaattc tacttgtaaa acataatcga aagatgatgt    26520
catttgtttt ttaaaattga actggcttta cgagtagaat tctacttgta aaacacaatc    26580
gagagatgat gtcatatttt gcacacggct ctaattaaac tcgctttacg agtaaaattc    26640
tacttgtaac gcatgatcaa gggatgatgt attggatgag tcatttgttt ttcaaaacta    26700
aactcgcttt acgagtagaa ttctacttgt aacgcacgcc caagggatga tgtcatttat    26760
ttgtgcaaag ctgatgtcat cttttgcaca cgattataaa cacaatcaaa taatgactca    26820 tttgttttttc aaaactgaac tcgctttacg agtagaattc tacttgtaaa acacaatcaa   26880
gcgatgatgt cattttaaaa atgatgtcat ttgttttttca aaactaaact cgctttacga   26940
gtagaattct acgtgtaaaa cacaatcaag ggatgatgtc atttactaaa ataaaataat    27000
tatttaaata aaaatgtttt tattgtaaaa tacacattga ttacacgtga catttacgat    27060
ggcgaacaat aatttcactt tttatattag gacacgacgt gtatatagga aagcttaagc    27120
gtttcaataa agccatggcg tacacgctaa gcttgcccag cttgcggctc tttgaaatct    27180
gtagttttcg gggagtaccg tcgttcttca gtgccacata cgtcaacttg cgatcgtaca    27240
ctttataata cgtgttgtag ttatttttttt ccagaaattc cctcataaag caatccttgg    27300 ataaagttt tgatccgtac agttggccac accggtccat gcacaggtac acacacgtga    27360
tggcgttttg aatgacgatg cgatttctgt caacggcaac gcgcttgaat atggtgtcga    27420
cgttgtccga ttcaatggtt ccgtaaacag ctccgtctgg atttactgcc aaaaactgcc    27480
ggttaataaa cagctggccg ggaatagacg tgcccgtgat gtgtgtcagc agagctgagc    27540
agtcagccat agaggctaga gctacaagtg ccagcaagcg atacatgatg aactttaagt    27600
ccccacagca aactggcgct tttatataaa aatttgggcc atttttggcg attagataat    27660
ttttgaagat tagataatat tgagattagt taataatttg tgtgattaga taactttta    27720 gggtattgcg cattataaat caaggtcgag ttgtataaac tgctctggcg tgtaaaactg    27780
cagacttaag ttttttgcaa acactcggtc tgaatcgcta aaatctttct gaccggtggt    27840
tagattaatt cggccagccg cgtcgcccac ataaaaagat tgttccttgt caatatgcgt    27900
aaactgtttg gccatctcgc gccacattcc cgtgtcgggc tttcgatgct catccttgtt    27960
gggcgacaca taaaacgata tgggcacgcc agtagctttt ttaatattct ctaatttata    28020
taataaatcg ctcgctttga ttttgccgga acctaaatgg gcttggttcg taaaaacaac    28080
taaatcgtag cctaattcgt acaaacgctt tagcttgtgt gcgcacggaa ggagctgcca    28140
gtcgtctggg ttttttggaa atttggaccg tgtctttgag ctaattagcg tgccgtccaa    28200
atcaaaagcc gcaattttgg ttcttttagc gccgtcatga accgcgtacg catacaaatc    28260
gggctgctgt aacgtccaca tggtgaatgc atcttactca aagtccatca attcgtacgc    28320
gtttgtgtcc aggtcgggcg ttgaaaaatt gtagcttgcc attagatcgg atagcgattc    28380
```

```
aaattttgta agcgtttgta gcgcacgttt ggcatcttgt ttaaaattac acgacgacag   28440
acagtaaaaa tattcctcga taagcatgac tacacccata tcactgttta agtgctcgac   28500
gtagttgttg catgttatgt cgcgtgtgcc gcgatacgcg tgatttcggt gaaaatcaca   28560
ccacaaccag tcggcgtgcg tgtaacaaag tcgacagcga aacaatttat cgttttccaa   28620
aaaatttaaa tactcgacag ttttgcagct tagattccgc gtttgattca ccttaaaatc   28680
gtcgtcagcc tctataatct cgggcaacag cttgccttgt tgcccatcg tatcgatcac    28740
ctcccccaag tggcccggtg ttatattaag tcgtttaaaa tcatttattg cttcctgcac   28800
gtcggcctgg taatttttga ccacgggcgt ggaaatcaat tgccgttgaa gggaaataat   28860
tcgtggtgtg ggtatcggcc gcctgttgca caattccacc agcggtggag gcaagggcgc   28920
attcacagca accgttgtca tttataagta atagtgtaaa aatgcaaata ttcatcaaaa   28980
cattgacggg caaaaccatt accgccgaaa cggaacccgc agagacggtg gccgatctta   29040
agcaaaaaat tgccgataaa gaaggtgtgc ccgtagatca acaaagactt atctttgcgg   29100
gcaaacaact ggaagattcc aaaactatgg ccgattacaa tattcagaag gaatctactc   29160
ttcacatggt gttacgatta cgaggagggt attaataata acaataataa aaaccattaa   29220
atatacataa aagttttttta tttaatctga catatttgta tcttgtgtat tatcgctaac   29280
cattaaaagt gctggagcca cagtgttgcg gcgagtcttt atagaagatc gttgtttggc   29340
tggaactgag cttttccttt tcctgctgcc gctaatggga gtgggcacgt actctgtagt   29400
agacggtgca acgggcaact tgagcgctac cgtcttaaat ttggccatac ttttagtgat   29460
gaaatcgcgc gttaacactt cgtcgtaaat gttacttagc agaggcgcaa cattgtgatt   29520
aaatgtctcg tttaacaagc tgtaaaactc cgaataaagc ttatcgcgca tttcgcagct   29580
ctccttcaat tctgccaaat ttgcgttggt aagcaccaca gtctgtcttt ttttgctcgc   29640
tggaattgct gcgttctcgc ttgaagacga cgatgtcgat cggtcggcca ttttttttgcc  29700
cagcttttca gtgtgatcaa aaatgaacac aaaatctgcc aattcgggct tgttttttcac  29760
caaatcccac atggccgggc tactaggcca ctcgggctgc ttgatcttag tgtaccaact   29820
gttaaacaaa atgtatttat tgttgttaat cactttcttc ttgcgtttgg acattttgcg   29880
ttcgtcttgc atgacaggca ccacgttaag gatatagtta atgttctttc tttccaagaa   29940
atttacaata acggccagct ggtccatgtt ggatttgttg taagagctcg attccagttt   30000
attcaacagc ttttcatttt tgcacacggc cgcagtctcc ggagattgtt gctccggcac   30060
gtttaccatg tttgcttctt gtaaaccttt gaaacaaccc gtttgtattc ttgatgtatt   30120
attttttttaa tgcccaacaa cctggcaatt cgtttgtgat gaagacacac cttacgcttc   30180
gaacatttgt cggtgattac tgtgaaatgg cctaaattag ctcttatata ttcttttata   30240
cgctcaaacg acacgatgtc caacatgtgc gcgcagacgt tttctgtgtt catcgtgtgc   30300
ttgagcgtgt tgatggcttc cctgaacagc gcttgtattt cgctgcgagt caagcagtcc   30360
gaatcacacc cgcctaagtg cgtgcaattt ttgggggggca tcgttgtcta tctttttcag   30420
agtggcgtag aaaaagtcct gcaattgcct attatcaaaa cgcgccttga cgctgcgcac   30480
aaaatcaaaa aattcaatgt aattgctgta atcgtacgtg atcagttgtt tgtcgttcat   30540
ataattaaag tatttgttga gcggcacgat ggccaggctg cgcgctattt cgcaattgaa   30600
gcgtcgcggt tttaacatta tacggtagtc attgccaaac gtgcccggca acaacttcac   30660
ggtgtacgtg ttgggtttgg cgttcacgtt aatcaagttg ccgcgcacga cgcctacgta   30720
```

```
tatcaaatac ttgtaggtga cgccgtcatc tttccattgt aacgtaaatg caacttgta   30780
gatgaacgcg ctgtcaaaaa accgccagt ttcttccaca aactcgcgca cggctgtctc   30840
gtaaactttt gcgtcgcaac aatcgcgatg acctcgtggt atggaaattt tttctaaaaa   30900
agtgtcgttc atgtcggcgg cgggcgcgtt cgcgctccgg tacgcgcgac gggcacacag   30960
caggacagcc ttgtccggct cgattatcat aaacaatcct gcagcgtttc gcattttaca   31020
tatttgacac ttaaaaaatt gcgcacacga gcaccatcgt ttgataccta attgcaacta   31080
tttacaattt atcagtttac gttgaacccg ttttaatttt ttagatccgt ccttgttcag   31140
ttgcaagttg actaaatgac aaaattttc ggttctgcaa aaccgccctt gtctgttcca   31200
cccgttgtat ttgaaaaaac ttttttcac gcggcgacaa ctgcttgtat aatattgccc   31260
aatgtaaaca tgcaaaattt tgttactctc gtcaaaacag cggttggcgt tccattccat   31320
aatttttta ttatttatca acgatggcca ttgtaaattg tcgtcattta tacgcatcat   31380
atgatttaac aaaagctttt cgtatagcgg aacttcaatt cccttggaac atttttcaaa   31440
cgataattta atttgtttct cggttggcag catttcatgc ttgattaaca atcgcctgac   31500
ttttatagcc acgtttatgt ctttgcacag caaatgtggg ttgtcgacaa tgtaatagtg   31560
caaagcattt gttacggcaa atgcgtagtt tgatttgacg acgcccttt tcttgacggg   31620
cattgcggct tttaaaatta cttgcaagca ttgtacgaat acctctttgt gtttaaacaa   31680
taatatggac aaacatcggc gaaacaattt gtaataatta tgaaatccca aattgcaggt   31740
tttaaacttc tttgttactt gtttataat aaataaaatt tgctgaccca tgtctgcgcc   31800
cacaactttta ttaaccatt tgtgcgcata ttgattgtct cgttgttccc aaccggaaaa   31860
ttgattgatc tcgagccacc ggcattggtc gtttgatacc gtcgttaacg ccgacgctcc   31920
tgcctgtttg attacgggtt ctaaaagacg aaacagcagc gtaaatttgt ttttgcgtcg   31980
gtagtatttt ggcaggcaat aatcaaaaaa atccgtaagc aattctctgc atctattaat   32040
attcgttgcg tacgaatcga gtttttcaaa aattactttg tttgtatgaa ataacgtttt   32100
gggcttctca caataataat cttcgttgta gaacagaaac ggtttgcgag aattggcacg   32160
tttgtccatg attggctcag tgtaacgatt gattcaaatc aaaattgaca acacgtttgc   32220
cgtaatgtgc accggttcgc acacgtttgc cgcgtatgta atccatgttt atttcgctgt   32280
cgcaattgat tacacgattg tgttgggcgg cgcgttttat tgaatttagg cgacgcgtcg   32340
acaactccaa aggattgtaa agcgcagatt tttccagagt aaacgagttt aagtggccac   32400
cgttgaacca ttccagagcc acgattgtgt acagcaaaaa gaatatttct ttgtcgacgt   32460
tttcaaacgc aaacttgttt tttaggcaat agtagtaaaa tttaacgaa ttgtataaat   32520
aaaacataaa attgccattt ttaaagtaaa attctacatc cgtgacgaac aaaaggttta   32580
ctattttgtt ctccaacaag tgtgccaatt ttcttaagta caccattgaa ttttgtcgt   32640
cgtccatctc gatcaacaac acgtacggcg ttttggaatt taaattatt ctaaaatttt   32700
cctgttgcaa cgattccaca gcgtccgacc aatatgacgc tgccacctct agacagatgt   32760
atttcttgga aaacacgtgt cgtttgataa cctcgctgat ggacgtgatc gattgtaaat   32820
acttttcaaa cgtcgcgtct tcccaaccac gcaccgaaac gggcgctgtc gtgtcgggct   32880
gatgtttgaa atccaaacca ctctgaatta acttggttgt gattcgtatg ctcaactgtt   32940
gacccaacgt gtagtgatct tcgtaggcgc gctcccacat cacgttacac acaaatttga   33000
cgagatcatc aacgtctttc tgttgcaaaa ttcgccgcaa acgcgccaca tcgcccttgt   33060
accaccgatc tcggcacaca agctgtagca tttttaaatc gtgatcgctc aagctattaa   33120
```

```
ttctggttag atttatatag tcgtcaatat cctcgggcgt ggtttgcgtc atgtctgtaa    33180
aacgtgcaaa atcaaacatt tttatgttgt agtcgaatct aacaaatcca tcggcgttca    33240
cttgcacttc gcgctttaca aaacgaggta gcgtgtaatc gaacccgttt aaatagattg    33300
cgtacaaaac cagcacttca tcttccagtt tgcacgcttg cggcaaaaat tgtgtggtgt    33360
gctccaaccg ggtgacaaac atgactatgg aaaataacgc ggaattcaac agacgactag    33420
agtacgtggg cacgatcgcc acaatgatga aacgaacatt gaacgtttta cgacagcagg    33480
gctattgcac gcaacaggat gcggattctt tgtgcgtgtc agacgacacg gcggcctggt    33540
tatgcggccg tttgccgacc tgcaattttg tatcgttccg cgtgcacatc gaccagtttg    33600
agcatccaaa tccggcgttg gaatatttta aatttgaaga agtctggcg caacgccaac    33660 acgtgggccc gcgttacacg tacatgaatt acacgctttt taaaaacgtc gtggccctca    33720
aattggtcgt gtacacgcgc acgctacaag ctaacatgta cgcggacggg ttgccgtatt    33780
ttgtgcaaaa ttttcagaa acaagctaca aacatgttcg tgtgtatgtt agaaaacttg    33840
gtgcgataca agtagcgaca ttatcagttt acgaacaaat tattgaagat acaataaatg    33900
aactcgtcgt caatcacgtt gattagataa tgtccgtgtt aaatgtgata tcttagatta    33960
cgagcgcgca ataaccatag tttaatcgaa gagaatagcc gtcgccacaa tggataatta    34020
caaattgcaa ttgcaagaat tttttgacca agcgcccgac aacgacgatc ccaactttga    34080
acatcaaacg cccaatctat tggcgcatca gaaaaaaggc atacagtgga tgattaacag    34140
agaaaaaaac ggccggccca acggcggcgt gcttgccgac gacatgggac tcggcaaaac    34200
gctctctgtg ctaatgttaa tcgcaaaaaa caactctcta caattgaaaa ctctaatagt    34260
gtgtcctttg tctttaatca atcattgggt aaccgaaaac aagaagcatg atttaaattt    34320
taacatttta aagtattaca aatctttgga tgccgacacg gttgagcatt accacattgt    34380
ggtgaccacg tacgacgttt tattggcaca tttcaaattg atcaaacaaa ataaacagtc    34440
aagtctgttt tcaacccgct ggcatcgagt tgttctagat gaagcgcata ttatcaaaaa    34500
ctgcaagacg ggcgtgcaca acgccgcgtg cgctttgacc gcaacaaacc gatggtgcat    34560
taccggcaca ccgatccaca acaagcattg ggacatgtac tcgatgatta attttttgca    34620
atgtcgtcct tttaacaatc caagagtgtg gaaaatgtta ataaaaaaca acgactctac    34680
aaatcgcata aaaagtatta ttaaaaaaat tgttttaaaa cgcgacaaat ctgaaatttc    34740
ttctaacatt cctaaacaca cggttgagta tgtacatgtt aattttaatg aagaagaaaa    34800
aacgttgtac gataaattaa agtgtgaatc ggaagaggcg tatgtgaagg ctgtggcagc    34860
gcgtgaaaac gaaaacgcac taagccgatt gcagcaaatg cagcacgtgt tatggctaat    34920
actgaaattg aggcaaatct gctgccaccc gtatttggcc atgcacggta aaatatttt    34980 ggaaacaaac gactgtttta aaatggatta tatgagcagc aagtgcaaac gagtgctcga    35040
cttggtagac gacattttga acacaagcaa cgacaagata atattggttt cgcaatgggt    35100
ggaatattta aaaatatttg aaaacttttt taaacaaaaa aacattgcta cgttaatgta    35160
cacgggccaa ttaaaagtgg aagacaggat tttggccgag acgacattca atgatgctgc    35220
caatactcaa catcgaattt tgctgctttc cattaagtgc ggcggcgtcg ggttaaactt    35280
aataggcgga aaccacattg taatgttgga gcctcattgg aacccgcaaa ttgaattgca    35340
ggcgcaagac cgaatcagtc gtatgggaca aacaaaaaac acgtacgtgt acaagatgct    35400
aaatgtggaa gacaacagca tcgaaaaata cattaaacaa cgccaagaca aaagagattgc    35460
```

-continued

```
gtttgtcaac acggtctttg aagagactct gctcaattac gaagacatta aaaattttt    35520
caacttgtag ctggtaagtc gtcatgaaca cccgatatgc tacttgctat gtttgcgacg   35580
agttggtgta cttgtttaag aaaacgttta gtaacatgtc cccttcggcc gctgcgtttt   35640
accaacggcg catggccatt gttaaaaacg gtatcgtgct gtgcccacgt tgttcgtcgg   35700
aactaaaaat tggcaacggc gtttcgattc caatttaccc ccaccgcgct caacaacatg   35760
cacgacggtc gcgttaagac gcaagcgctt cgagttttgg cccgctcgct acctccgctg   35820
tacgactcga ccgtcgatcg acacggctgc aaggtgttca cggtgcggcg ctacaacaga   35880
cgcgtaatcg actttgcggg cattcgcaac aaaacgctgg aaatcattaa acggataga    35940
aacttgccgc tcaacacaga atgcaatgtg aaagttgtcg acagtgcatg catgcgttgc   36000
agaaaaagtt tcgcagttta ccccgccgtt acctatctgc attgcggaca ttcgtgtctg   36060
tgcaccgact gcgacgaaac ggtaaacgtg acaacacgt gtcctaaatg taaaagcggc    36120
attagatata aattaaaata caaaactttg taacatgttg ccctacgaaa tggtgattgc   36180
cgtgttggtt tacttgtcgc cggcgcagat tctaaattta aaccttcctt ttgcatacca   36240
aaaaagtgtg ctgtttgcca gcaactctgc aaaagttaac gaacgcatca ggcggcgagc   36300
gcgtgacgac aacgacgacg accccctattt ttactacaaa cagttcataa agattaattt   36360
tttaactaaa aaataataa atgtttataa taaaactgaa aagtgtatta gagcgacgtt    36420
tgatggtcgg tatgtggtta cacgcgacgt tttaatgtgc tttgtaaaca agagttatat   36480
gaagcaattg ctgcgcgagg ttgacactcg cattcacta cagcaacttg ttaaaatgta    36540
tagtccagaa tttggttttt atgtaaatag caaaattatg tttgtgttaa ctgaatcggt   36600
gttggcgtct atttgtttaa acactcgtt cggcaaatgc gagtggttgg acaaaaatat    36660
aaaaactgtg tgtttacaat taagaaaaat ttgtattaat aataagcaac attcgacatg   36720
tctatcgtat tgattattgt catagttgta atatttttaa tatgtttttt gtacctatca   36780
aatagcaata ataaaaatga tgccaataaa acaatgctt ttattgatct caatcccttg    36840
ccgctcaatg ctacaaccgc tactactacc actgccgttg ctaccaccac taccaacaac   36900
aacaacagca tagtggcctt tcggcaaaac aacattcaag aactacaaaa ctttgaacga   36960
tggttcaaaa ataatctctc atattcgttt agccaaaaag ctgaaaaggt ggtaaatccc    37020
aatagaaatt ggaacgacaa cacggtattt gacaatttga gtccgtggac aagcgttccg   37080
gactttggta ccgtgtgcca cacgctcata gggtattgcg tacgctacaa caacaccagc   37140
gacacgttat accagaaccc tgaattggct tacaatctca ttaacgggct gcgcatcatt   37200
tgcagcaaac tgcccgatcc gccgccgcac caacaagcgc cctggggccc ggtcgccgat   37260
tggtaccatt tcacaatcac aatgcccgag gtgtttatga acattaccat tgtgctaaac   37320
gaaacgcagc attacgacga agctgcgtcc ctcacgcgtt actggctcgg cttgtatctg   37380
cccacggccg tcaactcgat gggctggcac cggacggcag gcaactcaat gcgcatgggt   37440
gtgccctaca cgtacagtca atcttgcgc ggatattcat tggcgcaaat taggcaagag    37500
cagggaatac aagaaatcct aaacacgatc gcgtttccgt acgtgactca aggcaacggc   37560
ttgcacgtcg attcgatata catcgatcac attgacgtgc gcgcttacgg ctatttgata   37620
aattcatact ttacgtttgc ctattacacg tactattttg gagacgaggt aatcaacacg   37680
gtgggtttga cgagagccat cgaaaacgtg ggcagtccg agggagttgt ggtgccaggc    37740
gtcatgtctc gaaacggcac gttgtactct aacgtgatag gcaactttat tacgtatccg   37800
ttggccgtcc attcggccga ttactccaaa gtgttgacca aactttcaaa aacatattac   37860
```

```
ggttcggttg tgggcgtaac gaataggttg gcttactacg aatccgatcc cacaaacaac    37920
attcaagcgc ccctgtggac catggcgcgg cgcatttgga atcggcgcgg cagaattatc    37980
aactataatg ccaacacggt gtcgtttgag tcgggtatta ttttgcaaag tttgaacgga    38040
atcatgcgca tcccgtcggg caccacgtcc acgcagtcgt tcagaccgac cattggccaa    38100
acggctatag ccaaaaccga cacggccggc gccattttgg tgtacgccaa gtttgcggaa    38160
atgaacaatt tgcaatttaa atcgtgcacg ttgttctacg atcacggcat gttccagcta    38220
tattacaaca ttggcgtgga accaaactcg ctcaacaaca caaacgggcg ggtgattgtg    38280
ctaagcagag acacgtcggt caacaccaac gatttgtcat ttgaagcgca aagaattaac    38340
aacaacaact cgtcggaagg caccacgttc aacggtgtgg tctgtcatcg cgttcctatc    38400
acaaacatca acgtgccttc tctgaccgtt cgaagtccca attctagcgt cgaactagtc    38460
gagcagataa ttagttttca acaatgtac acggccacgg cttcggcctg ttacaaatta    38520
aacgtcgaag gtcattcgga ttccctgaga gcttttagag ttaattccga cgaaaacatt    38580
tatgtaaacg tgggcaacgg cgttaaagcc ctgtttaatt atccctgggt aatggtcaaa    38640
gaaaataaca aagtgtcttt catgtcggct aacgaagaca ctactatacc atttagcgtt    38700
ataatgaatt ccttcacctc tatcggcgaa ccagctttgc aatactctcc atcaaattgc    38760
tttgtgtatg gaaacggttt caaattgaac aacagcacgt ttgatttaca atttattttt    38820
gaaattgtgt aattatattt agggagaatg tgatattcaa aagactgact gttaacacaa    38880
aagactgata ttgttgttgt tacaaaatag ataataaaac aaaaaataaa ttaaatatta    38940
tttatttatt aaactgttta attttaatgc taacgcgtac aaatcacgct gttccgacgt    39000
ggacatggaa ttgcgcagaa aagtcttgat agtgtcgatt tcttcgccgt catccacttc    39060
catatatttg atttcttcct cgatttgcat ttccaagttt gcgtattctt gcaaataata    39120
atctagtcgt tgggcgacct cgccaatttt aaataataca ttatccgaca ccaaatgcca    39180
gcgagtgact gtgcgctcca tcatcctggc acttttaat gtgaatatta aaaggttgtt    39240
gcatatatat cgttaaacgt ttatgtttac tttcacgtta gctcgtttca ttgatgtaaa    39300
catttagttt tataacagcg tcggtaattt tattttttaa agtaaacaga ccaaaatcaa    39360
aggtgtcttc gacaggtacg attattttcc cattgacact gttttcgtgc acagatataa    39420
ttttatcacc gttattattt ttgcccaaac acacgtactc gtttcttctc aagccaacta    39480
tttctaaaca attcactttt ctattatcgt gtacgcaatt aaaagtaaac gaagcgctac    39540
aattgtcgta ttctattaca attctgcggc atttataaaa tttattaatg ttgacgcaaa    39600
ttccatgcag cgcatccatt tcgtactgca aatgcggcgc aattaaaaaa tttcctcgtc    39660
gttgttaaca atcttgggcg ctaaaaagca cgccaacacg cccacgtctt taatgcaata    39720
ttccaatttg aacggcagtt cctcggacat gtatattgtc acggtgggcg ccaaaggagc    39780
ggctttagca aaatgacaca agtaatcgcc cgcaaaagtg tgcgttacgg tttgctttgc    39840
tttgagaacg gaaaagtttt cgttgtccgc gctcatctgc acgtccgccg agccaatgtc    39900
gccatttgct ctaaactgca gacccttctt ggaacacgac acaataatat cgtggtcgaa    39960
ttgcgtcatg tctttgcaca cctgcgcaaa ctcgacgctc gacatgtgga cgacgcaatc    40020
gtaatcgcta tccggaattc ccaaatgttc cacgtcgatg cacatcaact tgagcgtgta    40080
cgtgcagatt ctattgtcgt tgttgaacac gaacgccatc acatcgccct gatcttccgc    40140
tttcatcagt acagagctgc gctcgttaac gcatttgaca attttactta aactgtttat    40200
```

```
ggacacgttg agcggcacgt tgcggtcaca tctatatttt ttgaaaccct cggcgtgtag    40260
ttgcaacgac acgagcgcga catgcgaggt gtccataacc tgcatgctta cgcctcgatt    40320
atcacaatca aaagtagcgt gcggcagcag atccttaaaa gtttccacca gcctcttcaa    40380
aactgcgccg gttttaaatt ccgcttcgaa cattttttagc agtgattcta attgcagctg    40440
ctctttgata caactaattt tacgacgacg atgcgagctt ttattcaacc gagcgtgcat    40500
gtttgcaatc gtgcaagcgt tatcaatttt tcattatcgt attgttgcac atcaacaggc    40560
tggacaccac gttgaactcg ccgcagtttt gcggcaagtt ggacccgccg cgcatccaat    40620
gcaaactttc cgacattctg ttgcctacga acgattgatt ctttgtccat tgatcgaagc    40680
gagtgccttc gacttttttcg tgtccagtgt ggcttgtttt aataaattct ttgaaaatat    40740
tgtcgggtgt attattaaat agcatgtatg gtatgttgaa gatgggataa cgcttggcgt    40800
gcgggtcgtc atgatttcca ccgcgcacca catatttgcg ctcaatttta tcaaaattgg    40860
actggcgaga caaaaacgag acgggcgaca ggcatatttg ggcgtgcgta ccatcttcgg    40920
ccatccactc ggtcaggtct tcgctgcggt taaacacacc tttctgaccg tgaatgccac    40980
atatttttat tccttccaaa tcgttggtgg acgtgactat gactatttta agcataacgt    41040
tgtcgccgtt aaccaccatg ctggcgtcga gttttttcaat ttttttgattt ttaatttgtc    41100 taaagtaaac gtacactttg taaacgttaa aattgccgtt ggtgcacgtt tcaatttttgt    41160 accgtcggcc gtcgtacacc caattaatct ttgcgttgct caccaacaca ccggccatgt    41220
acagcacaag tccgtcgtct agcgcaacgt aattttttgtc gctactattc gtaaactttta    41280 ctaaacacga ctgcttgggg ccgaccacaa gcttgccctt caatttgttc actttgttgt    41340
tgtataaaca aatgggcagc gcaatgtgcg gaatgtacgg atcttcggcg gtcatgagtt    41400
tattgtctcg caccaacgtc cacaatttaa acatttatt gttgagcaaa atggacttgt    41460
ttaccgccac agagtagcca tttggtaaac ccgatacgca attttcctct ttgtactcaa    41520
acacgggcat ggcattcttt agattggtta gggacacaat caatttgggt acgggcgtgg    41580
tatgaaataa atgtataaaa ttacgataat aatactgctc caacttggac atgagcgatt    41640
tgacgtcatc gttttctacg atcgtacact gaataatggg attatagtat atagaatgtt    41700
tatagtggta ttcgtagggt gtcaacaata cgttaatgtc ggcttcgttg ttcacccgca    41760
actttttttt gatgcatatc attccttcgt gatgattaac gtaaagtatt ctgtctgtaa    41820
tcttcaattc gatgggcgcc atgtttcttt tcatagtgta cacgataaac gacgtgtttg    41880
attttaaaca ttttaaattt gtgggtctat cattaaacgc gatcagcaac gagtcgtctt    41940
gaacgtcgtt gaggtcgtcc acgaacgcga ccagattgtg ttttagcaaa tattgaaatt    42000
tttgcgcaac catttcgtag tccacgttgg gcaaacatgc gttgcggcaa aggaaaaact    42060
ttttgcccgc cacggtcatt tcgccgtgaa aaaaactgcc aataaatttc acaaaatcct    42120 tttttgctt caacattttc tggcgcatgc tgtcgttggt gattcgcgcc acctcgttgc    42180
cgacgcgata ttttaacacg ggcaacgaaa tttcaatatt gttattgctg ctgttgtcct    42240
gttgattggg aaagactttg cgttgcttgc taaaagtttt cgatacgcaa tatatgagac    42300
gcccgttgac tatacaatcg acaatctttt tcgactcttt gttgtacaag acgctttgaa    42360
ttttacgacg cttgttcgcc accgtgtacg cgtcgtcgtc ggccgtcttg tcgagaactc    42420
gttgatagtt ttgcaaaatt gtcgaagtta ataacagttc tatcaaatag gcgtgcttgt    42480
atacaatttt gttggccaaa ctgtctatag aatagtttat gtcgtgattc ataataattt    42540
ttatgtgttc cacgagttgt tgcttgtgaa gcgtgttgta ttcgaagaga aaatcgagcg    42600
```

```
gtttccattt gccgctgttg gccagatatg tttccagcac agaatttaaa tcttccgtca   42660
ctacgtaatc gctagcgtac acgtctcgag caaacaggac gtcgtcttgt ttgtcgtaaa   42720
ctagttggat tgcgcgattg atgtgcttct cttgatccac gttgccgtac aaaaacatgc   42780
gtttgcaatg tttggcgtat agcttgtcgt agaaattgtg caccaaaacg ttgttgttca   42840
tcattatgtt gggaaaactc aaaaatctgc cgtccagcat aaaagttccg ttaatattgt   42900
tgtttgcgtc gacatcgtcc gtttctctaa attgcttgtc taagcgcgtg ccgaatataa   42960
cgggcacaca tttatgcatt acgcaactga gctgttcatt aagagcgcaa cacaaataag   43020
acttgcgttc ttgaatagcg caaaaaagca tacgttcatt gctgtttgta gcgcaatcaa   43080
aagtatattt taatttgtat ttattttcaa ttctatcgta caactcgttg aaatcttgaa   43140
ccacgtccgt catcgtgaag cgattactgc gcactaatta tgtctaaacg tgttcgtgaa   43200
cggtcggttg tttcggatga acggccaaa cgcattcgac aaaacgaaca ctgtcatgcc    43260
aaaaatgaat cttttttggg gttttgcaac ttggaagaaa ttgattatta tcaatgttta   43320
aaaatgcaat acgttccgga ccaaaagttt gacaacgatt ttattttaac agtgtacaga   43380
atggccaacg tggtgacgaa acaagttaga ccgtataaca gtatcgacga aaagcaccat   43440
tacaacacgg tgcgtaacgt gttgatttta ataaaaaatg cgcgtttagt gcttagtaat   43500
agtgtcaaaa agcaatacta tgacgatgtg ttaaaattga aaaaaaatac agacttggaa   43560
tcgtacgatc cattgattac ggtctttta caaattggcg aatctgtaaa tgaagaaata    43620
caaaaactca gaaaagcttt ggtcaatatt tttactaata aacccgacaa gtcggatata   43680
aacaacccag atgtagtttc gtatcaattt attttttggca gagtacaaaa attgtataac   43740
agggcaatta acaaaaaac taaaactata attgtaaaac gtcctacaac tatgaacaga    43800
attcaaatag attggaaaac tcttttccgaa gacgaacaaa aaatgactag acaagaaatt   43860
gccgaaaaaa ttgtaaagcc ttgttttgag caatttggca ctatattaca catatacgta   43920
tgtcctttaa aacacaaccg aattattgtc gagtatgcaa actcagagtc ggtacaaaaa   43980
gccatgactg taaatgacga cactcgattt acagttacag agttttccgt ggttcagtac   44040
tacaacgtgg ccaaaacaga aatggtgaac cagcgaattg acataataag caaggacatt   44100
gaggatttaa gaaacgcttt aaaatcttac acataaatta aaatatcgaa caaaggaaaa   44160
aaacaattgt aacaaaaata atttacatta aaatttacaa gttttttttct agtgtcgtac   44220 ttttttacaa tgcgtctgtt gtccgtcgag cattgcaaac atattgtgga cggcgcaaaa   44280
tagcaaacaa aaggcacgtc cgcgctctcc cacgctattc taaaacgatg aatccatatt   44340 aattttcat tgtcgccaaa cgtcgctccg ctgcctcctt ccaataacaa atactcagaa    44400
acacaaacat gtacaattgc tgtcgcggcg ttaattgtcg ctgttttttcc aaatagtcta   44460 ttatgggaaa caaacacttg tcacaacaca aatactcgtt aattgtcaca accgacaagc   44520
acatttggca aaatgcgtcg caattttgt acggacgaga ttctatgcga agttcgttgt    44580
ccatgacgtc ttgggtccac tttttcaaca agacactttt atatttgtga tttgtacaac   44640
tttggtacgt gttagagtgt ttttgataag ctttgataag tttaaaactg ttggagtaag   44700
gccacgtcat tatgttctgc acctttttgtt taaaagacag aaattactat atgttcaaac   44760
tatttaaaga ttattggcca acgtgcacga cagaatgcca gatatgtctt gagaaaattg   44820
acgataacgg gggcatagtg gcaatgcccg cactggcat gttaaacttg gaaaagatgt     44880
ttcacgaaca atgtattcag cgttggcgtc gcgaacatac tcgagatccc tttaatcgtg   44940
```

```
ttataaaata ttattttaac tttcccccaa aaacactaga ggagtgcaac gtgatgcttc   45000
gagaaactaa agggtctata ggcgatcacg aaattgatcg cgtttacaaa cgcgtttatc   45060
aacgcgttac acaggaagac gccctggaca ttgaactcga ttttaggcat ttttttaaaa   45120
tgcaatcatg acgaacgtat ggttcgcgac ggacgtcaac ctgatcaatt gtgtactgaa   45180
agataattta ttttgatag ataataatta cattatttta aatgtgttcg accaagaaac   45240
cgatcaagtt agacctctgt gcctcggtga aattaacgcc cttcaaaccg atgcggccgc   45300
ccaagccgat gcaatgctgg atacatcctc gacgagcgaa ttgcaaagta acgcgtccac   45360
gtaacaatta ttcagatccc gataacgaaa acgacatgtt gcacatgacc gtgttaaaca   45420
gcgtgttttt gaacgagcac gcgaaattgt attatcggca cttgttgcgc aacgatcaag   45480
ccgaggcgag aaaacaatt ctcaacgccg acagcgtgta cgagtgcatg ttaattagac   45540
caattcgtac ggaacatttt agaagcgtcg acgaggctgg cgaacacaac atgagcgttt   45600
taaagatcat catcgatgcg gtcatcaagt acattggcaa actggccgac gacgagtaca   45660
ttttgatagc ggaccgcatg tatgtcgatt taatctattc cgaatttagg gccattattt   45720
tgcctcaaag cgcgtacatt atcaaaggag attacgcaga aagcgatagt gaaagcgggc   45780
aaagtgtcga cgtttgtaat gaactcgaat atccttggaa attaattacg gcgaacaatt   45840
gtattgtttc tacggacgag tcacgtcagt cgcaatacat ttatcgcact tttcttttgt   45900
acaatacagt cttgaccgca attcttaaac aaaacaatcc attcgacgta attgccgaaa   45960
atacttctat ttcaattata gtcaggaatt tgggcagctg tccaaacaat aaagatcggg   46020
taaagtgctg cgatcttaat tacggcggcg tcccgccggg acatgtcatg tgcccgccgc   46080
gtgagatcac caaaaaattt tttcattacg caaagtgggt tcgaaatccc aacaagtaca   46140
aacgatacag cgagttaatc gcgcgccaat cagaaaccgg cggcggatct gcagtttac   46200 gcgaaaacgt aaacaaccag ctacacgctc gagatgtgtc tcaattacat ttattggatt   46260
gggaaaactt tatgggtgaa ttcagcagtt attttggtct gcacgcacac aacgtgtagc   46320
atcgccagta tttaacagct gacctatttg ttaaacaagc attcttatct caataattgg   46380
tccgacgtgg tgacaattgt atccacaatc atgaaaaaag tagcgcttgg aaaaattatc   46440
gaaaacacag tagaaagcaa atataaaagc aacagtgtgt cgtcgtcatt gtcaacgggc   46500
gccagtgcaa aattgagttt aagcgaatat tacaaaactt ttgaagcaaa taagtgggc   46560 cagcacacta cgtacgacgt ggtcggcaag cgagattaca cgaaatttga caaattggtg   46620
aaaaaatatt gacatgctgc gatcaatcat gcgacgtttc aagagtacaa acaatctcag   46680
caaaaaaccc tccgattatt atgtagtgtt atgtccaaag tgttattttg tgacgtcggc   46740
cgaagtgagc gtggctgaat acatagaaat gcataaaaat tttaacacga aattcgccga   46800
tcggtgccct aacgatttta ttgtgaccaa ctctaaaagt tggaataatc atgaaaattg   46860
ttctgcccta ttttaccctc tgtgttaata agtttgttg tttgtatttt gtggttttat   46920
ttatttacgc tagatattgg gtttaaggtt cttagaaata gagttgtatt ttccctacca   46980 aagggatt gagcttcata taaatacaat attcgctcga caagcggttt atttcactcg   47040
gaggtattat atcaggcagt cgaacgtgcg cgatgaaaca tcccgtttac gctagatatt   47100
tggagtttga tgatgtagtg ttagatttga ctagtttaat attttagag tttgataacg   47160 ctcaaaatga agagtacatt attttatga atgtaaaaaa ggcgttttac aaaaactttc   47220
acattacttg tgatctgtcg cttgaaacgc tgaccgtgtt ggtgtacgaa aaagctcgcc   47280
taattgtgaa acaaatggag tttgagcagc cgccaaaactt tgttaatttt atcagtttca   47340
```

```
acgcgaccga caacgacaac tccatgataa tagacttgtg ttccgacgcg cgcataatcg   47400
tggccaagaa gctgacgccc gacgaaacgt atcatcagcg cgtgtccgga tttttggatt   47460
ttcaaaaacg taactgcata cctcggcccc caatcgagtc ggacccaaaa gtgcgagacg   47520
ccttggatcg tgaactagaa ataaaactat acaagtagaa aaaattaat ttattaatag    47580 ttgtaataat tatcttcgtc ctcatcttcg ctggtgtcat aatgcggtgg tgtgtttgtg   47640
ttttgtttta atcgtttgcg cgtcgacacc acttcgccga taggaaattt tttggatttc   47700
gcattaaatg ccctcttagc gacgcgccgt ttacgactac taaacatgtt gacgcgctcg   47760
tcgtcttcag tgtcataatc cgtgctagtg ttttcgttgt tattttctat gagacgatcg   47820
tttgatttag ttttcgtaga attgtccgcg ttatcgtcgc tttcgtcgat gtcgtcccta   47880
actatctcgt aggcggcttt gcgcggaatc caagattttg caatgtatct attttaacgt   47940
acttttcttc gagcgctttt ctagctttat gcatagcaat gtcttcgtcg ccgccgttca   48000
ttttatgata ctttgtaaac gtctcgacga ataactttt ggcgcgagga ggcattttt    48060 cattgtataa catatcggga atttgataca ttgtaattag aattaagcaa gttcgtcttc   48120
ggttgtactg tattcggttt ctgtatctgt agtggaatcc tctgtactag tagtagtgtc   48180
gctattgttg gcgtcaggcc ttggctgcca tttaccgtct atcaacatgt atttttcct    48240 aacagcacaa catgctagct tggtagctat ctgtgtcgac ttatatttt gtaaactacg    48300 atcgtagaat ttttcaaata tcctcttacc gttatagga aggttttgat aatatttagg    48360
caacatatca ataaaagaca atataaaaac tttgtgtttg tgttttattt atcacataaa   48420
atggacgtct ggcaagaatc acaaccaata ttagtgtttt tttcttaca ttacgagatt    48480 caacttgata ctaaaattaa ttattaatta aattaaatta aattttgaag catttttcg    48540 ctatcgtttt cagactcaaa attatcgacg ctatcgctat gaaaagcgta atatttgttg   48600
gctttgagat attctatatt ttgctcattt taacaataa acacgcgact cttttcgtcg    48660
cgtctcacca taacaccgtt tttacaaatg gaaatgtatt tgtaaacgg caacagagcg    48720 tcgcgagttt ttttaagtaa cagcttttgc tccgctgtgg cggccacaaa tattttacg    48780 ggcccgtcgt aattaatgtt taaattaaaa tttttaagtc gacgctcgcg cgacttggtt   48840
tgccattctt tagcgcgcgt cgcgtcacac agcttggcca caatgtggtt tttgtcaaac   48900
gaagattcta tgacgtgttt aaagtttagg tcgagtaaag cgcaaatctt ttttaaataa   48960
tagtttctaa ttttttatt attcagcctg ctgtcgtgaa taccgtatat ctcaacgctg    49020
tctgtgagat tgtcgtattc tagccttttt agttttcgc tcatcgactt gatattgtcc    49080
gacacatttt cgtcgatttg cgttttgatc aacgacttga gcagagacac gttaatcaac   49140
tgttcaaatt gatccatatt aactatatca acccgatgcg tatatggtgc gtaaaatata   49200 tttttaacc ctcttatact ttgcactctg cgttaatacg cgttcgtgta cagacgtaat    49260
catgttttct tttttggata aaactcctac tgagttgac ctcatattag accctcacaa    49320
gttgcaaaac gtggcatttt ttaccaatga agaatttaaa gttattttaa aaatttcat    49380 cacagattta aagaagaacc aaaaattaaa ttatttcaac agtttaatcg accaattaat   49440
caacgtgtac acagacgcgt cggtgaaaaa cacgcagccc gacgtgttgg ctaaaattat   49500
caaatcaact tgtgttatag tcacagattt gccgtccaac gtgtttctca aaagttgaa    49560 gaccaacaag tttacagaca ctattaatta tttaattttg ccccactta ttttgtggga    49620 tcacaatttt gttatatttt taaacaaagc tttcaattct aaacatgaaa acgatctggt   49680
```

```
tgacatttcg ggcgctctgc agaaaatcaa acttacacac ggtgtcatca aagatcagtt    49740
gcagagcaaa aacgggtacg cggtccaata cttgtacgcg acgtttctca acacggcctc    49800
gttctacgcc aacgtgcaat gtttaaatgg tgtcaacgaa attatgccgc cgcggagcag    49860
cgtaaagcgc tattatggac gtgatgtgga caacgtgcgt gcatggacca cgcgtcatcc    49920
caacattagc cagctgagta cgcaagtctc ggacgtccac attaacgagt catctaccga    49980
ctggaatgta aaagtgggtc tgggaatatt tcccggcgct aacacagact gcgacggtga    50040
caaaaaaatt attacatttt tacccaaacc taattcccta atcgactcgg aatgccttt     50100 gtacggcgac cctcggttta atttcatttg cttttgacaaa aaccgtttgt cgtttgtgtc    50160
acaacaaatt tattatttgt acaaaaatat tgacgcaatg gaggcgttgt ttaaatctac    50220
accattggtt tacgcgctgt ggcaaaaaca taaacatgag cagtttgcac agaggctaga    50280
gatgttgttg cgtgatttt gcttaattgc cagttcaaac gctagttatt tacttttaa     50340 acagcttaca cagctcatag ctaacgaaga aatggtgtgc ggagatgaag aaatattcaa    50400
tttaggcggc caatttgtag acatgattaa aagcggtgct aaaggcagtc aaaatctgat    50460
taaaagcacg caacaatacc gacagacttt aaatacagat attgaaactg tgtcttcacg    50520
agccaccacc agtttaaata gttacatatc ttctcacaat aaggtaaaag tgtgtggcgc    50580
cgacatatat cataacacgg ttgtgttaca gagcgtgttt attaaaaata actatgtttg    50640
ttacaaaaac gacgaacgta caatcatgaa tatttgcgct ttgccctctg agtttctgtt    50700
tccagaacat ttgctcgaca tgttcattga atgataatat aaatagagcg catttgattg    50760
catgcaatca gtgtttatt aattttagag caacatgtac gataaattta tgatctatct     50820
tcacttgaat gggctgcacg gagaagcaaa atactacaaa tatttaatgt ctcaaatgga    50880
ttttgaaaat caagtagccg atgaaatcaa gcggttttgt gaaactcgtc tgaaaccggc    50940
aatcagttgc aacactttaa ctgcggaaag tctcaatacg ctcgtagaca gcgtagtctg    51000
caaaaatgga ctgttaaatc cttacgccaa agaagtacag tttgctttgc aatatctttt    51060
tgacgatgac gaaatatcca acgagatca agatggcttt aaactatttt tattacataa     51120
ttatgacagg tgtgaaaata tggaagaata ttttttaatt aacaatttta gcatagcaga    51180
ctacgaattt gaagacatgt ttgaaattgt tcgtattgat tgtagagatc tgttattact    51240
tcttgctaaa tataatatgt aattaaaatt ttgtttgttt tattaaaatc ctggattaaa    51300
aaatgacgaa taatttgatt tgcgtgcacg ccaacaagat tcttcgtcat tatgatcaat    51360
gcgtgcatca agtttatgct tttgtaattg gcttctgacc actttagcca tttgagcgta    51420
tctgcattcg tcgtctagag tttcaaacac cagatcggcg caattataaa atccttcacc    51480
cacgggatct atgcgctgcc aacgcacata cattacaaat tgatttgacc tgtacggtat    51540
tactacgggt atagaataga ctagactgtt gtcacataat gaatcgcccg gatttggaat    51600
taaatttgaa tcgttaccac ctatgtattc taattcgttc caagttattg gattgcgacg    51660
atcccagttt gatttagtaa taaacacttc aaaataactg ggctcgtgta tggctgttgg    51720
acaaaaatga acattcatct gataaaccgg ttgatagcga tttaaatata gcgtatttgg    51780
cctccagttt ttaaaaggtt cgtccattcc gcttttatca ccaaacacag aattgcgatc    51840
gtttgaaccg gcaccgcaaa gtgtgtgcgg cacaacccct tgtttgatta ggtcaaaatc    51900
gtcataatta ggaccggcca cagccgcgta ttccatatac tgttgaaaca tgtattgcgc    51960
tgtggaagcg gccgccccgg attctaaatc gagagctcga tatttataat agactgattt    52020
gtaagcattg cggcacgcgg cgtcgggaat gttatcgcca ttgtcgggcc aataaaagtt    52080
```

```
tccatcttta aaacatttat attgacgggc cgtcggcacg gacaaatagc cgtgagagcg    52140
cactgccggc gcgtgaatcg cagcaaacaa tgcaattaat aatgcaatca ttatgattat    52200
acttatagaa cactaatcgg aataataacc gctgtcgtaa tcttggtcaa aaacgttatg    52260
ttgaaacata ataacacctt acagtaacat acaataaaac aacatagtat cgtatataat    52320
tataaacttt attttttcat tttatacaaa caaaatttat acgtattgtt agcacattga    52380
gtgtcatttt cgctgtctga actatcacaa tcatcgtcat catcatcatc attgtcatcg    52440
tcgtcgtcac gtttgcgttt gacactgcat tttttttggt taattttcac taacactggt    52500
tcttttcgat cgtacaattg attctgcatg tacttttgca tgatcgcggt aaaacacttt    52560
gcaattttat cctttgttc gtcgccaaat atttccagca actcgttcat aaatgtgcac    52620
aaaatgccca tgtgttttat ccagctgatt cgcattttca ctggatcgaa caaacgcaag    52680
gggtacgctt tttctgttac cttgccttcg atgtctatca aaggtacgg gatacgatct     52740 ccgttgccgg gcacaaaatc cgtgcctttg ttaaccaaaa tttctctaca atgcctagcc    52800
accgtaatca cgcgtctttt gggtgacgga ccctcattat cgtcagttga tttgcgtttt    52860
ttgcccgggt tatcgttata ggtcatacta aagctgtagt cggtcaacga ttttgatttg    52920
gcaaactcat catagtattc ataaaaacta gtctgtaaac tttgcaaaca tttgtccatg    52980
tccaaatgac gcaatatttg ttccactgcc gtcctaaacg cgattctcat aaaaacgggc    53040 atatccttt taactaacca cccttgtat acgatttat tctcactgtt gagatagcaa      53100
tattttttct tttttaatag tattaaaact ttcattaaat tttcaaatgc cattttgtaa    53160
ccgtccgtga atgagttatt aacgcgtgtc tcaacatgtg tgcatatttg ttttaatgtg    53220
tcggtttcgt tggatatttc gttatagtta aatgtgggca aaacaaatgt agaatctgtg    53280
tcgccgtaca caactttaaa agtgatgctg cccagattga attttctaa aatctcaggg     53340 tcgttgctca aaccttcaat cagagaaatg gccagccgca actgattgcg accaactcta    53400
gtgatgtagt ttgcaagcac tttgtaaaaa atgccataat aaccgtatat gctattggcg    53460
gtgcgcttca cggaattttg ttttgatcg tacagatcgt acaagaatgc cgattcgctt     53520
tgattgtcgc gattcttttt aaatttgcac ctttcgctta acaattttaa tagcaattta    53580
acaactattg cacgcgaatt gtggttcaaa tacacgttgc cgtcttcgca taaaattaaa    53640
ttggacaaac aagcacaaat ggctatcatt atagtcaagt acaaagaatt aaaatcgaga    53700
gaaaacgcgt tcttgtaaat gcctgcacga ggtttaaca cttgccgcc tttgtacttg      53760 accgtttgat tggcgggtcc caaattgatg gcatctttag gtatgttttt tagaggtatc    53820
aattttcttt tgagattaga aatacccgct gcggctttgt cggctttgaa ttggcccgat    53880
attattgaca gatcgttttt gttaaaaaaa tacgggtcag gctcctcttt gccggtgctc    53940
tcgttaatgc gcgtgtttgt gatggctgcg taaaagcacg ccacgctaat caaatgcgaa    54000
atattacata tcacgtcgtc tgtacacaaa cgatgcaata tacattgcga atatacagaa    54060
tcggccattt tcaatttgac aaacaatttt atcggcaaca tgcaatcctg cacgttgtac    54120
ttggcaatca cgtccagccg tcgagtgttg tacatcttga ccatttcggt ccaaggcaaa    54180
tcgattttgt tttcacccaa atagtaacta ctgattgtgt tcaattgaaa gttttcaact    54240
ttatgctgat tagaatcgct gctgaaaaat ttatacaaat caatgtgaat gtaatagtta    54300
aaataatacg tgtccacttt gttgcccaac ttgtttataa acagctttgt cgtcggcgcc    54360
gcagccggca aatcgtaacg ctttaatagc attttggttt tattcaatcg tccaagtata    54420
```

```
tagggcagat caaatacgtc tccgttaaaa tccaaaatca catcgggatt tgtaatttt    54480
atcatgtcaa aaaacgctgt aatcatgtcg atttcatttt gaaacatgac cacatacgtg   54540
tcatcgtcat aggtctctgg aatctgggtc ggcagcttgt gatacataaa acaaaatttt   54600
gcatactcgt cgttttttgta caccacaaat cctatagaca ttatgcaatc aaccgatgct  54660
ttcgacatgt tgtggccgtc cgaatgagtc tcaatgtcat agcacgacaa aacgggcatg   54720
atgccgctgg ttaaagtcat ttcatcgacc aactcaaagt cttcattaaa atgttgcaaa   54780
ttaaacatgc gcgtcgtcga tccaccgaca tagttatttt ggcagcgttg tgttttcttg   54840
aatcgcatat aggcgccttc cacaaacggc gtttgcatgt gtacgcgatt aacgttgtga   54900
agaaacttgt ccaaacacgc cgcgttgtcc gatggcgctg ctttgtttct ttcgtattta   54960
atcacgttta tcttgttcaa ataatttcct tccacgcccg gcgccacaaa cgtggtgtag   55020
ctgatgcact tgttgcggca agacggaaat atgtgcttgt cgtagcattg tttgtaagaa   55080
tacaaattta gttttacttt aaagtaaaac tgcagcactc gttctttgat atttgtatta   55140
caaaatgcaa acaagcaacc ttgttttcaa tcgtaatgca aacgaatgat acgaaacgta   55200
tcggctgaag taatattgaa ttctcctggt tttgcatatt ctgcaaagcg cgttttgagt   55260
tcattgtaag gatatatttt cattttaaaaa tatgcagcga tggcccaaat atggaggcac   55320
agacgtcaac acgcgcactg tacacgattt gttaaacacc ataaacacca tgagtgctcg   55380
aatcaaaact ctggagcggt atgagcacgc tttgcgagag attcacaaag tcgttgtaat   55440
tttgaaaccg tccgcgaaca cacatagctt tgaaccccgac gctctgccgg cgttgattat  55500
gcaattttta tcggatttcg ccggccgaga tatcaacacg ttgacgcaca acatcaacta   55560
caagtacgat tacaattatc cgccggcgcc cgtgcccgcg atgcaaccac cgccaccgcc   55620
tcctcaaccc cccgcgccac ctcaaccacc gtattacaac aattatccgt attatccgcc   55680
gtatccgttt tcgacaccgc cgccaacaca gccgccagaa tcgaacgtcg cgggcgtcgg   55740
cggctcgcaa agtttgaatc aaatcacgtt gactaacgag gaggagtctg aactggcggc   55800
tttatttaaa aacatgcaaa cgaacatgac ttgggaactt gttcaaaatt tcgttgaagt   55860
gttaatcagg atcgtacgcg tgcacgtagt aaacaacgtg accatgatta acgttatatc   55920
gtctataact tccgttcgaa cattaattga ttacaatttt acagaattta ttagatgcgt   55980
ataccaaaaa acaaacatac gttttgcaat agatcagtat ctgtgcacta acatagttac   56040
gtttatagat tttttacta gagtcttta tttggtgatg cgaacaaatt ttcagttcac    56100
cactttttgac caattgaccc aatactctaa cgaactttac acaagaattc aaacgagcat  56160
acttcaaagc gcggctcctc tttctcctcc gaccgtggaa acggtcaaca gcgatatcgt   56220
catttcaaat ttgcaagaac aattaaaaag agaacgcgct ttgatgcaac aaatcagcga   56280
gcaacataga attgcaaacg aaagagtgga aactctgcaa tcgcaatacg acgagttgga   56340
tttaaagtat aaagagatat ttgaagacaa aagtgaattc gcacaacaaa aaagtgaaaa   56400
cgtgcgaaaa attaaacaat tagagagatc caacaaagaa ctcaacgaca ccgtacagaa   56460
attgagagat gaaaatgccg aaagattgtc tgaaatacaa ttgcaaaaag gcgatttgga   56520
cgaatataaa aacatgaatc gccagttgaa cgaggacatt tataaactca aaagaagaat   56580
agaatcgaca tttgataaag attacgtcga aaccttgaac gataaaattg aatcgttgga   56640
aaagcaattg gatgataaac aaaatttaaa ccgggaacta agaagcagca tttcaaaaat   56700
agacgaaaact acacagaggt acaaacttga cgccaaagat attatggaac tcaaacagtc   56760
ggtatcgatt aaagatcaag aaattgccat gaaaaacgct caatatttag aattgagtgc   56820
```

```
tatatatcaa caaactgtaa atgaattaac tgcaactaaa aatgaattgt ctcaagtcgc   56880
gacaaccaat caaagtttat ttgcagaaaa tgaagaatct aaagtgcttt tagaaggcac   56940
gttggcgttt atagatagct tttatcaaat aattatgcag attgaaaaac ctgattacgt   57000
gccgatttct aaaccacagc ttacagcaca agaaagtata tatcaaacgg attatatcaa   57060
agattggttg caaaaattga ggtctaaact gtcaaacgcc gacgttgcca atttgcaatc   57120
agtttccgaa ttgagtgatt taaaaagtca ataatttct attgtaccac gaaatattgt    57180
aaatcgaatt ttaaaagaaa attataaagt aaagtagaa aatgtcaatg cagaattact    57240
ggaaagtgtt gctgtcacaa gtgctgtaag cgctttagta cagcaatatg aacgatcaga   57300
aaagcaaaac gttaaactta gacaagaatt cgaaataaaa ttaaacgatt tacaaagatt   57360
attggagcaa aatcagactg atttttgagtc aatatcagag tttatctcac gagatccggc   57420
tttcaacaga aatttaaatg acgagcgatt ccaaaacttg aggcaacaat acgacgaaat   57480
gtctagtaaa tattcagcct tggaaacgac taaaattaaa gagatggagt ctattgcaga   57540
tcaggctgtc aaatctgaaa tgagtaaatt aaacacacaa ctagatgaat taaactcttt   57600
atttgttaaa tataatcgta aagctcaaga catatttgag tggaaaacta gcatgcttaa   57660
aaggtacgaa acgttggcgc gaacaacagc ggccagcgtt caaccaaacg tcgaatagaa   57720
ttacaaaaat ttatattcat tttcatcttc gtcatacttc aacagtccca acacgttcat   57780
gttgtgattc tcgccgttct cgacagttac gtaaatagtt actttgatta aattatcttc   57840
cagcagcatt gagatttgat tgaaatccgc acatagcttt tgtagcgaat ccgcttcggt   57900 tttttttattt gtgttgacgt agaaaacaga tttgttccat ttgcccaagt cggaagaggt   57960
agaacagtca tccgaatcgg caatgttcaa ctcgtcgctt ttaaactgca caataaactt   58020
gttatcgccc atgtcatttt cttccaattc gcttttaac acatttacat tgtacgaagc     58080
aacgtgtttg ttcgatcgac taatgttgat ctttgcgttt gtgcaatttt gcaaatttga   58140
atatgcttcg ctttctttag cctcgcacaa ttcgatgcgc gtagagttga ccacgttcca   58200
attcatgtac acgtttgatc cattaaaaat ttgttgacac tttatactgt aaatggtaaa   58260
gatttggttt tcattgtctt ttaaatattt aaacacctca ttgatgtcgt cagaccccctt  58320 tatattgttc ttgaatagat ttattagtgt tttcgcattg acagaacatt ccacttgaac   58380
cacgtcggga tcgtcgttga gattttttgta cacaacctca aaaacaactt tgtacaaacc  58440
gctgttgatt tcttgtaga taaatttgta ctttacaata atattgacgc catcttcatt     58500
ttcaaaatgt ttgttagtca aatagtcgct catggggggtt gcagtttcaa tttccatttc  58560
acattctttg tattcgttga tctgaatcat ttgactaaac tttgttttca cataatttaa   58620
actaatgtca tagcacttgc cttcttccat gtctttgaaa gattgcgaat cgccgtagta   58680
ttcttgaatt ttgttgtcgg acattattcg aaaagtgtaa tggtattcat tatcgatact   58740
caacgtcatt ttgctcatca atttaccact aatccttttg taatttttctc taatcttctt  58800 ggggctactg gccatagcca tgcgttttat aagcggctca ccgctacttt ctccagacaa   58860
agatcttttg gtcgccatat tgctgttgtc gatatgtggg aatctatccg atggcaaata   58920
ctgaatggcg acgaaatcga agtgtcgcca gagcaccgtt cgttagcgtg gagggagttg   58980
attataaacg tggccagcaa cacgccgctc gacaacacgt tcagaacaat gtttcaaaaa   59040
gccgattttg aaaatttcga ctacaacacg ccgattgtgt acaatttaaa aacaaaaact   59100
ttaacaatgt acaacgagag aataagagcg gctctgaaca gacccgtccg atttaacgat   59160
```

```
caaacggtca atgttaatat tgcgtacgta tttttgttct ttatttgtat agttttgctg    59220
agcgtgttgg ccgtcttttt cgacacaaac attgcgaccg acacgaagag taaaaatgtt    59280
gcagcaaaaa ttaaataaac tcaaagatgg tttgaacacg ttcagcagca agtcggtggt    59340
ttgcgctcgc tcaaaattat ttgacaaacg cccaacgcgc agacctagat gttggcgaaa    59400
actatcagag atcgacaaaa agtttcacgt ttgccgacac gttgacacgt ttttggattt    59460
gtgcggcgga ccgggcgagt ttgccaacta taccatgtcg ttgaacccgc tttgcaaagc    59520
gtatggcgtc acgttgacaa caactcggt gtgcgtgtac aaaccgacag tgcgcaaacg     59580
caaaaatttc acaaccatta cggggcccga caagtcaggc gacgtgtttg ataaaaatgt    59640
tgtatttgag attagcatca agtgtggcaa cgcgtgcgat ctggtgttgg cagatggctc    59700
ggttgacgtt aatggacgcg aaaacgaaca agaacgtctc aactttgatt tgatcatgtg    59760
cgagacgcag ctaattttaa tttgcctgcg tcccggcggc aattgcgttt taaaagtttt    59820
cgacgcgttt gaacacgaaa cgatccaaat gctaaacaag tttgttaacc atttcgaaaa    59880
atgggtttta tacaaaccgc cttcttctcg gcctgccaat tccgaacgct atttaatttg    59940
tttcaataaa ttagttagac cgtattgtaa caattatgtc aacgagttgg aaaaacagtt    60000
tgaaaaatat tatcgcatac aattaaaaaa cttaaacaag ttgataaact tgttgaaaat    60060
ataacgtgtg tataaaaagc cagcggcttc aaatcaggca tcattcaaca tggattcgct    60120
agccaatttg tgcttgaaaa ccctgcctta caagtttgag ccgcctaagt ttttacgaac    60180
aaaatattgc gacgcatgtc gctacagatt tttaccaaaa ttttctgatg aaaaattttg    60240
tggacaatgc atatgcaaca tatgcaacaa tccaaaaaat atagattgtc catcatcata    60300
tatatcgaaa attaaaccga agaaagaaaa caagaaaata tatattacca gcaacaagtt    60360
taataaaacg tgcaaaaacg aatgtaatca acaatcaaac cggagatgtt taatttccta    60420
ttttacaaat gaaagttgta aagagctcaa ttgttgttgg tttaataaaa actgttacat    60480
gtgtttggaa tataaaaaga atttatacaa tgtaaatttg tatacgattg atggtcattg    60540
tccttcgttt aaagccgttt gttttttcatg tataaaaaga atcaaaacgt gccaagtttg    60600
caatcaacct ttattgaaaa tgtacaaaga gaagcaagaa gagcgtttga agatgcagtc    60660
gctgtacgca acgttggccg atgtagattt aaaaatatta gacatttacg atgtcgacaa    60720
ttattctaga aaaatgatat tgtgtgctca atgtcatata tttgcacgct gttttttgtac   60780
caataccatg caatgttttt gtcctcgaca gggttataag tgtgaatgta tatgccgacg    60840
atctaaatat tttaaaaata atgtattgtg tgttaaaagt aaagcggctt gttttaataa    60900
aatgaaaata aaacgtgttc caaaatggaa gcatagtgta gattatactt tcaaaagtat    60960
atacaagtta ataaatgttt aattttaagg atattgttat ggaataaact ataaaatgaa    61020
tttgatgcaa tttaattttt tgatactttc cacagacggt agattcagaa cgatggcaaa    61080
catgtcgcta gacaatgagt acaaacttga attggccaaa acggggctgt tttctcacaa    61140
taacctgatt aaatgtatag gctgtcgcac gattttggac aagattaacg ccaagcaaat    61200
taaacgacac acgtattcga attattgcat atcgtcaacc aacgcgttga tgttcaatga    61260
atcgatgaga aaaaaatcat ttacgagttt taaaagctct cggcgtcagt ttgcatcaca    61320
atccgtggtc gttgacatgt tggctcgtcg cggcttctat tattttggca aagccggcca    61380
tttgcgttgt tccggatgcc atatagtttt taaatataaa agcgtagacg acgcccaacg    61440
ccggcacaaa caaaattgca agtttctcaa cgcaatagaa gactattccg tcaatgaaca    61500
atttggcaaa ctcgatgttg cggaaaaaga aatactggct gccgatttga ttcctccgcg    61560
```

```
gctaagcgtt aaaccttcgg cgccgcccgc cgaaccgcta actcaacagg tctccgaatg   61620
caaagtttgt tttgatagag aaaaatcggt gtgtttcatg ccgtgccgtc acctggctgt   61680
gtgcacggaa tgttcgcgtc ggtgcaagcg ttgttgtgtg tgcaacgcaa aaattatgca   61740
gcgcatcgaa acattacctc agtaaacatt gcaaacgact acgacattct ttaaaaataa   61800
gctatatata aatattgcat tgtatgacaa aaaaattatt aacctactgc aaagtaaaac   61860
ttgtaaaagg cttttcaaaa aaatttgcga gtttattttg tcgctgcgtc gtgtcgcatc   61920
taagcgacga agacgacagc gacggtgatc gctattatca gtaataataac aattgtaatt   61980 tcatatacat aaatattgta aaataaaaga catattattg tacataatgt tttattgtaa   62040
ttaaattaat acaccaattt aaacacatgt tgatgttgtt gtgaataatt tttaaatttt   62100
tacttttttc gtcaaacact atggcgttgc tttcgattag ttttttcgtt agcatttcat   62160
ctaaaaaatc aaactgtttg cccggcgcgt ttagggattc tatggtgtag tcgggcgtgt   62220
cgctgtttag atattggtcc acttcgcgca ttatgtccaa gacgttgttc tgcaaatgaa   62280
tgagctttgt caccacgtcc acggacgtgt tcatgtttct tttttgaaaa ctaaattgca   62340
acaattgtac gtgtccacta tacaattcgg cttaatatac tcgtcggcgc aatcgtattt   62400
gcaatccaat ttcgtgttca acaaattggt gatgatatct ttgaacgtgc acgttttcaa   62460
tttgtcctta tcggccaacg caagtttcaa ttcgctctgt aaagtttcta aaattttgtc   62520
tttattgttg tcaaattcgt gcgtgttgcg ttccaaccac aatttgaacg gctcgtcgac   62580
aaaaatgctg cgcaacacct cgtacaactg tctgcctaac gtgtacactt gctcgtattc   62640
tttcatgctg acctctttgc taacgtacat tactaaaaaa tctacaagta ttttcaaaca   62700
tttgtaatag gcgacgtatt ttgatttaag ttttaaaccg tccaccgtgt attcgtccac   62760
gttcgcatcg accacttttc gattattatc gccgcttgtt gccggcgcgt cggcctgttc   62820
ggttttaact atatccggtt caatatttaa agtttcaaaa gatttaatgg cattcataaa   62880
atcatctttt tgctttggcg tggtcaatgg taaatctatc gaggagttgt cgtccgtgtg   62940
ctcttcgggc acgctgttca gacgtaacgt aatctttttg ggatcgtctt catcgggtat   63000
caaatcggct ttaattttat tagaattgag caacgacatg gtggtcgctt gtaaatttaa   63060
taaattaatt aaagactgaa attgtatatt gcacaaattt attttcattt ttattgatct   63120
tactattaat acgctggcag ttggtatgct tcatccattt ttgtgactag aaaatttgct   63180
aaaaaactga gctcgtcctg tgttaaaacg ttgtcgtcca cgaatctatg caatgtaaat   63240
gttacactga cattgtttaa caatgcatgt attaaaaaat caacctgtcg cctactgagt   63300
ttattagaag agtcgaccgt ttctactagt ttgtagattt tgttatttc aatttcattg    63360 tttaaaaaca tgttaactac tcgtttgagt ttaagcgaaa aatccttgtc cggatagact   63420
tgttcgcaca gccaattgct aagagtggtt ttgaccacgg acaccttggt ggtgaacgtc   63480
gtcgatttga ccagttcggt gaaaaagttt tcattaaat tggacatttt aacaaacact   63540
tatcaatcta ttgagctggt attttgtttt agaatcgcat caagcgcttg ctcgatctcc   63600 aattttttc ggacgctctt agctttatga ctcggtatgt cttctacggt agactcggtg   63660
ttcttactta taatggccgg gctgacgata ataaacacga gaaacaatat gagcagatac   63720
aaaaagatgc tgttttcctt tttgtcatac actaggctaa atatggccag tgcgcccaac   63780
aacaaatata aattcatttt tattcccttta ctctattcgt tgcgatagta caacaacgat   63840
tctcccgacg aaccggacga attgcgatta tgctgcgcgt cgtcgtcgtc gttgttgttc   63900
```

```
tcctcttcgc tgctcgtttc gtctaaacct atattgtatt tgttcaagta atgtttggtg   63960
cttgcggagg attcgtggtt cattaatttg gccacttttt gtaaaggcac gccgctattg   64020
tataggttac tgctcaaata atgtcttatc atgttgctgc gcggccgttc catctcgacg   64080
cccgactctt caaggagtcg cctgaaatct ttgaagggcg tcgaggtgtt tttagatatt   64140
tgcaaaatgg tcgggtttcg tgaataaatc tcgcgtgcca attccaacgg tttcattttg   64200
atgttgttga gtgtgttatt acgactgcgt tttcgcttta aattaatcgt gtcgctgtgc   64260
agttttcctc ttttaattag cacgttgaga tcgtccacgc tgagttggcg cgcttcgttg   64320
attcgcatac ccgtccctaa catgatgcaa aacactatcg cgcccctaat tagaccgcgg   64380
tcgtgaacat aatcgctgtt gagcatttta attttatcat taataaaatt taatatggta   64440
tctattacgt ttttaagcat taaattcttt tccttttccc tgatattttt gagctccttg   64500
tcgcgcggca gcataaccat gcggggaatt ttgtattcgg gcaagttcat catgttggtg   64560
taaaagttta tagtcaactg tagtgtttct ttggtgaccg agcgaagttc gagcatgcgc   64620
ctgcacagtt cttgggatc aatgagaagt gtttggtttt ctatcgagtc aaactccttg   64680
tccaacgagt acgacatgtc ttccaggtga acatcgtcta ccgagcagta cacaattta   64740 atgaatcgag acttgtaact ttttaaagtg gtgggcgcaa acggtttggg gaacatgtac   64800
ttgctccaca gactgttgtt tttcacctcg tcgggcgtgc atcgttgccg atcggtggcc   64860
aaatcgaaca cggactcgaa ccggggagcg gattgaattt ttattttcca agaattaaaa   64920
ttgttttcgt tgcgaacatt aaaaccgttc attgtggtta atcaaattta ttaaaaacaa   64980
aaggagaatc ggtgtcaata ctatccgaat attgttgttg ttctcttaat attacgaaat   65040
aatatattac atacagcagt aagaataaag ctataaaagc gactacacta attaaaatta   65100
taattcccgc cgacacgttg ctcgtcgtgt tgtcatagcc caccatgtcg tttattggca   65160
ttttgtgaac gggctcgcta aattgttgcg gttcgctggc agtatcgtcg ttgagcgcca   65220
atttcaacgg gatgtattcc accttttcgt ggttgcccaa ccgatagtag ggcacgtcca   65280
aattcatgtt tacaacttat ttgctaacag gaatttatgc aacaaaagtg gtttggcttt   65340
gatgagacgc aatttgaaat acttgctgca tttacgctta agattgtatt ccatgcgggc   65400
ggcggtgttg tagtcgtacg cgctcgcgct gtgatacacg agccgtaaat tggttgcgtt   65460
gcgcaaaaca ttggcgcctt gtttgttcga atgctgtttt atgcgtctgt taagattgct   65520
cgtgatgccc gtgtacaatt ttccattgtc ttgccgcaga atgtacacgc accacacctt   65580
gttggtgtac agagtcgtcg ccatgattat gcagtcgcc ctttcgtgtt cggccgagtg   65640
gcgttaggcg cagccgcggc aataatcgcg ttggcgtcct tgttgtaatt tatttgttga   65700
aaaataaaac gtcttagagt ttcgttttgg aacgccaatt cggtcaagct ctcctggcaa   65760
gcgcttttgg tcaaatgagc ggccggcgaa ttgaccgcgt tggcggccga cgttaagaag   65820
gtggcgttct ggaacatgct gggctgcttg ccggctcgcg tcgccagctc ggccatgtaa   65880
ttgaatatgt tggcagacgc agatagcggc gccaaaaacg caacgttctc ttttaaactc   65940
atgactcgcg ccctgttttt ttcgttcagc acgtagtggt agtaatcgcc gccgccggca   66000
aacagatcgt caatcacggc gttgatcaga tcgttgatca tgttgatgtg cggaaagcga   66060
cgcgactcga ctgcgctctg tatgtttggc ggcagagtgg cgtgcttgag caacagagtc   66120
atgtaattgt tggccagctg ctgattgaaa ggtaacggaa tgggaatgtt gcacgtcacc   66180
gcttccgcca ccatgtactg gacggccaga ctgagttgtt tggcggcctc ggccaaagcg   66240
tctttgccca acatatcagc gccaccgttg taaaactttt gcgcgtacgc cggcagcgaa   66300
```

```
tttagcacaa acgatggctg aaatatattt gaatcgctcg acagggactc ggccgcgttg   66360
ctctgtccca actcttttg caaccgaatc aggtggcgta tcatggtttc ctccgattca    66420
aaccgcttta ccacgtttac gctgattggg ttcgtgtcga tgcacatgtc acgaatagtg   66480
tttataaaaa gaatcatgag aggactaagt tctgacatgt cattgcacct gtaatatcta   66540
ataatctttt gaacaaaatc cacacatttg ttgtaccaaa tagattcacc ggcgtcgagc   66600
gtcggttctt tgctcttgtt gtacggtgca atcgctaccg agtttgtgct gttgctgcgg   66660
ctcgtgtaat ccatcctgtt gtcgcgcgtg gcgacggtcg taggcaccgt cgccggcggc   66720
acgtacccgg gcgcgttgta agtttgcgcg ctggtaaata tggccgttgc cggattagag   66780
ggatacctca gcggcggagg ggtgttgtaa taaaaattgc cacgttcatc tgtcatactt   66840
tttatttgta ctcttatgat tacaaaactc aatatacgga ttacttataa tatagttgtt   66900
gtgacaaaaa agcgataata aaattaacaa aattatcaac aagttaatca tggaaaattt   66960
ttcaacgttg aataacaaca acaaaatggc gcaggtcaac agcaccgttt gaaaactgac   67020
gcgccgacac aaaatgcttt cgcaatttct aaaagccaca ttaaacgaat tttcacctt    67080 gatataatca cgcagttctt ttttacaaca ttcgtcgcac aaaattaaca cctttataat   67140
gaggccgtcg gtgtgtatcg tttgaaatgt ccgcggttga ctgcctggat gaaattcaaa   67200
cgagtaccca gtggacacgt gtatctgtgc aaaataatgg gctaatatcg aggcgcccgt   67260
ttttttaacc tttacttttg atattttaat aacattaatg ttgttatttg cgtaatcaga   67320
gtttttattg tggtgatcat cgtacaaata atgaagcaac agttcactat cgtatttaat   67380
cttgtttagc gttgtcaagt ttttgtttct taggcgttgg agcgtctccg tcgtcgatat   67440
tttcttcgaa atcgagtcca acaacgtcgg cgtttccttc ttgctcatcg atagcggcgg   67500
cggaggcggc ctctccgtcg tcgtcattcg cggtttctac agtgcgtttg ggcgacgacg   67560
tgtgtacagc agcgtccgtc ttactattat cggaccgcca aattttgtt tgaaataaca   67620 tttggcccct gttcaacttt atttcggcgc agttaaacat tattgcatta agatcatatt   67680
cgccgttttg caccaaattg cacaaaacac catagttgcc gcacgacact gtagaatagg   67740 cgttttgta caacaatctg agttgcggcg agctagccaa cttgataata tgggcgccaa   67800
cgccccgttt ttttaagtaa tattcgtctt caattataaa atctagtacg ttttcatctt   67860
cactgttgat ttgggcgttc acgatgatgt ctggcgtaat gttgctcatg cttgcctttt   67920
ttcttataat agcgtttact ttaatgtatt tggcaattta ttttgaattt gacgaaacga   67980
ctttcaccaa gcggctccaa gtgatgactg aatatgtgaa gcgcaccaac gcagacgaac   68040
ccacacccga cgtaataggc tacgtgtcgg atattatgca aaacacttat attgtaacgt   68100
ggttcaacac cgtcgacctt tccacctatc acgaaagcgt gcatgatgac cggattgaaa   68160
tttttgattt cttaaatcaa aaatttcaac ctgttgatcg aatcgtacac gatcgcgtta   68220
gagcaaatga tgaaaatccc aacgagttta ttttgagcgg cgacaaggcc gacgtgacca   68280
tgaaatgccc cgcatatttt aactttgatt acgcacaact aaaatgtgtt cccgtgccgc   68340
cgtgcgacaa caagtctgcc ggtctttatc ccatggacga gcgtttgctg gacacgttgg   68400
tgttgaacca acacttggac aaagattatt ctaccaacgc gcacttgtat catcccacgt   68460
tctatcttag gtgttttgca aacggagcgc acgcagtcga agaatgtcca gataattaca   68520
cgtttgacgc ggaaaccggc cagtgtaaag ttaacgaatt gtgtgaaaac aggccagacg   68580
gctatatact atcatacttt ccctccaatt tgctcgtcaa ccagtttatg cagtgcgtaa   68640
```

```
atgggcgcca cgtggtgggc gaatgccccg cgaataaaat atttgatcgc aacttaatgt   68700
cgtgcgtgga agcgcatccg tgcgcgttta acggcgccgg acacacgtac ataacggccg   68760
atatcggcga cacgcaatat ttcaaatgtt tgaataataa cgagtcacaa ctgataacgt   68820
gcatcaaccg gatcagaaac tctgacaacc agtacgagtg ttccggcgac tccagatgca   68880
tagatttacc caacggtacg ggccaacatg tattcaaaca cgttgacgac gatatttcgt   68940
acaacagtgg ccaattggtg tgcgataatt ttgaagttat ttccgacatc gaatgtgatc   69000
aatcaaacgt gtttgaaaac gcgttgttta tggacaaatt tagattaaac atgcaattcc   69060
caactgaggt gtttgacggc accgcgtgcg tgccagccac cgcggacaat gtcaactttt   69120
tacgttccac gtttgccatt gaaaatattc caaaccatta tggcatcgac atgcaaacct   69180
ccatgttggg cacgaccgaa atggttaaac agttggtttc caaagatttg tcgttaaaca   69240
acgacgccat ctttgctcaa tggcttttgt atgcgagaga caaagacgcc atcgggctta   69300
acccgttcac cggcgagcct atcgactgtt ttggagacaa cttgtacgat gtgtttgacg   69360
ctagacgcgc aaacatttgt aacgattcgg gaacgagcgt tttaaaaacg ctcaattttg   69420
gcgatggcga gttttttaaac gtattgagca gcacgctgac cggaaaagat gaggattatc   69480
gccaattttg tgctatatcc tacgaaaacg gccaaaaaat cgtagaaaac gaacatttc   69540 agcgacgtat attgacaaat atactacagt cggacgtttg tgccgaccta tatactacac   69600
tttaccaaaa atatactaca ctaaactcta aatatactac aactccactt caatataacc   69660
acactctcgt aaaacggccc aaaaatatcg aaatatatgg ggcaaataca cgtttaaaaa   69720
acgctacgat tccaaaaaac gctgcaacta ttccgcccgt gtttaatccc tttgaaaacc   69780
agccaaataa caggcaaaac gattctattc taccctgtt taacccttt caaacgaccg   69840 acgccgtatg gtacagcgaa ccaggtggcg acgacgacca ttgggtagtg gcgccgccaa   69900
ccgcaccacc tccaccgccc gagccagaac cagagccaga acccgagcca gaacccgagc   69960
cagagttacc gtcaccgcta atattagaca acaaagattt atttttattca tgccactact   70020 cggttccgtt tttcaagcta accagttgtc atgcggaaaa tgacgtcatt attgatgctt   70080
taaacgagtt acgcaacaac gttaaagtgg acgctgattg cgaattggcc aaagacctat   70140
cgcacgtttt gaacgcgtac gcttatgtgg gcaatgggat tggttgtaga tccgcgtacg   70200
acggagatgc gatagtggta aaaaaagaag ccgtgcctag tcacgtgtac gccaacctga   70260
acacgcaatc caacgacggc gtcaaataca accgttggtt gcacgtcaaa aacggccaat   70320
acatggcgtg tcccgaagaa ttgtacgata caacgaatt taaatgtaac atagaatcgg   70380
ataaattata ctatttggat aatttacaag aagattccat tgtataaaca ttttatgtcg   70440
aaaacaaatg acatcattcc ggatcatgat ttacgcgtag aattctactt gtaaagcaag   70500
ttaaaataag ccgtgtgcaa aaatgacatc agacaaatga catcatctac ctatcatgat   70560
catgttaata atcatgtttt aaaatgacat cagcttatga ctaataattg atcgtgcgtt   70620
acaagtagaa ttctactcgt aaagcgagtt tagttttgaa aaacaaatga gtcatcatta   70680
aacatgttaa taatcgtgta taaggatga catcatccac taatcgtgcg ttacaagtag   70740
aattctactc gtaaagcgag ttcggttttg aaaaacaaat gacatcattt cttgattgtg   70800
ttttacacgt agaattctac tcgtaaagta tgttcagttt aaaaaacaaa tgacatcatt   70860
ttacagatga catcatttct tgattatgtt ttacaagtag aattctactc gtaaagcaag   70920
tttagtttta aaaacaaat gacatcatct cttgattatg ttttacaagt agaattctac   70980
tcgtaaagcg agtttagttt tgaaaaacaa atgacatcat ctcttgatta tgttttacaa   71040
```

| | | | | | |
|---|---|---|---|---|---|
| gtagaattct | actcgtaaag | cgagtttagt | tttcaaaaac | aaatgacatc | atcccttgat | 71100 |
| catgcgttac | aagtagaatt | ctactcgtaa | agcgagttga | attttgatta | caaatatttt | 71160 |
| gtttatgata | gcaagtataa | ataaccgcac | aaagttaaat | ttttttcatt | tacttgtcac | 71220 |
| catgtttcga | atataccata | ataacacaac | tgtgcccggt | tgtttagtgg | gtgacattat | 71280 |
| tcaagttcgt | tataaagatg | tatcacatat | tcgcttttg | tcagattatt | tatctttgat | 71340 |
| gcctaacgtt | gcgattgtaa | acgaatatgg | acctaacaac | cagttagtaa | taaaacgcaa | 71400 |
| aaacaaatcg | ctgaaaagct | tgcaagattt | gtgtctggac | aaaatagccg | tttcgctcaa | 71460 |
| gaaaccttt | cgtcagttaa | aatcgttaaa | tgctgtttgt | ttgatgcgag | acattatatt | 71520 |
| ttcgctgggt | ttaccaatta | ttttaatcc | ggctttgcta | caaagaaaag | tgccgcagcg | 71580 |
| cagcgtggga | tatttcatga | attcaaaatt | ggaaaggttt | gccaattgtg | atcgggtca | 71640 |
| tgtcgttgaa | gagaaacaat | tgcagagtaa | tttgtatata | gattatttt | gtatgatttg | 71700 |
| tggtttaaat | gttttaaaa | taaagaata | acaatttaca | cattgttta | ttacatggat | 71760 |
| aatgttgttt | gtttgacatt | aaaggttatc | atggtgcaat | gattaataat | aaaacaatat | 71820 |
| tatgacatta | ttttcctgtt | attttacaat | ataaaatcac | accaattgtg | caagttttta | 71880 |
| ttatttgttt | gtcgacggtc | gaggggtcag | cggcgtgtgc | aacaataaaa | aacatgaagc | 71940 |
| tgttaacaat | tttgatttta | ttttattcat | ttttatgaa | tttgcaagcg | ctaccagatt | 72000 |
| accatcaagc | aaataggtgt | gtgttgctgg | gaactcgcat | tggatggaac | gatgacaata | 72060 |
| gccaagatcc | caacgtatat | tggaaatggt | gttaaataaa | agtgaatata | ttttttataa | 72120 |
| aatttttat | ttaaaattcc | aagtaatccc | tgcaaacatt | aaacactgta | ggtattttta | 72180 |
| aatcttgcca | catgcgaaca | acgcacggcc | tgtcgtcgaa | caccgctatt | acattatatt | 72240 |
| ttcctctgat | atagttgtta | aacaattta | attttaataa | ataatcttta | caagtatcgt | 72300 |
| ctgaaggcct | cataaacaat | ttatatgatt | taatatcaaa | atactttca | atccagtttc | 72360 |
| gagtgggctg | ttcacaaatt | acgcttctcc | cgctcataaa | cacgataatt | gcgtcgtggc | 72420 |
| aatttgccaa | atacttaacg | caagtaataa | cgtctaagcg | ggcttcatct | tgagcaactc | 72480 |
| tattatcaaa | atcataaaac | gatctatttg | tgggcaaagc | tactgtaccg | tctaaatcac | 72540 |
| ataatacagc | gcggggaaat | ttgtcgccga | caggaacgta | atattcgaaa | ttatttacct | 72600 |
| ttagaaactt | tttatattgc | tttttaatag | tttctggatt | taatgaaat | ttatcagagc | 72660 |
| gtttataatt | gcgttcaaga | gccgtttcca | aagaaacgtc | catcaaacgc | gttaaaaaat | 72720 |
| ggtaattatg | cgttgcggcc | attttttgcc | acatgtccac | cgattgagtg | ttcaaattag | 72780 |
| tgtcgctgac | aaccacgttg | gcaccacatt | ttgcggcttt | taaaaactgt | tcaatgcaca | 72840 |
| ttttggtaat | ttgttcttct | ttagtttgtc | tacatttccg | cgattggtta | tagaaagcgt | 72900 |
| tcagttttgt | ataatcgccg | tttaaaaaca | acttaacgcg | cacgtcgtct | ctgttgattt | 72960 |
| ctgtatagcc | ttttaaactt | ttggcatacg | tgcttttgcc | cgaacccgaa | atgcctatca | 73020 |
| acaccaacaa | ttgttttgaa | gaaggcaatt | taattgttgg | agcaagttta | ttatttaatg | 73080 |
| cctgcttagt | cgatacaaat | tttataatat | ttttgatcat | tttaattttt | tcaggctcgg | 73140 |
| ttaattttaa | aaattcgctc | tccacatcga | tcgtttgtgc | tttacgacat | ctgtacgcta | 73200 |
| aacatttcca | cggcaaagtt | tgcaccagtt | cgttgaaacg | ctgttgattc | aaagtcaaac | 73260 |
| ccgacaccat | aatatttatt | gtagactcgt | tggtgaacgt | gtttctagca | tcaacgtacg | 73320 |
| gtttaatgac | acttttaaa | tgcgggaaaa | gagctagaaa | gtcatcgtgt | tcgccattta | 73380 |

```
taacaagctg cgccaattta gtaggatttt cagcacggct ctgattttg tgcatgttca    73440
aatacacgtc gcttttaatc ttgcatagtg gcgcgttgtt tttatcgtaa actacaaatc   73500
cttcttccaa attttcaac tgggccgcgt gttcgacaca ttcttgcaca gacgtaaact    73560
cgtaacattt ggggtatttg caaaacggca aattggaaca gtaaaaataa tcgcccgttt   73620
cgttgtttct gcttgccaaa taccacaacg ttggctgttc atcgtaaacg gttacaattc   73680
tgttgtgttt gcttgttaac tcaaacatgt gagtcgacgc gcagtctaaa tattcgttac   73740
acaacgcttg aaattgattg tgggcctcgt caagttgaag agcttgcaaa actaaacgtt   73800
taaacgtcac gtctgacacg caaaggtttt ctgcaaaagc acttcctcgg gtgctggcat   73860
gccattcgcc gttgtacttg tagatttaa ttaaacttcc gtcgattttt tcgtaaaact    73920
taaaattctc cttcgattgg aacagtttgt gatgagcatc ttcgccgccg atattttgta   73980
gcaattcttg aaaattaaag aaacgatcga agaacgcga cacaacggcg tacgtgcggc    74040
tgttaagaat taaccgcga cattccacga ccacaggatg atctcgatcg cgttcaaacg    74100
attcgtaatt aagaaccatc aaatcgtgtt cggtataatt tttaattttg actttaaact   74160
tgtcacaaag atttttcact ccgccgtttg caagtagacg cgaaacgtgc aacatgattg   74220
ctgtttaata atgcatacca atgctaaact gtctattata taaagtgcag tgataacttt   74280
gttatcaacg cgttcgatgc cgacatatat aaacgcaatg taacagtttt tgctagtacc   74340
atcgcataca acattatgaa tacaagggg tgtgttaata ataataaaat gatatttatg    74400
aatgctttgg gcttgcaacc tcaaagtaaa ttgaaaatta ttgcacataa aatactagaa   74460
aaatgtaaac gtgacgcgta cacgcgtttc aagggcgtaa aggcgatcaa gaatgaacta   74520
aaaacataca atcttacgtt gcaacaatac aacgaggcgc tcaatcagtg cgctttaaac   74580
gatagccgat ggcgcgacac aaataattgg catcacgata ttgaagaagg tgtgaaaata   74640
aacaagagac atatatatag agttaatttt aattctaaaa cccaagaaat tgaagaatat   74700
tattacatta aagtagaatg ttatgtaaac agttaattaa tctacattta ttgtaacatt   74760
tgtggtaata gtggcgttgg ttatacattt atatgattgt aatgttgtgt actcgttttg   74820
taataaattt ttgtgtttaa tcaattcaat atttttattt gataaaacct tatttcgct   74880
actcaatttg gcgttttag acgcaagttt tgcgtaatcg tcattgagcg attttagcgc    74940
cttttcagtt gtaattcgtt tcagttgcaa ttcttaaaa gatttatgca tgttgttgta   75000
gtcgctttta atttgtcta acttttcttg catagaaacg cttgtttgtt gtaatttgtc    75060
taaatctaat tgttgtttaa tgttgagctg cgtttgttcg gcaatgtcta cctgtagttt   75120
ttttagtatc gcttgtgctt cagacagcat agtgtcgtcg gcatttgcgt tgttgtcttc    75180
tgcgtcgtcc aacagacttt tttcaaacaa cacactggcc aaagaggccg catcaaaatt    75240
agcgtttatt ttattccatt gtgcgacact cgacgcgctg catttaatca catccacaac   75300
gtttcggttt acgctgtaaa cgttgaaatg caaactttca accctacaca agggacatgg   75360
tacttttttt cgttttctaa tcttgcgtat acacattgag cataattgat gtttgcacgt    75420
gtctagttct aatacgggta ttatagtcaa tctgtctatt ggttgcagaa aataatttt    75480
aatttctgca accgaaaaac aaatgttgca ttgcaattta acaaactcca tttttagacg   75540
gctattcctc cacctgcttc gcctgcaaca ccaggcgcag gacctgccac tgcgccgccg    75600
cccagagtag cgttaggatt tgctcttggt ataagtcgt tgcgcaaaaa gttgttttct    75660
gaattgatta tttggtatcc caaaacagc ggaacgtacg tcgggtattc ttcgtatccg    75720
ctaagcgttc tgtccagctc acgtgtgtcg ccttcaaatt tcaaaacgtt tctaatttgc    75780
```

```
aaacgattgg gttgacttct cataatgtca ctgcttctta tcgggttgta caactcgggg   75840
ccgtcgggca cagacgcgac cagacccgtt tcgtcaatta tacacgtggc gcaatttcta   75900
aacctcaatt cctccgtgtc gatttgcaag tactcgggcg ctactgcgcg tcgaatcaaa   75960
ttttgcaaaa atccactgta attgttaaat aattgatcgc cagcaccgcc tcgaagcgct   76020
cgggcgttgg tcacgtcaaa gaaacgcaat tcgtctcgcg acaccgcga  acaaaacgtg   76080 ttcgggtttg tggtgtccag aatgcttttt gtagttgcgt aaacgctgtg tataacgcgt   76140
tgcgtgttgc ttgtgaaacc ttcggtatat tttagattgt cgcatatagt gttaactgcg   76200
ttttcgttgt tatatatcaa atgaaagatt agctgttcgg cttgcatcat actgtttaga   76260
ttaaacacgt cttggtaatt ggttgcgctt ggaattaaaa ttcgcttgat acctcttct   76320 ttatttccaa ctaaatgcct agcgatcgtc attttgaatt gattgtcgtc ttcgtcgaaa   76380
atgggcaaaa ccattttga  cattttaaaa cgttttatga ggtggttgtt gcaaataaac   76440
catccatcgt catgatacgc gtcgggcgaa cacggcgatt tgtatgttat gcacgcgtcg   76500
aacgacacga tggacgcgaa aatgcagcga ttaactctca tttgtcgcgg cgccataccc   76560
acgggcacta gcgccatatt gttgccgtta taaatatgga ctacggcgat tttgtgattg   76620
agaaagaaat ctcttattca ataaatttta gccaagattt gttgtataaa attttaaatt   76680
cttatattgt tcctaattat tcgctggcac aacaatattt cgatttgtac gacgaaaacg   76740
gctttcgcac tcgtatacct attcagagcg cttgcaataa cataatatca agcgtgaaaa   76800
agactaattc caaacacaaa aaatttgttt attggcctaa agataccaac gcgttggtgc   76860
cgttggtgtg gagagaaagc aaagaaatca aactgcctta caagactctt tcgcacaact   76920
tgagtaaaat aattaaagtg tacgtttacc aacacgataa aattgaaatc aaatttgaac   76980
atgtatattt ttcgaaaagt gacattgatc tatttgattc cacgatggcg aacaagatat   77040
ccaaactgct gactttgttg gaaaatgggg acgcttcaga gacgctgcaa aactcgcaag   77100
tgggcagcga tgaaattttg gcccgcatac gtctcgaata tgaatttgac gacgacgcgc   77160
ccgacgacgc gcagctaaac gtgatgtgca acataattgc ggacatggaa gcgttaaccg   77220
acgcgcaaaa catatcaccg ttcgtgccgt tgaccacgtt gattgacaag atggcccctc   77280
gaaaatttga acgggaacaa aaaatagtgt acggcgacga cgcgttcgac aacgcgtccg   77340
taaaaaaatg ggcgctcaaa ttggacggta tgcggggcag aggtctgttt atgcgcaatt   77400
tttgcattat tcaaaccgac gatatgcaat tctacaaaac caaaatggcc aatctgtttg   77460
cgctaaacaa cattgtggcc tttcaatgcg aggttatgga caaacaaaag atttacatta   77520
cagatttgct gcaagtgttt aaatacaaat acaacaatcg aacacagtac gaatgcggcg   77580
tgaacgcgtc atacgctata gatccggtga cggccatcga atgtataaac tacatgaaca   77640
acaacgtgca aagcgtcacg ttgaccgaca cttgccccgc aattgaattg cggtttcagc   77700
aattttttga tccaccgcta cagcagagca attacatgac cgtgtccgtg gacgggtatg   77760
tcgtgctcga caccgagttg agatacgtca aatataaatg gatgccaaca accgagttag   77820
agtatgacgc cgtgaataag tcgtttaaca cactcaatgg gccattgaac ggtctcatga   77880
ttttaaccga cttgccggag ttactgcacg aaaacattta cgaatgtgta atcacggaca   77940
cgacaataaa cgtgttgaaa catcgtcgcg accgaatcgt gccaaattaa agcacgttaa   78000
gcggatacaa cgggcagtcc gagctgttaa agtcaataca accatcgtta acaaacgaat   78060
acgcattgtt gtgacagctg aggatataaa aaggaataga gaagtaattg caatgaaata   78120
```

```
tcccgttaca attccacggc acagcgtatg ttgctcgagt tctatcagtt gcacacaacg   78180
gcctaagaaa atttattaat gcttcatttg tatctatatt agaaggataa tacataggtt   78240
cgcccaaagg actgggagaa ggcggcggcg aaggtgtagg tgtaggagga ataggagaag   78300
gcggcggcga aggtgtaggt gttggaggaa taggagaagg cggcggcgaa ggtgtaggtg   78360
taggaggaat aggagaaggt ggaggtgtag gtgtaggtgt tggaggtata ggtgttggag   78420
gaggtgtagg tgtaggtgtt ggaggtatag gtgttggagg aggtgtaggc gaaggtggag   78480
aaggtgtagg agtaggtgga ggtgtaggta acggtacaat tggtggagat gtaggtggtg   78540
gtacaattgg tggatttgga tacaattcct gaatgtcgtc taatattttt aaagttaata   78600
aaattattat aaataaattt aatattatta ttattattat tatcacaata atgtaccaca   78660
tgttgcttaa atataaaaat taaacaaaga atgttgtatt attgcaaatt taacaatttt   78720
ttgtattctc cccatgtcat gcgttcgtaa tgagcgggcg gttttttatt tctttgtatc   78780
cacttgtaat cgttaatgtg gttgtgaaaa gtcatactga cgtaggccat taaattttc    78840 atgagcatat tatttgacac aactgcaaca tctgcgcctg ccgtttcttg ctggtacgaa   78900
tcgacaaacg taatgtctgt gccgtatttt tctttgtcaa gtgcaatttc tataagctca   78960
atgtggtaaa tgatgaaacc tttgacgttc atataatgat cgcggcacat ggcgcactgt   79020
agtatgaaaa atacgttgta aaatagcacc ttcattgttt tcaactgctg catgacaaaa   79080
tctaaactgc ttttgtctcg cgtatacacc atatcgtcga tgatgagact gagaaagtgc   79140
atggtgtccc atatggtagt aaacgtgtaa gtaaaactct gggctggca cgaacgcaaa    79200 ttgagttctg tggttttgtc cataaattct atgcgaaact gttgcaagtc catgtcgggg   79260
gatgcgttaa tggcccattc gatcaactgc tgcacctcgt acttttgaat gtctttgtat   79320
ttcatcaaac acgcaaaatg gtataagtaa gttgcttgcg aagacaacag tttggtgagg   79380
tgcgtcgatt tagaggctcg caaaaggtct atgagacgaa acgaatacaa cagatagctg   79440
tctttgtaac gagaaaaaag cggcgtcagc ggtatcatgg cgactagcaa aacgatcgtg   79500
ctgtacttgt gtcaggcgcc ggccacagcg tcgttgtacg ttagcgcaga cacggacgcc   79560
gacgagccta ttatttattt cgaaaatatt acagaatgtc ttacgacga ccaatgcgac     79620 aagtttactt atttttgctga actcaaacag gagcaagcct tatttatgaa aaagtatac    79680 aaacacttgg tgcttaaaaa cgagggtgct tttaacaaac accacgtatt gttcgatgca   79740
atgattatgt ataagacata tgtgcatttg gtcgacgagt ctgcgttcgg aagcaacgtt   79800
atcaactatt gcgaacagtt tatcacggcc atttttgaaa ttttttacgct cagcagtaaa   79860 atcgtcgtgg ccgtgcccgt caattgggaa aacgataatt taagtgtact tttgaaacat   79920
ttgcacaacc taaatctcat tggaattgaa attgtaaatt aaaacaaatc atgtggggaa   79980
tcgtgttact tatcgttttg ctcatactgt tttatcttta ttggacgaat gcattaaatt   80040
tcaattcctt aaccgagtcg tcgcccagtt tagggcagag cagcgactcg gtggaattag   80100
acgagaacaa acaattaaac gtaaagctga ataacggccg ggtggccaac ttgcgcatcg   80160
cacacggcga taataaattg agccaagtgt atattgccga aaaccgcta tctatagacg     80220 acatagtcaa agagggctcc aacaaggtgg gcactaacag cgttttctg ggcaccgtat     80280 acgactatgg aatcaaatca ccaaacgcgg ccagcacatc tagtaatgta accatgacgc   80340
gcggcgccgc aaactttgat atcaaggaat tcaagtccat gtttatcgta ttcaagggtg   80400
tgacgcccac taaaactgta gaggacaatg gcatgttgcg attcgaagtc gacaacatga   80460
ttgtgtgttt gatcgacccc aacacggcgc cgctgtccga acgagaggtg cgcgaattgc   80520
```

```
gcaaatctaa ttgcactttg gtgtacacaa gaaacgcggc agctcagcaa gttttattgg   80580
aaaataactt taccgtcatt aatgctgaac aaaccgccta tctcaaaaac tataaatcat   80640
acagagaaat gaattaataa aacaaaaagt ctatttatat aatatattat ttattaacat   80700
acaaaatttg gtacactagt gttcaaatcg tttctgttca acgccattgt catgttataa   80760
aacacatttg tagttttatt gtaattattt ttaaatttat ttttaatttg ctgtaataaa   80820
acttgttcat taaatacaaa agactttgaa ctacttgcgt ttatattctt tttataattg   80880
tactgaacaa acgaggggtg caaaaagttt ttgaaatgct gcacggcaat acctatcatc   80940
tcctccattt tgtcctctcc tattgtaata gtggcactgc gcaccgtttt aatgtttaga   81000
atgtaaatga gcgcatacag cggactattg ttggtgctca agcacattag gttgtgctta   81060
tgcatagggt cgttgctcag cagcgttttt tatactacaa agcccgtttt ggggtcgcgt   81120
ctgtacatta gtacgtgcga caaaaacaaa cgcaccggcg tcacaagcga ctcgtaatac   81180
atgctttcta tcggaaactg tttgacttg atgtgttcgt acacggagcc ggcaaacttg   81240
acgctgtcta caaacttatg gttcgtgtaa acaatcaaaa atctgtcttg tacaccgtcg   81300
tcataatcgt ccacgtacag cggcttgttg ttaacaatta acattttgta gttggcttca   81360
tactttagca gcccttggta ttttctgctc ttggaatcgc tcttgctcga atcggcatgc   81420
ttcttaaagt acgactcgct gcattgtttc aactcgttga tagtgtacaa ctgcgagttg   81480
agtttgctca cttccttgtc gctcgtttcc ttgttggact ctccgctgtg gttgtcatcg   81540
tcaaacttgt gcatcaacac caaatagtcc aacagctcaa aaaacgacga cttgcccgaa   81600
cccggttcgc cgggcatgta aatagccttc tttccgtaat ctacgggaat ggccaaacta   81660
gcggcgaaat gcatcaacat aatcgcgttc gcgtgattaa aattggtgaa gcgtttaaag   81720
tacaaatagc cttcgacaat cttttcaaa taattgtacg agtactcctt caagtccact   81780
ttggacatga tgatgcgcat gtagaatcga gtcagccaag tgggcaaatc gtccgtgctg   81840
cgcgccaata tgattttgtc ccaccacaca ttgtacttct tcaagatcat taacgcgtcg   81900
gcgtggtgcg tgtaaaattt ggaaatgtta tccgattctt caaactgaac atcgggttca   81960
cgtgcaacat catcgcgcaa ttcggttaaa acaaacgtt tatcattaaa cttgtccatc   82020
aacatgtcga catattcgat tttgtgaatt gttcgataca agtactgaat aattttgttg   82080
tgttctttgg aaaaaaactc tccgtgttgg ttaacaaatt cgctgttcgt gcgaatcaac   82140
gtggtcgaca cgtacgtttt gttagtaaaa attagcatcc aaatcaattc gctcaattct   82200
gcatcgttac cgaacatgtc cgccatcaag cagacttta gcgcttttct attgatcttt   82260
attttcttgt agcatttgca ttttggtcga gatcccgata ccgttgaccg acacggtttg   82320
cattttaggt tgtgcaacat gtcggaaacc ctgttcttgt ttacgtacag agcgagcgta   82380
atcagatttt catcgtccaa attccacaaa tcgcgaaaca ggttgtttaa cgcgactcgc   82440
atatcggctt ggcatgtgtt gcaattgccc atgtagttaa ctatggccgt gttagttttt   82500 agcatttta catctcggca catttggcg atgtgataag ttctataaat gctgagctcg   82560
tcggcgctag tagatagcat gtaattaaac gcgtcctcgg gcaaatactt ttcgtcggtg   82620
ggcttcttga atgtctgcgg caacgtgtg cccaacaaaa atggacagct cgaatgaaag   82680
ctgttggtga acacgttgta cacaccgtgc gttgtcaagt acaagtattt ccaattgtta   82740
aattttatgt tgctcaactt gtaacaattg cttttggtca atttgaatag gtcatcctct   82800
ttctttacaa tttgataatg tttgccgttg aaaaccaaat tgactccggt cactacgttt   82860
```

```
tccaatttc taaagaatcc tttacacaca atgtcaggcg gcaagtttag cgccatcaca    82920
ttctcgtacg tgtacgccca caattcatcg tgatccaaaa tttcgttttt agccgactga    82980
gtcaaatata tcatgtagtg tatgccaaaa taatagccca acgatacgca caatttggta    83040
tcgtcaaagt caaaccaatg attgcaggcc ctattaaaca ctattttctc ttgtttttg     83100
taaggctcac atcgcttcaa agcttcattc aaagcttctt tgtcgcaggc aaataatgat    83160
tcacacaaaa gttccaaaaa cagtttgatg tcggtttctc tgtacgagaa attttcgttc    83220
ttggtcaata tcttccacag tacatagatt aaaaaatcaa aatttttaaa tttgcttttt    83280
tcaaagtatt gttgtagaag gtttggatcg ttggctcgtt cgtgggtcgc caaaacttta    83340
accatgttct cgtgaattgc tataagcccc aaattgattt gcgtttgaat gtagtctgca    83400
tttcgctgc tcgccgatat aatgggtacg atgcgcggtt ttctggaacg cgtgtcgctc     83460
aagtccacgt cgttttgtc aaaattgttg ttctcgaaca ctctgaggct tttgaggttg     83520
acgttgacga tatgcttgta cttgggcacc gtaatgcatt cctccaaatt aatgtcgtcc    83580
ctaatgtaat tgaaaaaatt tttatccgaa ttgaccagct cgccattaac tttgcacgtg    83640
gccacagtgc cgtcggccat tttgagtata acaagtctt cgtgagaatc gtcaaacttg     83700
gtttttccat ttacaaacag cgtttgcggc ggatcgtgat tcgtgcgcag gctgagctcg    83760
acgttgagaa acatttagg gtcaaacaca aacaaatcca cagggcctag ttttttgttg     83820
tgtatgattg gtatcgtggg ttcgatgaca attccaaatt ttatatttaa aaacagctgc    83880
catccgttaa aagagaaagc ttgcttttg ggccagttgg gccaataata gtaatcgccc     83940
gcttgcacgc atttgttaat gtatccaggg tcggtgctct tgaaaaaatc ttcaaaatta    84000
atatacttt gtatgatgtc atagtgcttc ttcaaaatga aggttttac aaaaatgcaa      84060
aaatcgttac tttccaacac ccagtcgtgg ccgtctaatg tttgagctgc gtgtttctct    84120
gcaggttctt cggtgtcttc gcaagatgcg cccatgtcgt gtttcgcgca cggaccgtta    84180
aagttgtttc taattgtgtt taagaactgt tgaaagttgt tgacgtactc aaacaatcta    84240
cgtgttcctg ttcgcgtgtt tctaatgatt aaatgatttg catcttgcaa gttgttaatc    84300
tcgtacgttt tgtcttgagg cacgtttttc aaaaaaaatt gtaaatgtt gtcaatcatg     84360
ttggctatcg tgtttgtact tttcgtgtta atttatttaa taatttcgat caaaaatcac    84420
catccattct tacatagaat agaaacgcta atacaagatt tcaacaacac attgttgttt    84480
ggcgcgtatg tacagattta cgatttaagc acgcccgccc gcaccgaacg attgtttatt    84540
attgcgcccg aaaatgtggt gttgtataat tttaacaaaa cgctctatta ttacttggac    84600
tcggcgaacg tgttttgtcc caacgagttt agcgtgacca cgttcacgca atccactatt    84660
aaaacgatca acgagacggg aatatatgcc accgcatgca cgccggtcag cagcttgacg    84720
ctaattgaac attttgcaac attaaaaaat aacgtgcccg atcacacgct cgttctcgat    84780
gtggtcgacc aacagattca gttttcaata ctcgacatta tcaattattt gatttacaat    84840
ggctacgtgg atttgttggc cgaataacgc gtatatagac gcttgtacgt tcatcgtagt    84900
aatcatttta atacatttga ttgaactaaa catacatctg caatgggtga agagtcact     84960
aaattttgca atggaaaacg gcgataaaga agacagcgac aatgaataga gtttatattt    85020
ttatttaata aaatattgtt cgtaatccat aatgttttgt attatttcat tgtgataatg    85080
ttcccaatct tgcacggggg tggggcatcg tttgactttg acgtagaaat cgtacgcgta    85140
gttattagtt ggcagatcgt cgacaagtgt gatcgacttg aaaaagttta cattttatc     85200
gctcaaatat ttaattacaa tttttggcga tttgggtata ttgttgtcgg atcgatgatt    85260
```

```
gtgaatgtca aaaacaaatt tattttcaat gaaacgcttt tttaaattgt aatctacaat    85320
agcgttgtgt gaattttgaa ctaaatcaga gcgttcttct tgaacggtgg aaccttcgct    85380
gataatgata tcaaaatagc cttccaaatc gacgtctcgc atcgagtgtg ctacatgatc    85440
tctactgcca tacgaccaca agactaaaac gcaacccatc tcgtgcaact cctgcaagct    85500
gtcatacaca aacggatctc gaatctcaac ttgctcctct tcggttatga gagtgctgtc    85560
caaatcaaac acgaccacgt gcggaaatcc ccacgtcaaa gattcgcttt tgagagagac    85620
cactttgtag tgtggcaata gaaaccattc tttaagaaac gaatacattg gcggtttgtt    85680
gctaagcacg cacatgtggc ccaacactgg cgttttgaat gcgcgtttaa tattgtgcct    85740
gatgtcgcgc atgtcgtcgg cgggcgcttt gaatatttgc atacagtaat tgtaattgtt    85800
ttctatgatc ttgcacagct gcgggtcgtt gcaaaattga atattacat attcaaaaaa    85860 tttatacttt tcaaagccaa ggtatttgag gtcggcgtac tcgcttaaaa cgagaacatg    85920
tcgtttgatg atggcgtcgt taaggcgcaa acagatccat ttgctttgaa gcgaggaggc    85980
cataatgtac aaaaatggac cagttacgcc ttatttaaac tgtttaaaga gtttcgtata    86040
aacaaaaact actctaaact aatagatttc ttaacagaaa attttcccaa caacgtcaaa    86100
aacaaaacgt tcaacttttc gtctaccggc catctgtttc actcgttgca cgcgtacgtg    86160
cccagcgtca gtgatttggt gaaagagcgc aaacaaattc gattgcagac agaatatttg    86220
gcaaagctgt tcaacaacac aataaacgat ttcaaactgt acactgagct gtacgagttt    86280
atcgaacgga ccgaaggcgt cgattgctgt tgtccgtgcc agctattgca caagagtcta    86340
ctcaacacca aaaattacgt ggaaaactta aattgcaaac tgtttgacat aaagccgccc    86400
aaatttaaaa aggaaccttt tgacaacatt ctttacaagt attccctaaa ttacaaaagt    86460
ttgttgttga aaaaaaagga aaaacatacc agcactgggt gtacacgcaa aaagaaaatc    86520
aaacacaggc aaatattgaa tgataaagtt atttatttac aaaacagtaa taaaaataaa    86580
ctatttgagc ttagcgggct tagtttaaaa tcttgcagac atgattttgt aacagtcgaa    86640
agccaaacga gggcaggcga cgaaatcgct tcgttcattc gctactgtcg gctgtgtgga    86700
atgtctggtt gttaatagta gcgtgttctg taacttcggc gacctgtcga tgaacggctc    86760
ctggatcttc tgtatgtgcg gggtctaccc gggcggcgtc tgtaacccga gcttctgcgc    86820
ctgcgtgtcg aaccatatgt ggtaccggtt gaagaacggc gacggcgacg ataaaccatg    86880
tttaaattgt gtaatttatg tagctgtaat ttttacctta ttaatatttt ttacgctttg    86940
cattcgacga ctgaactccc aaatatatgt ttaactcgtc ttggtcgttt gaattttgt    87000 tgctgtgttt cctaatattt tccatcacct taaatatgtt attgtaatcc tcaatgttga    87060
acttgcaatt ggacacggca tagttttcca tagtcgtgta aaacatggta ttggctgcat    87120
tgtaatacat ccgactgagc gggtacggat ctatgtgttt gagcagcctg ttcaaaaact    87180
ctgcatcgtc gcaaaacgga atttcggtac cgctgttgat gtattgttgc ggctgcaaca    87240
tttgtatctt ttcgccgcgc tcgatcaaca attcttcaag agtggtgcgt tgtcgcgct    87300 gtaaagccac gttttgtaac agcactattt tcgcatatct cataatcgga ctgttgaaac    87360
agcgtgcaaa cgacgaccgc ataatatcga cggtcgtcaa gtcgattgtg gtcgaaggca    87420
tctccaacag agatcgcacg gcgtccaaca gcgtgtccgt ttgaacctgc gtcatttgcg    87480
gtctgcacgt gtagtcgtca aacgtggttt cgagcagttt gaacaacgaa tgatactttt    87540
ccgatcgcag caaaaatatc atggtcatga ccacgtcgct gattttgtat tctgtagaac    87600
```

```
tggtgctgtt caacgaatag tgatggatta gtttgcgagc agcatttctg tatcggcgca   87660
tgttgatcaa ctcttcggaa ggctgcgcgg gcgcggcggc gttggctcgc gcaaacaaat   87720
ttattacggg acgcggcgta ggctgcgcgg acgctggcgc ggcgacgacg tccgcgtttc   87780
ccgccgcgta ctgagacgct atggcagcgt tgttatttaa aattgtgttt tgcgatttgc   87840
gagccacgtg catcataaaa tttatcaaca cgtcggtgtt caactgcacg ctttgatgtt   87900
cgtcgcagag caaaggaaat agctggggcc atatcgccaa ttgcataggc tcgtctatttt  87960 ttaaccgcaa tttgtttatt tccaaataca acgcgatagc gctcatcgtg accgacgacg   88020
cacacttact ctgtaactat cacttggatc gtgttgtcgt aaacgcttcc caaaaagtct   88080
aacacgttga ccgtttcgat tctattcaac ttaattgtgg acgcgttggc ttgcatcggt   88140
tccaacagac tgcgcgctcc gacagattga gtagacaaaa ttttttaaact ttccgtctta  88200 tgggcgtaa tgtcgttgat taacaacgac gcagccgttt gagaggccgc agtgttgatg    88260
gtttgcaaca tgtcgacggc cgccatttgc gtttgcgccg aaggtcttgc tggcggcctg   88320
ttgcggcggt ttcttcgtgc ttgcgacatg ttgtcgtcag tgtccatatc ggtatcatt   88380 attgaagcaa tcatggttga gttcgataag cagagatatt tcgttgtcca attggtactt   88440
ggtaatgatg tgccttataa atgtttcggg cacaatcatt tctgtcatta gcacgttaca   88500
aatatctatt ttgatcaatt tcaatttatg aattaacaga ttaatgtttt cgtccgagta   88560
cttgctcatg atgaaacgac aaacgttgcg gagttccaac tccgctaccg gatacgcttt   88620
gttgggcaaa ctctctaaat agtgtctcaa ataaaagccg atcaatacgg tggacgctat   88680
tttgttaacc tttttcattt tagtattgcg gcccatttct atcatgaagt ttttaaacgg   88740
tagcaacagc ctgtctccgt tagcaacagt ggagcagccg ttgcattgcg cgctcaaaat   88800
actcaacacg cgctcgtgat cttcttggcg caatccgacg gttgcttttt tgcattcttt   88860
gacaaatggc acgcacatgt cgcgtttcgt gtacaaagaa tacgctttgt cgcaaatcaa   88920
gttatagaaa aattgcacaa atatctgcgt aatcaagttg ttttcgttaa taatgtcact   88980 ttcgttttttg taatcggttc gaagcaacac gtacaacatc agaggcatgc cgaacatggg   89040
tcttaaaaaa atgtcccaac cattttgcaa gcccgcgtcg agggtgctca gcgaggacgc   89100
caagtatttg catttgcact caaaacattg aattttgttt gcgggcttgc acgactgaca   89160
catgatcgca tccacgtcgg gtgccggcgt cggattgtaa tatttttgca agtattgcat   89220
aatggtccta aaatggggta cctgtttgat aaactcgtcg cgcaaaaata tcgaaaaat   89280 gttttttaca ttgtgtatgt tgtctgtgtt gttggcttga ttctcaaaac tactcttat    89340 ggaaacaata catttgttaa attctgtgaa aaagtaaga cctttactgt ccacgatcaa    89400
gctttggttg aaatattttg aaaataaaaa acacaacgaa tcgatttcat cttgtaacaa   89460
ttgcgcttca aaacacacgt tttcaaagcg gtcgtaaatg ttaaaccttaa actgtattg   89520 taatctgtaa gcgcacatgg tgcattcgat ataaccttat aatatgaacg attccaattc   89580
tctgttgatt acgcgtttgg cagcgcaaat actgtccaga acatgcaaa cggtggatgt    89640 gattgttgac gacaaaacgc tcagtttgga agaaaaaata gacacgttga ccagcatggt   89700
gttggctgta aatagcccgc cgcaatcgcc gccgcgggta acatccagcg acctggccgc   89760
atcgatcatt aaaaataaca gcaaaatggt gggcaacgat tttgaaatgc gatacaacgt   89820
gttgcgtatg gccgtcgttt ttgttaagca ttatcccaag tattacaacg agacgaccgc   89880
cggtttagtt gccgaaatag aaagtaatct gttgcaaat caaaattatg taaaccaagg    89940
caattatcag aacattgagg gttacgatag tttattaaat aaggcggaag agtgttatgt   90000
```

```
taaaattgat agactattta aagagagcat taaaaaaatc atggacgaca cggaagcgtt    90060
cgaaagagaa caggaagcgg agagattgag ggccgaacaa actgccgcaa acgctcttct    90120
ggagaggcga gcgcagacgt ccgcagacga tgtcgttaat cgtgccgacg ccaatattcc    90180
cacggcattt agcgatccgc ttccaggccc cagcgcgccg cggtacatgt acgaaagttc    90240
agagtcggac acgtacatgg aaaccgcccg acgtaccgcc gaacattaca ccgatcagga    90300
caaagactac aacgcggcgt acactgccga cgagtacaat tccctggtca agacggttct    90360
tttgcgttta atcgaaaagg cgctggccac tctaaaaaat cggttgcaca taacaactat    90420
tgatcaattg aaaaagttta gagattatct gaatagcgat gctgatgctg agaatttca    90480 aatatttta aaccaggaag attgtgtgat actgaaaaat tgtcaaatt tagcgtcaaa    90540 gtttttcaac gttcgttgcg tggccgacac gttagaggta atgttggaag cgcttcgcaa    90600
taatattgag ttggtgcagc ctgaaagcga tgccgtacgg cgaatagtca taaaaatgac    90660
gcaagaaatt aaagattcga gcacgccgct gtacaacatt gccatgtaca aaagcgatta    90720
tgacgccata aaaaacaaaa acattaaaac cttgttcgac ttgtacaacg acaggctgcc    90780
aatcaatttc ttggacacgt ccgcaaccag tccagttcgc aaaacttccg gcaagagatc    90840
tgcggaagac gacttgttgc cgactcgcag cagcaaacgt gccaatagac ccgaaattaa    90900
tgtaatatcg tcagaagacg agcaggaaga tgatgacgtt gaagatgtcg actacgaaaa    90960
agaaagtaaa cgcagaaaat tagaagacga agattttctc aaattaaaag cattagaatt    91020
tagcaaggac attgtcaacg aaaagcttca aaaaattatt gtggtcaccg acggtatgaa    91080
acggctgtac gaatactgca actgcaaaaa ttctttagag actttaccga gcgccgctaa    91140
ctatggcagc ttgctcaaaa ggctaaacct gtacaatctc gatcatatcg aaatgaatgt    91200
aaatttttac gagttgctgt ttccattgac actgtacaat gacaatgata acagtgacaa    91260
aacgctttct catcaattgg taaattacat atttttggcc agtaactatt ttccaaaactg    91320 cgctaaaaac ttcaactata tgcgcgaaac ttttaacgtg tttggcccgt ttaaacaaat    91380
cgactttatg gtcatgtttg ttataaaatt taacttttta tgcgacatgc gtaattttgc    91440
caaattaatc gacgagctgg tgcccaacaa acagcccaac atgagaattc acagcgtgtt    91500
ggtcatgcgg gataaaattg ttaaactagc ttttagtaat ttacaatttc aaaccttttc    91560
aaagaaagac aagtcgcgca acacaaaaca tttgcaaaga ctaataatgt tgatgaacgc    91620
aaactacaat gttatataat aaaaaattat aaaatatttt taattttat ttatattcag    91680 tacatttaca catattaaca tattgtttat acaaattctt ataatcatta tgatttaaat    91740
tgaattgttg tctaaacaaa ttaaacactt tattaaacaa taacttttcg ttgtaatttt    91800
ttactttgca catgttataa caaaaaatta aaatttcat catgtctgat tgtctatgg    91860 cgtcacagtt gcttttaatg taatcgcaag ttaaccactc aaaaggaccc ttttctattt    91920
ttaatttgtt taaatctttta taatcagact tcagtttgta aattagattt ccacatcgaa    91980
taataaatcc ttccagcggg ctttggggaa acattaaaga cttgaaattt aacctttcta    92040
caaaatcgtt gtacaaatat ttgtgacacg gaatagtatt aaaccccacg ttagtcaaca    92100
actcttgcgc ctccacaaag ggcacaaact ccccgccgta taattgaatt tcgtaagcgt    92160
agtatttcaa actctctttc tggtccacgt agttaattac gttaatgggt gtcgttttg    92220 cgtcgtcttt ccaacccatt aattcgccgt agacaataaa accgtcattg aaccgcgcct    92280
gaagcgatcg catgcacgtt tctaaatctt ttcgaatgcg gtaataattc ataaaattgc    92340
```

-continued

| | |
|---|---|
| cgtccggtct gtaagtgttt cttgacccgt acgtaatttt attttggttg caaatgattc | 92400 |
| tgaaattaca accgtccaac ttttcttgaa cataaatttc tttgtcggcc aacgtacctt | 92460 |
| ttttaccttg atctagatgc gacacagatg gataaatttg atacacaatt ttattctcat | 92520 |
| cttcgggcat tacgggtccg cgttcattta acgcgtacat gacaatgttg tggcgaatgt | 92580 |
| cggtgcgctc cggcggttct ggcacgtggt gcagtctgtc ctgcaattgt tgcttccatt | 92640 |
| gttgaaaata ttcggtccat tcttgttgat actcgccgcg ttgcatgagt tttacgtaca | 92700 |
| gttttaaaag tttgacattc tttacaaata acgttagagt ttcgtcgatt ttgtatcctc | 92760 |
| cattattttt gtttaaatcc aatacattta aatcgttcac taccagttga ttgttttat | 92820 |
| ccatcgtaat ttttatctca tcgcccacgt tgaacaacat gtttaaaatt ttggtggatt | 92880 |
| tcggcgcacg tttataatct aaataatatt caacgtacac gtaattgaac atgagctgca | 92940 |
| acaatccttt ggcattgttc aaaattttgt atctcatcaa agtataaata atttcacca | 93000 |
| tcgacaccgt catcaacttg gttacaaact cgtacaattg caagttttca ataccgtatt | 93060 |
| tgtctttaaa atcttcacgt ttactgaaca tgcttaattc gggagatttt ccagtcaaaa | 93120 |
| tgccaattaa tcccgtgtac aagtcaacgt atttgacatc gttgcccgat tcatcttttg | 93180 |
| catgtcgatt tttcaaaagc tctttattgt cgataaattt ttcaaaggtc tctcgatcac | 93240 |
| atttagtgta aatatggtag tcagtgtcgc tgctttcgac cgcgtatccc ttggcatggc | 93300 |
| tgcccgtatc aatgcaaatg tacaccatgt tagaatgtgc tgcttactgt gcctgtatca | 93360 |
| agccttatat acctcaaaat atttcacatt tttgcatcat cgtaaaatat acatgcatat | 93420 |
| aattgtgtac aaaatatgac tcattaatcg atcgtgcgtt acaagtagaa ttctactggt | 93480 |
| aaagcaagtt cggttgtgag ccgtgtgcaa acatgacat cataactaat catgtttata | 93540 |
| atcatgtgca aaatatgaca tcatccgacg attgtgtttt acaagtagaa ttctactcgt | 93600 |
| aaagcgagtt taaaaatttt gtgacgtcaa tgaaacaacg tgtaatattt tttacaatat | 93660 |
| ttaagtgaaa cattatgact tccaataatt ttgtggatgt ggatacgttt gcaagacaat | 93720 |
| tgattacaga taaatgtagt gctctaatca aagtgcggat ctgttgccgg caaacatttt | 93780 |
| agagattgta gagaaggcca gagacaagta ttttgagggc caactcaaaa aaactatgaa | 93840 |
| tacattaaaa aattattttt acgaaaaaat atatggacga ttcgatagat tataaagatt | 93900 |
| ttaacagacg catcctattg atagttttta aattcgcttt aaacaagagc acaatacttt | 93960 |
| ccatcgtaca aagagatcat cgagtggcca ttaaacgttt aaacaaaatt aaccccgatt | 94020 |
| taaagagttc tccgcgcaat gcttcagcat tacaatgaat gtttggaaaa tctagacaat | 94080 |
| ccagtcacgg acgaacatca tttgttgaca aaagagttgc tacaaaaata tttatcgaag | 94140 |
| cgtttgaata cagttacacc aacactaatg ccatcagcat ggacaaaaca gatgaatttg | 94200 |
| attttattaa accggcattg aaacctttgc cagatgcaag accgccatcg cttttggcca | 94260 |
| acgtgatgaa cgaacgtaaa agaaaattac aaaacaccaa ctcaacggca aaatgtttgc | 94320 |
| taccagcacc accgccacaa ttgcgtaaac ttgaaaaaaa gaatcattta ttgcctttgt | 94380 |
| tttctttgta attatattgt tgcatttcta tttctaatat catagttttc taataaagta | 94440 |
| gtttcatatt tttgttttg tacagtaatt gtttcttggt ttaacaagat cacaaccaat | 94500 |
| aacataaaga ataacacaat cataacaaaa attaaaaagc cgcatactac tagaacaaat | 94560 |
| tcttaatta gcgatcggtt tctatttaca aattggccga gctgatcgcc ttcagtcggc | 94620 |
| gagttgtggg cttggatgat gtcgacgata ttgttgccgg cgcgaccgcc tgtcgctctc | 94680 |
| gatataatgt cggccgccgt cggtttcatg atgtgcttaa ctacaaataa tagttgtact | 94740 |

```
tgacgggcgt caccgtgatg ccgctgctaa aacctccgtc cgttaagacg cgttgcgtta   94800
caaaattaat gtttgtccga ttagcgtagt cggaataatc aaacgtgttg ggcggactaa   94860
aatcgggcat gttgatgggc acaatgccgc tggagctgat agcaatgctg tcgttcttgc   94920
aaaacagccg aattttttg tagggctctg ctttattcgg cgcagacgac accatctggt    94980
caaagttgtt caattttatg attacgttgg gtaccaattg ataggggaaa attattttct   95040
ggaacatttt gacaaagtcc acaaccgttt ggctatagtc gggaatgccg agcaaagact   95100
gcgcctgttt aatgtatttg agactggagc ggtttactgt agcgcaattg gatggcacgt   95160
cgcccttcat aagccggcgc gttctctccc aattcaattt gttgtacaaa ttatcaatct   95220
cctcgtgcgg cagattgatt acatagcgcg cgggctgttt gcgatattga agatgcaaa   95280 aaatgcgttt caacgacaat atcttcacca tggtggacgt ttccagattg aaacataaca   95340
aaaagtcatt gctttccacc aattctttaa aatgagacag cggaatttca caagcgatcg   95400
gtcgcaaatt gcttttatt ggaggcggaa cgctttgacc gttgcggttt tttagtaacg    95460
cgctgcacgc agattgcatg tccgtttcgg gatacgtaaa ctcgatggga catttggggt   95520
tttcatggtg aacgatcata gtgttgcaat aaaacaagtt gttggtcagg agcacgctaa   95580
aaacacgcgt ttcgcccgca ccgatttcgg tgatgggtac caacgggttc cagtagacta   95640
tggtggcgga cgctgttttt tttggcgatc gactgtctat gttaacatca tgctcgtgcc   95700
tgtacactag cacagaattg aattttggaa attgttttt gtcaatgtac aaccggtcgt    95760
cgtctgtggg cacgtacacg atcaagtttt cgattaattt gttgcctacg tcgctttgcg   95820
gttccaccaa attgtgaggg aacgcaaaaa agcgatcgct aatacaaact gaatctgaa    95880 acgggcactc catcgtgatg tatatgtctt acttcattag actttagatt attttaattt    95940
gtgaactcgt accgtattca atagggtgtc gggcacgtaa ttgtaatggt aaaacagatc   96000
ctgttgaaca cgtgcgttgt tcactacgat tgaaatgcaa aaatacatca agtacataaa   96060
cactatgatt agaaaggtag cagacagaaa atatttcatc tttaaatctt atgctagttg   96120
aataaaatac atagtacttt tatacgttta tttatatttg ttttctttgt tataaccgta   96180
attgtaaaac ttgtgatcgt gctcgccagg cataattct ttgcacatca gcttgcgaat    96240
atatgtgaca tcttcgtaca ccgatttctt gatgttacca tcgtgaagcg ttgtcggctt   96300
gagaggtttg cggtcgttgt tgtaaaaatt ttgcaccgaa taattatcca tagtgcagca   96360
caggcaatgt cactgatgca tatgctttaa tttttattg cattcagtta ttatatgatt    96420
taataaacgt acacaatagc acgtttatcg gttaaagata actttcaata tataaaagtg   96480
tttgaattgc gagaccgtca acataacgtt tatcaacgcg atgactaaac gacaatttgc   96540
tttgctgttt gtgtggcacc acgacaacca atttgtttgc aacacggacg aatacccgtt   96600
ttggcacaac attgaatacc atgcacggcg ctataaatgc atcgttttgt actgtgtgga   96660
aaacgacgga tcgctacaac tgcccgtttg caaaaacata aatctcataa attataaaaa   96720
agcgtatcct cattattatg gaaactgtgt tgacagtata gtgaaacgtg ctggcaaaaa   96780
ttgattatat gaaagtaact gcaatgttaa accccacct gttggacgtc gcgtacaatt    96840
atttgctgtt gatggacatg gattgtgtgg tgcaaagcgt gcaatggaaa caattgtcaa   96900
ccgacacgta ttgttttgag ccgttttacg actctcaaat taaatggttg tacgcgccca   96960
aaagcggaca aagttttgat agttatcttg aaaactatgc aactctaatt cgagtcaaac   97020
aagtgcagca acatcgaaaa gaattaatac tgcattgtgt ggattttctt acaatgaaag   97080
```

```
caaatgacaa ttttatggtg ttcaaaaatt atattaacat gattataaaa gtgtatttgc   97140
aattttacaa ttacagattt cccatcaatt ttgaggacaa cacgatgaaa ccttgtgtaa   97200 atttaactttt tagacgtggc ggcagttgga aaactcaact gcaacccgta tgcaattatg   97260
tttacaaaag taaaaatatg ccaaaattta ttaaataaaa caattaatt taaacaagcg    97320 tttttattga caatactcac atttgatatt atttataatc aagaaatgat gtcatttgtt   97380
ttcaaaattg aactggcttt acgagtagaa tttacttgt aaaacacaat caagaaatga    97440 tgtcatttttt gtacgtgatt ataaacatgt ttaaacatgg tacattgaac ttaattttttg  97500 caagttgata aacatgatta atgtacgact catttgtttg tgcaagttga taaacgtgat    97560
taatatatga ctcatatgtt tgtgcaaaaa tgatgtcatc gtacaaactc gctttacgag   97620
tagaattcta cttgtaacgc atgatcaagg gatgatgtca tttgtttttt taaaattcaa    97680
ctcgctttac gagtagaatt ctacttgtaa aacacaatcg agggatgatg tcatttgtag   97740
aatgatgtca tttgtttttc aaaccgaac tcgctttacg agtagaattc tacttgtaac    97800
gcaagatcgg tggatgatgt cattttaaaa atgatgtcat cgtacaaact cgctttacga   97860
gtagaattct acgtgtaaaa cacgattaca gcacttcgta gttgtatcga aaattgttca   97920
atggctcttt gttaatgtcg taattgatta atatgtcgta caatttggcg gcgttgtgtt   97980
tgcacacgac cgttttttagt tcttgaaaca ttttttcgtg tatgtttagc atgttgtatt   98040
tcagagtgcg atgtgtaatg ctggtgacga gcatcaaaat gataaaatct aaagcggcta   98100 attttgtaatc ccgttcatac gctctgtaat cgccaacaac tctgtggcca gatcttttta   98160
gattttgaca ggcgttatgg tacgaattga taatatttac tatagtttct cttgttatcg   98220
gtttgtcgat taaactgtta acaaacatca cgttgcccaa gcgcgacggt ttagacaccg   98280
acttgttttt tgtctgttca aatttgtaca aattaaaaac gctcatagac tggtcgtcag   98340
gcagtgtgtc gttatacaaa caaaatggta aaacgtttaa ttcgacaaac gacgagcaca   98400
ttaaagtttg ttggctgtta acgtcctggg gatgtaaact gttattcata acgtaacaca   98460
cttcaatgtc ggaatgcttg ttttcaaatt tgtccttgtc tacagtttca atggtgattg   98520
agcgaggttt gagtttatt tctaaattca tttggatatt ttcaatatgg tataccaccg    98580
acacgttgtg agccagcgat ccttgattgg ttttaatcat attcaaaata ttcatgatat   98640 ggttgaaaaaa agagtctgtc aaaacgtttg tgtcgttgtt aaatatcgct ttccagggtt  98700
tactgttgcg tgactcaacg acggccgtgt aacataacaa gcgcgccagt tgcatgtgcg   98760
acaacttaat gttatcaatg tcggtgatgt ttggcaccag attttcattg ccgtcttcca   98820
gtagcgtgct cagttcggtc gagtagttat tcaacgatcg attgtgcgat tcaaacaagt   98880
ttactatcgc aggttgtaca tagtttttta tgtcgtcaaa ttgaattata tcgatcttgt   98940
ccttgttctc cagcataaac gacaaatttt ttaggtcgaa tttaatattt ggcgcgtttt   99000
cgttggactt tttgtaattt aacaacatcg ccaacagttt gtgtaactcg ccgttagctt   99060
gatctttgct aaacagttta ttggtagcgt aattcacgtt gtcgttcaaa aacagcaact   99120
cgttgatgat catttttttgt aaaagcgcgt acttgctcat gttgacagaa tctcttacat   99180
ttcagttgta aacgcgtctg tacaaattgg ccatgcgatt cggaatgcac acggggatcg   99240
tgcgagccag tgccgtttgg cgaaatagca tttttttcata gccgctcgaa caatcgcacg   99300
cgtccggcga aaattgcacc gtgttcaaat tcatattcaa ccggccgtcg ttgcatagat   99360
aaggcctcga tgttcccgta tcgtccacca agtctctgta cgtgctcacg catgtttgag   99420
acacgacaaa atctccgccg gcggagaaaa cgtgaaccaa gcccagtgcg ggatcgcatt   99480
```

```
ctatcaagtc cggagcctgc gcgtttacca aagcgtcgga ggcgttgcaa aagccatcct   99540
ggcaggtcaa ctcgtttgca gcgctggaga tcacgcagtt gtctctacac tgctgatccg   99600
tcacgcacgg taaccggttc aatgaacaat ctacgcctcg attgcgctga aacgtaaaat   99660
ttaacggcgg cgcttccaac tcgttaatgt gcatgtatgc atcttgcaaa ataaattttt   99720
gaacaaattt aaacgtgtac atgtacacga ttagtataat taccagtaga ataagtattt   99780
gccaaaagtt caacatgatc gtcttaactg agtgtgaaaa gcgtggtgtg acgcacgaaa   99840
tgactggttg cgcaaaaaat aaaccggggt ctatataact cggcgtcgac cgcgttcatt   99900
tttaccgtca tgcatctgac ggctaatgta ttgctcgttc ctaacgcgct caaaaagcgg   99960
gacgtgaaat acatttataa tacctatttg aaaaattaca gtgtaattga aggtgtgatg  100020
tgttgcaatg gcgattgttt ggccgtggtg gtgttggacc gaaatcagct gcaaaacacg  100080
gacatggaag tgttggagag tttagaatac actagtgaca acattgaact gttatgcgaa  100140
aaaatatgtg tgatagttga taattacgac aagtattacc aaaaaaattg tgtataaata  100200
aaataccaaa ttttattata tcattttgtt ttatttaata attaaagaat acaacgccac  100260
atctattcct agtacaacaa ataatttgat tattattttt gagtgcacat taaaaaataa  100320
caaacagtgt aaaaatacta cagaataata caatacataa atattatagt aaatagctgc  100380
aattttgata gcgtaattta tactttgata ttttttcaacg tacaacgtta aatgttgata  100440
cgcattattc acaaataaca aaattttttct aatatgccat ttgtccgcaa ttgttttttgc  100500 gatatcaaag ccttttttcaa acaattgaaa aattgcaaac aaaaccacgt acatgacgtt  100560
atacatagtg ttaaagttttt tacataacaa ttctataatg aagaaaattg ctaaacacgg  100620
catgagcgcg cacataatcg cgttggccgc aaatatctcg tacgtacaaa aatactcgga  100680
cattctccaa taagtaaaat gcattttgct attatactgt tgtttcttct agtgattatt  100740
gcaatagtgt acacgtatgt agacttgata gatgtgcacc atgaagaggt gcgttatcct  100800
attacggttt ttgacaacac acgcgcgccg cttattgaac cgccgtccga aatagtaatc  100860
gaaggcaatg cacacgaatg tcacaaaact ttgacgccgt gcttcacaca cggcgattgc  100920
gatctgtgcc gcgaaggatt agccaactgc cagttgtttg acgaagatac aatagtcaag  100980
atgcgtggag atgacggcca agaacacgag acgcttattc gagcgggaga agcgtactgc  101040 ttggcttttgg atcgagaacg cgcccgatcg tgtaaccccca acacgggtgt gtggttgttg  101100
gccgaaactg aaactggttt cgctcttttg tgcaactgct tacggcccgg acttgttacg  101160
cagctcaaca tgtacgaaga ctgcaacgtg cccgtgggct gcgcgcctca cggccgtatc  101220
gacaatatca acagcgcttc gatccggtgc gtgtgcgacg acgggtacgt gagcgactat  101280
aacgccgaca ccgaaactcc gtattgccgt ccgcgcaccg tgcgcgacgt aatgtacgac  101340
gagagttttt ttccgcgggc gccatgcgca gacggccaag ttcgtctgga tcatccggcg  101400
ctcaatgatt tttaccgcag acactttaga ctcgaagaca tttgcgtgat cgacccttgc  101460
tcggtggacc cgattagcgg gcaacgcaca tcgggacgct tatttcacca accaaccgta  101520
aatggtgtgg gaatcaacgg atgcaattgt ccggccgatg acgggttact gcccgtgttt  101580
aatcgacaca ccgccgacac gggcatggtt agacaaagcg accgcaccgt cgcgaacgct  101640
tgcttgcagc cgtttaacgt gcacatgtta tcgttgcgtc atgtggatta caaatttttc  101700
tggggccgca gcgaccacac cgagtttgcc gacgcggaca tggtgtttca agcgaatgtc  101760
aaccaactca gtcacgaacg gtatcgagcg atttttgtact cgttgctcga gtcgcacccg  101820
```

```
gacgtaacag aaatcgtaac agtcaacatg ggtgtcatga aaatttccgt gtcatacgat   101880
accacattga aaaatatact attaccatct tctgttttta ggctatttag atttaaagaa   101940
agtggcactg ctcagccggt atgcttcttt ccaggcgtag gacggtgcat aaccgtcaat   102000
tccgattcgt gcatcaggcg acacgctggt ggtcaagtgt ggaccgcaga aacgttcacc   102060
aactcgtggt gtgtactgag tcgtgaaggt acgcatataa aagtttggag tcgcgcgtca   102120
cgatatccac gcggagacgc gcctgcagcg ttaagattgc gcggcttctt tctgaacaac   102180
gatcgcgaac gaaacacaat aagagcggtc actacaggcg acatgaccca agggcaacaa   102240
atagacgcat taacccaaat acttgaaact taccccaact actctgtata acaacatgag   102300
cattttaaaa gttgtagaag cgtgcaattt ggcacacact tttttaaaat tgggttattt   102360
atttagggcc aagacttgtt tggatatcgc tttagataat ttggaactat tgcgtcgaaa   102420
gactaacata aaagaagtgg cagtcatgtt aaacaagaaa actacagagt gtttgcaatt   102480
gaaacgaaaa atagataaaa aaattgcaca acgtgtttta ataaaaattt acactatcaa   102540
atgatgacat cataacgggt tcaatattct gtgtgcaaaa ataaatgaca tcatatttca   102600
aacttgtttt acgcgtaaaa ttctactggt aaaacaagtt tgagatatga tgtcatcatc   102660
acaaataata gtatgtaata aaataaacat atttgtgtgt aaatataatt tattacaaat   102720
aaattttaca ttgaatcaat ctgtcttcgt gtttgttgta aggtcttcga atcttgtgtt   102780
tcagcccctc gggatggtca aaatgcgccg tagtaattgt taatggatct ttcaacgatt   102840
ttttgcccat ggcgagtgtg acaaacgcgg ccacgacaaa cagcaggata atcagtttca   102900
tggtgttcta tattcgacaa tatatgggtc gcttctaaat caccttgtcc ccaaaagcct   102960
cttttatagt tttttagaac acgttgtgta ttccaacagt aattgttcca tctctttcaa   103020
cagccattca gcatccggtc gttgactgta atcatgctga attaatttac aaacaatttc   103080
ggtcaattta ggatggcctt gggataaact tgccggcatt tgctgtacat tgtttctaaa   103140
gttagttagc gtagtttcgc gttccaaagc agtcttgaag ggcattatca attcgaataa   103200
aacaatgccc aaactataca tgtcattttt gggggtgtac acttttttga tttgttctgg   103260
tgcagcgtac aaagttatat tttgagggtt gttttttgata aacgttttgt atagactgcc   103320
aaacatgccg cccacataca aatcaaagtc gggcccagtc atgaaaatat cttcgggatt   103380
aatattgtgg tgcacgatat ttacggaatg aatcgctttc acggcgctca ccaaatcaac   103440
aaacttgcta atataaaagc caaaatccgc cggaacttta atgttggtct ttgcaaaagt   103500
ttgcaaattg cgttgtttca aatagtcgct caacatgtac tcgtttagag gcgacgcaat   103560
atatatgcgg tgctgccgcg gattcaaata aaccaattgt tcgggtttca tggtatacag   103620
ttaagtgtta acgcgtcact aaattcagac acgagcgcac gccctatata catcaatttt   103680
atcgcacaag atgcttaacg cgatctgttt ataaactaaa acgcactgca ataaatttta   103740
gcaagcattt gtatttaatc aatcgaaccg tgcactgata taagaattaa aaatgggttt   103800
gtttgcgtgt tgcacaaaat acacaaggct gtcgaccgac acaaaaatga gtttcccta   103860 tgttgcgttg tcgtacatca acgtgacgct gtgcacctac accgccatgt tggtgggata   103920
catggtaaca ttcaatgact ccagcgaatt gaaatattta caatactggt tgctgttgtc   103980
gtttttgatg tccgtggtgc taaacgctcc gactctgtgg acgatgctca aaaccacaga   104040
agcccatgaa gtaatttacg aaatgaagct gttccacgcc atgtacttta gtaacgtgct   104100
gttgaattat gtggtgtttt tggacaatca aatgggtaca aatttgtttt ttgttaacaa   104160
tttaattcac tgttgtgtac ttttatgat atttgttgaa ttgcttatcc tgttgggcca   104220
```

```
cacaatgggc acgtacacgg attatcaata tgtcaaatcg tgttatatgg ttatattgtt   104280
tgtttcagtt atgagtgtta ctattgttat gggtttagag tgtttgaaaa cgaaactaat   104340
tgataacagt ttgatgttta acgcgtttgt gtgcgctttg tacattgtga ttgcaataat   104400
gtggtcttta aaaataatt tgactagtta ttacgtttca aatttacaaa gtattcaagt    104460
tgttccgttt tcatacaacg atccgccgcc accgttctct aacattgtaa tggatgacat   104520
aaaaaataaa aataatttta taaaaatgtt tttattcttt tcacaattct gtaaattcta   104580
aacaaaaaat ataaatacaa acttattatg ttgtcgtcta aataaacatc aatttgtaaa   104640
tctggacacc tattcatatc attgatatta cagtctacta tacaacaatt aaaactaacc   104700
aaattatctt tacaacaatt aaagcaatta aaacaattta ataatcttc attgtcgtcg    104760
tataagttta tttgcactgt agacggtgtt acacagcgat ccattcgacg ttcgtgttcg   104820
atcaactttc tcgccaactt gtaccataaa aattgtttgg acaaaagtt ttccaacaat    104880
ggtaacggcc aattcaacgt gacgatgcgc acgtcctcgg gtatgcattt gttaaaaaac   104940
acacagctcg ctttaccaaa cgaaagcaaa ggtactaaat atggcgccat tggctgattt   105000
gttattccaa gataattaca aataaactga tccgtcgtgg ggtgataact ggcaggtgtc   105060
agctttaaat aatcttcaac gttgttgtcg cgcaaaagtc tgcattttac acgcgttgtt   105120
aatcccacga cttttgcatg taaaatcgga tccaaatact gcagaatcgt gtctataatt   105180
tctaatggta aacgtatgcg ttttgctcgt gggcgctttg taacgctcga catcctaata   105240
acaactaaca caaaactaaa atgatactca atatattgct tttacagttc atctttaggt   105300
ttaaactgtg cgtttatcgc gttgagcaag tcgccgttat cggcatcaat ctcccaagca   105360
aacaggccgc ccaatttatt tcggtcgaca tatttaactt ttcctaacac agagtcgacg   105420
ctgtcaaacg aaatcaaatc acctttactt ttatcgaaaa cgtacgacgc ttgagcggcg   105480
ctgtcaaacg tgtacacata attgttgaga tctttttgaa tttgacgata atctacaaca   105540
ccgtcctccc acgtgcccga ccccggcccg ttgccagtgc cggaaaaata gttgtcattc   105600
gtataatttg ttacgccggt ccagccgcgg ccgtacatgg cgacgcccac aattattttg   105660
ttgggatcga cgccttgttt cagtaacgca tcgacagcgt agtgtgtagt gtatagctct   105720
tccgagttcc aacttggcgc gtagactgtt gtttggtagc ccaaatccgt gtttgaccaa   105780
gccccttaa atcgtaact catgagaaat atttgccta atgactttg cgcttcggcg      105840
tagtttacca cggcaatctt gtcgtaaccc gcgcttatag cgcttgttaa ttcgtaaacc   105900
ctgccggttt gcgcttcgag gtcgtctagc attgcgcgca gctcctccaa caacaaaatg   105960
tatgttttgg cgtcaccgtc cgcatcgccc aacgacgggt tagcccttt gccgcccgga    106020
aactcccaat cgatgtctac accgtcaaag aatttccaca cttgcagaaa ttccttaacc   106080
gaatctacaa aaacgtttct tttttcaaca tcgtgcataa aataaaatgg gtctgataga   106140
gtccagcctc ctattgaagg aagaattttt aaatgggggt ttgctaattt tgccgccatc   106200
aactgtccaa aattgccttt atacggctcg ttccaagcgg acacacctt tgggggtttt    106260
tgtacggcgg cccacggatc gtgaatggca actttgaaat cttcgcgtcc cttgcacgat   106320
ctttgcaaag attcaaagct tccgggtatc gttttgaggg cgtcgtttat tccatcgccg   106380
ccgcagatgg gtatgaaacc atacaacaag tgtgataaat ttggcaaggg aactttgtct   106440
acgggaaagt tgcgcccgta cacaccccac tcaacaaagt acgcagcgac aattttatcc   106500
tctctcctgc caggtttgtt gttttccagc catgtgtatt cgagcggtgc cagatggccg   106560
```

```
ccgtcggtgt ctgcgacttt gaccaacacg ggatcgctca cggaacagcc gtcctcattg    106620
caaagtttga cacgcatgtt aaattgcccg ctcacaagaa ctttaatggt agcccttta    106680 ctttcggcgt cgccttttcca tacctgctgc tcgtcaaaca acacgtacgc tatgtcgcca    106740
atgtcgccgt tccagacgtt ccaactgact tgaacgtcga cttgttcttt aggctttatt    106800
aaattttcgt aagcggtggc ctcgtaattt atttctacga gcgcataatt gcgatcggcc    106860
caatcgatca ccggcgtgcc gggaatcgcg ttagaaacgg cgaccaacca caaaacgttt    106920
aacaatttgt acaacatttt aatttatctt aattttaagt tgtaattatt ttatgtaaaa    106980
aaatgaacaa aatttttgttt tatttgtttg tgtacggcgt tgtaaacagc gcggcgtacg    107040
accttttgaa agcgcctaat tattttgaag aatttgttca tcgattcaac aaagattatg    107100
gtagcgaagt tgaaaaattg cgaagattca aaattttcca acacaattta aatgaaatta    107160
ttaataaaaa ccaaaacgat tcggccaaat atgaaataaa caaattctcg gatttgtcca    107220
aagacgaaac tatcgcaaaa tacacaggtt tgtctttgcc tattcagact caaaatttt    107280 gcaaagtaat agtcctagac cagccaccgg gcaagggcc ccttgaattc gactggcgtc    107340
gtctcaacaa agtcactagc gtaaaaaatc agggcatgtg tggcgcctgc tgggcgtttg    107400
ccactctggc tagtttggaa agtcaatttg caatcaaaca taaccagttg attaatctgt    107460
cggagcagca aatgatcgat tgtgattttg tcgacgctgg ctgtaacgg ggcttgttgc    107520 acacagcgtt cgaagccatc attaaaatgg gcggcgtaca gctggaaagc gactatccat    107580
acgaagcaga caataacaat tgccgtatga actccaataa gtttctagtt caagtaaaag    107640
attgttatag atacattacc gtgtacgagg aaaaacttaa agatttgtta cgccttgtcg    107700
gccctattcc tatggccata gacgctgccg acattgttaa ctataaacag ggtattataa    107760 aatatgttt caacagcggt ctaaaccatg cggttctttt agtgggtat ggtgttgaaa    107820 acaacattcc atattggacc tttaaaaaca cttggggcac ggattgggga gaggacggat    107880
ttttcagggt acaacaaaac ataaacgcct gtggtatgag aaacgaactt gcgtctactg    107940
cagtcattta ttaatctcaa cacactcgct attttggaaca taatcatatc gtctcagtag    108000
ctcaaggtag agcgtagcgc tctggatcgt atagatcttg ctaaggttgt gagttcaagt    108060
ctcgcctgag atattaaaaa actttgtaat tttaaaaatt ttatttata atatacaatt    108120 aaaaactata caattttta ttattacatt aataatgata caattttat tattacatt    108180 aatattgtct attacggttt ctaatcatac agtacaaaaa taaaatcaca attaatataa    108240
ttacaaagtt aactcatga ccaaacatga acgaagtcaa tttagcggcc aattcgcctt    108300
cagccatgga agtgatgtcg ctcagactgg tgccgacgcc gccaaacttg tgttctcca    108360 tggtggttat gaggttgctt ttttgttggg caataaacga ccagccgctg gcatctttcc    108420
aactgtcgtg ataggtcgtg ttgccgatgg tcgggatcca aaactcgacg tcgtcgtcaa    108480
ttgctagttc cttgtagttg ctaaaatcta tgcattgcga cgagtccgtg ttggccacccc   108540 aacgcccttc tttgtagatg ctgttgttgt agcaattact ggtgtgtgcc ggcggattgg    108600
tgcacggcat cagcaaaaac gtgtcgtccg acaaaaatgt tgaagaaaca gagttgttca    108660
tgagattgcc aatcaaacgc tcgtccacct tggccacgga gactatcagg tcgtgcagca    108720
tattgtttag cttgttgatg tgcgcatgca tcagctcaat gttcattttc agcaaatcgt    108780
tttcgtacat cagctcctct tgaatatgca tcaggtcgcc tttggtggca gtgtctccct    108840
ctgtgtactt ggctctaacg ttgtggcgcc aagtgggcgg ccgcttcttg actcggtgct    108900
cgactttgcg tttaatgcat ctgttaaact tgcagttcca cgtgttttta gaaagatcat    108960
```

```
atatatcatt gtcaatcaaa cagtgttcgc gtgtcaccga ctcggggtta tttttgtcat    109020
ctttaatgag cagacacgca gcttttattt ggcgcgtggt gaacgtagac ttttgtttga    109080
gaatcatact cacgccgtct cgatgaagca cagtgtccac ggtcacgttg atggggttgc    109140
cctcagcgtc caaaatgtat acctggcact cgtccgtgtc gtcctggcac tcgagcctgc    109200
tgtacatttt cgaagtggaa atgccgcatc gccacgattt gttgcacgtg tggtgcgcaa    109260
agtgattgtt attctgccgc ttcaccaact ctttgccttt gacccactgg ccgcggccct    109320
cgttgtcgcg aaaacagtcg tcgctgtcac tgccccaacg gtcgatcagc tcttcgccca    109380
cctcgcactg ctgcctgatg ctccacataa gcaaatcctc tttgcccaca ttcagcgttt    109440
tcatggtttc ttcgacgcgt gtgttgggat ccagcgagcc gccgttgtac gcatacgcct    109500
ggtagtaccc cttgtagccg ataatcacgt tttcgttgta gtccgtctcc acgatggtga    109560
tttccacgtc cttttgcagc gtttccttgg gcggggtaat gtccaagttt ttaatcttgt    109620
acggacccgt cttcatttgc gcgttgcagt gctccgccgc aaaggcagaa tgcgccgccg    109680
ccgccaaaag cacatataaa acaatagcgc ttaccatctt gcttgtgtgt tccttattga    109740
agccttggtg tgactgattt actagtagca ttgaggcatc ttatataccc gaccgttatc    109800
tggcctacgt gacacaaggc acgttgttag attaataatc ttatctttttt atcttaattg    109860 ataagattat ttttatctgg ctgttataaa aacgggatca tgaacacgga cgctcagtcg    109920
acatcgaaca cgcgcaactt catgtactct cccgacagca gtctggaggt ggtcatcatt    109980
accaattcgg acggcgatca cgatggctat ctggaactaa ccgccgccgc caaagtcatg    110040
tcaccttttc ttagcaacgg cagttcggcc gtgtggacca acgcggcgcc ctcgcacaaa    110100
ttgattaaaa acaataaaaa ttatattcat gtgtttggtt tatttaaata tctgtcaaat    110160
tacaatttaa ataataaaaa gcgtcctaaa gagtattaca cccttaaatc gattattagc    110220
gacttgctta tgggcgctca aggcaaagta tttgatccgc tttgcgaagt aaaaacgcaa    110280
ctgtgtgcga ttcaggagag tctcaacgag gctatttcga ttttgaacgt tcatagcaac    110340
gatgcggccg ccaacccgcc tgcgccagac attaacaagt tgcaagaact gatcaagat     110400 ttgcagtctg aatacaataa aaaaattacc tttaccactg atacaatttt ggagaattta     110460
aaaaatataa aggatttaat gtgcctgaat aaataataat aagggttttg tacgatttca    110520
acaatgaact tttgggccac gtttagcatt tgtctggtgg gttatttggt gtacgcggga    110580
cacttgaata acgagctaca agaaataaaa tcaatattag tggtcatgta cgaatctatg    110640
gaaaagcatt tttccaatgt ggtagacgaa attgattctc ttaaaacgga cacgtttatg    110700
atgttgagca acttgcaaaa taacacgatt cgaacgtggg acgcagttgt aaaaaatggc    110760
aaaaaaatat ccaatctcga cgaaaaaatt aacgtgttat taacaaaaaa cggggtagtt    110820
aacaacgtgc taaacgttca ataaacgctt atcactaagt taatatacta aaaatcacat    110880
agtcactaca atatttcaaa atatgaagcc gacgaataac gttatgttcg acgacgcgtc    110940
ggtcctttgg atcgacacgg actacatttta tcaaaattta aaaatgcctt tgcaggcgtt    111000
tcaacaactt ttgttcacca ttccatctaa acatagaaaa atgatcaacg atgcgggcgg    111060
atcgtgtcat aacacggtca aatacatggt ggacatttac ggagcggccg ttctggtttt    111120
gcgaacgcct tgctcgttcg ccgaccagtt gttgagcaca tttattgcaa acaattattt    111180
gtgctacttt taccgtcgtc gccgatcacg atcacgctca cgatcacgct cgcgatcacg    111240
ttctcctcat tgcagacctc gttcgcgctc tcctcattgc agacctcgtt cgcgatctcg    111300
```

-continued

```
gtcccggtct agatcgcggt cacgttcatc gtctcccagg cgagggcgtc gacaaatatt  111360
cgacgcgctg gaaaagattc gtcatcaaaa cgacatgttg atgagcaacg tcaaccaaat  111420
aaatctcaac caaactaatc aattttttaga attgtccaac atgatgacgg gcgtgcgcaa  111480
tcaaaacgtg cagctcctcg cggcgttgga aaccgctaaa gatgttattt tgaccagatt  111540
aaacacattg cttgccgaga ttacagactc gttacccgac ttgacgtcca tgttagataa  111600
attagctgaa caattgttgg acgccatcaa cacggtgcag caaacctgcg caacgagttg  111660
aacaacacca actctatttt gaccaattta gcgtcaagcg tcacaaacat caacggtacg  111720
ctcaacaatt tgctagccgc tatcgaaaac ttagtaggcg gcggcggcgg tggcaatttt  111780
aacgaagccg acagacaaaa actggacctc gtgtacactt tggttaacga aatcaaaaat  111840
atactcacgg gaacgctgac aaaaaaataa gcatgtccga caaaacacca acaaaaaagg  111900
gtggcagcca tgccatgacg ttgcgagagc gcggcgtaac aaaaccccca aaaaagtctg  111960
aaaagttgca gcaatacaag aaagccatcc tgccgagca acgctgcgc accacagcag  112020 atgtttcttc tttgcagaac cccggggaga gtgccgtttt tcaagagttg gaaagattag  112080
agaatgcagt tgtagtatta gaaaatgaac aaaaacgatt gtatcccata ttagatacgc  112140
ctcttgataa ttttattgtc gcattcgtga atccgacgta tcccatggcc tattttgtca  112200
ataccgatta caaattaaaa ctagaatgtg ccagaatcag aagcgattta ctttacaaaa  112260
acaaaaacga agtcgctatc aacaggccta agatatcgtc ttttaaattg caattgaaca  112320
acgtaatttt agacactata gaaactattg aatacgattt acaaaataaa gttctcacaa  112380
ttactgcacc tgttcaagat caagaactaa gaaaatccat tatttatttt aatattttaa  112440
atagtgacag ttgggaagta ccaaagtata tgaaaaaatt gtttgatgaa atgcaattgg  112500
aacctcccgt cattttacca ttaggtcttt agatttggta aggctagcac gtcgacatca  112560
tgtttgcgtc gttgacctca gagcaaaagc tgttattaaa aaaatataaa tttaacaatt  112620
atgtgaaaac gatcgagttg agtcaagcgc agttggctca ttggcgttca aacaaagata  112680
ttcagccaaa acctttggat cgtgcagaaa ttttacgtgt cgaaaaggcc accaggggac  112740
aaagcaaaaa tgagctgtgg acgctattgc gtttggatcg caacacagcg tctgcatcgt  112800
ccaactcgtc cggcaacatg ttacaacgac cagcgctttt gtttggaaac gcgcaagaaa  112860
gtcacgtcaa agaaaccaac ggcatcatgt tagaccacat gcgcgaaatc atagaaagta  112920
aaattatgag cgcggtcgtt gaaacggttt tggattgcgg catgttcttt agccccttgg  112980
gtttgcacgc cgcttcgccc gatgcgtatt tttctctcgc cgacggaacg tggatcccag  113040
tggaaataaa atgtccgtac aattaccgag acacgaccgt ggagcagatg cgtgtcgagt  113100
tggggaacgg caatcgcaag tatcgcgtga acacaccgc gctgttggtt aacaagaaag  113160
gcacgcccca gttcgaaatg gtcaaaacgg atgcgcatta caagcaaatg caacggcaga  113220
tgtatgtgat gaacgcgcct atgggctttt acgtggtcaa attcaaacaa aatttggtgg  113280
tggtttctgt gccgcgcgac gaaacgttct gcaacaaaga actgtctacg gaaaacaacg  113340
cgtacgtggc gtttgccgtg gaaaactcca actgcgcgcg ctaccaatgc gccgacaagc  113400
gacggctttc attcaaaacg cacagctgca atcacaacta gtggtcaa gaatcgatg  113460 ctatggtcga tcgcggaata tatttagatt atggacattt aaaatgtgcg tactgtgatt  113520
ttagctcaga cagtcgggaa acgtgcgatt ctgttttaaa acgcgagcac accaactgca  113580
aaagttttaa cttgaaacat aaaaactttg acaatcctac atactttgat tatgttaaaa  113640
gattgcaaag tttgctaaag agtcaccact ttagaaacga cgctaaaaca cttgcctatt  113700
```

```
ttggttacta tttaactcat acaggaaccc tgaagacctt ttgctgcgga tcgcaaaact  113760
cgtcgcccac caaacacgat catttaaacg actgtgtata ttatttggaa ataaaataaa  113820
cctttatatt atatataatt cttttattta tacatttgtt tatacaattt tatttacgac  113880
aaatattgac tcgttgttca gaaagtttaa taagcttgtc aatttcttcg gcttgcaaag  113940
ggctgccaac gcgttcgttt tgaatgcgcg taatccggtt tacggtattg ttggcgcgaa  114000
caataaactc ctcaactggc aaattaacaa ttttgtttgc gtactcattg tgcactgcgg  114060
ccaggttttg tagaatgttt tcgggaaaaa tggcaattct attaaatttg acatgttttt  114120
gattgtatac atagttttga tattcttcca gcgtaggata tttgtttaaa ctcttgacgc  114180
attcaatgta caatttgtgc agtgacaaaa ttctgttaaa atccaaacga gaacatttct  114240
caaaagttat ttcttgaccg ttgaaatgta cactttgcaa ttgtttcaat aaactgtcgt  114300
aaaaagtttt tccttcttca agcacaaacg cggggcgcat cgtgttatct acaacgctta  114360
tgtacttgtc aaaatcttca attatatgat agaaatacaa atatctctcc gcgtttatgg  114420
acgtgtcgtt taaaacatgt tcgtcaacaa ctccgttatg atttactttc aaaaatttca  114480
aatcttgcaa agcgtccgcg ttggtcaact tgttgataat aaatttgtct ttgcattcaa  114540
acgctctgtt tgcaatccac tccacagcgt ccaaaacgga catgcgttta aacatgttga  114600
tacgttttag acaatacgct cgttttttta ccgcctcaac gttcacgtcc gtgtagtcgc  114660
accattgcag gatttgcaac atgtcctcgg caaaatgcgc gaactgccgc agcttttcct  114720
ttccaaaatg ttgattgtcg tgtttaaaaa gcaacgttga aatttccgag acataccaca  114780
aagccgtggg caattttact ttgatcagcg gctccatagc caggttgctg aacccgatca  114840
tgcattccgt gttgttaatg cggtaaatga catagcgttt aaagtagtcc tttacattat  114900
cgtcaatgta ttctgcgtcg tttatgtgct tgtacagcaa atagtacata aggcccgcgt  114960
taaacgcgac cttttttagcg tcaaaatacg tgcacgccaa cacgtaatcg ttgtattcgt  115020
cgaattgctc gttgggcact atggcgcccg taaaagggcg tctgctgcgc ggtgacaaac  115080
gcgttccatg ctgaatcaac tgcttcaaac tttccaaatt ataacaatat tcaattgaat  115140
ttttaatctc tttatttttgg ctccataaaa gaggaaactc gagtcggctt ttaaacttgg  115200
tcaaactgcc ctgaattgtt tcaaacaagt tgtaatgtgt taacaatatg gccggcacac  115260
cgctatcgtt ggctaaaata caatcgggga atcgaatatt ttctacgttg ctgtaatcgt  115320
acgcttcgtc gtcgtcgttg gcaacaacat cgtcggtttc ggcgttaacg ctcgctaact  115380
tgttctgata gtgtaaattt ttcattacat caaaagcgta tgacttgttg cgattgtgca  115440
aataatttat ggccgtgcta atggtgctgt cgataatttt atcaaaattg agaacatcgg  115500
cgttatacaa cgttttataa aattctgttg acttgaacgt gtttacaaac tcattttat  115560 ttttaatctg gtcaaaattc atactagaat tgttagtttg tttgatttcg ctgaatagcc  115620
gctggcggag acgcttcagc ttgtccacct cgtttaacac gttggcgtcc gtcggcatgg  115680
aattgataaa tttgaaccga acaaaagaca gcagttcatc ttttttcgat ataaaatttt  115740
cggttgtaat gatatcgtag ttaaattctt tggttaaatt gacccattcg accatttcat  115800
cgttgcgata aatcttgcag tccgagttgt tgacaaacgc cgaggcaacg gacaaatcaa  115860
tctgttccgt gttattattg atggcataaa acacaatgcg ttcgaaacta acggtttttt  115920
cgtttagcaa attttttgcaa acgtttgcct catttttggaa aatttggccg tcggtcacca  115980
tgtacaaaag tttcaacttg ccgtcgagca agtttatatt cttgtgaatc cactttatga  116040
```

```
attcgctggg cctggtgtca gtaccctcgc cattgcggcg caaataacga ctcttgacgt   116100
ctccgatttc ttttggcgg caataagcac tccaatgcaa atacaaaact ttgtcgcaac    116160
tactgatgtt ttcgatttca ttctgaaatt gttctaaagt ttgtaacgcg ttcttgttaa   116220
agtaatagtc cgagtttgtc gacaaggaat cgtcggtggc gtacacgtag tagttaatca   116280
tcttgttgat tgatatttaa ttttggcgac ggattttat atacacgagc ggagcggtca    116340
cgttctgtaa catgagtgat cgtgtgtgtg ttatctctgg cagcgcgata gtggtcgcga   116400
aaattacacg cgcgtcgtaa cgtgaacgtt tatattataa atattcaacg ttgcttgtat   116460
taagtgagca tttgagcttt accattgcaa aatgtgtgta atttttccgg tagaaatcga   116520
cgtgtcccag acgattattc gagattgtca ggtggacaaa caaaccagag agttggtgta   116580
cattaacaag attatgaaca cgcaattgac aaaacccgtt ctcatgatgt ttaacatttc   116640
gggtcctata cgaagcgtta cgcgcaagaa caacaatttg cgcgacagaa taaaatcaaa   116700
agtcgatgaa caatttgatc aactagaacg cgattacagc gatcaaatgg atggattcca   116760
cgatagcatc aagtatttta aagatgaaca ctattcggta agttgccaaa atggcagcgt   116820
gttgaaaagc aagtttgcta aaattttaaa gagtcatgat tataccgata aaaagtctat   116880
tgaagcttac gagaaatact gtttgcccaa attggtcgac gaacgcaacg actactacgt   116940
ggcggtatgc gtgttgaagc cgggatttga gaacggcagc aaccaagtgc tatctttcga   117000
gtacaacccg attggtaaca aagttattgt gccgtttgct cacgaaatta cgacacgggg   117060
actttacgag tacgacgtcg tagcttacgt ggacagtgtg cagtttgatg gcgaacaatt   117120
tgaagagttt gtgcagagtt taatattgcc gtcgtcgttc aaaaattcgg aaaaggtttt   117180
atattacaac gaagcgtcga aaaacaaaag catgatctac aaggctttag agtttactac   117240
agaatcgagc tggggcaaat ccgaaaagta taattggaaa attttttgta acggttttat   117300
ttatgataaa aaatcaaaag tgttgtatgt taaattgcac aatgtaacta gtgcactcaa   117360
caaaaatgta atattaaaca caattaaata atgttaaaa tttattgcct aatattattt     117420
tgtcattgct tgtcatttat taatttggat gatgtcattt gttttttaaaa ttgaactggc  117480
tttacgagta gaattctacg cgtaaaaacac aatcaagtat gagtcataat ctgatgtcat  117540
gttttgtaca cggctcataa ccgaactggc tttacgagta gaattctact tgtaatgcac   117600
gatcagtgga tgatgtcatt tgttttttcaa atcgagatga tgtcatgttt tgcacacggc  117660
tcataaactc gctttacgag tagaattcta cgtgtaacgc acgatcgatt gatgagtcat   117720
ttgttttgca atatgatatc atacaatatg actcatttgt ttttcaaaac cgaacttgat   117780
ttacgggtag aattctactt gtaaagcaca atcaaaaaga tgatgtcatt tgttttttcaa  117840
aactgaactc gctttacgag tagaattcta cgtgtaaaac acaatcaaga aatgatgtca   117900
tttgttataa aaataaaagc tgatgtcatg ttttgcacat ggctcataac taaactcgct   117960
ttacgggtag aattctacgc gtaaaacatg attgataatt aaataattca tttgcaagct   118020
atacgttaaa tcaaacggac gttatggaat tgtataatat taaatatgca attgatccaa   118080
caaataaaat tgtaatagag caagtcgaca atgtggacgc gtttgtgcat attttagaac   118140
cgggtcaaga agtgttcgac gaaacgctaa gccagtacca ccaatttcct ggcgtcgtta   118200
gttcgattat tttcccgcaa ctcgtgttaa acacaataat tagcgttttg agcgaagacg   118260
gcagtttgct cacgttgaaa ctcgaaaaca cttgttttaa ttttcacgtg tgcaataaac   118320
gctttgtgtt tggcaatttg ccagcggcgg tcgtgaataa tgaaacgaag caaaaactgc   118380
gcattggagc tccaattttt gccggcaaaa agctggtttc ggtcgtgacg gcgtttcatc   118440
```

```
gtgttggcga aaacgaatgg ctgttaccgg tgacgggaat tcgagaggcg tcccagctgt 118500
cgggacatat gaaggtgctg aacggcgtcc gtgttgaaaa atggcgaccc aacatgtccg 118560
tctacgggac tgtgcaattg ccgtacgata aaattaaaca gcatgcgctc gagcaagaaa 118620
ataaaacgcc aaacgcgttg gagtcttgtg tgctatttta caaagattca gaaatacgca 118680
tcacttacaa caaggggggac tatgaaatta tgcatttgag gatgccggga cctttaattc 118740
aacccaacac aatatattat agttaaataa gaattattat caaatcattt gtatattaat 118800
taaaatacta tactgtaaat tacatttttat ttacaatcat gtcaaagcct aacgttttga 118860
cgcaaatttt agacgccgtt acggaaacta acacaaaggt tgacagtgtt caaactcagt 118920
taaacgggct ggaagaatca ttccagcttt tggacggttt gcccgctcaa ttgaccgatc 118980
ttaacactaa gatctcagaa attcaatcca tattgaccgg cgacattgtt ccggatcttc 119040
cagactcact aaagcctaag ctgaaacccc aagcttttga actcgattca gacgctcgtc 119100
gtggtaaacg cagttccaag taaatgaatc gttttttaaaa taacaaatca attgttttat 119160
aatattcgta cgattctttg attatgtaat aaaatgtgat cattaggaag attacgaaaa 119220
atataaaaaa tatgagttct gtgtgtataa caaatgctgt aaacgccaca attgtgtttg 119280
ttgcaaataa acccagtatt atttgattaa aattgttgtt ttctttgttc atagacaata 119340
gtgtgttttg cctaaacgtg tactgcataa actccatgcg agtgtatagc gagctagtgg 119400
ctaacgcttg ccccaccaaa gtagattcgt caaaatcctc aatttcatca ccctcctcca 119460
agtttaacat ttggccgtcg gaattaactt ctaaagatgc cacataatct aataaatgaa 119520
atagagattc aaacgtggcg tcatcgtccg tttcgaccat ttccgaaaag aactcgggca 119580
taaactctat gatttctctg gacgtggtgt tgtcgaaact ctcaaagtac gcagtcagga 119640
acgtgcgcga catgtcgtcg ggaaactcgc gcggaaacat gttgttgtaa ccgaacgggt 119700
cccatagcgc caaaccaaa tctgccagcg tcaatagaat gagcacgatg ccgacaatgg 119760
agctggcttg gatagcgatt cgagttaacg cttttggcagt cacggtcagc gttttgatgg 119820
cgatcacgtt gagcgagtgc actaacgcgg ctttgtaagt ctctcccaac atgcgcacgg 119880
tcacgcgccg agtcgtgcta agcaacatgt gtttcatggc cggaatgaga gaagtgttaa 119940 ttttttttcaa catgctttta aacccggaca ttagcatatc aaagccaatg tccgtagcaa 120000
taccgaaaac gagcgcgtaa tcttccaaaa acgatgttat aattgactcc aagtcttggt 120060
cgctgattga acgtcgagc gcctcgaaat gttcgacacg tgcacgttcg ttaccgcggt 120120
aattgtatgc gatcggagtt ttagtaaagc cggtttcggc cgtgtacgtg atctggacgg 120180
gcgacccgtt gacgatcatg cccaaatcgt ttagtgttgg attttttgtta aaaagttttt 120240 caaattccaa gtctgtggcg ttatcgcgca cgctgcgcca ttgcgctagt attgcgttgg 120300
agtccacgtt gggtcgtggc ggtagtatgc tggaaggcgc tttgtaatca aaatcgcgca 120360
gttcgctaaa aatgttgttg gccagcattt tgaaagtgac aaagatcgtg tcgcccagca 120420
cgaatccgat gagcgattcc caccatctaa acgaacaacc gccgttgaat agctctctgc 120480
cgaaacgtcg acagtaggct tcgttgaatt cgcctttaaa gcgttcggga acaagggggc 120540
cgggatcggg ccgaacgtta aaagccggca catcgtccac gccatgatc gtgtgttctt 120600 cggtgcgcaa gtatgggctg ttaaagtaca ttttggacag cgagtccact aagatgcatt 120660
tgttgtcgag cgtgtatcta aactcggcag actgaacttg ggtttcggcg ccttcacgca 120720
tggccgccgc cctgtccagg tggtagcacg cgggctgcgc gtaacccacg ctagtctcgg 120780
```

```
aggtctgcat gtacatgaac ggcgtcgtgt tggacacgac gccggtttcg tgaaacggat  120840
agcagctcat gcttacacac ccgcgcttgc tgaaagccag tttgacggcc agcgctttgt  120900
cggccaattt cggcggcaca taataatcgt cgtcacttga cgcgggacgc agcgtgtagt  120960
cgattagtat atgcggaaac ctggtgcgcc atctcgaaat aaactcgaga cgatgcatat  121020
gtatggcata cctactggca ttagttaaat cgacggctgt taaaaccgcc atgttatata  121080
ggacttaaaa taaacaacaa tatataatga aatatttatt agattatatt atagcaatac  121140
atttacattt attataacaa tacttttat ttaatctgat tatattataa cgatacattt  121200
ttatttagac attgttattt acaatattaa ttaactttt atacattttt aaatcataat  121260
atataatcat ttcgttgtgc atttcaaagc ttttgatagc ttcaaagtaa tacatgaatt  121320
tagagtattc aggaaaatga taaacgttgg taaacccgca tttggtacaa tataacacgg  121380 gattttata atacagttta gtttttttac acaatttgca atagttgtta gttgtaggtt  121440
tcaaaggaaa cgtgattgcg ccgtccaata cctgggtaaa cttttgact ttaacagtgg  121500 caaacacggt tcctttgata cccgaaaatc ggttgtcttg cagagcggcc atcatttcgc  121560
ttggctcttg aagtataaaa cagttgacgt catccaccac gtcgggtctg gtgcacatgc  121620
ttcggtagcg ctgcaacact atattggtgt atgtttccct gagaacgaga ccgccggtgg  121680
tgctaagatc gattgtttga atgcgctcgt tgggctcttt gtgatttcga attatgcgcc  121740
gaattatttc aaacactttg cagttgtgat cgtcaattct caattctta acttccgtcg  121800 tgtgctctaa acttacaggg aaaatgtatt ggtaaaaaaa cctctctctg gctaaatagc  121860
tgaggtcgac caaattgata gaaggatata ttcgtacga ggtttttgga acgttgtgat  121920
atagatagca tttttgacag cagatgtcta tgcggtcagg atcgtccaac ggcttttcga  121980
tgtgaaccac aacatacaaa aaccattcgc gcgtgttgtc tttgaatcta taattgcaag  122040
tggtgcatcg cgaatcgctc atgtgctcca tagtcttctt gtatttcaca ggcctgcttg  122100
caaatttgcc cgtcatgcgc atatctttgc tgtttatgta gcccataatg taattggtgg  122160 aaaatttag cgtggctttc atgatgtcgc gttctaaatc gctcatgaaa tgcatacgta  122220
gatcgcgctc ttgttttgaaa tccagtttgt cgctgtacgc gggcaaacct tcaaacttgt  122280
tcccaaactc gggcggcaca aaatatccat ctttttctgtt gacgactggt ttttttactta  122340 caatgctgct gtgctccaac ggcttggccg gagaggtgca cataggctgt ttaggcggag  122400
agatgcgcgt aggtggtttg atgttagatt ttggcggcgg acgaacaggc gacggcggcg  122460
agttggcggc aggcgctggc aaagatttgg cacgacccct gccccggtc cttggcgcgt  122520 caaaaatgtt attctctcga aaaaaacggt tcattgtaac tgttagttag cactcagaaa  122580
tcaacacgat actgtgcacg ttcagccatc gagaggcttt atatatggaa accttatcta  122640
tagagataag attgtatatg cgtaggagag cctggtcacg taggcacttt gcgcacggca  122700
ctagggctgt ggaggggaca ggctatataa agcccgtttg cccaactcgt aaatcagtat  122760
caattgtgct ccggcgcaca cgctcgcttg cgcgccggat agtataagta attgataacg  122820
ggcaacgcaa catgataaga accagcagtc acgtgctgaa cgtccaggaa aatataatga  122880
cgtcaaactg tgcgtcatcg ccatattcgt gcgaggcaac gtccgcttgc gcagaagctc  122940
agcaggtaat gatcgataac tttgtttct ttcacatgta caacgccgac atacaaattg  123000
acgcaaagct gcaatgcggc gtgcgctcgg ccgcgtttgc aatgatcgac gataaacatt  123060
tggaaatgta caagcataga atagagaata aatttttta ttactatgat caatgtgccg  123120
acattgccaa acccgaccgt ctgcccgatg acgacggcgc gtgctgtcac catttttattt  123180
```

-continued

```
ttgatgccca acgtattatt caatgtatta aagagattga aagcgcgtac ggcgtgcgtg   123240
atcgcggcaa tgtaatagtg ttttatccgt acttgaaaca gttgcgagac gcgttgaagc   123300
taattaaaaa ctcttttgcg tgttgtttta aaattataaa ttctatgcaa atgtacgtga   123360
acgagttaat atcaaattgc ctgttgttta ttgaaaagct ggaaactatt aataaaactg   123420
ttaaagttat gaatttgttt gtagacaatt tggttttgta cgaatgcaat gtttgtaaag   123480
aaatatctac ggatgaaaga ttttttaaagc caaagaatg ttgcgaatac gctatatgca   123540
acgcgtgctg cgttaacatg tggaagacgg ccaccacgca cgcaaaatgt ccagcgtgca   123600
ggacatcgta taaataagca cgcaacgcaa aatgagtggt ggcggcaact tgttgactct   123660
ggaaagagat cattttaaat atttattttt gaccagctat tttgatttaa aagataatga   123720
acatgttcct tcagagccta tggcatttat tcgcaattac ttgaattgca cgtttgattt   123780
gctagacgat gccgtgctca tgaactattt caattacttg caaagcatgc aattgaaaca   123840
tttggtgggc agcacgtcga caaacatttt caagtttgta aagccacaat ttagatttgt   123900
gtgcgatcgc acaactgtgg acattttaga atttgacacg cgcatgtaca taaaacccgg   123960
cacgcccgtg tacgccacga acctgttcac gtccaatccc cgcaagatga tggcttttcct  124020
gtacgctgaa tttggcaagg tgtttaaaaa taaaatattc gtaaacatca caactacgg    124080
ctgcgtgttg gcgggcagtg ccggtttctt gttcgacgat gcgtacgtgg attggaatgg   124140
tgtgcgaatg tgtgcggcgc cgcgattaga taacaacatg catccgttcc gactgtatct   124200
actgggcgag gacatggcta agcactttgt cgataataat atactaccgc cgcacccttc   124260
taacgcaaag actcgcaaaa tcaacaattc aatgtttatg ctgaaaaact tttacaaagg   124320
tctgccgctg ttcaaatcaa agtacacggt ggtgaacagc actaaaatcg tgacccgaaa   124380
acccaacgat atatttaatg agatagataa agaattaaat ggcaactgtc cgtttatcaa   124440
gtttattcag cgcgactaca tattcgacgc ccagtttccg ccagatttgc ttgatttgct   124500
aaacgaatac atgaccaaaa gctcgatcat gaaaataatt accaagtttg tgattgaaga   124560
aaacccgct atgagcggtg aaatgtctcg cgagattatt cttgatcgct actcagtaga    124620
caattatcgc aagctgtaca taaaaatgga ataaccaac cagtttcctg tcatgtacga    124680
tcatgaatcg tcgtacattt ttgtgagcaa agactttttg caattgaaag gcactatgaa   124740
cgcgttctac gcgcccaagc agcgtatatt aagtattttg gcggtgaatc gtttgtttgg   124800
cgccacggaa acgatcgact ttcatcccaa cctgctcgtg taccggcaga gttcgccgcc   124860
ggtccgtttg acgggcgacg tgtatgttgt tgataagaac gaaaaagttt ttttggtcaa   124920
acacgtgttc tcaaacacgg tgcctgcata tcttttaata agaggtgatt acgaaagttc   124980
gtctgacttg aaatcccttc gcgatttgaa tccgtgggtt cagaacacgc ttctcaaatt   125040
attaatcccc gactcggtac aataatatga tttacactga tcccactact ggcgctacga   125100
ctagcacaga cgtcgtccgt ccacaaacta tttaaacagg ctaactccaa acatgttctt   125160
gaccatcttg gctgtagtag taattattgc tttaataatt atatttgttc aatctagcag   125220
taatggaaac agctcggggg gtaatgtacc tccaaacgcc ctgggggtt ttgtaaatcc    125280
tttaaacgct accatgcgag ctaatccctt tatgaacacg cctcaaaggc aaatgttgta   125340
gataagtgta taaaaaatga aacgtatcaa atgcaacaaa gttcgaacgg tcaccgagat   125400
tgtaaacagc gatgaaaaaa tccaaaagac ctacgaattg gctgaatttg atttaaaaaa   125460
tctaagcagt ttagaaagct atgaaactct aaaaattaaa ttggcgctca gcaaatacat   125520
```

```
ggctatgctc agcaccctgg aaatgactca accgctgttg gaaatattta gaaacaaagc  125580
agacactcgg cagattgccg ccgtggtgtt tagcacatta gcttttatac acaatagatt  125640
ccatcccctt gttactaatt ttactaacaa aatggagttt gtggtcactg aaaccaacga  125700
cacaagcatt cccggagaac ccattttgtt tacggaaaac gaaggtgtgc tgctgtgttc  125760
cgtggacaga ccgtctatcg ttaaaatgct aagccgcgag tttgacaccg aggctttagt  125820
aaactttgaa aacgacaact gcaacgtgcg gatagccaag acgtttggcg cctctaagcg  125880
caaaaacacg acgcgcagcg atgattacga gtcaaataaa caacccaatt acgatatgga  125940
tttgagcgat tttagcataa ctgaggttga agccactcaa tatttaactc tgttgctgac  126000
cgtcgaacat gcctatttac attattatat ttttaaaaat tacggggtgt ttgaatattg  126060
caaatcgcta acggaccatt cgcttttttac caacaaattg cgatcgacaa tgagcacaaa  126120
aacgtctaat ttactgttaa gcaaattcaa atttaccatt gaagattttg acaaaataaa  126180
ctcaaattct gtaacatcag ggtttaatat atataatttt aataaataat taaataaat  126240
acaatgtttt tattaattat atttttaata ttaattaaaa gtattaatat ttaaaaaaat  126300
gaatcaaatt catctaaagt gtcacagcga taaaatttgt cctaaagggt attttggcct  126360
caacgccgat ccctatgatt gcacggcgta ttatctgtgt ccgcataaag tgcaaatgtt  126420
ttgcgaatta aatcacgaat ttgacttgga ctccgccagc tgcaagccta tcgtgtacga  126480
tcacacgggc agcgggtgta cggctcgcat gtatagaaac ttgttactat gaagagcggg  126540
tttccagttg cacaacacta ttatcgattt gcagttcggg acataaatgt ttaaatatat  126600
cgatgtcttt gtgatgcgcg cgacattttt gtaggttatt gataaaatga acggatacgt  126660
tgcccgacat tatcattaaa tccttggcgt agaatttgtc gggtccattg tccgtgtgcg  126720
ctagcatgcc cgtaacggac ctcgtacttt tggcttcaaa ggttttgcgc acagacaaaa  126780
tgtgccacac ttgcagctct gcatgtgtgc gcgttaccac aaatcccaac ggcgcagtgt  126840
acttgttgta tgcaaataaa tctcgataaa ggcgcggcgc gcgaatgcag ctgatcacgt  126900
acgctcctcg tgttccgttc aaggacggtg ttatcgacct cagattaatg tttatcggcc  126960
gactgttttc gtatccgctc accaaacgcg tttttgcatt aacattgtat gtcggcggat  127020
gttctatatc taatttgaat aaataaacga taaccgcgtt ggttttagag ggcataataa  127080
aagaaatatt gttatcgtgt tcgccattag ggcagtataa attgacgttc atgttggata  127140
ttgtttcagt tgcaagttga cactggcggc gacaagatcg tgaacaacca agtgactatg  127200
acgcaaatta attttaacgc gtcgtacacc agcgcttcga cgccgtcccg agcgtcgttc  127260
gacaacagct attcagagtt ttgtgataaa caacccaacg actatttaag ttattataac  127320
catcccaccc cggatggagc cgacacggtg atatctgaca gcgagactgc ggcagcttca  127380
aacttttttgg caagcgtcaa ctcgttaact gataatgatt tagtggaatg tttgctcaag  127440
accactgata atctcgaaga agcagttagt tctgcttatt attcggaatc ccttgagcag  127500
cctgttgtgg agcaaccatc gcccagttct gcttatcatg cggaatcttt tgagcattct  127560
gctggtgtga accaaccatc ggcaactgga actaaacgga agctggacga atacttggac  127620
aattcacaag gtgtggtggg ccagtttaac aaaattaaat tgaggcctaa atacaagaaa  127680
agcacaattc aaagctgtgc aaccccttgaa cagacaatta atcacaacac gaacatttgc  127740
acggtcgctt caactcaaga aattacgcat tatttactta atgatttgc gccgtattta  127800
atgcgtttcg acgacaacga ctacaattcc aacaggttct ccgaccatat gtccgaaact  127860
ggttattaca tgtttgtggt taaaaaaagt gaagtgaagc cgtttgaaat tatatttgcc  127920
```

```
aagtacgtga gcaatgtggt ttacgaatat acaaacaatt attacatggt agataatcgc  127980
gtgtttgtgg taacttttga taaaattagg tttatgattt cgtacaattt ggttaaagaa  128040
accggcatag aaattcctca ttctcaagat gtgtgcaacg acgagacggc tgcacaaaat  128100
tgtaaaaaat gccatttcgt cgatgtgcac cacacgttta aagctgctct gacttcatat  128160
tttaatttag atatgtatta cgcgcaaacc acatttgtga ctttgttaca atcgttgggc  128220
gaaagaaaat gtgggtttct tttgagcaag ttgtacgaaa tgtatcaaga taaaaattta  128280
tttactttgc ctattatgct tagtcgtaaa gagagtaatg aaattgagac tgcatctaat  128340
aatttctttg tatcgccgta tgtgagtcaa atattaaagt attcggaaag tgtgcagttt  128400
cccgacaatc ccccaaacaa atatgtggtg gacaatttaa atttaattgt taacaaaaaa  128460
agtacgctca cgtacaaata cagcagcgtc gctaatcttt tgtttaataa ttataaatat  128520
catgacaata ttgcgagtaa taataacgca gaaaatttaa aaaaggttaa gaaggaggac  128580
ggcagcatgc acattgtcga acagtatttg actcagaatg tagataatgt aaagggtcac  128640
aattttatag tattgtcttt caaaaacgag gagcgattga ctatagctaa gaaaaacaaa  128700
gagttttatt ggatttctgg cgaaattaaa gatgtagacg ttagtcaagt aattcaaaaa  128760
tataatagat ttaagcatca catgtttgta atcggtaaag tgaaccgaag agagagcact  128820
acattgcaca ataatttgtt aaaattgtta gctttaatat tacagggtct ggttccgttg  128880
tccgacgcta taacgtttgc ggaacaaaaa ctaaattgta aatataaaaa attcgaattt  128940
aattaattat acatatattt tgaatttaat taattataca tatattttat attatttttg  129000
tcttttatta tcgaggggcc gttgttggtg tggggttttg catagaaata acaatgggag  129060
ttggcgacgt tgctgcgcca acaccacctc ctcctcctcc tttcatcatg tatctgtaga  129120
taaaataaaa tattaaacct aaaaacaaga ccgcgcctat caacaaaatg ataggcatta  129180
acttgccgct gacgctgtca ctaacgttgg acgatttgcc gactaaacct tcatcgccca  129240
gtaaccaatc tagacccaag tcgccaacta aatcaccaaa cgagtaaggt tcgatgcaca  129300
tgagtgtttg gcccgcagga agatcgctaa tatctacgta ttgaggcgaa tctgggtcgg  129360
cggacggatc gctgccgcga caaactgttt tttctacttc atagttgaat ccttggcaca  129420
tgttggttag ttcgggcgga ttgttaggca acaaggggtc gaatgggcaa atggtaacat  129480
ccgactgatt tagattgggg tcttgacgac aagtgcgctg caataacaag caggcctcgg  129540
cgatttctcc ggcgtctttta ccttgcacat aataacttcc gccggtgtta ttgatggcgt  129600
tgattatatc ttgtactagt gtggcggcgc taaacaagaa atagccgccg gtggccaaga  129660
gtatgcccgt tcctcctact tttaagcttt gcatgtaact atgtagacgg gggttttgct  129720
gcagtgcgtt ttgaacacct tcgggcgtgc gcacgttggt ttccgggaag ttttgtttga  129780
ctgcattgga tcgcgtctgc ttggtgtggt aattaaagtc tggcacgttg tccacgcgcc  129840
gcaattggct caatgagttt atttgagggt ctgaaatgcc ctgaaatact ccgcgtatgt  129900
tggggacatc attgttacga gtaattctgt ttatgtctga agtgctcaca aactggttgt  129960
tagatagttg atagcccggc tgaaatctgt tgtttccaat gttgcgtaca ctgggcgcgt  130020
tgagcacatt tgtgaaaccg gcgggagtgc ttgttaaaag acgcgtatta tcagtaataa  130080
aactggcctg attaggatac aatttattga ctgcgcgaag atttgaaaaa aaactcatt  130140 taaagcaaac ttatttaata aatatatcac agtaaaggtt ttgcaaaact gccgtcgtca  130200
atacaacacg gcagcggcgt catgttggta aaatctaatc ttctccttgc tttagattct  130260
```

```
gggcgagaag gcgcatttgt tgtgtaagtt atttcgacgt ctgcattatt tgttgtgtaa    130320
ggtatctcga cgtatgaagc aactttaaca ttgttataat ttttttttaaa tattgatgcg    130380
ctccacggcg cgcgttgata cggatgatat ctctccattg tatgatcgct aaatttatat    130440
accgttccaa taaatatgtt aaacccaac atgttaatta taatattcat aatagtttgt    130500
ttgttttcaa taattatttt tactgttttg aaatctaaaa gaggtgacga tgacgaatca    130560
gacgacgggt tcagttgcta taacaaacca attggagtaa attttccgca tcctactaga    130620
tgtgacgctt tctacatgtg tgtcggttta aatcaaaaat tagagttaat ctgccctgaa    130680
ggatttgaat ttgatccaga tgttaaaaat tgtgttccta tatcagatta tggatgtacc    130740
gctaaccaaa actaaaaata aaataaaatt tatatagatt aatgaaataa aatttatata    130800
gattaataaa ataaaattta tttaatatat tatactattt atattattta caacacttaa    130860
cgtctagaca taacagtttg taacttagaa actaaatcag agttactgcg ctcaaactct    130920
gaaaatttgg cttgagactc ggccacctgc ttacgcaatt gttcttgcag attattcaca    130980
gtcgattgca actcttctga tttcttggta gattcttgca agtcatagtt tgccttttgt    131040
aaatctaatt cggcgacagc atgcttgtgt ttaagcataa tgtagtcgct gtttaacatg    131100
gtcattttat gttcaacttg gctggtcttg gctcgcagct cggacagttc ttttttgcaat    131160
tgctccacat agttcaagtc cgtggtgtga ttgttgaccg tgttatttc taaaagctcg    131220
cgccaatgct gtttgatgga atcctggtta cgagtgacgt taatgggcat aaattctaca    131280
tacccgtgct tattgtacac gcgacaatct gatgaagtag cgctgcaaaa acatttgtac    131340
acagaattgt ccataattat cttgacataa cacttgaaac acacagcatg ttacaatga    131400
atcgaagtca caaacgagga atttacgttt ttagtgtctt taaaagtagt aaaacaaata    131460
ttacacgaaa cctctacttc ttcttcgggt tctgattgct gctgctgctg ctgctgcggc    131520
tgcggagact gcggcgaggc aaacaaatct ggcgactgtg gtattacgta attcggcgaa    131580
taagatggac tataagtggg agaccttggg gcaatctcat tcatcagctg agcctcaaga    131640
tctaaaccctc gttgcagagc cctctgcgca gctgtctccg acgcaatgtt atcctggtac    131700
tgctgggcag tgatgtcggg aaaccgttca cgatccacat tttcactatt aattagtatg    131760
acgtcatcct cttgacttaa tagcggatcg tcattgctaa tgttaacctg accgtgcacg    131820
taatacgtga caccctgacg atggtaggtg cgcgtcaacg gctcgttgac gttcccgata    131880
atctgcacgt tttcttcgct gacacgctgc tcctgacgcc gctcctgacg gcgatggctg    131940
cgactgcttg aagacggctg gctgcgactg cttgaagacg gctgggcttc gggagatgtt    132000
gtaaagttga tgcggcgacg gctgagagac agcctgtggc ggcggctgct gctgggagtg    132060
gcggcgttga tttggcgact catggctggg ctggtaggat actgttcact aggctgtgag    132120
gcttgaactg tgcttacgag tagaacggca gctgtattta tactgtttat cagtactgca    132180
cgactgataa gacaatagtg gtgggggaac ttgccaggca aaaatgaact ttttgtaat    132240
gcaaaaagt tgatagtgta gtagtatatt gggagcgtat cgtacagtgt agactattct    132300
aataaaatag tctacgattt gtagagattg tactgtatat ggagtgtcag gcaaaagtga    132360
acttttttgc attgcaaaaa aattcatttt aaatttatca tatcacaggc tgcagttct    132420
gttatctgtc ccccactcag gcgtgcagct ataaaagcag gcactcacca actcgtaagc    132480
acagttcgtt gtgaagtgaa cacggagagc ctgccaataa gcaaaatgcc aagggacacc    132540
aacaatcgcc accggtctac gccatatgaa cgtcctacgc ttgaagatct ccgcagacag    132600
ttgcaagaca atttggacag cataaaccgc cgagacagaa tgcaagaaga acaagaagaa    132660
```

```
aacctgcgct atcaagtgcg tagaaggcag cgtcaaaacc agctccgctc catacaaatg  132720
gaacagcagc gaatgatggc ggaattaaac aacgagccgg tgattaattt taaatttgag  132780
tgtagtgtgt gtttagaaac atattcccaa caatctaacg atacttgtcc tttttttgatt  132840 ccgactacgg gcgaccacgg ttttgtttc aaatgcgtca tcaatctgca aagcaacgcg  132900
atgaatattc cgcattccac tgtgtgctgt ccattgtgca atacccaggt aaaaatgtgg  132960
cgttccttaa agcctaacgc tgttgtgacg tgtaagtttt acaagaaaac tcaagaagat  133020
gttccgcccg tgcagcagta taaaaacatt attaaagtgc tacaagaacg gagcgtgatt  133080
agtgtcgaag acaacgacaa taattgtgac ataaatatgg agaatcaggc aaagatagct  133140
gctttggaag ctgaattgga agaagaaaaa aatcacagtg atcaagtagc ttctgaaaac  133200
cgacagctga tagaagaaaa tactcgtctc aatgaacaga ttcaagagtt gcagcatcag  133260
gtgaggacat tggtgccgca acgtggcatt acggttaatc agcaaattgg ccgtgacgac  133320
agtgcgccag ccgagctgaa cgagcgtttt cgctcacttg tctattcgac tatttcagag  133380
ctgtttattg aaaatggcgt tcatagtatt caaaattatg tttatgccgg aacttctgct  133440
gctagttcat gtgatgtaaa tgttactgtt aattttgggt ttgaaaatta atgtgatatg  133500
aaatgtatat ataaaaatga tggaataaat aataaacatt tttatacttt ttatgttttt  133560
tttatttcat gtgattaaga aacttttaag atggatagta gtaattgtat taaaatagat  133620
gtaaaatacg atatgccgtt acattatcaa tgtgacaata acgcagataa agacgttgta  133680
aatgcgtatg acactatcga tgttgacccc aacaaaagat ttataattaa tcataatcac  133740
gaacaacaac aagtcaatga aacaaataaa caagttgtcg ataaaacatt cataaatgac  133800
acagcaacat acaattcttg cataataaaa atttaaatga catcatattt gagaataaca  133860
aatgacatta tccctcgatt gtgttttaca agta                              133894

<210> SEQ ID NO 2
<211> LENGTH: 45
<212> TYPE: DNA
<213> ORGANISM: artificial
<220> FEATURE:
<223> OTHER INFORMATION: vp39-F forward primer

<400> SEQUENCE: 2
gcttctaata cgactcacta tagggtcgta tccgctaagc gttct                    45

<210> SEQ ID NO 3
<211> LENGTH: 45
<212> TYPE: DNA
<213> ORGANISM: artificial
<220> FEATURE:
<223> OTHER INFORMATION: vp39-R reverse primer

<400> SEQUENCE: 3
gcttctaata cgactcacta tagggacgca acgcgttata cacag                    45

<210> SEQ ID NO 4
<211> LENGTH: 43
<212> TYPE: DNA
<213> ORGANISM: artificial
<220> FEATURE:
<223> OTHER INFORMATION: 45510 forward primer

<400> SEQUENCE: 4
cttctaatac gactcactat agggacagcg tgtacgagtg cat                      43
```

```
<210> SEQ ID NO 5
<211> LENGTH: 45
<212> TYPE: DNA
<213> ORGANISM: artificial
<220> FEATURE:
<223> OTHER INFORMATION: 46235 reverse primer

<400> SEQUENCE: 5
gcttctaata cgactcacta tagggatctc gagcgtgtag ctggt            45

<210> SEQ ID NO 6
<211> LENGTH: 44
<212> TYPE: DNA
<213> ORGANISM: artificial
<220> FEATURE:
<223> OTHER INFORMATION: 90292 forward primer

<400> SEQUENCE: 6
gcttctaata cgactcacta tagggtaccg ccgaacatta cacc             44

<210> SEQ ID NO 7
<211> LENGTH: 43
<212> TYPE: DNA
<213> ORGANISM: artificial
<220> FEATURE:
<223> OTHER INFORMATION: 90889 reverse primer

<400> SEQUENCE: 7
gcttctaata cgactcacta tagggtctat tggcacgttt gct              43

<210> SEQ ID NO 8
<211> LENGTH: 45
<212> TYPE: DNA
<213> ORGANISM: artificial
<220> FEATURE:
<223> OTHER INFORMATION: ec-27-F forward primer

<400> SEQUENCE: 8
gcttctaata cgactcacta tagggaaagc agacactcgg cagat            45

<210> SEQ ID NO 9
<211> LENGTH: 45
<212> TYPE: DNA
<213> ORGANISM: artificial
<220> FEATURE:
<223> OTHER INFORMATION: ec-27-R reverse primer

<400> SEQUENCE: 9
gcttctaata cgactcacta tagggttgag tggcttcaac ctcag            45

<210> SEQ ID NO 10
<211> LENGTH: 44
<212> TYPE: DNA
<213> ORGANISM: artificial
<220> FEATURE:
<223> OTHER INFORMATION: dbp-F forward primer

<400> SEQUENCE: 10
gcttctaata cgactcacta tagggcgctc gctagttttg ttct             44

<210> SEQ ID NO 11
<211> LENGTH: 44
<212> TYPE: DNA
<213> ORGANISM: artificial
<220> FEATURE:
<223> OTHER INFORMATION: dbp-R reverse primer
```

```
<400> SEQUENCE: 11
gcttctaata cgactcacta tagggaaaga tcggaaggtg gtga              44

<210> SEQ ID NO 12
<211> LENGTH: 45
<212> TYPE: DNA
<213> ORGANISM: artificial
<220> FEATURE:
<223> OTHER INFORMATION: gfp-F forward primer

<400> SEQUENCE: 12
gcttctaata cgactcacta tagggctgac cctgaagttc atctg             45

<210> SEQ ID NO 13
<211> LENGTH: 44
<212> TYPE: DNA
<213> ORGANISM: artificial
<220> FEATURE:
<223> OTHER INFORMATION: gfp-R reverse primer

<400> SEQUENCE: 13
gcttctaata cgactcacta tagggaactc cagcaggacc atgt              44

<210> SEQ ID NO 14
<211> LENGTH: 45
<212> TYPE: DNA
<213> ORGANISM: artificial
<220> FEATURE:
<223> OTHER INFORMATION: cat-F forward primer

<400> SEQUENCE: 14
gcttctaata cgactcacta tagggacggc atgatgaacc tgaat             45

<210> SEQ ID NO 15
<211> LENGTH: 45
<212> TYPE: DNA
<213> ORGANISM: artificial
<220> FEATURE:
<223> OTHER INFORMATION: cat-R reverse primer

<400> SEQUENCE: 15
gcttctaata cgactcacta tagggatccc aatggcatcg taaag             45

<210> SEQ ID NO 16
<211> LENGTH: 68
<212> TYPE: DNA
<213> ORGANISM: artificial
<220> FEATURE:
<223> OTHER INFORMATION: vp80-KO-F forward primer

<400> SEQUENCE: 16
ctgtattgta atctgtaagc gcacatggtg cattcgatat aaccttataa tgtgtgctgg     60
aatgccct                                                              68

<210> SEQ ID NO 17
<211> LENGTH: 71
<212> TYPE: DNA
<213> ORGANISM: artificial
<220> FEATURE:
<223> OTHER INFORMATION: vp80-KO-R reverse primer

<400> SEQUENCE: 17
aaatgtactg aatataaata aaaattaaaa atattttata atttttatt taccgttcgt     60
```
atagcataca t                                                    71

<210> SEQ ID NO 18
<211> LENGTH: 21
<212> TYPE: DNA
<213> ORGANISM: artificial
<220> FEATURE:
<223> OTHER INFORMATION: 89507 forward primer

<400> SEQUENCE: 18
agcggtcgta aatgttaaac c                                         21

<210> SEQ ID NO 19
<211> LENGTH: 25
<212> TYPE: DNA
<213> ORGANISM: artificial
<220> FEATURE:
<223> OTHER INFORMATION: 91713 reverse primer

<400> SEQUENCE: 19
tgtataaaca atatgttaat atgtg                                     25

<210> SEQ ID NO 20
<211> LENGTH: 34
<212> TYPE: DNA
<213> ORGANISM: artificial
<220> FEATURE:
<223> OTHER INFORMATION: gfp-NheI-F forward primer

<400> SEQUENCE: 20
ccaaaccgct agcaacatgg tgagcaaggg cgag                           34

<210> SEQ ID NO 21
<211> LENGTH: 49
<212> TYPE: DNA
<213> ORGANISM: artificial
<220> FEATURE:
<223> OTHER INFORMATION: gfp-SphI reverse primer

<400> SEQUENCE: 21
aggaaagggc atgcttaacg cgtaccggtc ttgtacagct cgtccatgc           49

<210> SEQ ID NO 22
<211> LENGTH: 40
<212> TYPE: DNA
<213> ORGANISM: artificial
<220> FEATURE:
<223> OTHER INFORMATION: pvp80-StuI-F forward primer

<400> SEQUENCE: 22
ggaacaaagg cctgagctca aagtaagacc tttactgtcc                     40

<210> SEQ ID NO 23
<211> LENGTH: 35
<212> TYPE: DNA
<213> ORGANISM: artificial
<220> FEATURE:
<223> OTHER INFORMATION: vp80-XbaI-R reverse primer

<400> SEQUENCE: 23
ccttctatct agattatata acattgtagt ttgcg                          35

<210> SEQ ID NO 24
<211> LENGTH: 35
<212> TYPE: DNA
<213> ORGANISM: artificial

```
<220> FEATURE:
<223> OTHER INFORMATION: vp80-SacI-F forward primer

<400> SEQUENCE: 24
ttatcttgag ctcaatatga acgattccaa ttctc                           35

<210> SEQ ID NO 25
<211> LENGTH: 69
<212> TYPE: DNA
<213> ORGANISM: artificial
<220> FEATURE:
<223> OTHER INFORMATION: vp80-FLAG-R1 reverse primer

<400> SEQUENCE: 25
caacagagaa ttggaatcgt tcttatcgtc gtcatccttg taatccatat tataaggtta    60
tatcgaatg                                                             69

<210> SEQ ID NO 26
<211> LENGTH: 62
<212> TYPE: DNA
<213> ORGANISM: artificial
<220> FEATURE:
<223> OTHER INFORMATION: vp80-FLAG-R reverse primer

<400> SEQUENCE: 26
ccttctatct agattactta tcgtcgtcat ccttgtaatc tataacattg tagtttgcgt    60
tc                                                                    62

<210> SEQ ID NO 27
<211> LENGTH: 23
<212> TYPE: DNA
<213> ORGANISM: artificial
<220> FEATURE:
<223> OTHER INFORMATION: M13-F forward primer

<400> SEQUENCE: 27
cccagtcacg acgttgtaaa acg                                         23

<210> SEQ ID NO 28
<211> LENGTH: 23
<212> TYPE: DNA
<213> ORGANISM: artificial
<220> FEATURE:
<223> OTHER INFORMATION: M13-R reverse primer

<400> SEQUENCE: 28
agcggataac aatttcacac agg                                         23

<210> SEQ ID NO 29
<211> LENGTH: 20
<212> TYPE: DNA
<213> ORGANISM: artificial
<220> FEATURE:
<223> OTHER INFORMATION: GenR reverse primer

<400> SEQUENCE: 29
agccacctac tcccaacatc                                             20

<210> SEQ ID NO 30
<211> LENGTH: 71
<212> TYPE: DNA
<213> ORGANISM: artificial
<220> FEATURE:
<223> OTHER INFORMATION: vp39-KO-F forward primer
```

```
<400> SEQUENCE: 30
tcgggcacag acgcgaccag acccgtttcg tcaattatac acgtggcgca taccgttcgt    60
ataatgtatg c                                                         71

<210> SEQ ID NO 31
<211> LENGTH: 70
<212> TYPE: DNA
<213> ORGANISM: artificial
<220> FEATURE:
<223> OTHER INFORMATION: vp39-KO-R reverse primer

<400> SEQUENCE: 31
gtttatttgc aacaaccacc tcataaaacg ttttaaaatg tcaaaaatgt accgttcgta    60
tagcatacat                                                           70

<210> SEQ ID NO 32
<211> LENGTH: 33
<212> TYPE: DNA
<213> ORGANISM: artificial
<220> FEATURE:
<223> OTHER INFORMATION: vp39-SacI-F forward primer

<400> SEQUENCE: 32
aaggttctct agattagacg gctattcctc cac                                 33

<210> SEQ ID NO 33
<211> LENGTH: 32
<212> TYPE: DNA
<213> ORGANISM: artificial
<220> FEATURE:
<223> OTHER INFORMATION: vp39-XbaI-R reverse primer

<400> SEQUENCE: 33
ttatcttgag ctcaatatgg cgctagtgcc cg                                  32

<210> SEQ ID NO 34
<211> LENGTH: 39
<212> TYPE: DNA
<213> ORGANISM: artificial
<220> FEATURE:
<223> OTHER INFORMATION: vp39-StuI-F forward primer

<400> SEQUENCE: 34
ggaacaaagg cctgagctct tagacggcta ttcctccac                           39

<210> SEQ ID NO 35
<211> LENGTH: 34
<212> TYPE: DNA
<213> ORGANISM: artificial
<220> FEATURE:
<223> OTHER INFORMATION: lef-4-XbaI-R reverse primer

<400> SEQUENCE: 35
ccttctatct agattaattt ggcacgattc ggtc                                34

<210> SEQ ID NO 36
<211> LENGTH: 39
<212> TYPE: DNA
<213> ORGANISM: artificial
<220> FEATURE:
<223> OTHER INFORMATION: cg-30-XbaI-F forward primer

<400> SEQUENCE: 36
aaggttctct agattaatct acatttattg taacatttg                           39
```

```
<210> SEQ ID NO 37
<211> LENGTH: 61
<212> TYPE: DNA
<213> ORGANISM: artificial
<220> FEATURE:
<223> OTHER INFORMATION: vp39-FLAG-SacI-R reverse primer

<400> SEQUENCE: 37
ttatcttgag ctcaatatgg attacaagga tgacgacgat aaggcgctag tgcccgtggg      60
t                                                                     61

<210> SEQ ID NO 38
<211> LENGTH: 72
<212> TYPE: DNA
<213> ORGANISM: artificial
<220> FEATURE:
<223> OTHER INFORMATION: vp1054-KO-F forward primer

<400> SEQUENCE: 38
gtactgaaag ataatttatt tttgatagat aataattaca ttattttaaa cgtgttcgac      60
caagaaaccg at                                                         72

<210> SEQ ID NO 39
<211> LENGTH: 45
<212> TYPE: DNA
<213> ORGANISM: artificial
<220> FEATURE:
<223> OTHER INFORMATION: vp1054-KO-R1 reverse primer

<400> SEQUENCE: 39
agggcgaatt ccagcacact ttattacgtg gacgcgttac tttgc                     45

<210> SEQ ID NO 40
<211> LENGTH: 71
<212> TYPE: DNA
<213> ORGANISM: artificial
<220> FEATURE:
<223> OTHER INFORMATION: vp1054-KO-R2 reverse primer

<400> SEQUENCE: 40
gataagaatg cttgtttaac aaataggtca gctgttaaat actggcgatg taccgttcgt     60
atagcataca t                                                          71

<210> SEQ ID NO 41
<211> LENGTH: 41
<212> TYPE: DNA
<213> ORGANISM: artificial
<220> FEATURE:
<223> OTHER INFORMATION: vp1054-Rep-F forward primer

<400> SEQUENCE: 41
ggttgtttag gcctgagctc ctttggtacg tgttagagtg t                         41

<210> SEQ ID NO 42
<211> LENGTH: 36
<212> TYPE: DNA
<213> ORGANISM: artificial
<220> FEATURE:
<223> OTHER INFORMATION: vp1054-Rep-R reverse primer

<400> SEQUENCE: 42
tcctttcctc tagattacac gttgtgtgcg tgcaga                               36
```

<210> SEQ ID NO 43
<211> LENGTH: 67
<212> TYPE: DNA
<213> ORGANISM: artificial
<220> FEATURE:
<223> OTHER INFORMATION: p6.9-KO-F forward primer

<400> SEQUENCE: 43
gcttcgttca ttcgctactg tcggctgtgt ggaatgtctg gttgttaagt gtgctggaat    60
tcgccct                                                              67

<210> SEQ ID NO 44
<211> LENGTH: 70
<212> TYPE: DNA
<213> ORGANISM: artificial
<220> FEATURE:
<223> OTHER INFORMATION: p6.9-KO-R reverse primer

<400> SEQUENCE: 44
aatattaata aggtaaaaat tacagctaca taaattacac aatttaaact accgttcgta    60
tagcatacat                                                           70

<210> SEQ ID NO 45
<211> LENGTH: 32
<212> TYPE: DNA
<213> ORGANISM: artificial
<220> FEATURE:
<223> OTHER INFORMATION: Ac-p6.9-F forward primer

<400> SEQUENCE: 45
tttgaattca tggttgcccg aagctccaag ac                                  32

<210> SEQ ID NO 46
<211> LENGTH: 34
<212> TYPE: DNA
<213> ORGANISM: artificial
<220> FEATURE:
<223> OTHER INFORMATION: Ac-p6.9-R reverse primer

<400> SEQUENCE: 46
tttgcggccg cttaatagta gcgtgttctg taac                                34

<210> SEQ ID NO 47
<211> LENGTH: 29
<212> TYPE: DNA
<213> ORGANISM: artificial
<220> FEATURE:
<223> OTHER INFORMATION: Se-p6.9-F forward primer

<400> SEQUENCE: 47
tttgaattca tgtatcgtcg tcgttcatc                                      29

<210> SEQ ID NO 48
<211> LENGTH: 34
<212> TYPE: DNA
<213> ORGANISM: artificial
<220> FEATURE:
<223> OTHER INFORMATION: Se-p6.9-R reverse primer

<400> SEQUENCE: 48
tttgcggccg cttaatagtg gcgacgtctg tatc                                34

<210> SEQ ID NO 49
<211> LENGTH: 22

-continued

```
<212> TYPE: DNA
<213> ORGANISM: artificial
<220> FEATURE:
<223> OTHER INFORMATION: 86596 forward primer

<400> SEQUENCE: 49
gggcttagtt taaaatcttg ca                                            22

<210> SEQ ID NO 50
<211> LENGTH: 21
<212> TYPE: DNA
<213> ORGANISM: artificial
<220> FEATURE:
<223> OTHER INFORMATION: 86995 reverse primer

<400> SEQUENCE: 50
aattcaaacg accaagacga g                                             21

<210> SEQ ID NO 51
<211> LENGTH: 21
<212> TYPE: DNA
<213> ORGANISM: artificial
<220> FEATURE:
<223> OTHER INFORMATION: 45122 forward primer

<400> SEQUENCE: 51
gcaatcatga cgaacgtatg g                                             21

<210> SEQ ID NO 52
<211> LENGTH: 22
<212> TYPE: DNA
<213> ORGANISM: artificial
<220> FEATURE:
<223> OTHER INFORMATION: 46441 reverse primer

<400> SEQUENCE: 52
cgataatttt tccaagcgct ac                                            22

<210> SEQ ID NO 53
<211> LENGTH: 30
<212> TYPE: DNA
<213> ORGANISM: artificial
<220> FEATURE:
<223> OTHER INFORMATION: pp6.9-F forward primer

<400> SEQUENCE: 53
ggtcgacgta ccaaattccg ttttgcgacg                                    30

<210> SEQ ID NO 54
<211> LENGTH: 34
<212> TYPE: DNA
<213> ORGANISM: artificial
<220> FEATURE:
<223> OTHER INFORMATION: pp6.9-R reverse primer

<400> SEQUENCE: 54
ggtcgacgga tccgtttaaa ttgtgtaatt tatg                               34

<210> SEQ ID NO 55
<211> LENGTH: 21
<212> TYPE: DNA
<213> ORGANISM: artificial
<220> FEATURE:
<223> OTHER INFORMATION: 75834 forward primer

<400> SEQUENCE: 55
```

```
cttcttatcg ggttgtacaa c                                              21

<210> SEQ ID NO 56
<211> LENGTH: 20
<212> TYPE: DNA
<213> ORGANISM: artificial
<220> FEATURE:
<223> OTHER INFORMATION: 76420 reverse primer

<400> SEQUENCE: 56
gcgtatcatg acgatggatg                                                20
```

BACULOVIRUS-BASED PRODUCTION OF BIOPHARMACEUTICALS FREE OF CONTAMINATING BACULOVIRAL VIRIONS

CROSS-REFERENCE TO RELATED APPLICATIONS

This application is a continuation of U.S. Ser. No. 13/390,806, filed Feb. 16, 2012, now U.S. Pat. No. 8,993,317, which is the U.S. national stage application of International Patent Application No. PCT/EP2010/061456, filed Aug. 5, 2010, the disclosures of which are hereby incorporated by reference in their entirety, including all figures, tables and amino acid or nucleic acid sequences.

The Sequence Listing for this application is labeled "Seq-List.txt" which was created on Feb. 9, 2012 and is 117 KB. The entire contents of the sequence listing is incorporated herein by reference in its entirety.

The present invention relates to methods for the production of biopharmaceuticals implementing a baculovirus-based system. These methods advantageously allow the production of biopharmaceuticals with reduced or no contaminating baculoviral virions.

Over the past two decades the baculovirus-insect cell technology has become a very frequently used eukaryotic expression system for the production of recombinant proteins, not only for scientific purposes, but more and more for human and veterinary medicine (Condreay and Kost, 2007, van Oers, 2006). In particular, recombinant baculoviruses derived from *Autographa californica* multicapsid nucleopolyhedrovirus (AcMNPV) are widely employed for large-scale production of heterologous proteins in cultured insect cells. The main reasons for the frequent application of this system are: (1) high levels of expression of foreign proteins, (2) insect cells are able to grow in a suspension culture and thus are easy to scale up, (3) the proteins synthesized in insect cells are processed and modified post-translationally, (4) well-developed manipulation techniques for the viral vectors resulting in a flexible expression system, and 5) non-pathogenic to humans, as the baculovirus host range is restricted to insects and invertebrates. Recombinant baculovirus vectors are being used for the production of individual proteins, as for sub-unit vaccine purposes, but also for higher order structures containing one or more proteins, such as enzyme complexes, viruses or virus-like particles.

Virus-like particles (VLPs) are highly organised structures that self-assemble from virus-derived structural proteins. These stable and versatile nano-particles possess excellent adjuvant properties capable of inducing innate and acquired immune responses (Ludwig & Wagner, 2007). During the past years, VLPs have been applied in other branches of biotechnology taking advantage of their structural stability and tolerance towards manipulation to carry and display heterologous molecules or serve as building blocks for novel nanomaterials. For immuno-therapeutic and prophylactic applications, many types of virus-like particles (VLP) have been successfully produced in baculovirus-infected insect cells (Noad & Roy, 2003, van Oers et al., 2006, Ramqvist et al., 2007). The first commercial achievement of baculovirus VLP technology for use in humans is the human papillomavirus (HPV) vaccine recently marketed by GlaxoSmithKline, prophylactic against HPV strains 16 and 18. The L1 protein of each of these types of HPV was expressed via a recombinant baculovirus vector and the resulting VLPs were combined to produce the vaccine Cervarix™ (Harper et al., 2006).

Today, there is a huge effort to develop baculovirus-derived influenza virus-like particles as well as influenza subunit-vaccines as a new generation of non-egg and non-mammalian cell culture-based candidate vaccine. Non-replicating influenza virus-like particles are effective in eliciting a broadened, cross-clade protective immune response to proteins from emerging H5N1 influenza isolates giving rise to a potential pandemic influenza vaccine candidate for humans that can be stockpiled for use in the event of an outbreak of H5N1 influenza (Bright et al., 2008). An influenza subunit vaccine produced in insect cells is close to FDA approval (Cox and Hollister, 2009). Similar strategies could in principle be applied for vaccines against the pandemic influenza such as the recent outbreak of Swine flu.

For gene therapy purposes, baculovirus-insect cell technology is also being applied for the production of infectious adeno-associated virus vectors (e.g. Urabe et al., 2002) and lentiviral vectors (Lesch et al., 2008). For the production of AAV vectors insect cells are co-infected with three recombinant baculoviruses—one producing the AAV replicase (REP) proteins, one carrying the cap functions for producing the AAV viral structural proteins (VP1, VP2. VP3), and a third baculovirus comprising an AAV-ITR vector with the ability to carry and transfer transgenes. Recently an improved version of this production had been published which is based on the use of only recombinant baculoviruses, one of them carrying the rep and cap functions of AAV (Smith et al. 2009). The produced AAV vector is indistinguishable from that produced in mammalian cells in its physical and biological properties. The yield of the AAV-ITR vector particles approached $5 \times 10^4$ per Sf9 insect cell demonstrating that the system is able to produce high quantities of AAV vectors in a simple manner. Currently, clinical trials with baculovirus-derived AAV vectors are underway for instance for lipoprotein lipase deficiency (Amsterdam Molecular Therapeutics B.V.). As an alternative, scalable approach to produce lentiviral vectors (Lesch et al., 2008) mammalian 293T cells were transduced simultaneously by four recombinant baculoviruses produced in insect cells to express all elements required for generation of a safe lentivirus vector. The unconcentrated lentiviral titers in mammalian cell culture media were on average $2.5 \times 10^6$ TU $ml^{-1}$, comparable to titers of the lentiviruses produced by conventional four-plasmid transfection methods. In addition, there is a general effort to convert lentiviral vector production methods into better scalable insect cell-based technologies.

Tjia et al., 1983 discovered that BVs can be internalized by mammalian cells and even some of the viral DNA reached the cell nucleus. Further studies showed that baculoviruses can enter mammalian cells and mediate expression of *Escherichia coli* chloramphenicol acetyl-transferase under the Rous sarcoma virus promoter (Carbonell et al., 1985). These findings led to the development of novel baculovirus-based gene delivery vehicles for mammalian cells (Boyce & Bucher, 1996, Hofmann et al., 1995, Condreay and Kost, 2007, Kaikkonen et al., 2008). Today, there is strong evidence that baculovirus-derived gene delivery vectors can mediate transient and stable expression of foreign genes in mammalian cells following antibiotic selection (Lackner et al., 2008).

There is still poor knowledge about transcriptional activities of baculovirus promoters in mammalian cells. It has been demonstrated that the transactivator protein IE1 of AcMNPV is functional in mammalian cells (Murges et al., 1997) as well as the early-to-late (ETL) promoter (Liu et al., 2006a,b). Among the other imperfectly explored areas is the interaction of baculoviruses with components of the mammalian immune system. AcMNPV virus is able to induce antiviral cytokine production, which protects cells from infection with vesicular stomatitis virus and influenza virus (Abe et al., 2003, Gronowski et al., 1999). AcMNPV is also recognized by Toll-like receptor 9 on dendritic cells and macrophages, and AcMNPV induces antitumor acquired immunity (Kitajima & Takaku, 2008). These results suggest that AcMNPV has the potential to be an efficient virus or tumor therapy agent which induces innate and acquired immunity. In spite of universally positive effects of AcMNPV on components of the humoral and adaptive cell-mediated immunity in mice, the interaction of baculoviruses with the human immune system can be slightly different. Additionally, immunoadjuvant properties of AcMNPV should be fully separated from immune response against target vaccine/biopharmaceuticals produced in insect cells.

These features of baculoviruses are strongly disadvantageous in cases where baculoviruses are utilized for the production of vaccines or viral vectors for therapeutical purposes (e.g. AAV, lentivirus). Contamination of the produced biopharmaceuticals with both types of baculovirus virions—budded virions (BVs) and occlusion-derived virions (ODVs) should, therefore, be avoided. In general, the recombinant proteins can be produced in insect cells as cytosolic, membrane-bound, or extra-cellularly secreted proteins. The latter secreted proteins are highly "contaminated" with baculoviral BVs present in the culture medium. It can be very difficult to separate undesirable baculovirus virions from produced recombinant biopharmaceuticals in some production and purification configurations. It has been shown for instance that these BVs can cause problems during the purification process of AAV vectors produced with baculovirus-insect cell technology (personal communication O. Merten, Genethon). On the other hand, there are also ODVs, always formed inside the nuclei of infected cells, in all conventional baculovirus-insect cell expression systems, even if occlusion bodies are not formed, due to replacement of the polyhedrin open reading frame by a desired gene. Analogously, these virions can co-purify with intracellularly produced recombinant proteins or VLPs during purification process.

In summary, the separation of recombinant proteins and, especially, VLPs from baculovirus particles, requires a lot of effort and occurs at high costs. In addition, it results in reduced efficiency of recombinant protein production. Therefore, the development of an improved baculovirus-insect cell technology allowing high expression of heterologous proteins while eliminating baculovirus BV and ODV production is highly desirable, and is the topic of this patent application. Such a baculovirus virion-free production system would represent a significant improvement over existing systems for the production of all kinds of biopharmaceuticals in insect cells.

The present invention is based on the identification of efficient baculovirus-insect cell based methods for producing biopharmaceuticals with reduced amounts or absence of baculovirus virions.

An object of the present invention thus provides a method for the production of a biopharmaceutical product, comprising:
(a) infecting a biopharmaceutical-producing insect cell with at least one baculovirus, said at least one baculovirus comprising a genome coding for said biopharmaceutical product, and (b) maintaining the biopharmaceutical-producing insect cell under conditions such that the biopharmaceutical product is produced,
wherein each genome of said at least one baculovirus is deficient for at least one gene essential for proper baculovirus virion assembly or wherein said biopharmaceutical-producing insect cell comprises an expression control system allowing the inactivation of at least one gene essential for proper baculovirus virion assembly.

In an embodiment, the invention relates to the above method, wherein said at least one gene essential for proper baculovirus virion assembly is made deficient in said genome by mutation, for example by way of nucleotide substitution, insertion or deletion.

In another embodiment, the invention relates to the above method, wherein the biopharmaceutical-producing insect cell is a recombinant insect cell comprising a construct expressing a dsRNA specific for the at least one gene essential for proper baculovirus virion assembly, the dsRNA being optionally expressed under the control of an inducible promoter.

In a further embodiment, the invention relates to the above method, wherein the at least one baculovirus is produced before step (a) in a baculovirus-producing cell expressing a complementing copy of the at least one gene essential for proper baculovirus virion assembly.

In yet another embodiment, the invention relates to the above method, wherein the at least one gene essential for proper baculovirus virion assembly is selected from vp80, vp39, vp1054 and p6.9.

In another embodiment, the invention relates to the above method, wherein the deficiency or inactivation of the at least one gene essential for proper baculovirus virion assembly does not affect very late gene expression from said baculovirus in comparison to very late gene expression from the wild-type baculovirus vector.

In yet another embodiment, the invention relates to the above method, wherein the at least one baculovirus is preferably derived from AcMNPV or *Bombyx mori* (Bm) NPV.

In a further embodiment, the invention relates to the above method, wherein the biopharmaceutical product is a recombinant protein, a recombinant virus, a virus-derived vector, or a virus-like particle.

In another embodiment, the invention relates to the above method, wherein the biopharmaceutical product is a recombinant AAV vector. Furthermore, the invention relates to the above method, wherein the biopharmaceutical product is a vaccine. Representative examples of vaccines than can be produced with the method of the present invention include, but are not limited to, influenza virus-like particles or influenza subunit vaccines, and vaccines against Human papillomavirus.

In a further embodiment, the invention relates to the above method, wherein the biopharmaceutical product is coded by at least one gene introduced in the recombinant baculovirus genome under the control of a baculovirus promoter, preferably the p10 or polyhedrin promoter.

Another object of the invention provides the use of a baculovirus-insect cell system for the production of a biopharmaceutical product wherein the baculovirus-insect cell system comprises a biopharmaceutical-producing insect cell infected with at least one recombinant baculovirus, wherein:
the, or each, recombinant baculovirus comprises a recombinant baculovirus genome that encodes the biopharmaceutical product, or at least one component of the biopharmaceutical product, and the recombinant baculovirus genome is deficient for at least one gene essential for proper assembly of said baculovirus, or the biopharmaceutical-producing insect cell comprises an expression control system allowing the inactivation of the at least one gene essential for proper baculovirus virion assembly.

Yet another object of the invention relates to a bacmid comprising a baculovirus genome, wherein said genome is deficient for a gene essential for proper baculovirus virion assembly, preferably wherein the genome of said baculovirus is deficient for vp80, vp39, p6.9 or vp1054. In a particular aspect, said bacmid is derived from AcMNPV and is lacking the vp80 ORF.

A further object of the invention relates to a recombinant AcMNPV baculovirus vector, wherein the genome of said baculovirus is deficient for a gene essential for proper baculovirus virion assembly, preferably wherein the genome of said baculovirus is deficient for vp80, vp39, vp1054 or p6.9. In a particular aspect, the invention relates to a recombinant AcMNPV baculovirus lacking the vp80 ORF.

The invention has also as an object an insect cell infected with the above mentioned recombinant AcMNPV baculovirus.

Another object of the invention relates to an insect cell, comprising a construct expressing a dsRNA specific for a gene essential for proper baculovirus virion assembly, preferably directed against vp80, vp39, vp1054 and/or p6.9, said construct being preferably integrated in the genome of the insect cell.

A further object of the invention relates to an insect cell comprising an expression cassette coding for a gene essential for proper baculovirus virion assembly. In particular, the invention relates to said insect cell, wherein the gene coded by the expression cassette is vp80, vp39, vp1054 and/or p6.9.

Another object of the invention relates to a method for the production of a baculovirus deficient for at least one gene essential for proper baculovirus virion assembly, comprising the step of transfecting an insect cell comprising an expression cassette coding for a gene essential for proper baculovirus virion assembly, with a bacmid comprising a baculoviral genome, wherein said genome is deficient for a gene essential for proper baculovirus virion assembly, preferably wherein the genome of said baculovirus is deficient for vp80, vp39, p6.9 and/or vp1054, wherein the gene essential for proper baculovirus virion assembly deficient in said bacmid is the gene coded by the expression cassette comprised in said insect cell.

The present invention relates to the production of biopharmaceuticals in insect cells by implementing a baculoviral system, but without coproduction of contaminating baculovirus virions. The methods of the invention simplify the downstream processing of biopharmaceuticals produced in insect cells to a large extent.

Thus, the invention relates to methods for the production of a biopharmaceutical product implementing a baculoviral system designed to avoid the production of contaminating baculoviral virions. The method of the present invention comprises the infection of biopharmaceutical-producing insect cells with at least one baculovirus coding for said biopharmaceutical product.

Baculoviruses are enveloped DNA viruses of arthropods, two members of which are well known expression vectors for producing recombinant proteins in cell cultures. Baculoviruses have circular double-stranded genomes (80-200 kbp) which can be engineered to allow the delivery of large genomic content to specific cells. The viruses used as a vector are generally *Autographa californica* multicapsid nucleopolyhedrovirus (AcMNPV) or *Bombyx mori* (Bm) NPV (Kato et al., 2010).

Baculoviruses are commonly used for the infection of insect cells for the expression of recombinant proteins. In particular, expression of heterologous genes in insects can be accomplished as described in for instance U.S. Pat. No. 4,745,051; Friesen et al (1986); EP 127,839; EP 155,476; Vlak et al (1988); Miller et al (1988); Carbonell et al (1988); Maeda et al (1985); Lebacq-Verheyden et al (1988); Smith et al (1985); Miyajima et al (1987); and Martin et al (1988). Numerous baculovirus strains and variants and corresponding permissive insect host cells that can be used for protein production are described in Luckow et al (1988), Miller et al (1986); Maeda et al (1985) and McKenna (1989).

According to the present invention, any genome derived from a baculovirus commonly used for the recombinant expression of proteins and biopharmaceutical products may be used. For example, the baculovirus genome may be derived from for instance AcMNPV, BmNPV, *Helicoverpa armigera* (HearNPV) or *Spodoptera exigua* MNPV, preferably from AcMNPV or BmNPV. In particular, the baculovirus genome may be derived from the AcMNPV clone C6 (genomic sequence: Genbank accession no. NC_001623.1—SEQ ID NO:1).

The terms "Biopharmaceutical", "Biopharmaceuticals" and "Biopharmaceutical Product" are intended to define medical drugs produced using biotechnology. As such, biopharmaceuticals may correspond to recombinantly produced drugs such as recombinant proteins, notably recombinant hormones or recombinant proteins for use as vaccines, viruses, for example therapeutic recombinant AAV or other viral vectors for use in gene therapy, as well as virus-like particles (or VLPs). Such biopharmaceuticals are intended to be administered to a subject in need thereof for the prophylactic or curative treatment of a disease condition in said subject which may be of either human or animal origin.

A biopharmaceutical product may correspond to a single chain protein or peptide, for example in the case of a therapeutic recombinant protein, or may be a complex structure such as a virus or a virus-like particle. In the latter two cases, the components of the complex may be expressed from several recombinant baculoviruses, each carrying at least one component of the complex structure, or from a single baculovirus whose genome has been genetically modified by the insertion of sequences encoding all the components of the complex. For example, for the production of a recombinant AAV, a system comprising three baculoviruses may be used: a baculovirus coding for the AAV Rep proteins, a baculovirus coding the AAV Cap proteins and a baculovirus coding the AAV-ITR genome comprising a therapeutic gene between the two AAV ITRs. A system comprising two baculoviruses is also available now, for which the DNA sequences coding for the AAV Rep proteins and the AAV Cap proteins are provided by one baculovirus.

In a preferred embodiment of the invention, the heterologous gene(s) encoding the biopharmaceuticals are placed under the control of a baculoviral promoter. For example, the heterologous gene(s) is (are) placed under the control of the polyhedrin or p10 promoter, or of any other baculoviral promoter commonly used for expression in an insect cell (e.g. ie-1, p6.9, gp64 or the *Orchyia pseudotsugata* (Op) MNPV ie-2 promoter). In a preferred embodiment of the invention, the baculoviral promoter is selected from very late expression promoters, for example from the p10 and polyhedrin promoters, preferably under the control of the polyhedrin promoter.

In the method of the present invention, at least one gene essential for proper baculovirus virion assembly is either absent from the genome of the recombinant baculovirus(es) implemented in the above described method, or its expression is prevented. The inventors have shown that the deletion or inactivation of such genes results in the reduction, or even the complete absence, of budded virions and/or occlusion derived virions, the two forms of a baculovirus.

A "gene essential for proper baculovirus virion assembly" is a gene whose deficiency or inactivation in a baculovirus-producing cell negatively impacts the number of BVs and ODVs produced from said cell. Such a gene may be identified as provided in the herein below examples. In particular, one can use double stranded RNAs specific for a particular baculoviral gene to assess the impact of the absence of said particular gene on the production of BVs and ODVs, for example by detecting the expression of a reporter gene present in the baculoviral genome in the cell culture, and thus determine the spreading or absence of spreading of the baculovirus (single-infection phenotype). Alternatively baculovirus virions may be detected by the presence of baculoviral structural proteins or genome sequences in the culture medium when sampling for BV production. Both virion types may be detected by electron microscopy.

In a preferred embodiment of the invention, the gene essential for proper baculovirus virion assembly is selected from vp80, vp39, vp1054 and p6.9. More preferably, the gene is selected from vp80 and vp39, said gene being preferably vp80.

The invention provides the inactivation of genes essential for proper baculovirus virion assembly. Several strategies may be implemented for this purpose, and in particular: the mutation, for example by deletion, of the selected gene(s) in the recombinant baculovirus genome; or the reduction of the expression of the selected gene by an expression control system provided in the biopharmaceutical-producing insect cell intended to be infected by the baculovirus.

Preferably, the expression control system involves the down-regulation by RNA interference of the expression of the protein(s) encoded by the selected gene(s).

In one embodiment of the invention, the genome of the at least one baculovirus implemented in the method of the invention is deficient for at least one gene essential for proper baculovirus virion assembly, in particular for a gene coding for vp80, vp39, vp1054 and/or p6.9, preferably for vp80 and/or vp39, and even more preferably for vp80. More particularly, said genome is derived from AcMNPV, more particularly from AcMNPV clone C6 genome sequence (Genbank accession no. NC_001623.1—SEQ ID NO: 1). Accordingly, in one aspect the invention provides the method as defined above, wherein the baculoviral genome is an AcMNPV genome, in particular an AcMNPV clone C6 genome, deficient for the gene coding for vp80, vp39, vp1054 and/or p6.9, preferably for vp80 and/or vp39, and even more preferably for vp80. As is well known in the art and specified in Genbank accession no. NC_001623.1, these genes are positioned as follows in AcMNPV clone C6 genome (i.e. in SEQ ID NO:1): positions 89564-91639 for vp80; positions 75534-76577 for vp39 (complementary sequence); positions 45222-46319 for vp1054; positions 86712-86879 for p6.9 (complementary sequence).

It should be noted that in case the biopharmaceutical product is a complex product comprising various subunits each encoded by different baculoviruses, the genomes of all the implemented recombinant baculoviruses are deficient for the selected essential gene, so as to avoid complementation of one genome by another. In other words, when several baculoviruses are used to infect the same biopharmaceutical-producing insect cell, each of these baculoviruses are deficient for the same gene(s) essential for proper baculovirus virion assembly.

According to the present invention, a gene may be made deficient by mutating said gene. A mutation of a gene essential for proper baculovirus virion assembly is a modification of said gene that results in the complete absence of a functional essential gene product. Accordingly, said mutation may result in the introduction of one or several stop codons in the open reading frame of the mRNA transcribed from the gene essential for proper baculoviral virion assembly or may correspond to the deletion, either total or partial, of the gene essential for proper baculovirus virion assembly. A gene essential for proper baculoviral virion assembly may be mutated by way of nucleotide substitution, insertion or deletion in the sequence of all or a part of the wild type gene (for example in the sequence provided in Genbank Accession No. NC_001623.1, for a genome derived from AcMNPV). The mutation may correspond to the complete deletion of the gene, or to only a part of said gene. For example, one may delete at least 50%, more preferably at least 60%, more preferably at least 70%, more preferably at least 80% and even more preferably at least 90% of the gene essential for proper baculoviral virion assembly.

The mutant baculoviral genome may be produced using standard methods well known in the art, such as site-directed mutagenesis (see, e.g., Sambrook et al. (1989)) and Lambda red recombination (Datsenko & Wanner, 2000). The gene essential for proper baculovirus virion assembly may in particular be deleted as provided in the below examples. In summary, one can make use of the mutant LoxP sites described by Suzuki at al. (2005), by replacing either totally or in part the gene essential for proper baculovirus virion assembly with a reporter gene flanked by mutant LoxP sites by recombination. The reporter gene (for example the gene coding for chloramphenicol acetyl transferase (cat) is then excised by implementing a recombination with Cre recombinase.

This embodiment is illustrated in the below examples and is detailed for baculoviruses whose genome has been modified by deleting a 2074-bp fragment of the vp80 ORF in the AcMNPV genome. This particular genome is part of the present invention, but is given as a non limiting example of what is a mutant baculoviral genome according to the invention.

It should be noted that recombinant engineering of the baculovirus genome may result in the insertion of several sequences like cloning sites or recombination sites (for example one remaining LoxP site after recombination with Cre recombinase). This is irrelevant as long as the resulting genome is made deficient for the selected gene essential for proper baculovirus virion assembly.

In this embodiment, wherein the genome of the at least one baculovirus is deficient for at least one gene essential for proper assembly of baculovirus virion, the production of recombinant budded baculovirus particles needed for the initial infection of the cells producing the bio-pharmaceuticals requires the implementation of special cells rescuing the deficient gene, i.e. these baculovirus-producing cells express the selected gene. In other terms, the baculovirus-producing cell expresses a complementing copy of the at least one gene essential for proper baculoviral virion assembly which is deficient in the baculovirus genome. For example, a Sf9-derived cell line constitutively producing the product of the gene essential for proper assembly of the baculovirus virion may be established. This recombinant cell line is used for production of baculovirus seed stock while conventional insect cell lines like Sf9, Sf21 or High-five cell lines can be infected with the produced baculovirus for heterologous expression of the biopharmaceutical product. Accordingly, the invention also relates to an insect cell modified so as to express a gene essential for proper baculovirus assembly, said gene being mutated in a baculovirus used for the production of biopharmaceuticals, as defined above. Such a cell line used for the production of the mutant baculovirus vector implemented in the method of the present invention is referred to as a "baculovirus-producing cell". When the baculovirus genome is deficient for a gene essential for proper baculovirus virion assembly, the baculovirus-producing insect cell must provide and express said gene in order to complement the deficiency and to produce an infectious baculovirus. In a particular embodiment, the insect cell used for the production of the baculovirus is modified by transfection with an expression cassette coding for at least one gene essential for proper baculovirus virion assembly. In an embodiment, said expression cassette is integrated in the genome of said cell. One may also use insect cells transiently transfected with at least one plasmid comprising the expression cassette. The term "expression cassette" denotes a construct comprising the coding sequence of a gene of interest functionally linked to expression control sequences. Such an expression cassette may be a plasmid comprising the ORF of a gene essential for proper baculovirus virion assembly placed under the control of a promoter functional in the selected insect cell, and does not contain baculoviral genome sequences other than the gene essential for proper baculovirus virion assembly to be complemented and optionally the promoter sequence allowing the expression of said gene (in particular, an expression cassette is not a bacmid or any other baculoviral entire genome). Exemplary expression control sequences may be chosen among promoters, enhancers, insulators, etc. In one embodiment, the complementing gene is derived from the genome of the baculovirus in which the gene essential for proper baculovirus virion assembly has been made deficient. In another embodiment, the complementing gene originates from the genome of a different baculovirus species than the baculovirus genome used for the production of biopharmaceuticals. For example, the baculovirus used for the production of biopharmaceuticals may be derived from the AcMNPV genome, and the complementing gene introduced in the baculovirus-producing cell is derived from BmNPV or SeMNPV. More specifically, the baculovirus genome may be made deficient for vp80, vp39, vp1054 and/or p6.9 and the baculovirus-producing cell may comprise a copy of a gene from BmNPV or SeMNPV able to complement these genes (e.g. as provided in the examples, p6.9 is deleted in the AcMNPV genome and the baculovirus-producing cell provides a rescuing copy of the SeMNPV p6.9 gene).

The invention thus also provides a method for the production of a baculovirus deficient for at least one gene essential for proper baculovirus virion assembly, comprising the step of transfecting an insect cell comprising an expression cassette coding for a gene essential for proper baculovirus virion assembly, with a bacmid comprising a baculoviral genome, wherein said genome is deficient for a gene essential for proper baculovirus virion assembly, preferably wherein the genome of said baculovirus is deficient for vp80 or vp39, p6.9 and/or vp1054, wherein the gene essential for proper baculovirus virion assembly deficient in said bacmid is the gene coded by the expression cassette comprised in said insect cell. According to this method, the gene deficient in the baculoviral genome is complemented by the gene expressed in the insect cell. The cells transfected with the bacmid are maintained in conditions such that baculovirus virions are produced. These produced baculovirus virions, which comprise a genome where at least one gene essential for proper baculovirus virion assembly is lacking, are then collected for their subsequent use for infecting biopharmaceutical-producing insect cells for the production of the biopharmaceutical.

In the embodiment where the genome of the baculovirus is deficient for at least one gene essential for baculovirus virion assembly, the biopharmaceutical-producing insect cell must be unable to complement the deficiency of said gene. Otherwise, the deficiency would be rescued by the biopharmaceutical-producing cell and BVs and ODVs might be produced. The presence or absence of a gene essential for proper baculovirus assembly may be monitored for example by checking said cell by a PCR specific to said gene or by detection of the protein product of this gene (for example by western-blot with an antibody specific to said gene product). Cells expressing a functional product of the gene essential for proper baculovirus virion assembly which has been made deficient in the genome of the implemented baculovirus intended to infect said cell must be disregarded as biopharmaceutical producing cells.

In another embodiment of the invention, the expression of the gene essential for proper assembly of baculovirus virions is controlled by an expression control system. The term "expression control system" defines a modification of the baculovirus-producing insect cell system/the biopharmaceutical-producing cell system and/or yet another adaptation of the viral genome, resulting in the specific regulation of the gene essential for proper baculovirus virion assembly. This system may be an inducible expression system (for example Tet-On, Tet-Off, ecdysone-based systems (Dai et al., 2005) or baculovirus homologous region (hr) containing elements, such as the hr2 system described by Aslanidi et al. (2009), allowing the desired triggering or shutdown of the essential gene, an RNA interference expressing construct or a combination of these.

In a particular embodiment, the expression of the gene essential for proper assembly of baculovirus is inactivated by RNA mediated silencing, or RNA interference (Salem & Maruniak, 2007, Kanginakudru et al., 2007). Preferably, an insect-cell derived cell line, in particular a Sf9-derived cell line, is established by stably transforming such a cell with a construct coding for a gene-specific double stranded RNA (dsRNA) to silence the expression of the gene essential for proper baculovirus virion assembly. This dsRNA expressing cell line is used for the expression of the biopharmaceutical product after infection with the recombinant baculovirus(es) carrying the gene coding for said biopharmaceutical product. In this embodiment, seed stock recombinant baculovirus(es) may be produced with conventional Sf9, Sf21 or High-Five cell lines (i.e. without the need of a complementing copy of the gene in the cell), since in this case the baculovirus genome comprises the wild-type gene essential for proper baculovirus virion assembly.

In yet another embodiment of the invention, the gene essential for proper baculovirus virion assembly is placed under the control of an inducible promoter, allowing either the expression or repression of said gene under controlled conditions.

In a preferred embodiment, the number of baculovirus virions produced in the method of the present invention is reduced by at least 50% in comparison to the number of baculovirus otherwise produced by the biopharmaceutical-producing cell using a baculovirus genome comprising all the genes essential for proper baculovirus virion assembly. More preferably, the number of baculovirus virions is reduced by at least 60%, at least 70%, at least 80%, at least 90% and most preferably by at least 95% in comparison to a wild type baculovirus genome.

As discussed above, the use of insect cell/baculovirus systems for the production of biopharmaceuticals in the prior art is characterized by the coproduction of huge quantities of recombinant baculoviruses (and may be over $10^8$ pfu/ml) in parallel to the biopharmaceutical product, needing carefully developed and optimized downstream processing protocols to inactivate and eliminate this baculovirus contamination. Inactivation can be performed by the addition of a detergent step leading to disintegration of the lipid layer of the contaminating baculovirus, such as used for the purification of virus-like particles for vaccine purposes (porcine parvovirus-VLPs (Maranga et al. (2002)) or rotavirus-VLPs (Mellado et al. (2008)) or the purification of different serotypes of AAV (Smith et al. 2009).

Further efficient separation steps have been used: centrifugation (Wang et al. (2000); Maranga et al. (2002); Mellado et al. (2008)), microfiltration (Tellez (2005)), negative elimination of baculovirus proteins (e.g. Mellado et al. (2008)) or positive affinity chromatography (retention/capture of a biopharmaceutical—flow through of the contaminating proteins, such as capture of the vp7 protein of rotavirus by Concanavalin A chromatography (Mellado et al. (2008)), capture of the immunogenic chimeric rVP2H infectious bursal disease virus particles by immobilized metal-ion affinity chromatography (Wang et al. (2000)) or capture of different AAV serotypes by immunoaffinity chromatography using camelid antibodies (Smith et al. 2009). In particular, due to the use of highly specific immunoligands, the use of immunoaffinity allows the complete separation of the to be purified biopharmaceutical (e.g. specific AAV) from any contaminant, and in the case of the baculovirus system, from the huge contamination by baculovirus due to the concomitant production of baculovirus in parallel to the biopharmaceutical.

These references present very clearly the need of these different process steps for inactivating and eliminating residual baculovirus contaminants, because without these steps, the biopharmaceutical product is still considerably contaminated by various baculovirus proteins and cannot be used for clinical purposes.

The method of the present invention allows a significant reduction of the number of contaminating baculovirus virions, or even a complete absence. As a consequence, a reduced number of purification steps will be necessary for getting a biopharmaceutical for clinical purposes (or even no purification step if no baculoviral virion is produced). Thus, the biopharmaceutical production and purification protocol is simplified because by using the method of the present invention, the need for eliminating residual baculovirus virion is greatly reduced. In case a simplified purification protocol is still to be applied, the skilled artisan may select at least one of the above identified methods and protocols to obtain a purified biopharmaceutical product.

Preferably, the selected essential gene is a gene whose inactivation does not affect baculoviral very late gene expression, compared to the original baculovirus vector. In the AcMNPV genome (and other alpha-baculoviruses), the p10 and polyhedrin promoters are the very late expression promoters and it should be noted that in baculovirus/insect cell production systems, the heterologous gene is most commonly inserted under the control of these very strong promoters allowing expression of very large amounts of recombinant proteins. The inactivation of a gene essential for proper baculovirus virion assembly, which does not affect very late gene expression is thus preferred. The term "does not affect very late gene expression" denotes the fact that the level of recombinant protein expression from very late baculovirus promoter comprised in the genome of a baculovirus modified according to the invention is at least 70% in comparison to the levels obtained from a non-modified genome, more preferably greater than 80%, more preferably greater than 90%. It should be mentioned that the level of expression of a biopharmaceutical product from a very late baculoviral promoter may even be greater than 100% of the level obtained with the non-modified vector in the method of the present invention.

Among the genes tested by the inventors, the vp80 gene is particularly preferred since its deletion does not affect very late expression, while it totally prevents production of BVs and results in a significant reduction in the number of intracellular nucleocapsids, the precursors of ODVs.

Very late expression may be evaluated by placing a reporter gene, for example a gene coding for a GFP, in particular egfp, or a luciferase gene, under the control of the polyhedrin or p10 promoter in a wild type AcMNPV vector and in a mutant AcMNPV genome from which the essential gene has been inactivated, and by comparing the expression of the product of the reporter gene from both genomes. Preferably, very late expression from the vector with a mutated baculovirus backbone is at least 60% of the expression level obtained with the wild type AcMNPV vector and preferably higher than 80%, more preferably higher than 90%, as measured from a reporter gene under the control of either p10 or polyhedrin gene promoters.

The invention also relates to a method for screening baculoviral genes, the inactivation of which could be useful for producing biopharmaceuticals without contaminating baculovirus virions in an insect cell—baculovirus system as defined above, comprising:

a) providing a cell culture of cells containing a baculoviral genome;

b) contacting said cell culture with means for inactivating at least one test baculoviral gene of said baculoviral genome, for example with RNA interference; and c) testing virion formation from said cell culture in comparison to virion formation from a cell culture not contacted with said means;

wherein a test gene is selected as potentially useful for producing biopharmaceuticals if its inactivation results in a reduction of baculoviral virion formation.

In a particular embodiment, the method for screening of the invention further comprises step d) of testing very late gene expression from the cell culture contacted with said means in comparison to very late gene expression from a cell culture not contacted with said means;

wherein a test gene is selected as potentially useful for producing biopharmaceuticals if its inactivation results in a reduction of baculoviral virion formation and if it does not affect very late gene expression from said baculoviral genome.

The invention also relates to a method for screening baculoviral genes, the inactivation of which could be useful for producing biopharmaceuticals without contaminating baculovirus virions in an insect cell—baculovirus system as defined above, comprising:

inactivating at least one test gene of a baculoviral genome (for example by deletion of said test gene in said genome);

evaluating baculoviral very late gene expression from said baculoviral genome as defined above;

determining production of baculoviral virions from cells containing said baculoviral genome;

wherein a gene is selected as potentially useful for the production of biopharmaceuticals if its inactivation results in a reduction in the production of baculoviral virions, and does not affect very late gene expression from said baculoviral genome, as defined above.

In a particular embodiment of the method for screening a baculoviral gene, the inactivation of which could be useful for producing biopharmaceuticals, the inactivation of the test gene is carried out with dsRNA specific for said test gene. In particular, the candidate baculovirus gene can be identified by knocking down its expression by RNA interference to test its role in virion formation.

The invention will now be illustrated with the following examples, which are provided as non limiting exemplary embodiments of the invention.

LEGENDS TO THE FIGURES

The patent or application file contains at least one drawing executed in color. Copies of this patent or patent application publication, with color drawing(s), will be provided by the Office upon request and payment of the necessary fee.

FIGS. 1A-1D. dsRNA-mediated gene silencing screening. Insect Sf9 cells were seeded in 24-well tissue culture plates ($2 \times 10^5$ cells/well) in 1 ml Sf-900 II SFM culture medium at 28° C. After two hours, the culture medium was removed, and the cells were infected with recombinant baculovirus carrying the egfp gene under control of the polyhedrin promoter (AcMNPV-EGFP) under standard conditions.

(A) Determination of very late gene expression level using fluorescent microscopy. Cells were infected at MOI=10 $TCID_{50}$ units/cell and transfection with gene-specific dsRNA for vp1054, vp39, vp80, dbp and ec-27 was performed at 1 h post infection (p.i.). The level of very late gene expression was checked by EGFP-specific fluorescence at 48 h p.i. dsRNAs specific for egfp and cat sequences were used as RNAi controls. (B) Measurement of very late gene expression levels by an immunoblotting-based assay. The cells were infected with AcMNPV-EGFP at MOI=1 and transfection with gene-specific dsRNA was also performed at 1 h p.i. The level of very late gene expression was analyzed by using a rabbit anti-EGFP polyclonal antiserum at 48 h p.i. Anti-vp39 and anti-α-tubulin antibodies were used as internal controls. (C) Titration and detection of produced budded virions in dsRNA-treated cells. Budded virions were harvested at 36 hours p.i., and used either for end-point dilution assays to measure titers of infectious virions, or for PCR-based detection to check the presence of virus particles. (D) Presence of occlusion-derived virions and rod-shaped structures in vp39- and vp80-down-regulated cells. The cells were harvested 36 hours p.i., lysed, and the cell lysates were ultracentrifuged through a cushion of 40% sucrose solution (45,000 rpm for 1 hour, Beckman SW55). Pellets were resuspended in demi-water and analyzed by negative staining electron microscopy. The bars represent 100 nm.

Figure 2A:
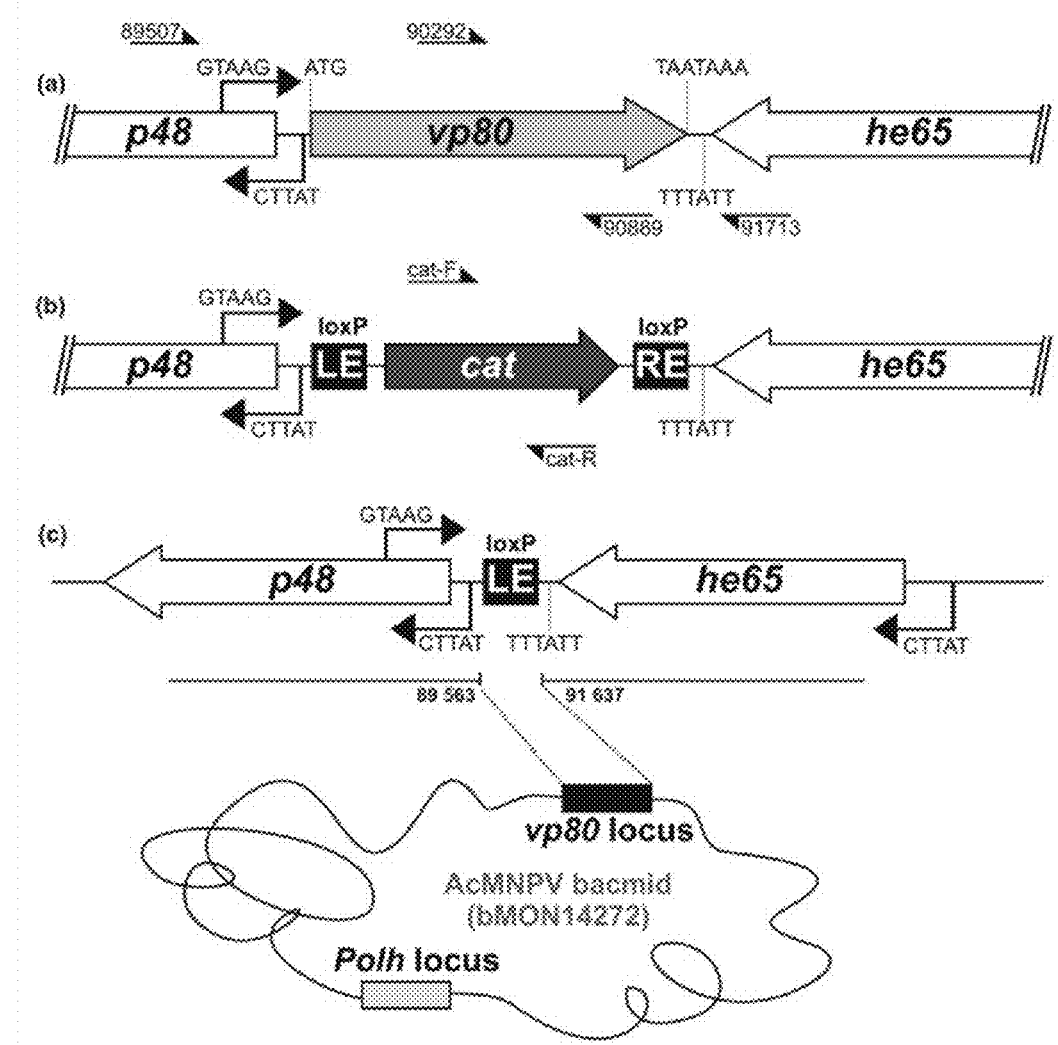
Figure 2B:
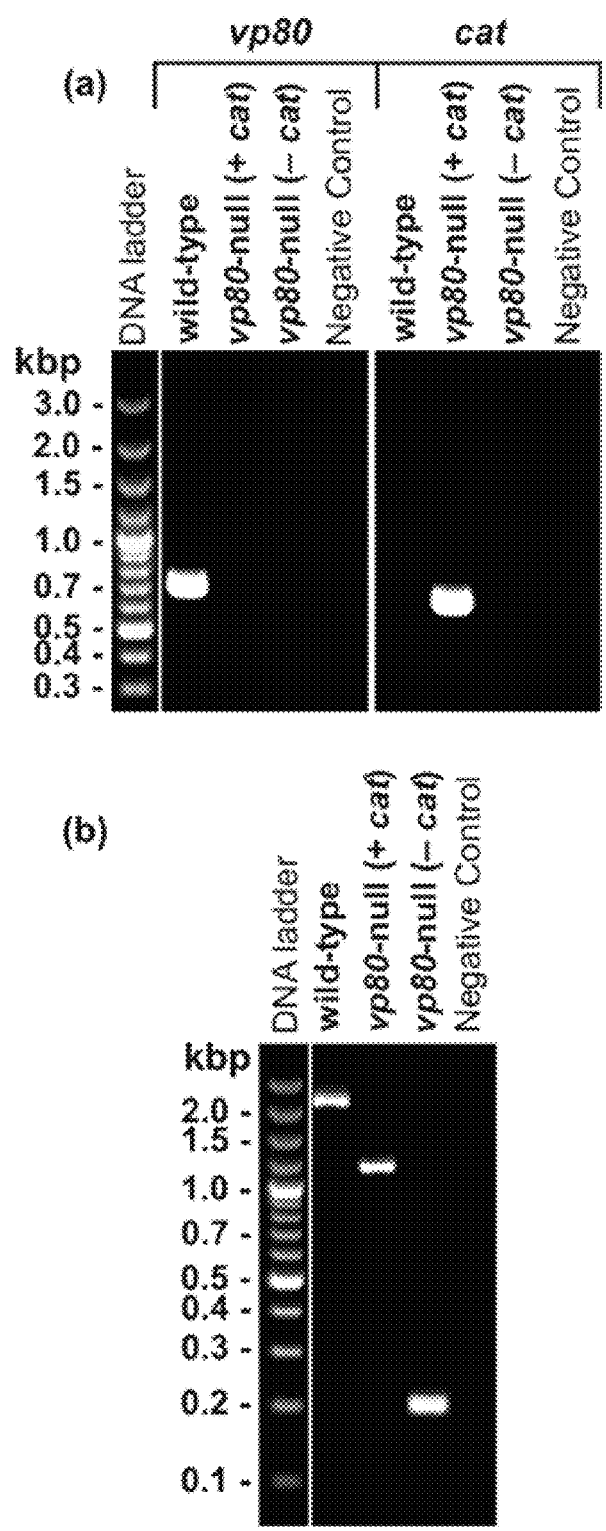

FIGS. 2A-2B. Construction of the AcMNPV vp80-null bacmid. (A) Strategy for construction of a vp80-null bacmid containing a complete deletion of the AcMNPV vp80 open-reading frame via homologous recombination in *E. coli*. At the first step, a 2074-bp fragment encompassing the vp80 ORF was deleted and replaced with a sequence cassette containing the chloramphenicol (cat) resistance gene flanked by modified loxP (LE and RE) sites. Subsequently, the antibiotic resistance gene (cat) was eliminated from the bacmid sequence using the Cre/loxP recombination system. The promoter sequence of the p48 gene and the polyadenylation signal of the he65 gene remained intact. Oligonucleotide pairs were used in PCR analysis of the wild-type locus and two vp80 knock-out genotypes to confirm the deletion of the vp80 ORF and the correct insertion/deletion of the chloramphenicol resistance gene cassette, as indicated by unilateral arrows. Their names are designated according to nucleotide sequence coordinates. Primers for cat gene cassette amplification are named cat-F and cat-R. (B) PCR-based detection of the presence or absence of sequence modifications in the vp80 locus in the original AcMNPV bacmid (Ac-wt), Ac-vp80null(+cat), and Ac-vp80null(−cat) bacmids. The top figure confirms the vp80 gene deletion and the insertion of the cat cassette into the vp80 locus with primer pairs 90292/90889 and cat-F/cat-R. The bottom figure shows PCR-based verification of the correct recombination processes in the vp80 locus using the 89507/91713 primer pair.

Figure 3C:
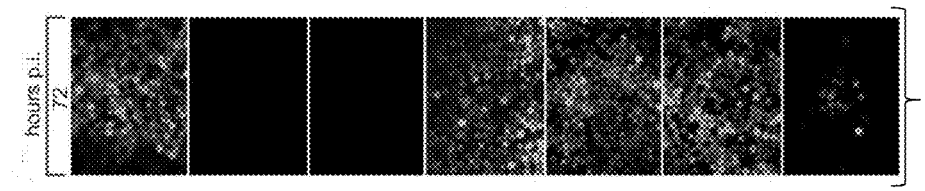
Figure 3B:
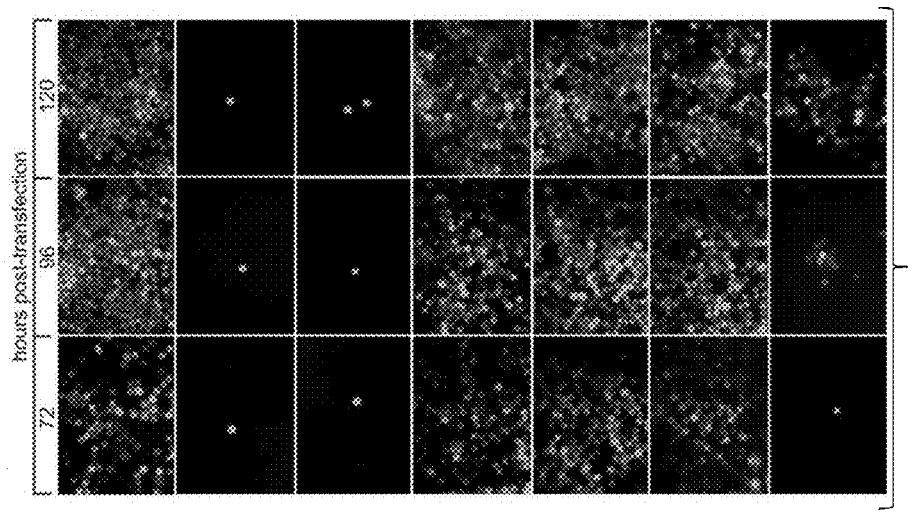
Figure 3A:
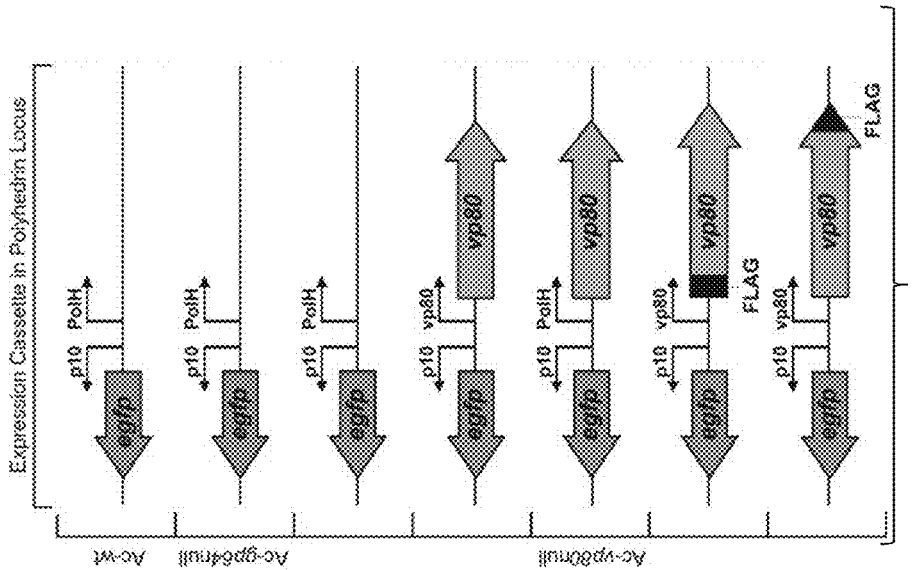
Figure 4A:
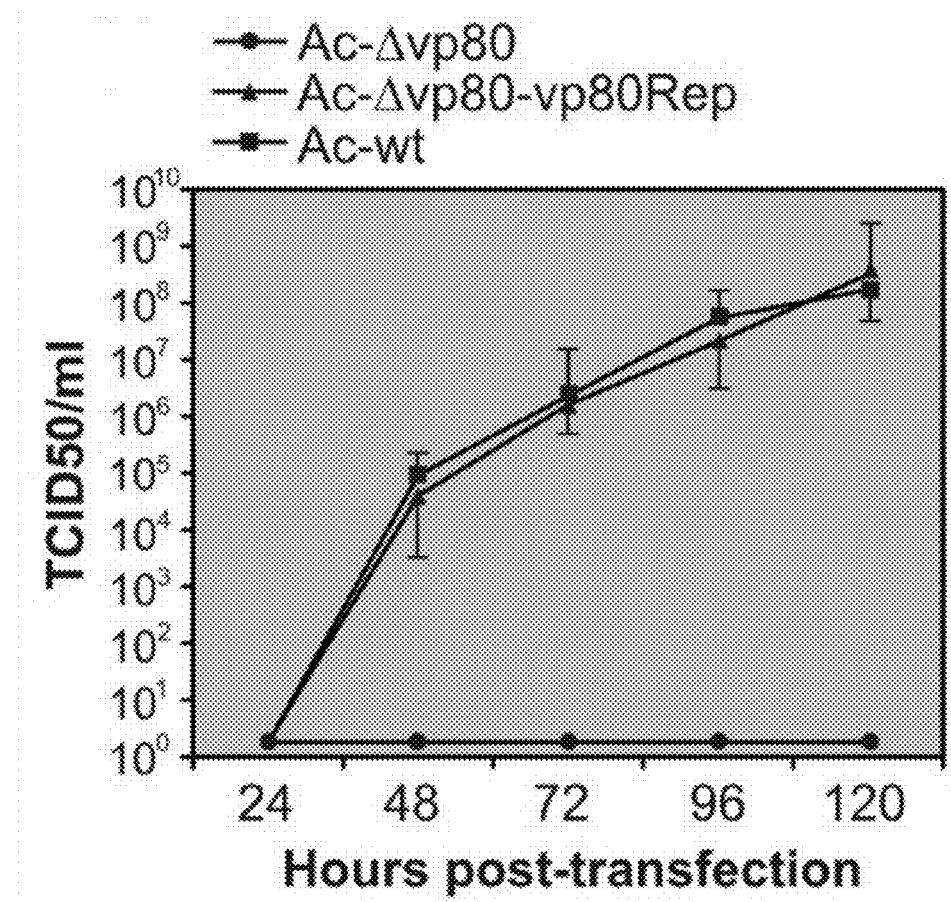
Figure 4B:
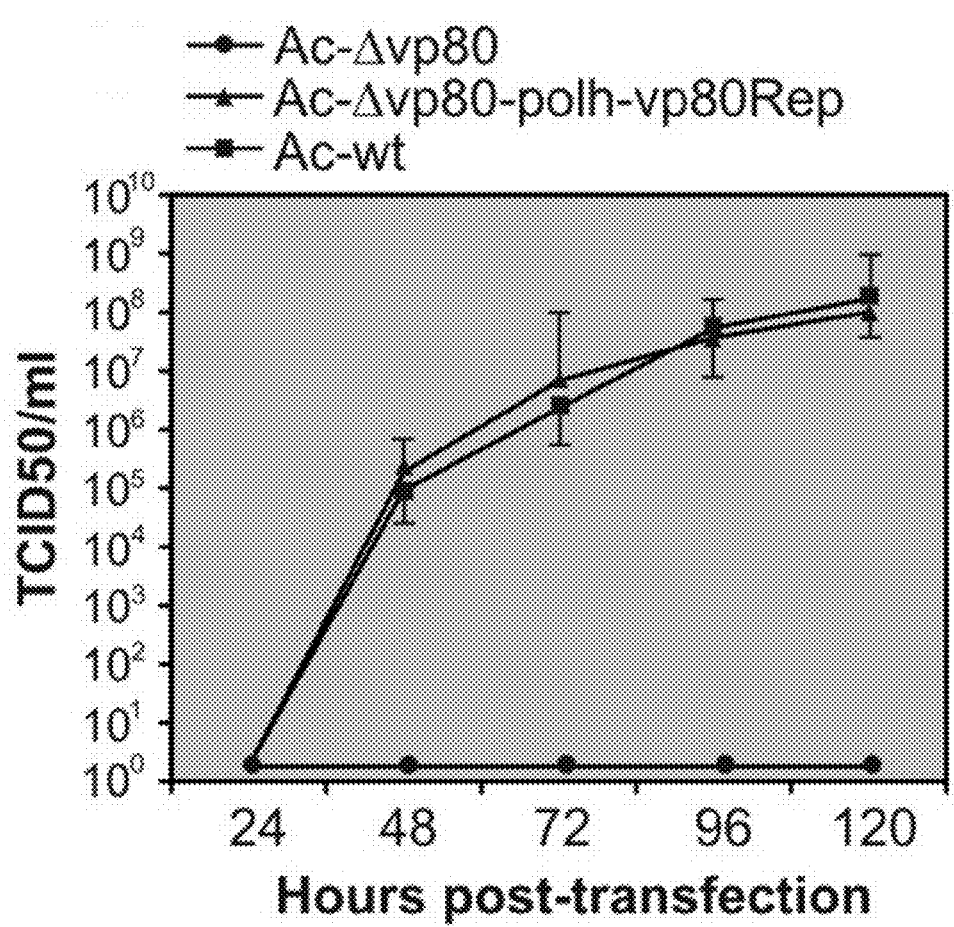
Figure 4C:
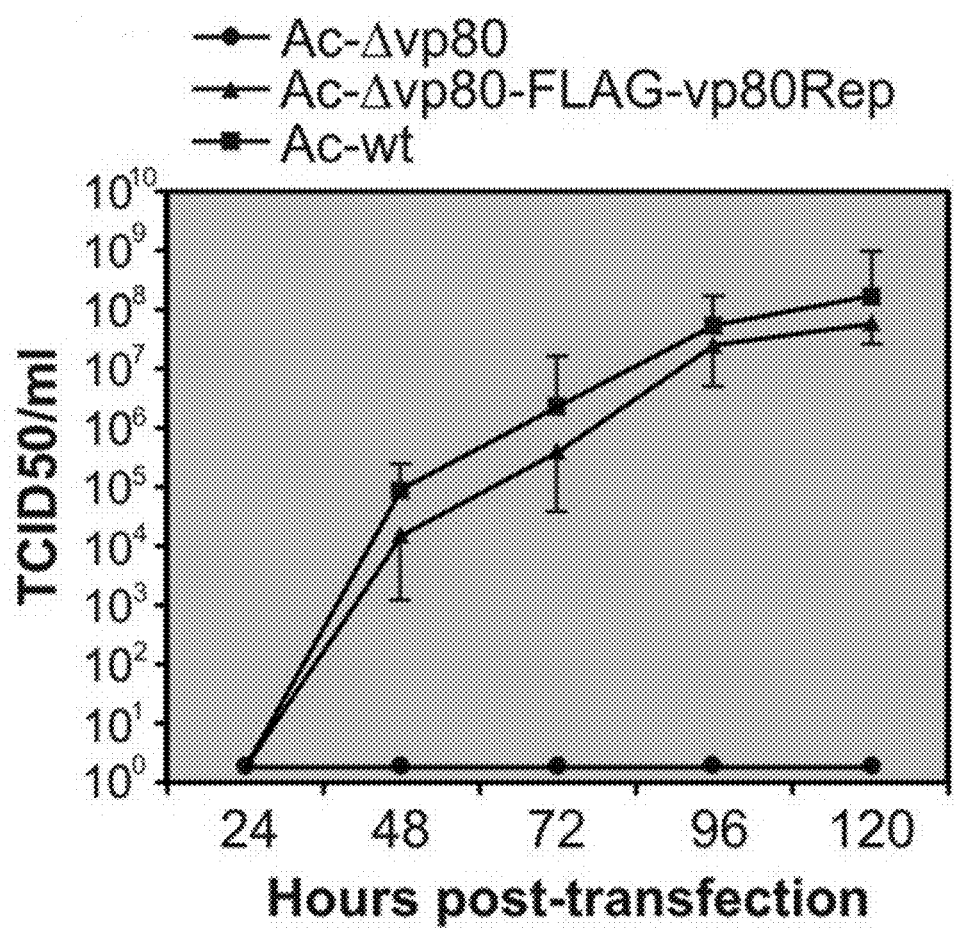
Figure 4D:
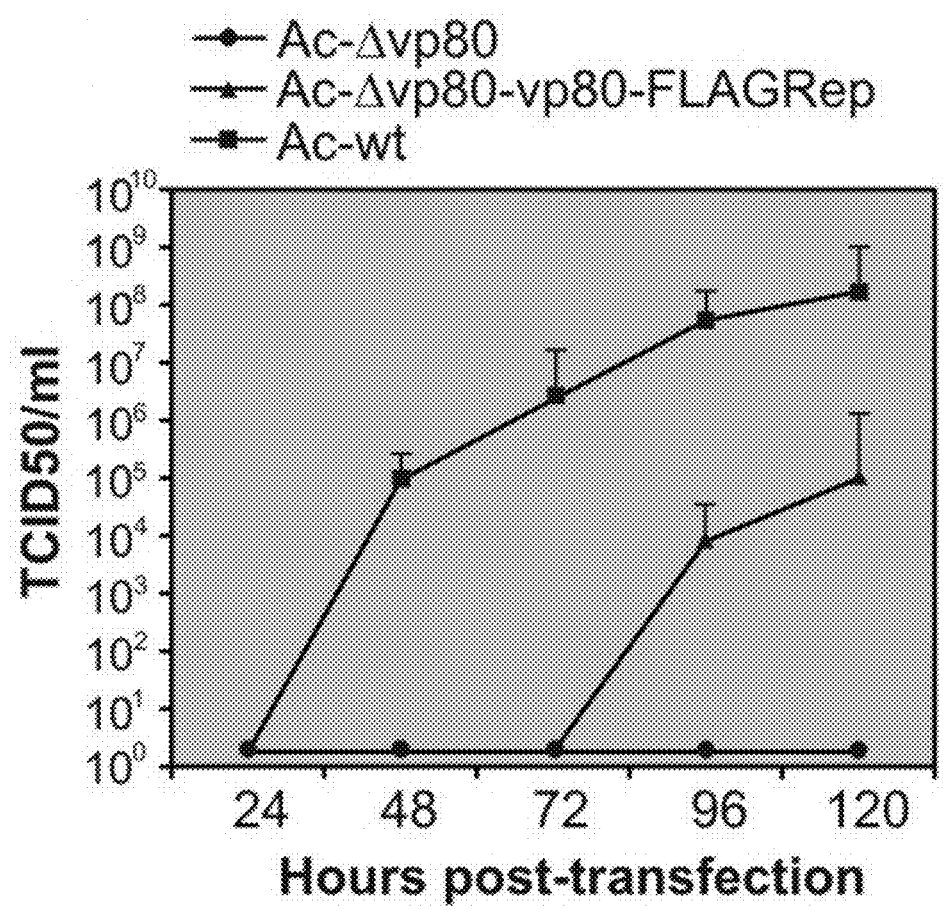

FIGS. 3A-3C. Viral replication capacity of AcMNPV-vp80 knockout and repaired bacmid constructs using transfection-infection assays. (A) Schematic representation of expression cassettes transposed into the polyhedrin locus. Four repair constructs were made (vp80 driven by its native promoter, vp80 driven by the polyhedrin promoter, N-terminally FLAG-tagged vp80 and C-terminally FLAG-tagged vp80, both expressed from its native promoter). The bacmid genome backbones used for transfection assays are indicated on the left. As positive control of viral replication the wild type AcMNPV (bMON14272) bacmid was used. The Ac-gp64null bacmid was used as negative control representing a prototype bacmid with a "single-cell infection" phenotype. (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection.

FIGS. 4a-4d. Growth curves of AcMNPV-vp80null repaired bacmid constructs generated from transfection time-course assays. Sf9 cells were transfected with 5.0 μg of DNA from each repair bacmid. (a) vp80 driven by its native promoter, (b) vp80 driven by the polyhedrin promoter, (c) N-terminally FLAG-tagged vp80, and (d) C-terminally FLAG-tagged vp80, both expressed from the vp80 promoter. Cell culture supernatants were harvested at the indicated time points post-transfection and analysed for the production of infectious budded virus by a $TCID_{50}$ end-point dilution assay. Infectivity was determined by monitoring EGFP expression. The points indicate the averages of titers derived from three independent transfections, and the error bars represent the standard deviation.

Figure 5A:
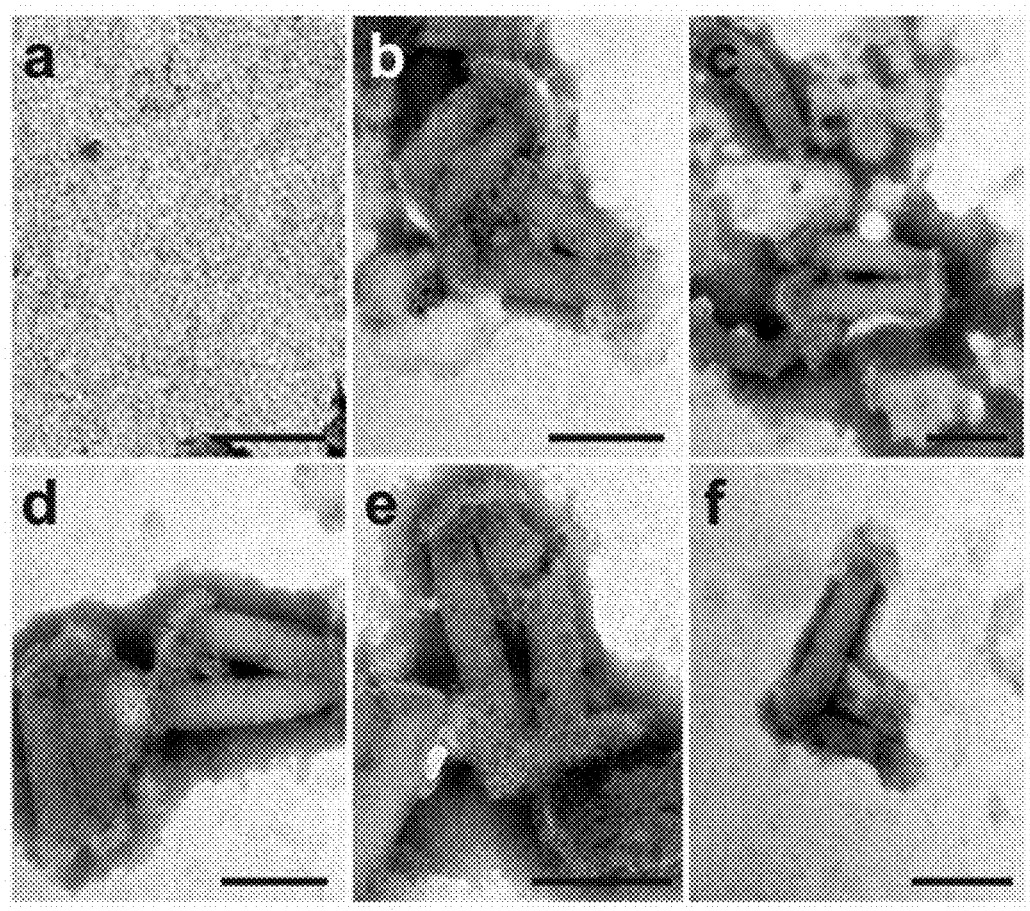
Figure 5B:
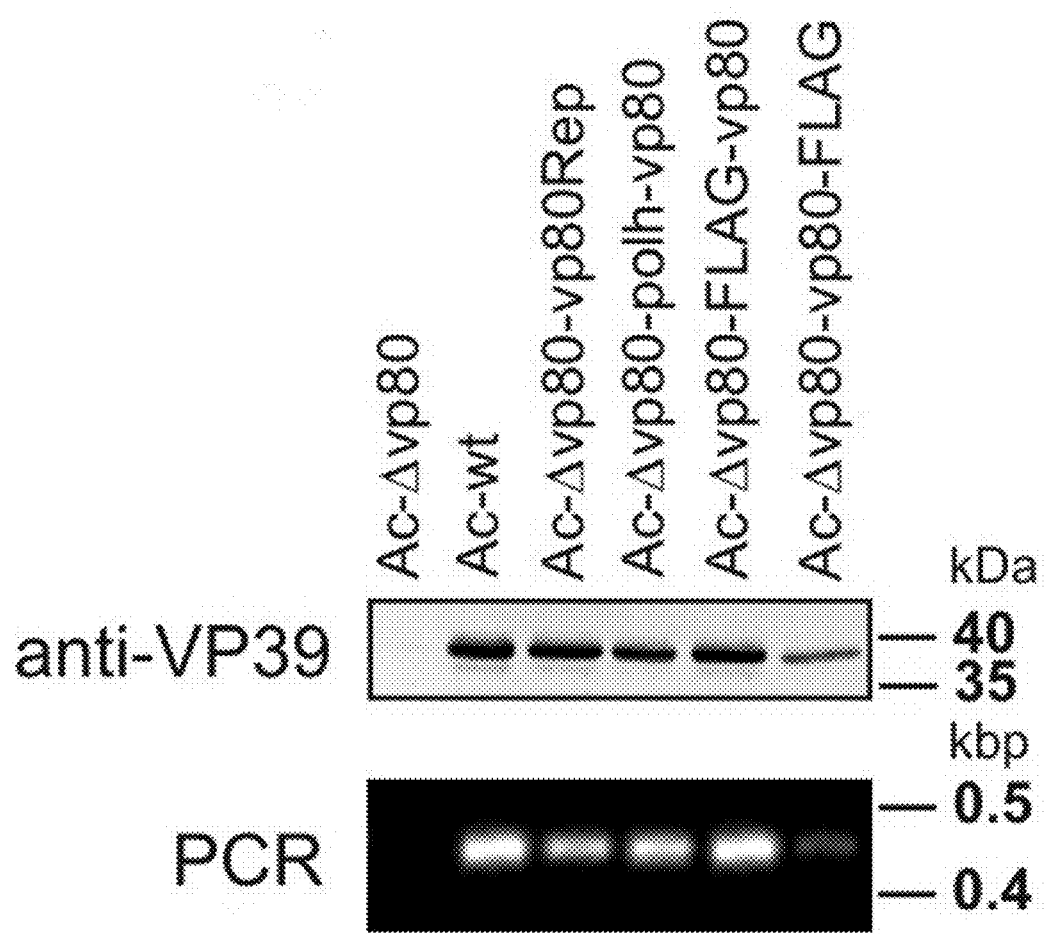

FIGS. 5A-5B. The AcMNPV-vp80null mutant is unable to produce any infectious/non-infectious budded virions. The Sf9 cells were independently transfected with 20 μg of bacmid DNA of Ac-Δvp80 (a), Ac-wt (b), Ac-Δvp80-vp80 (c), Ac-Δvp80-pH-vp80 (d), Ac-Δvp80-FLAG-vp80 (e), or Ac-Δvp80-vp80-FLAG (f). Five days p.t., the budded virus-enriched cell culture supernatants were ultracentrifuged and budded viruses were observed by negative staining electron microscopy (A). The bars represent 200 nm. Parallelly, harvested budded virions were also either separated on SDS-PAGE, blotted and immuno-detected using anti-VP39 antibody or used for PCR-based detection to detect the presence of viral particles (B).

FIGS. 6A-6H. The null bacmid mutant in the vp80 gene forms small numbers of nucleocapsids, and is deficient in production of occlusion-derived virions. The Sf9 cells transfected either with Ac-Δvp80 (A to D), Ac-Δvp80-vp80 (E, F), or Ac-wt (G, H) were fixed, stained, embedded and thin-sectioned as described in Materials and Methods. (A) Representative overview of Sf9 cell transfected with Ac-vp80null bacmid mutant. (B) The Ac-vp80null mutant does form lower numbers of nucleocapsids in the virogenic stroma (C), and no occlusion-derived virions in the ring zone of transfected cells (D). On the other hand, repair bacmid construct Ac-Δvp80-vp80 fully regenerates formation of plenty of nucleocapsids in the virogenic stroma (E), as well as normally-appearing occlusion-derived virions in the ring zone of transfected cells (F). Representative images of the virogenic stroma (G) and the ring zone (H) of cells transfected with Ac-wt bacmid. Bars represent 500 nm. Abbreviations: Nc, nucleocapsid; NM, nuclear membrane; Nu, nucleus; RZ, ring zone; Mi, mitochondrion; ODV, occlusion-derived virions; VS, virogenic stroma.

Figures 7A, 7B:
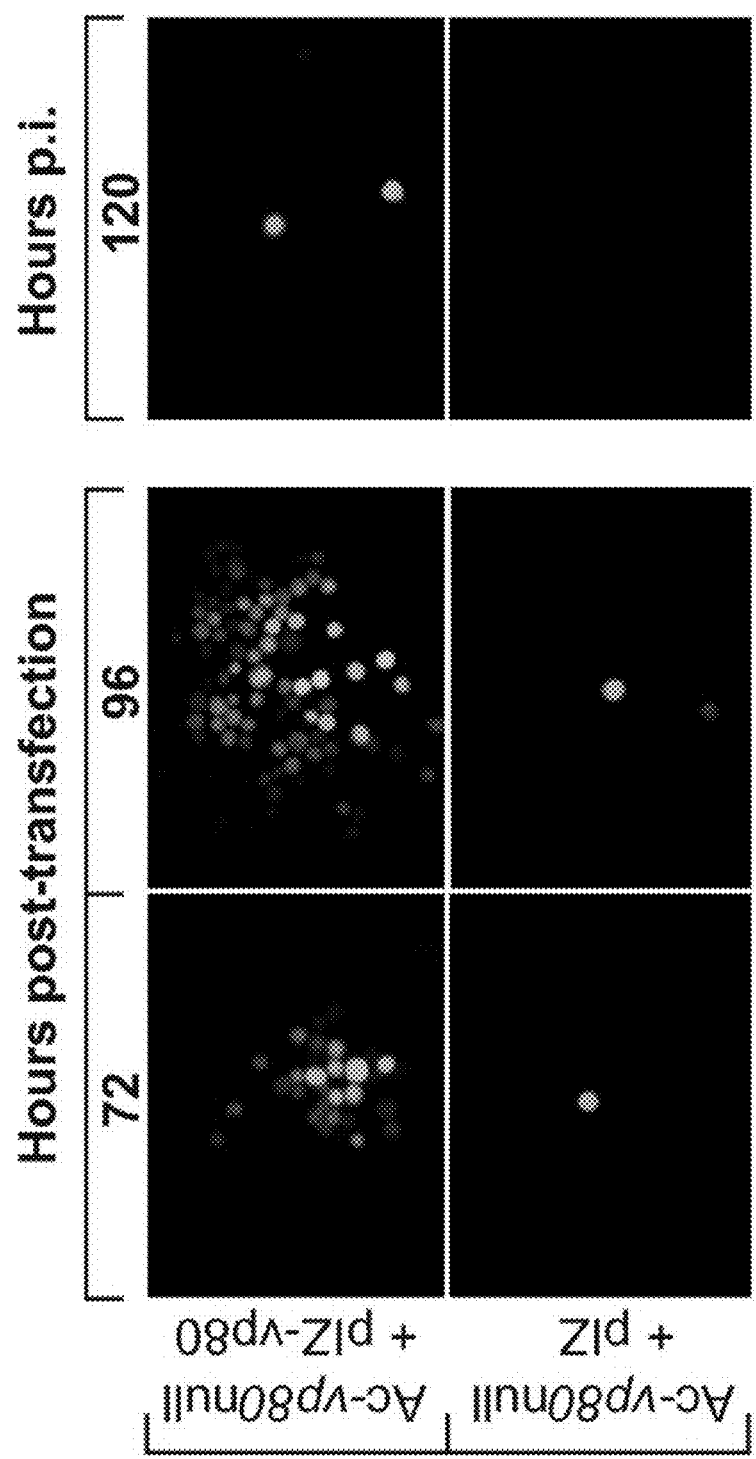

FIGS. 7A-7B. Functional complementation of the Ac-vp80null bacmid mutant using the trans-acting vp80 gene. The Sf9 cells were transfected with either pIZ-flag-vp80 (A) or pIZ (B) vector, and subjected to Zeocin-based selection. Three weeks post-transfection, polyclonal Zeocin resistant populations of cells were seeded to a new 6-well plate and transfected with the Ac-vp80null bacmid mutant to check complementation activity. Virus propagation was monitored by EGFP-specific fluorescence at 72 h and 96 h p.t. At 120 hours p.t., the cell culture supernatants were collected to initiate a secondary infection in untreated (wild-type) Sf9 cells (right panel). EGFP was detected at 72 hours p.i. to signal the progress of infection. EGFP was detected at 120 hours p.i. to signal the progress of infection.

Figure 8A:
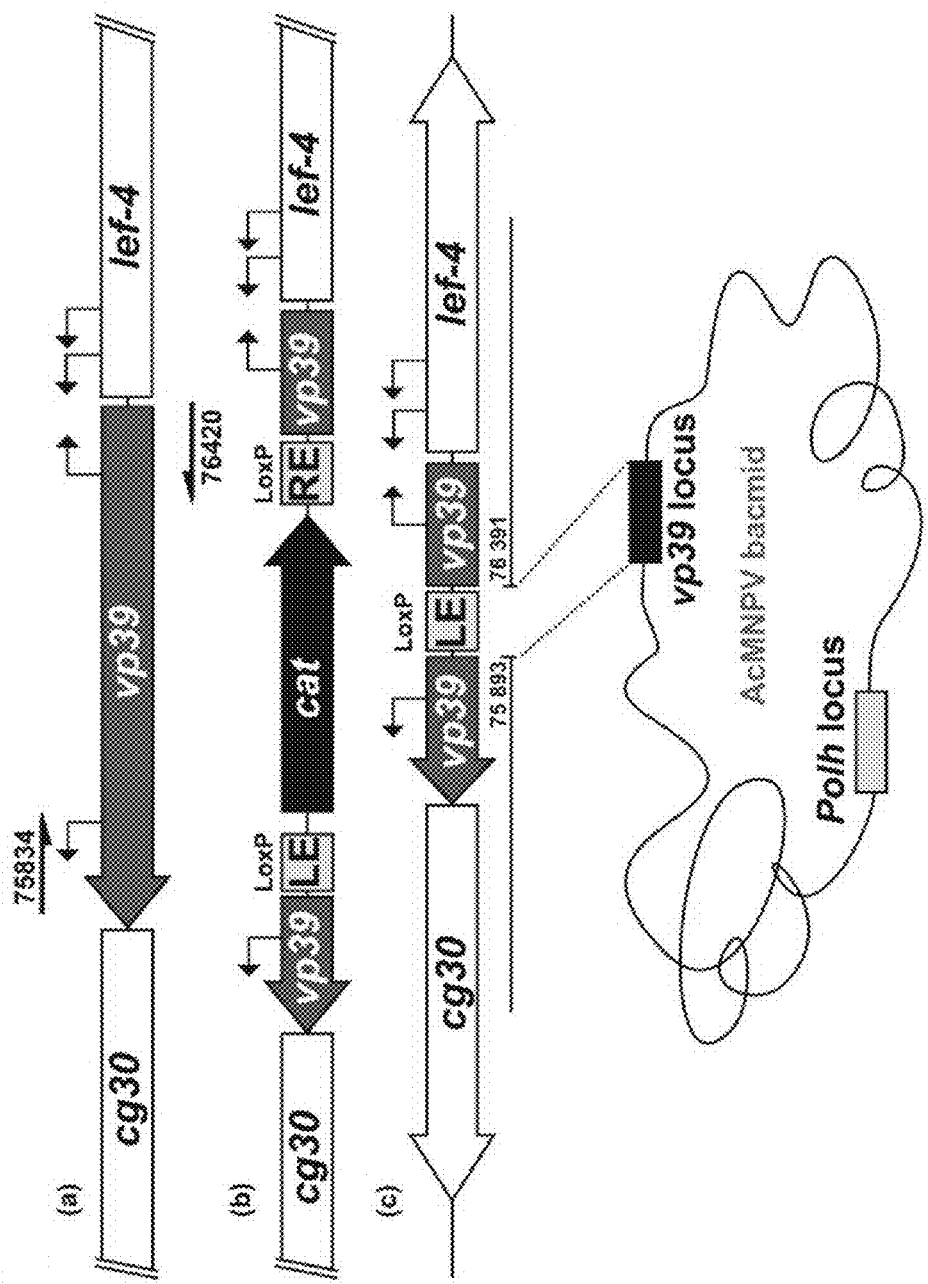
Figure 8B:
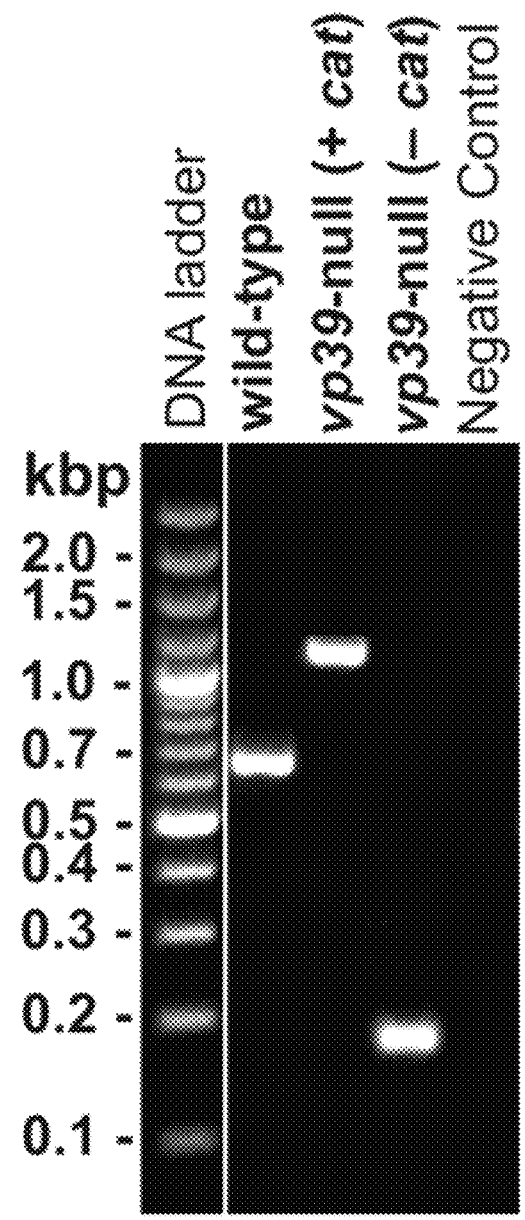

FIGS. 8A-8B. Construction of an AcMNPV vp39-null bacmid. (A) Strategy for construction of a vp39-null bacmid containing a partial deletion of the AcMNPV vp39 open-reading frame via homologous recombination in *E. coli*. At the first step, an internal 498-bp fragment of the vp39 ORF was deleted and replaced with a sequence cassette containing the chloramphenicol (cat) resistance gene flanked by modified loxP (LE and RE) sites. Subsequently, the cat gene was eliminated from the bacmid sequence using the Cre/loxP recombination system. The promoter sequences of the lef-4 and cg-30 genes were not affected. Arrows indicate the positions of oligonucleotide pairs used in PCR analysis of the wild-type locus and two vp39 knock-out genotypes to confirm the partial deletion of the vp39 ORF and the correct insertion/deletion of the cat gene cassette. Primers names are designated according to the nucleotide sequence coordinates. (B) PCR-based detection of the presence or absence of sequence modifications in the vp39 locus of Ac-wt, Ac-vp39null(+cat), and Ac-vp39null(−cat) bacmids. The figure shows the PCR-based verification of the correct recombination processes in the vp39 locus using the 75834/76420 primer pair.

FIGS. 9A-9C. Determination of viral replication capacity of AcMNPV-vp39 knockout and repaired bacmid constructs using transfection-infection assays. (A) Schematic representation of expression cassettes, Tn7-based transposed into the polyhedrin locus. (1) vp39 expressed from the polyhedrin promoter, (2) a double gene vp39 and lef-4, both driven by their native promoters, (3) a double gene vp39 and cg-30 both driven by the polyhedrin promoter, and finally (4) a double gene construct of N-terminally FLAG-tagged vp39 driven by the polyhedrin promoter and the cg-30 ORF expressed from both its native and also the more upstream polyhedrin promoter. The parental bacmid genome backbones used for transfection assays are indicated on the left. The wild type AcMNPV (bMON14272) bacmid was used as positive control of viral replication. (B) Time course fluorescence microscopy showing the propagation of the infection in Sf9 cells transfected with indicated bacmid constructs. Viral progressions were checked by EGFP detection at indicated times post transfection. At 168 hours p.t., the cell culture supernatants were collected to initiate a secondary infection. (C) Secondary infection assay. EGFP detection was performed at 72 hours p.i. to measure progress of the infection.

Figure 10A:
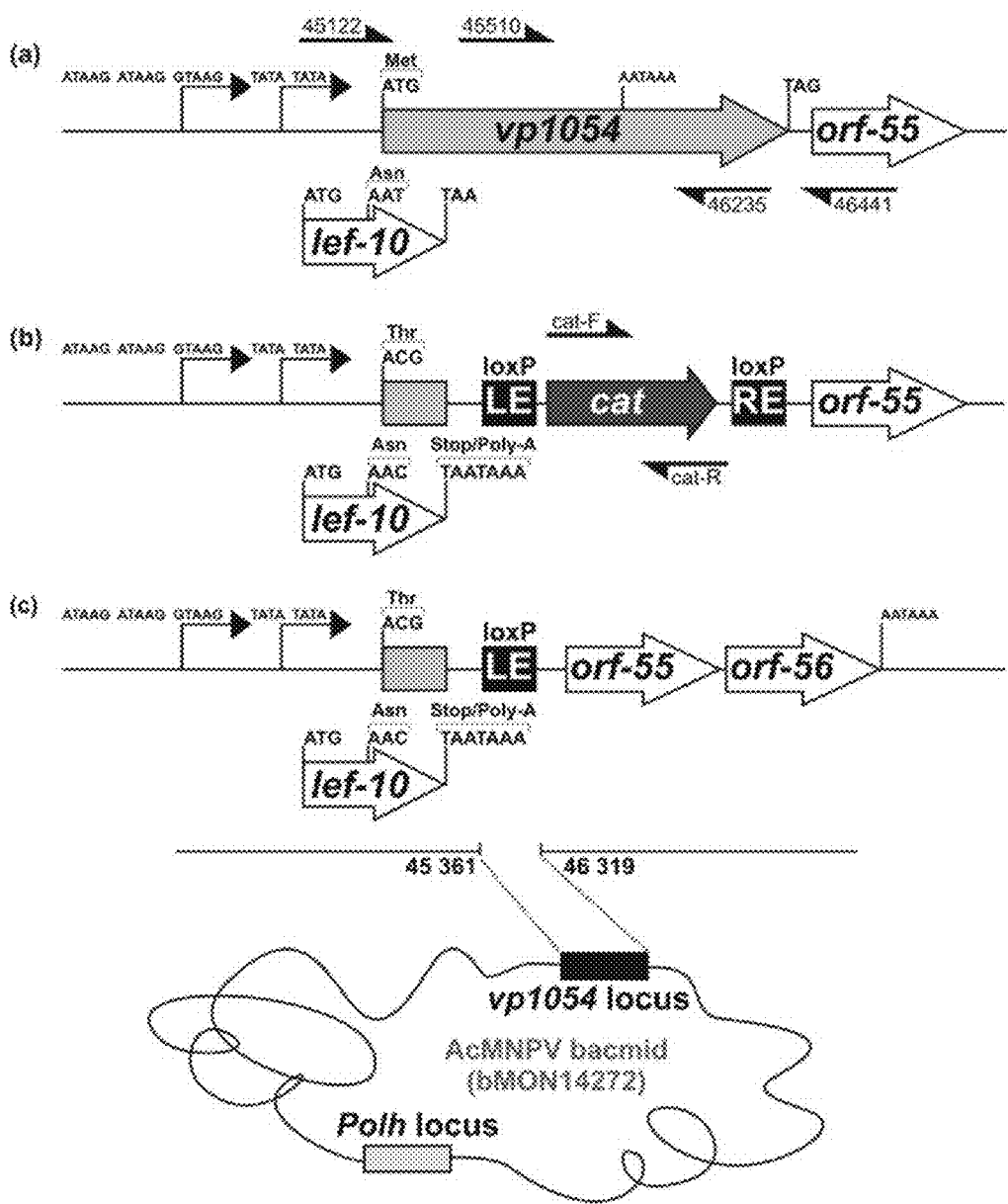
Figure 10B:
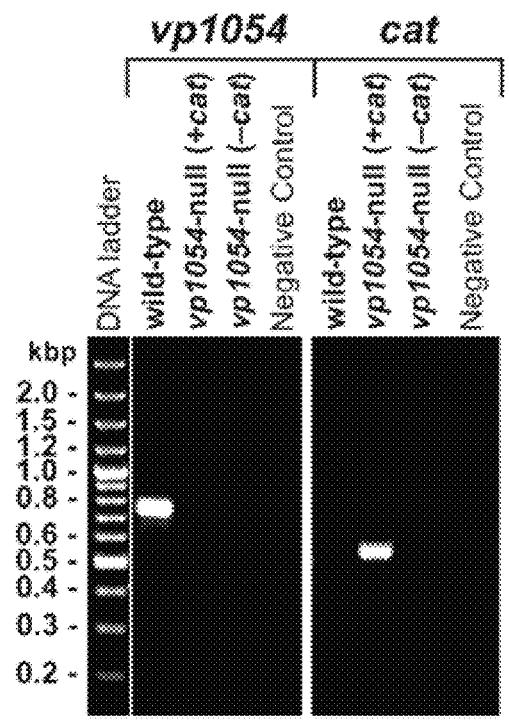
Figure 10B:
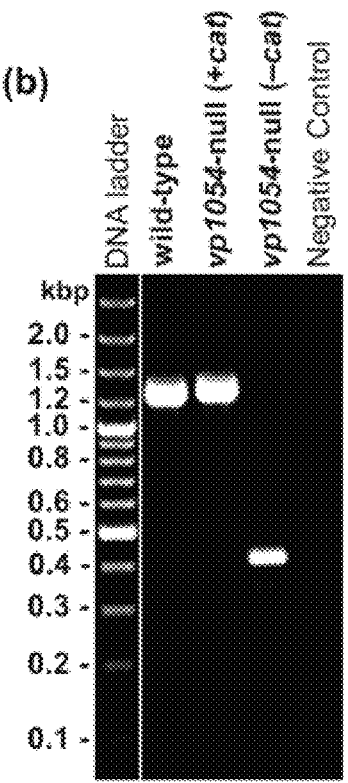

FIGS. 10A-10B. Construction of an AcMNPV vp1054-null bacmid. (A) Strategy for the construction of a vp1054-null bacmid containing a deletion of the AcMNPV vp1054 open-reading frame via homologous recombination in *E. coli*. A 955-bp sequence from the 3"-end of the vp1054 ORF was deleted and replaced with a cat sequence cassette flanked by modified loxP (LE and RE) sites. At the same time, a single point mutation was introduced to change the first translation codon ATG→Met to ACG→Thr, to prevent translation into a C-truncated VP1054 protein. It also meant that the internal AAT codon no. 32 of lef-10 was mutated to AAC, both encoding Asn. Subsequently, the cat gene was eliminated using the Cre/loxP recombination system. The promoter sequence of vp1054/lef-10 was not affected in the bacmid construct. Since the polyadenylation signal of the lef-10 gene was removed, a novel synthetic poly-A signal combined with stop codon (TAATAAA) was introduced at the 3"-end of the lef-10 ORF. Arrows represent locations of oligonucleotide pairs used in the PCR analysis of the wild-type locus and two vp1054 knock-out genotypes to confirm the deletion of the vp1054 ORF and correct insertion/deletion of the cat cassette. (B) PCR-based detection of the presence or absence of sequence modifications in the vp1054 locus of Ac-wt, Ac-vp1054null(+cat), and Ac-vp1054null(−cat) bacmids. The top figure is showing confirmation of the vp1054 gene deletion and insertion of the cat cassette into vp1054 locus using primer pairs 90292/90889 and cat-F/cat-R. The bottom figure shows CR-based verification of the correct recombination processes in the vp1054 locus using the 89507/91713 primer pair.

Figures 11A, 11B, 11C:
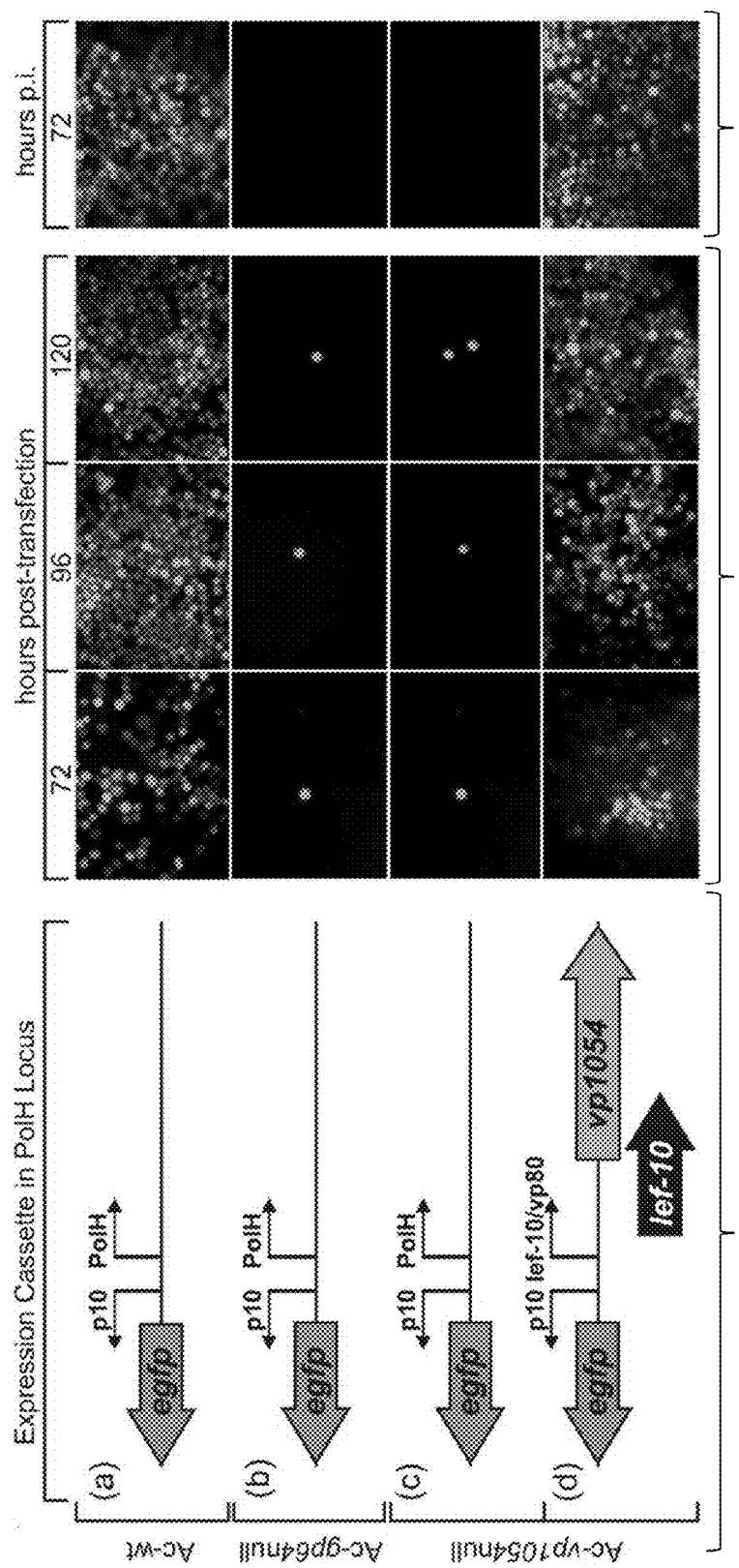

FIGS. 11A-11C. Viral replication capacity of AcMNPV-vp1054 knockout and repaired bacmid constructs using transfection-infection assays. (A) Schematic representation of expression cassettes transposed into the polyhedrin locus. The bacmid genome backbones used for transfection assays are indicated on the left. Two Ac-vp1054null-derived constructs were made: first construct carrying only egfp marker gene under control of p10 promoter, and second construct carrying both egfp marker and overlapping lef-10/vp1054 locus directed from their natural promoter sequences (d). As positive control of viral replication the wild type AcMNPV (bMON14272) bacmid was used (a). The Ac-gp64null bacmid was used as negative control representing a prototype bacmid with a "single-cell infection" phenotype (b). (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection.

Figure 12A:
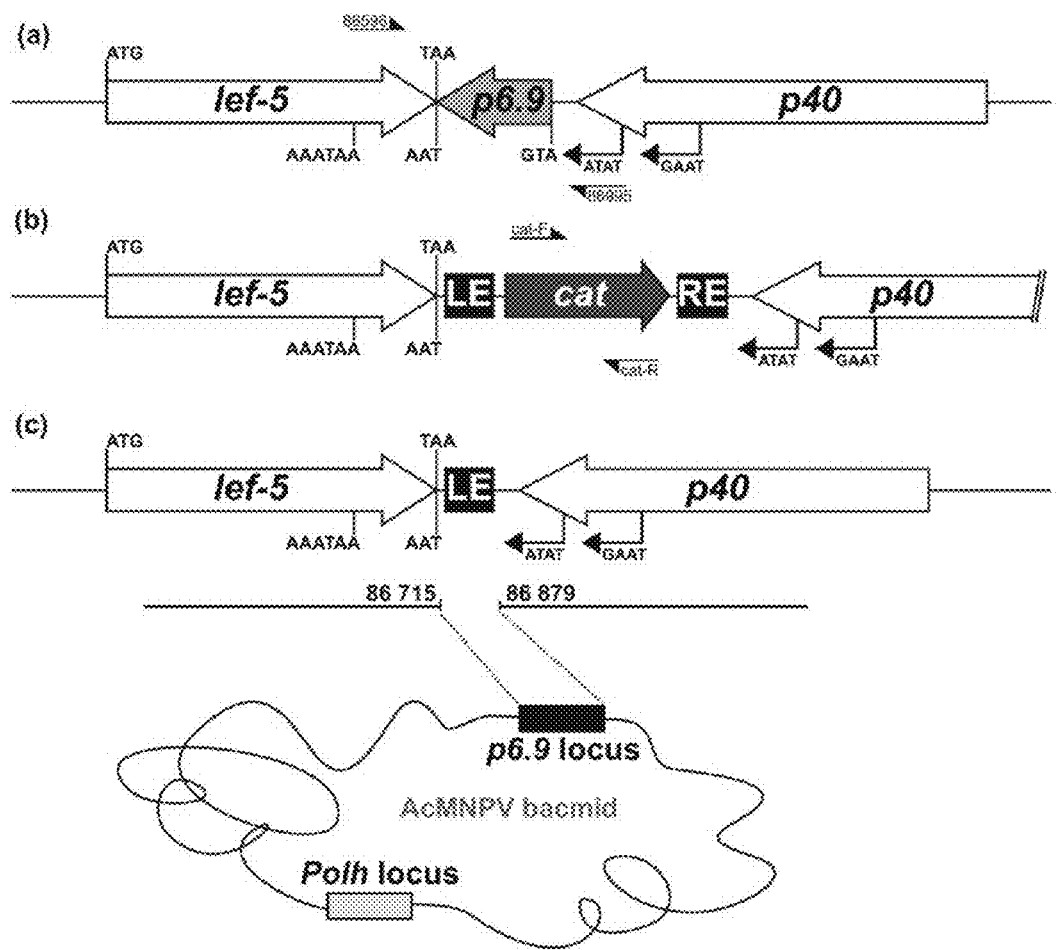
Figure 12B:
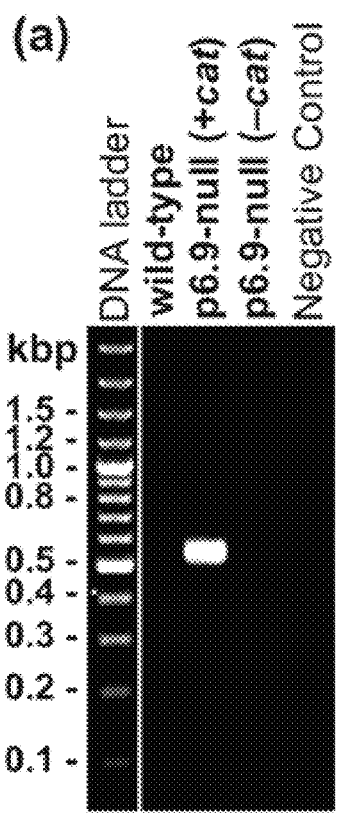

FIGS. 12A-12B. Construction of an AcMNPV p6.9-null bacmid. (A) Strategy for construction of a p6.9-null bacmid containing a complete deletion of the AcMNPV p6.9 open-reading frame via homologous recombination in E. coli. A 164-bp fragment of the p6.9 ORF was deleted and replaced with a cat resistance gene flanked by modified loxP (LE and RE) sites. Subsequently, the cat gene was eliminated from the bacmid sequence using Cre/loxP recombination. The promoter sequence of p6.9 gene was left unaffected, since its sequence is overlapping with the p40 ORF. Arrows represent locations of primer pairs used in the PCR analysis of the wild-type locus and two p6.9 knock-out genotypes. (B) PCR-based detection of the presence or absence of sequence modifications in the p6.9 locus of Ac-wt, Ac-vp6.9null(+cat), and Ac-vp6.9null(−cat) bacmids. The top figure shows the insertion of the cat cassette into the p6.9 locus using primer pairs cat-F/cat-R. The bottom figure shows PCR-based verification of the correct recombination processes in the p6.9 locus using the 86596/86995 primer pair.

FIGS. 13A-13O. Viral replication capacity of AcMNPV-p6.9 knockout and repaired bacmid constructs using trans-fection-infection assays. (A) Schematic representation of expression cassettes transposed into the polyhedrin locus. Two repair constructs were made (AcMNPV p6.9 and SeMNPV p6.9 genes, both driven by the AcMNPV p6.9 promoter). The bacmid genome backbones used for transfection assays are indicated on the left. As positive control of viral replication the wild type AcMNPV (bMON14272) bacmid was used. The Ac-gp64null bacmid was used as negative control representing a prototype bacmid with a "single-cell infection" phenotype. (B) Time course fluorescence microscopy showing the propagation of the infection in Sf9 cells transfected with indicated bacmid constructs. Progress of viral infection was checked by EGFP detection at indicated times post transfection. At 120 hours p.t., the cell culture supernatants were collected to initiate a secondary infection. (C) Secondary infection assay. EGFP was detected at 72 hours p.i. to signal the progress of infection. (D) Comparisons of growth curves of AcMNPV-p6.9null (a), AcMNPV-p6.9null rescued with AcMNPV p6.9 (b), and AcMNPV-p6.9null rescued with SeMNPV p6.9 (c) constructs with wild-type (Ac-wt) bacmid. Sf9 cells were transfected with 5.0 µg of DNA from each bacmid, cell culture supernatants were harvested at the indicated time points post-transfection and analysed for the production of infectious budded virus by a $TCID_{50}$ end-point dilution assay. Infectivity was determined by monitoring EGFP expression. The points indicate the averages of titers derived from three independent transfections, and the error bars represent the standard deviation.

Figure 14A:
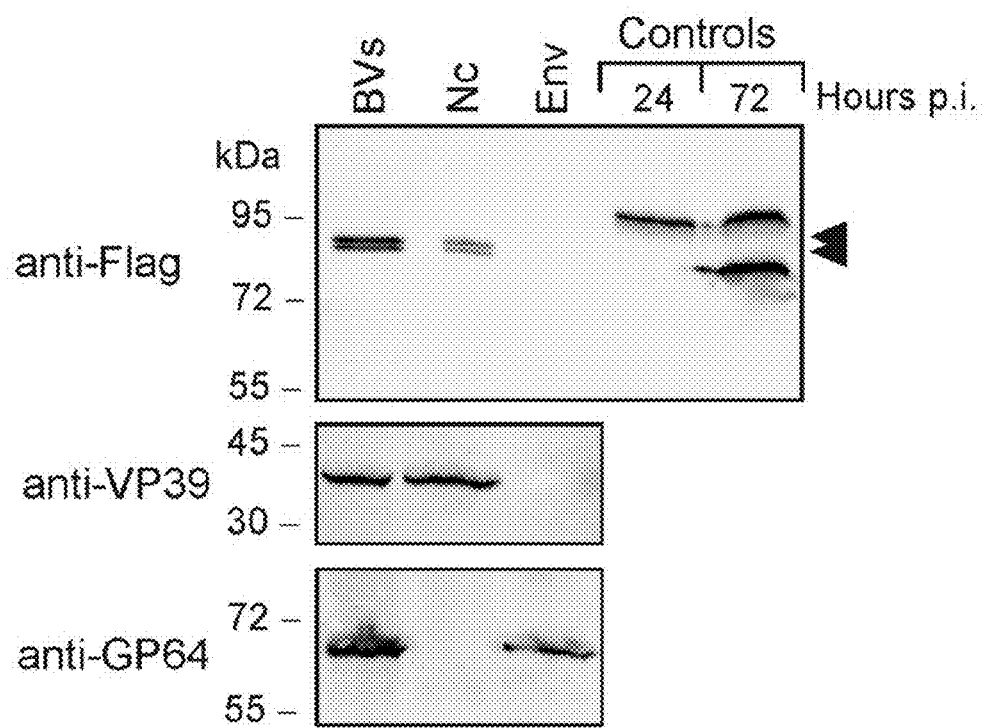
Figure 14B:
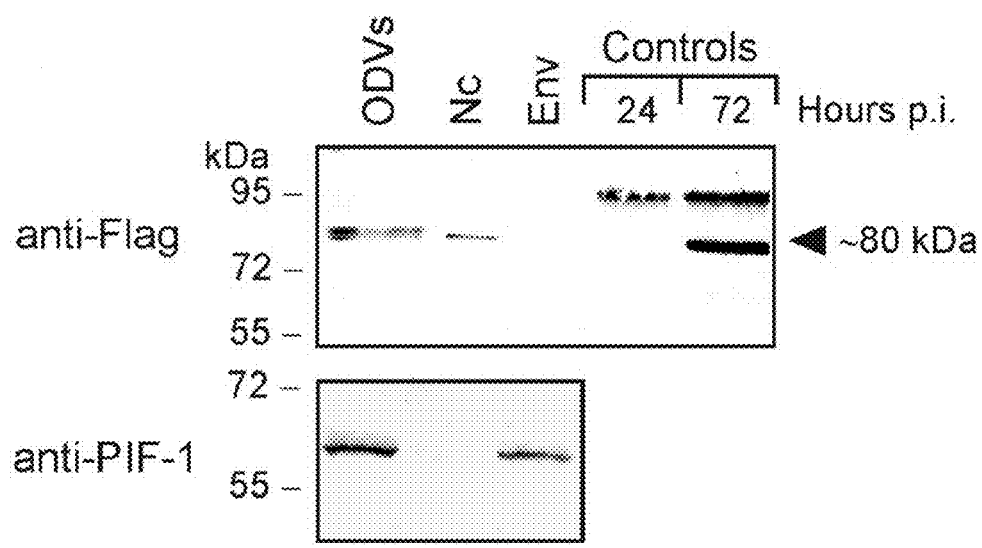

FIGS. 14A-14B: Western blot analysis of Flag:vp80 in cells, BV and ODV. (A) Time course of vp80 expression in infected insect cells. Sf9 cells were infected with the Ac-Δvp80-Flag•vp80 repair virus, and harvested at indicated time points. Flag•VP80 was detectable by western blot analysis from 12 h to 72 h p.i. as a band of approximately 95 kDa. In addition, a second Flag•VP80-specific band of ~80 kDa accumulated from 48 h until 72 h p.i. Tubulin was used as an internal loading control. (B) The VP80 associates with the nucleocapsid fraction of BV. Two days p.i., BVs were purified by isokinetic ultracentrifugation in a sucrose gradient and separated into nucleocapsid (Nc) and envelope (Env) fractions by Nonidet-P40-based extraction. Flag•VP80 was detected in the Nc fraction as a double-band with molecular weights between the two variants (80-kDa and 95-kDa) detected in infected Sf9 cells (upper panel). Correct separation into Nc and Env fractions was controlled by anti-VP39 and anti-GP64 antibodies (bottom panels). (C) VP80 is also a structural component of ODV-nucleocapsids. Sf9 cells were co-infected with Ac-Δvp80-Flag•vp80 (MOI=25) and AcMNPV strain E2 (MOI=5) viruses. Five days p.i., ODVs were released from occlusion bodies and subsequently separated into nucleocapsid (Nc) and envelope (Env) fractions. Western blot analysis showed that VP80 is present in the DV Nc fraction as a single band of ~80 kDa. Proper fractionation into Nc and Env fractions was controlled using anti-PIF-1 antiserum (bottom panel).

Figure 15A:
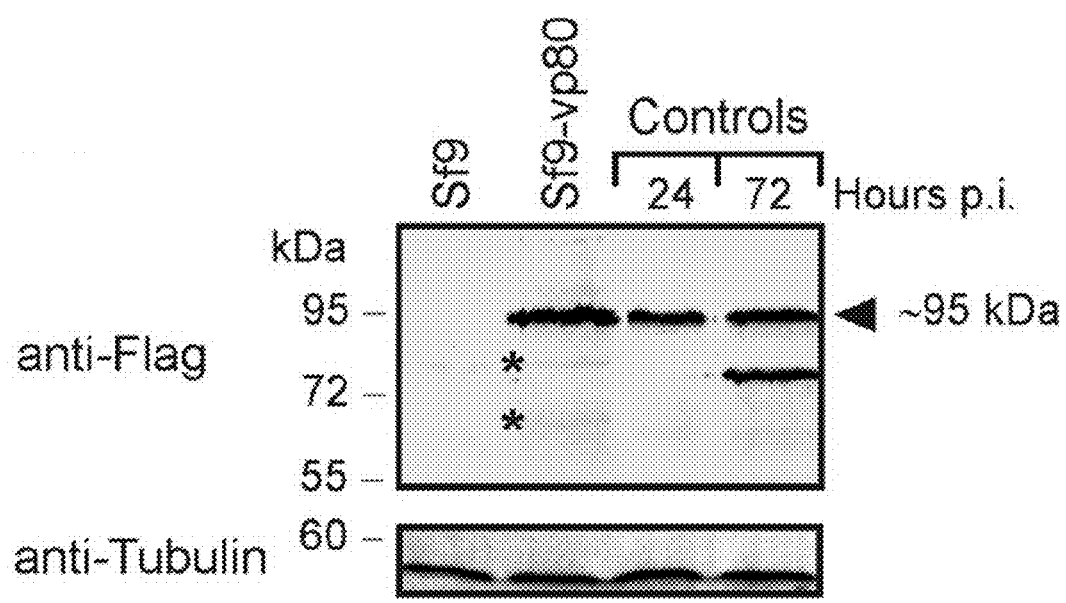
Figure 15B:
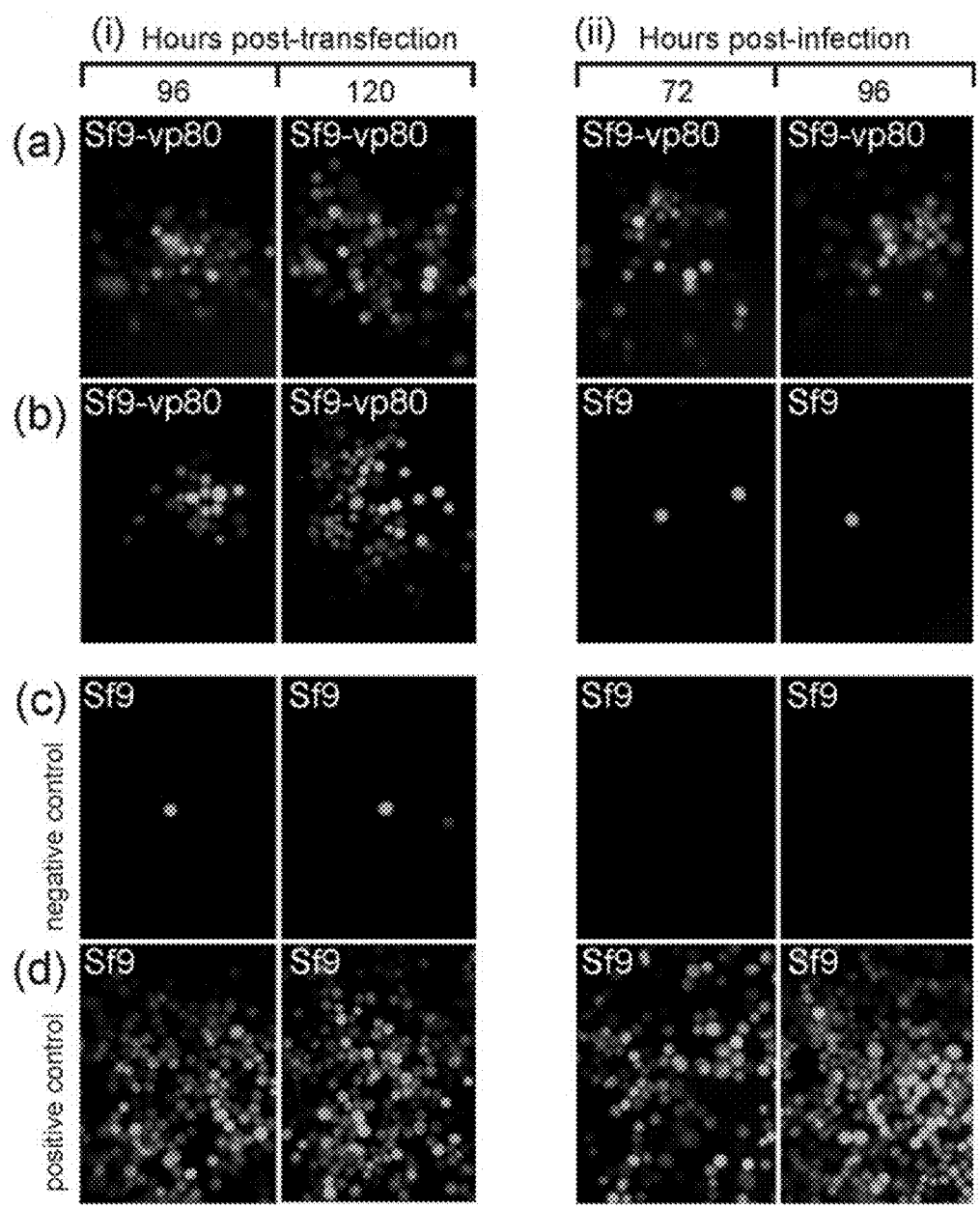
Figure 15C:
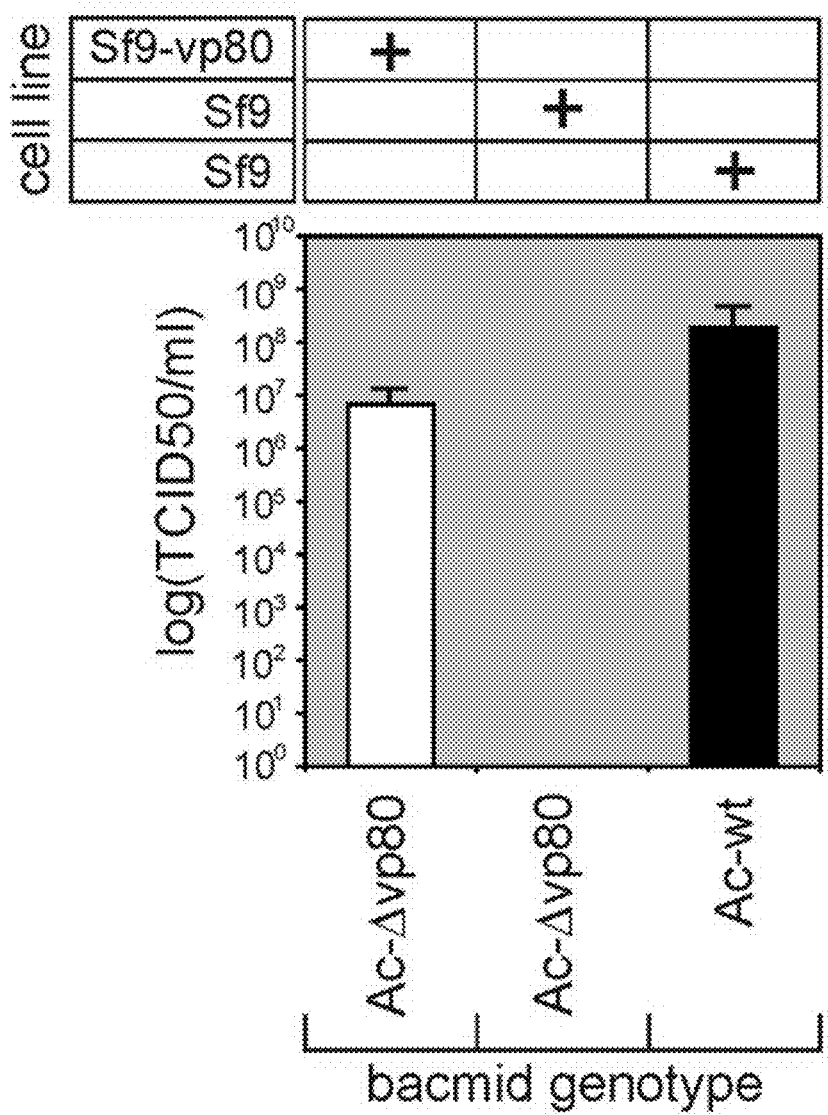

FIGS. 15A-15C. Functional complementation of the Ac-vp80null bacmid defective in BV production by trans-complementation. (A) Detection of FLAG:VP80 in a transgenic Sf9-derived cell line (Sf9-vp80) by Western analysis. Tubulin was used as an internal loading control. (B) Time-course fluorescence microscopy (EGFP) to follow the infection in Sf9-vp80 cells transfected (i) or infected (ii) with the Ac-Δvp80 bacmid (a,b). At 120 h p.t., the cell culture supernatants were collected to initiate a secondary infection in either Sf9-vp80 (a) or Sf9 (b) cells (panels on the right side). As negative control Ac-Δvp80 was propagated in Sf9 cells (c), Ac-wt propagated in Sf9 cells (d) was used as positive control. (C) Comparative release of infectious BV virions. Sf9-vp80 cells were transfected with the Ac-Δvp80 bacmid and Sf9 cells with either the Ac-Δvp80 (negative control) or the Ac-wt (positive control) bacmid. BVs were quantified in cell culture supernatants at 6 days p.t. by end point dilution. Representative results of three independent assays with error bars giving the SD are shown.

Figure 16A:
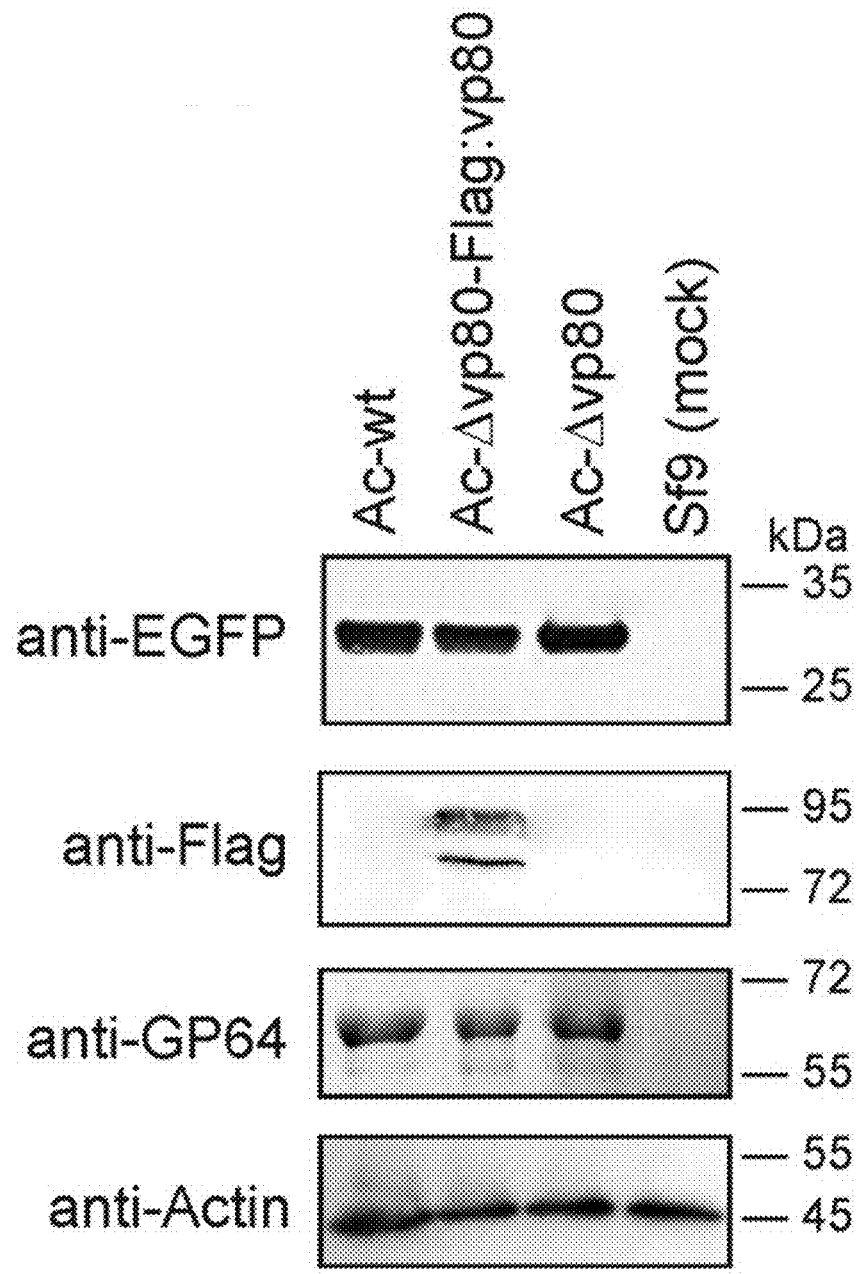
Figure 16B:
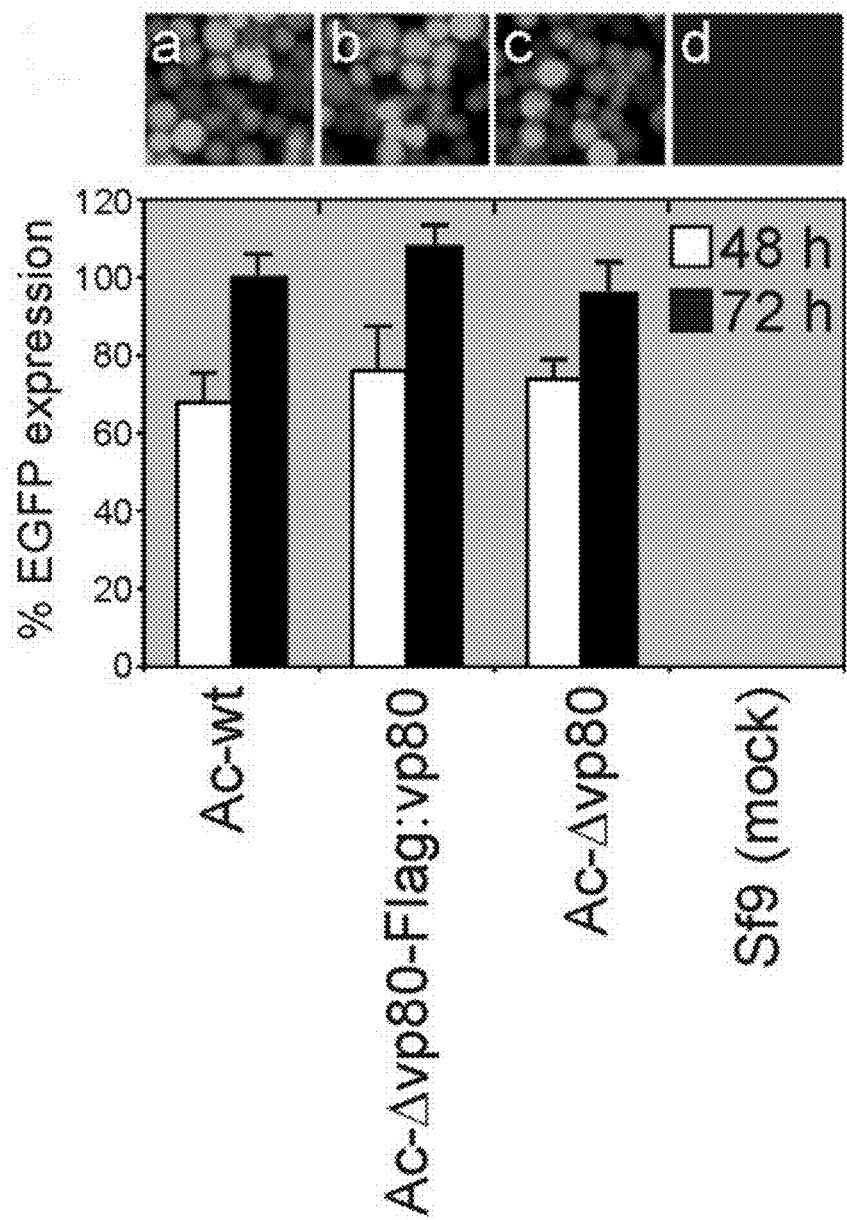
Figure 16C:
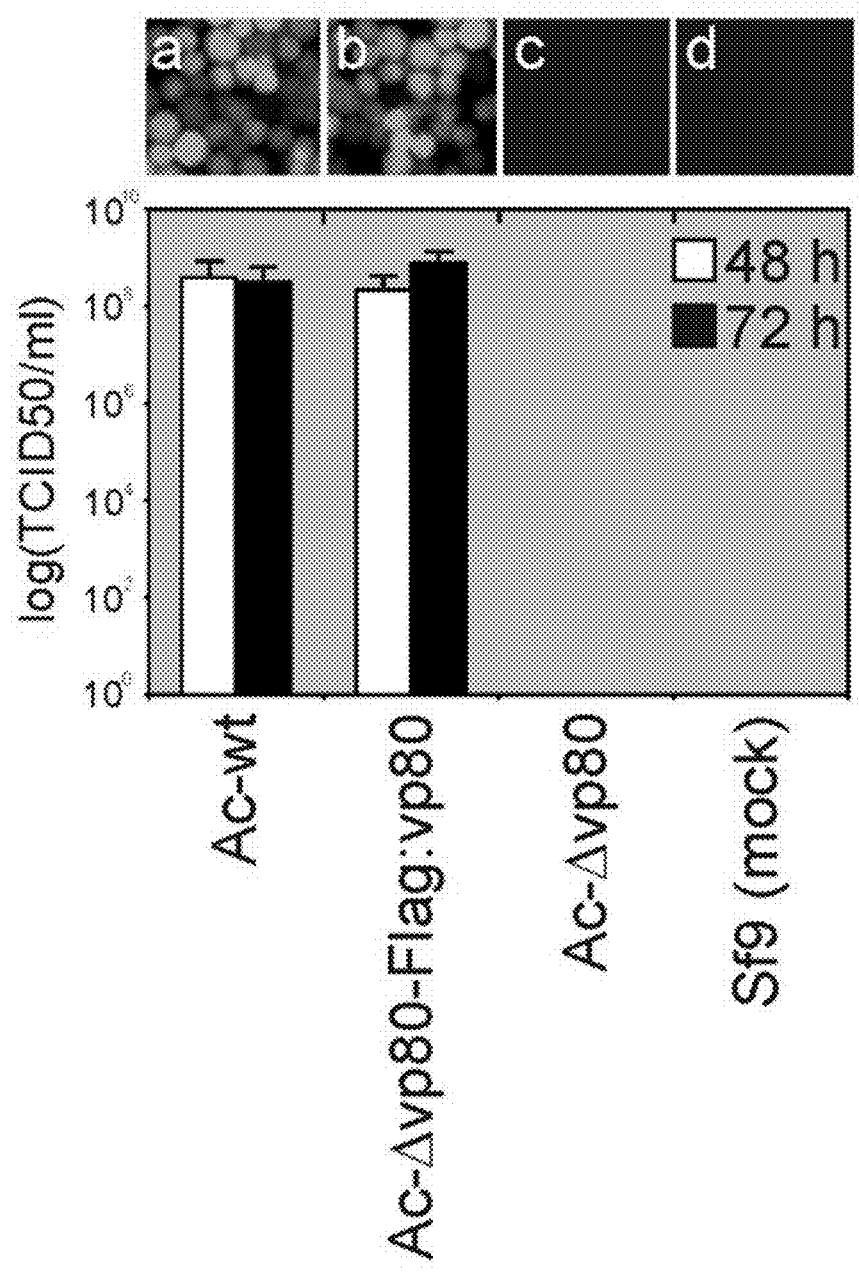

FIGS. 16A-16C. Analysis of foreign gene expression by trans-complemented, replication-deficient baculovirus seed. Sf9 cells were infected with Ac-wt, Ac-Δvp80-Flag:vp80 or Ac-Δvp80 virus seed (MOI=10 $TCID_{50}$ units per cell), all expressing egfp from the very late p10 promoter. (A) At 48 h p.i. the presence of EGFP, Flag:VP80 and GP64 was analyzed by Western blotting. Actin was used as an internal loading control. (B) Photomicrographs of cells expressing EGFP 72 h p.i. (top), and relative amount of EGFP measured by ELISA at 48 and 72 h p.i. (bottom) (C) Photomicrographs of cells expressing EGFP 72 h p.i. (top), and analysis of BV released to test for revertant genotypes by $TCID_{50}$ titration (bottom). The results of three independent assays are shown with error bars (SD) (B and C).

FIGS. 17A-17D. The novel baculovirus-insect cell technology approach designated for the production of biopharmaceuticals free of contaminating baculoviral virions. (A) Insect cell engineering to express an essential viral factor (vp80) to complement a vp80 mutation in the virus. The transgenic Sf9 cells encode the vp80 ORF and a resistance gene allowing antibiotics-based selection of the transgenic cells. (B) Generation of an Ac-Δvp80 bacmid defective in production of BV and ODV virions. The bacmid lacks the entire vp80 ORF. (C) Production of a baculovirus seed stock by trans-complementation in the engineered Sf-vp80 cells. The Sf9-vp80 cells are transfected with the Ac-Δvp80 bacmid to produce trans-complemented virus progeny. After budded virus propagation, high-titer virus stocks are produced in the Sf9-vp80 packaging cells. (D) Baculovirus-based recombinant protein expression. Conventional Sf9 cells are infected with the trans-complemented budded virus progeny. Recombinant protein is expressed from very late baculovirus promoters (p10 or polh) allowing high levels of expression, while no contaminating baculovirus virions (BV/ODV) are produced.

EXAMPLES

Example I

Materials and Methods
Insect Cells and Viruses

Spodoptera frugiperda (Sf9) cells were maintained in SF900-II serum-free medium (Invitrogen) under standard conditions. Recombinant bacmid-derived AcMNPV virus (AcMNPV-EGFP) carrying an egfp reporter gene under control of the very late polyhedrin promoter transposed into the polyhedrin locus was obtained from Pijlman et al. (2006). The virus was propagated and its titers were determined by an end-point dilution assay in Sf9 cells.

In Vitro Synthesis of dsRNA

The method used to synthesize dsRNA is similar to that described by Ramadan et al. (2007) with minor modifications. All DNA templates were PCR amplified using primers with twenty-five nucleotide overhangs homologous to the T7 RNA polymerase promoter sequence 5"-gcttctaatacgact-cactataggg-3". The sequences of the primers indicated below are given in Table 1. The following primers were used for amplifying these genes: primers vp39-F and vp39-R for vp39; primers 45510 and 46235 for vp1054, primers 90292 and 90889 for vp80; primers ec-27-F and ec-27-R for odv-ec27; and primers dbp-F and dbp- for dbp. To test the efficiency of the RNAi studies we made dsRNA against egfp with primers gfp-F and gfp-R, and to have a negative control we made dsRNA with primers cat-F and cat-R for the chloramphenicol acetyl transferase (cat) gene.

The PCR products were purified using the Illustra GFX PCR DNA and Gel Band Purification Kit (GE Healthcare, Buckinghamshire, UK) and were used as templates for dsRNA in vitro synthesis using the T7 RiboMAX™ Express RNAi System (Promega, Madison, Wis., USA) according to manufacturer's protocol. Briefly, approximately 1 µg of purified DNA templates were used for RNA synthesis at 37° C. for 4 h. After synthesis, DNA templates were removed by digestion with DNase. Complementary RNA strands were annealed by incubation at 70° C. for 10 min followed by slow cooling to room temperature (~30 min). Non-annealed (single-stranded) RNA molecules were degraded by RNase A treatment (30 min, 37° C.). Finally, the dsRNA was isopropanol precipitated, resuspended in DEPC-treated sterile water to a final concentration of 0.5-1 mg/ml, and its purity and integrity were checked by agarose gel electrophoresis. The dsRNA was kept at −80° C. in aliquots of 40 µl. Immediately before transfection, the dsRNA was thawed on ice.

RNAi Procedure in Baculovirus-Infected Insect Cells

Sf9 cells were seeded in 24-well tissue culture plates ($2 \times 10^5$ cells/well) in 1 ml Sf900-II culture medium without serum at 28° C. After two hours, the culture medium was removed, and the cells were infected with recombinant baculovirus AcMNPV-EGFP at a multiplicity of infection (MOI) of 10 $TCID_{50}$ units/cell for 1 h, under standard conditions. One hour post infection (p.i.), dsRNA (20 µg/well) was introduced into the cells by Cellfectin™-based (Invitrogen) transfection in Grace's serum-free medium. After 4 h, the transfection mixture was replaced with Sf900-II serum-free medium. The cells were incubated for a total of 48 h p.i. at 28° C. and then harvested by centrifuging at 1000×g for 5 min for Western blot and electron microscopy analysis. However, one fifth of the culture medium was harvested at 36 h p.i., and used for titration of budded virions by end-point dilution assays or for PCR-based detection of viral DNA. In all the experiments, dsRNA corresponding to the cat gene was taken as negative control. On the other hand, egfp gene-specific dsRNA was used as positive control for the RNAi procedure.

SDS-Polyacrylamide Electrophoresis and Western Blotting

For immuno-detection, the Sf9 cells were disrupted in 125 mM Tris-HCl, 2% sodium dodecyl sulfate (SDS), 5% 2-mercapthoethanol, 10% glycerol, 0.001% bromophenol blue, pH 6.8 at 95° C. for 10 min. Proteins were separated in 10% SDS-polyacrylamide gels, and subsequently transferred to Immobilon-P membranes (Millipore) by semi-dry electroblotting. Membranes were blocked for 30 min in 1×PBS containing 2% fat-extracted milk powder, followed by incubation for 1 h at room temperature with either rabbit polyclonal anti-GFP antiserum (Molecular Probes), rabbit polyclonal anti-VP39 antiserum, or monoclonal anti-α-tubulin antibody (Sigma-Aldrich), all diluted 1/2000 in 1×PBS containing 0.2% milk power. After washing (3×10 min) in 1×PBS, the membranes were incubated with 1/4000 dilution of either goat anti-rabbit IgG or rabbit anti-mouse IgG antibodies conjugated with alkaline phosphatase (Sigma). After final washing (3×10 min) in AP buffer (100 mM Tris-Cl [pH 9.5], 100 mM NaCl, 5 mM $MgCl_2$), the blots were developed with 5-bromo-4-chloro-3-indolyl phosphate nitroblue tetrazolium (NBT)/5-bromo-4-chloro-3-indolyl-phosphate (BCIP) (Bio-Rad) according to the manufacturer's instructions.

Preparation of Viral Genomic DNA and its PCR-Based Detection

Two-hundred microliters of cell culture medium were collected at 36 h p.i. and used for preparation of viral DNA. The cells and cell debris were removed from samples by centrifuging at 1000×g for 5 min. Supernatants containing budded virions were quantitatively transferred to new sterile tubes and centrifuged again at 12000×g for 90 min. Pelleted BVs were re-suspended in 200 µl TE buffer (10 mM Tris-HCl [pH 7.5], 1 mM EDTA) containing Proteinase K (540 µg/ml), and incubated at 55° C. for 2 h. A phenol:chloroform:isoamyl alcohol (25:24:1) and a chloroform extraction were subsequently performed. The DNA was precipitated by adding an equal amount of isopropanol and the pellet was washed with 70% ethanol. The DNA pellet was dissolved in 15 µl sterile water, and 2 µl of the final DNA solution was applied to PCR-based detection of the vp39 gene sequence using primers mentioned above. All PCR reactions were performed in 25 µl volumes including: 2 µl DNA, 200 µM dNTPs, 10 pmol of each primer, 1.5 mM $MgCl_2$ and 1.5 U GoTaq DNA polymerase (Promega). Amplification conditions were as follows: an initial denaturation at 94° C. for 2 min, after which 30 cycles of denaturation (30 s at 94° C.), primer annealing (20 s at 60° C.) and primer extension (25 s at 72° C.). The termination cycle was 7 min at 72° C. Negative controls were included in all PCR amplifications to test for contaminants in the reagents. Aliquots (3.0 µl) of the PCR products were analysed by electrophoresis in 1.2% (w:v) agarose gels, with 1×TAE buffer, stained with ethidium bromide (0.5 µg/ml).

Generation of an Antibiotic Resistance Gene-Free AcMNPV vp80-Null Bacmid

To determine whether the VP80 protein has an essential role in the context of viral progeny production, we constructed an AcMNPV bacmid (derived from bMON14272 (from Invitrogene)) with a deletion of the vp80 ORF by homologous recombination in E. coli. To accomplish this, a cat gene flanked by mutant LoxP sites (Suzuki et al., 2005) was amplified using PCR primers vp80-KO-F and vp80-KO-R (see Table 1) from a plasmid comprising a cat gene flanked by mutant LoxP sites. The resulting PCR fragment, which contained the cat gene flanked by mutant LoxP sites and AcMNPV ~50-bp homology sequences to the 5' or 3' proximal region of the vp80 ORF, was treated with DpnI and gel-purified to eliminate the template plasmid. The PCR product was then transformed into DH10β *E. coli* cells containing bMON14272 (Invitrogen) and the Lambda RED recombinase-producing plasmid pKD46 (Datsenko & Wanner, 2000), which had been prepared in the following manner. Transformed DH10β-bMON14272/pKD46 *E. coli* cells were grown in 50-ml LB (2.0% peptone, 0.5% yeast extract, 85.5 mM NaCl, [pH 7.0]) cultures with kanamycin (50 µg/ml), ampicillin (100 µg/ml) and L-arabinose (1.5 mg/ml) at 30° C. to an $OD_{600}$ of ≈0.6 and then made electrocompetent by a standard procedure. The electroporated cells were incubated at 37° C. for 3 h in 3 ml LB medium and plated on LB-agar containing chloramphenicol at a concentration of 6.5 µg/ml. After 48-h incubation at 37° C., the chloramphenicol-resistant colonies were streaked to fresh LB-agar medium with 34 µg/ml chloramphenicol. The plates were incubated at 37° C. overnight, and colonies resistant to chloramphenicol were selected for further confirmation of the relevant genotype by PCR. Primers 90292 and 90889 were used to confirm the absence of the vp80 ORF, and primers cat-F and cat-R were employed to verify the presence of cat cassette into bacmid (detailed sequences in Table 1).

To eliminate the introduced antibiotic resistance gene (cat) from the bacmid backbone, a Cre/LoxP recombinase system was employed. A Cre recombinase-carrying plasmid pCRE obtained from Jeanine Louwerse (LUMC Leiden, The Netherlands) was introduced into DH10b-bMON14272-vp80null *E. coli* cells, and CRE expression was subsequently induced by the addition of isopropyl thiogalactoside (IPTG). Briefly, the electroporated cells were incubated at 37° C. for 3 h in 3 ml of LB medium (2.0% peptone, 0.5% yeast extract, 85.5 mM NaCl, [pH 7.0]) and plated on LB-agar medium containing 50 µg/ml kanamycin, 100 µg/ml ampicillin and 2 mM IPTG. After 24-h incubation, colonies resistant to kanamycin and ampicillin were selected for further verification of the desired genotype by PCR. In PCR-based analysis, primers 89507 and 91713 (Table 1) were used to verify elimination of cat gene from bacmid backbone. Positive clones were also confirmed by DNA-sequencing.

To recover transposition competence, the helper transposase-encoding plasmid pMON7124 (Invitrogen) was re-introduced into DH10β-bMON14272-vp80null *E. coli* cells. Finally, the egfp reporter gene was introduced into the vp80-null bacmid to facilitate observation of its behaviour in insect cells. Briefly, the egfp reporter gene was amplified using PCR oligonucleotides gfp-NheI-F and gfp-SphI-R (Table 1) from plasmid pEGFP-N3 (Clontech). The PCR product was cloned into plasmid pJet1.2/Blunt using Clone-JET™ PCR Cloning Kit (Fermentas) according to manufacturer's protocol. Subsequently, the egfp ORF was excised from error-free pJet1.2-egfp with NheI and SphI and subcloned into NheI/SphI-digested pFastBacDUAL (Invitrogen), to generate plasmid pFB-egfp. An expression cassette containing the egfp reporter gene under transcriptional control of the very late p10 promoter was transposed from pFB-egfp into polyhedrin locus of vp80-null bacmid as described in the Bac-to-Bac manual (Invitrogen). In the resulting genome, the complete vp80 ORF has been removed (see FIG. 2). This corresponds to the deletion of 2074 bp from nucleotide positions 89564 to 91637 in the AcMNPV clone C6 genome provided in SEQ ID NO: 1.

Construction of Repaired vp80-Null Bacmids

To prepare vp80 repair donor vectors, we modified plasmid pFB-egfp (noted above) by removing the polyhedrin promoter and replacing it with a fragment containing the vp80 promoter region and the vp80 ORF. First, a 2300-bp fragment containing both the vp80 promoter and ORF sequence was amplified using primers pvp80-StuI-F and vp80-XbaI-R (Table 1) from bacmid bMON14272 template, and cloned into vector pJet1.2/Blunt (Fermentas) to form pJet1.2-pvp80-vp80. After DNA sequence verification, the vp80 cassette was excised from pJet1.2-pvp80-vp80 by StuI/XbaI double digestion, and then subcloned into Bst1107I/XbaI-digested and gel-purified pFB-egfp to generate donor plasmid pFB-egfp-pvp80-vp80. Parallelly, a donor plasmid pFB-egfp-polh-vp80, where vp80 ORF is driven by the very late polyhedrin promoter (polh) was constructed. To this aim, a 2105-bp fragment carrying the vp80 ORF was amplified using primers vp80-SacI-F and vp80-XbaI-R (Table 1) and cloned into pJet1.2/Blunt, to generate pJet1.2-vp80. In the final step, the vp80 ORF was cut out (SacI/XbaI) from pJet1.2-vp80, and subcloned into SacI/XbaI-digested pFB-egfp, to create pFB-egfp-polH-vp80.

To overcome a problem associated with the unavailability of anti-VP80 antibody, FLAG tag decoration (N- and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transferred into pFB-egfp in a similar way as previous constructs.

The inserts of all developed donor plasmids were transposed into the vp80-null bacmid following the Bac-to-Bac protocol (Invitrogen). Screening of transposition-positive constructs into the polh locus was done by a triplex PCR-based assay employing a M13 forward and reverse primers and a gentamicin resistance gene-specific primer GenR (Table 1).

Transfection-Infection Assay

Bacmid DNAs were prepared from 1.5-ml over-night bacterial cultures of 2 to 3 independent colonies carrying the bacmid with the inserted heterologous gene according to the Bac-to-Bac manual (Invitrogen) and were analyzed in parallel. For transfections, 1 µg of each bacmid DNA preparation was used to transfect $1 \times 10^6$ Sf9 cells in a 6-well plate by the Cellfectin™-based transfection protocol as described in the Bac-to-Bac (Invitrogen) manual. From 72 h to 120 h post transfection (p.t.), viral propagation was checked by fluorescence microscopy. At 120 h p.t., the cell culture medium was centrifuged for 5 min at 2000×g to remove cell debris, and this clarified supernatant was used to infect $1.5 \times 10^6$ Sf9 cells in 6-well plates. After 72 h p.i., the spread of virus infection was again monitored by fluorescence microscopy. In all experiments, a wild-type bMON14272 bacmid carrying the egfp reporter gene under control of the p10 promoter was used as positive control. A bMON14272-gp64null bacmid also carrying the egfp reporter gene under control of the p10 promoter served as negative control, since it has lost the ability of cell-to-cell movement of the infection (Lung et al., 2002).

Time-Course Characterization of Viral Propagation in Cell Culture

Time course analyses were performed to compare budded virus production of the AcMNPV-vp80null virus and the various repair constructs in comparison to the wild type AcMNPV bacmid (Ac-wt) all containing egfp. Briefly, the Sf9 cells were seeded in 6-well tissue culture plates ($1 \times 10^6$ cells/well in 1 ml Sf900-II culture medium without serum at 28° C.). After two hours, the culture medium was removed, and the cells were transfected with 5 µg bacmid DNA, under standard conditions as recommended in the Bac-to-Bac manual (Invitrogen). Cell culture supernatants were harvested at 24, 48, 72, 96 and 120 h p.t., and analysed for the production of infectious budded virus by an end-point dilution assay to determine the tissue culture infective dose 50 ($TCID_{50}$). Infection was determined by monitoring egfp expression (from the p10 promoter). The average values of infectious titers derived from three independent transfections were calculated and plotted into graphs.

Transmission Electron Microscopy

Insect Sf9 cells were seeded in 25T flask ($3.5 \times 10^6$ cells/flask), and transfected with 20 µg either the Ac-Δvp80, rescue Ac-Δvp80-vp80 or Ac-wt bacmid construct. After 48 h p.t., the cells were harvested and prepared for transmission electron microscopy as described previously (van Lent et al., 1990). Samples were examined and photographed with a Philips CM12 electron microscope.

Budded Virus Production Assay

Insect Sf9 cells were seeded in two 25T flasks ($3.5 \times 10^6$ cells/flask), and transfected with 20 µg either Ac-Δvp80, Ac-Δvp80-vp80, Ac-Δvp80-pH-vp80, Ac-Δvp80-FLAG-vp80, Ac-Δvp80-vp80-FLAG, or Ac-wt bacmid construct. Five days p.t., the BV-enriched cell culture supernatants were harvested, and ultracentrifuged through a cushion of 10% sucrose solution (25,000 rpm for 1.5 hour, Beckman SW32). Pelleted budded virions were resuspended in sterile demi-water, and prepared for either negative staining electron microscopy, SDS-polyacrylamide electrophoresis, or PCR-based detection (as mentioned above).

Purification of ODVs and Rod-Shaped Structures from Infected Cells

The presence of ODVs and rod-like structures in infected/transfected insect cells was analyzed by electron microscopy (EM). For this purpose, insect cells were harvested 48 h p.i., lysed and the cell lysates were ultracentrifuged through a 40% sucrose cushion in TE (1 mM Tris-HCl pH 7.4, 0.1 mM EDTA) buffer (45,000 rpm for 1 hour, Beckman SW55). Pellets were resuspended in sterile demi-water and analyzed by negative staining EM as described previously (van Lent et al., 1990).

Development of Transgenic Sf9-Derived Cell Line Expressing vp80

To develop a cell line, which produces the VP80 protein, a 2105-bp fragment carrying the vp80 ORF was amplified using primers vp80-SacI-F and vp80-XbaI-R (Table 1) and cloned into pJet1.2/Blunt, to generate pJet1.2-vp80. In the next step, the vp80 ORF was cut out (SacI/XbaI) from pJet1.2-vp80, and subcloned into SacI/XbaI-digested pIZ (Invitrogen), to create pIZ-vp80. The resulting plasmid vector pIZ-vp80 was linearized with Eco57I, and gel-purified. Sf9 cells were seeded in a six-well plate ($1 \times 10^6$ cells/well), and transfected with 10 µg of the linearized vector. After 24 hours post-transfection, cells were selected by cell culture medium containing Zeocin™ (300 µg/ml) for 2 to 3 weeks, until no control Sf9 cells survived under the same conditions. Cells were then propagated as an uncloned cell line.

Generation and Characterization of a AcMNPV vp39-Null Bacmid

To study the role of the vp39 gene in the context of viral progeny production and the nucleocapsid assembly process, we constructed an AcMNPV bacmid (bMON14272) with a deletion of vp39 by homologous recombination in *E. coli* according to the same procedure as noted above for the AcMNPV vp80null bacmid construct. Since the sequence of the vp39 ORF is overlapping with promoter sequences of both flanking ORFs (cg-30 and lef-4), only an internal part of the vp39 ORF could be deleted, to avoid de-regulations of cg-30 and lef-4 expression. To reach this, a cat gene flanked by mutant LoxP sites was amplified using PCR primers vp39-KO- and vp39-KO-R (Table 1) from a plasmid comprising a cat gene flanked by mutant LoxP sites. The resulting PCR fragment, which contained the cat gene flanked by mutant LoxP sites and ~50-bp sequences homologous to an internal region of the vp39 ORF, was treated with DpnI and gel-purified to eliminate the template plasmid. The PCR product was then transformed into DH10β *E. coli* cells containing bacmid bMON14272 (Invitrogen) and Lambda RED recombinase-producing plasmid pKD46 (Datsenko & Wanner, 2000) prepared in the above mentioned manner. In the final step, colonies resistant to kanamycin were subjected to PCR-based analysis using primers 75834 and 76420 (Table I) to verify insertion/elimination of the cat gene from the bacmid backbone. Positive clones were further verified by DNA-sequencing of the obtained PCR products. According to this protocol, an internal part (498 nt=166 aa) of the vp39 ORF was removed, coordinates: 75894-76391 as indicated in FIG. 9.

Construction and Analysis of Repaired vp39-Null Bacmids

To prepare a vp39 repair donor vector, we modified plasmid pFB-egfp (noted above) by introduction of the vp39 ORF under control of the polyhedrin promoter. Initially, a 1073-bp fragment was amplified using primers vp39-SacI-F and vp39-XbaI-R (see Table I for primer sequences) from the bMON14272 template, and cloned into vector pJet1.2/Blunt (Fermentas) to form pJet1.2-vp39. After DNA sequence verification, the vp39 ORF was excised from pJet1.2-vp39 by SacI/XbaI double digestion, and then subcloned into SacI/XbaI-digested and gel-purified pFB-egfp to generate donor plasmid pFB-egfp-vp39. After an unsuccessful attempt to rescue AcMNPV vp39null with pFB-egfp-vp39, a set of novel donor plasmids was prepared. First, a 2498-bp fragment containing vp39 and lef-4 ORFs was PCR-generated using primers vp39-StuI-F and lef-4-XbaI-R from bacmid bMON14272 template, and cloned into vector pJet1.2/Blunt (Fermentas) to form pJet1.2-vp39-lef-4. After DNA sequence confirmation, the fragment containing vp39 and lef-4 ORFs was excised from pJet1.2-vp39-lef-4 by StuI/XbaI double digestion, and then subcloned into StuI/XbaI-digested and gel-purified pFB-egfp to generate donor plasmid pFB-egfp-vp39-lef-4.

Parallelly, donor plasmid pFB-egfp-vp39-cg30 was constructed, where both vp39 and cg-30 ORFs are driven from the very late polyhedrin promoter, and the cg-30 ORF can also use its native promoter situated inside the 3"-end of the vp39 ORF. Briefly, a 1868-bp fragment carrying both vp39 and cg-30 ORFs was amplified using primers cg30-XbaI-F and vp39-XbaI-R (noted above) and cloned into pJet1.2/

Blunt, to generate pJet1.2-vp39-cg30. The vp39/cg-30 cassette was subcloned as SacI/Xba into pFB-egfp, to create pFB-egfp-vp39-cg30. Additionally, a similar donor vector pFB-egfp-FLAG-vp39-cg30 was constructed, where vp39 ORF is N-terminally FLAG-tagged. The same strategy was employed to develop this vector, only the reverse primer vp39-FLAG-SacI-R was used to amplify vp39/cg-30 cassette instead of the vp39-XbaI-R primer.

All developed donor plasmids were transposed into vp39-null bacmid following the Bac-to-Bac kit protocol (Invitrogen) and screened as detailed above for vp80 repair bacmids. The functional analysis was performed as described above for the vp80 constructs.

Generation and Analysis of AcMNPV vp1054-Null Bacmid

To verify the essential role of the vp1054 gene in the context of viral progeny production and nucleocapsid assembly, we constructed an AcMNPV bacmid (bMON14272) with a deletion of vp1054 by homologous recombination in E. coli according to the same procedure as for the vp80null bacmid construct with minor alternations. Since the vp1054 ORF is overlapping with the essential lef-10 ORF, we could not remove the whole vp1054 ORF, but only a 955-bp nucleotide 3"-end part of the ORF. To prevent translation of the C-truncated VP1054 mutant in insect cells, we decided to mutate the first translation codon ATG→Met to ACG→Thr. This single nucleotide substitution also changed an internal codon no. 32 (AAT) to AAC of lef-10 ORF, however, both are encoding the same amino acid (Asn). To accomplish this, we first amplified the 5"-end of the vp1054 ORF using primers vp1054-KO-F and vp1054-KO-R1 from bacmid bMON14272 (Invitrogen). The 214-bp PCR product contained a mutation of the ATG start codon of the vp1054 ORF, introduced a synthetic stop/poly-A signal sequence for the lef-10 ORF, and has a 3"-end sequence homology overhang to the cat cassette to facilitate the second PCR, and a 49-bp homology sequence to the 5"-end of vp1054 ORF to mediate Lambda RED-directed homologous recombination in E. coli. After gel-purification and DNA quantification, the 214-bp fragment was used as forward primer in a second step PCR with reverse primer vp1054-KO-R2 with a plasmid comprising a cat gene flanked with mutant LoxP sites as template. The resulting 1230-bp PCR fragment, which contained the cat gene flanked by mutant LoxP sites, a mutated 5'-end of the vp1054 ORF and ~50-bp sequences homologous to the 5' or 3' proximal region of the vp1054 ORF, was treated with DpnI and gel-purified to eliminate the template plasmid. Recombination of this PCR product with the bMON14272 bacmid was performed as described above for the vp80 mutant. Kanamycin resistant colonies were verified by PCR with primer pairs cat-F/cat-R, 45510/46235, and 45122 and 46441 to check the insertion/elimination of the cat gene from the bacmid backbone. Insertion sites were also confirmed by DNA-sequencing. This method resulted in the deletion of 955 bp from nucleotide positions 45365 to 46319 in the AcMNPV clone C6 genome provided in SEQ ID NO: 1. All primer sequences are given in Table 1.

Construction of a Repaired vp1054-Null Bacmid Construct

To prepare vp1054 repair donor vector, we modified plasmid pFB-egfp (noted above) by removing the polyhedrin promoter and replacing it with a fragment containing the vp1054 promoter region and the vp1054 ORF. First, a 1714-bp fragment containing both the vp1054 promoter and ORF sequence was amplified using primers vp1054-Rep-F and vp1054-Rep-R from bacmid bMON14272 template, and cloned into vector pJet1.2/Blunt (Fermentas) to form pJet1.2-pvp1054-vp1054. After DNA sequence verification, the vp1054 cassette was excised from pJet1.2-pvp1054-vp1054 by StuI/XbaI double digestion, and then subcloned into Bst1107I/XbaI-digested and gel-purified pFB-egfp to generate donor plasmid pFB-egfp-pvp1054-vp1054. The developed donor plasmids were transposed into the vp1054-null bacmid following the Bac-to-Bac protocol (Invitrogen) and screened. Recombinant bacmids were analyzed as detailed above for vp80 bacmids.

Generation and Analysis of AcMNPV p6.9-Null Bacmid

To verify the essential role of p6.9 in the context of viral progeny production, we constructed an AcMNPV bacmid (bMON14272) with a deletion of p6.9 by homologous recombination in E. coli. To accomplish this, a chloramphenicol resistance gene (cat) flanked by mutant LoxP sites was amplified using PCR primers p6.9-KO-F and p6.9-KO-R from a plasmid comprising a cat gene flanked by mutant LoxP sites. Mutant viruses were obtained following the same procedure as for the other mutants. For the PCR-based analysis of the finally obtained mutant clones the primer pairs cat-F and cat-R and 86596 and 86995 were used to check insertion/elimination of cat gene from bacmid backbone. Positive clones were also confirmed by DNA-sequencing. This method results in the deletion of 164 bp from nucleotide positions 86716 to 86879 in the AcMNPV clone C6 genome provided in SEQ ID NO: 1. Table 1 for primer sequences.

Construction and Functional Analysis of Repaired p6.9-Null Bacmids

To prepare p6.9 repair donor vectors, the pFB-GFP-p6.9 vector was used, which was constructed by Marcel Westenberg (Wageningen University). To make this vector, the AcMNPV p6.9 promoter sequence was amplified from the plasmid pAcMP1 (Hill-Perkins & Possee, 1990) with primers pp6.9-F and pp6.9-R using the high-fidelity Expand long-template PCR system (Roche). The PCR product was cloned as SalI fragment into pFastBac1 (Invitrogen), from which the polyhedrin promoter was deleted in advance by fusing the Bst1107I to the StuI site, to obtain pFB1-p6.9. The p6.9 promoter from pFB1-p6.9 was recloned as SnaBI/BamHI fragment into the Bst1107I and BamHI sites of pFastBacDUAL (Invitrogen), thereby deleting the polyhedrin promoter. Subsequently, the egfp reporter gene was cloned downstream of the p10 promoter into the XmaI site to obtain pFB-GFP-p6.9. Finally, the p6.9 genes of AcMNPV and Spodoptera exigua (Se)MNPV were PCR amplified from either the AcMNPV bacmid (bMON14272) or SeMNPV genomic DNA by using the high-fidelity Expand long-template PCR system and primers generating EcoRI and NotI at the 5' and 3' ends, respectively (Table 1). The PCR products were cloned downstream of the p6.9 promoter in the EcoRI/NotI sites of pFB-GFP-p6.9. All generated clones were sequenced to verify the incorporated p6.9 sequences.

The expression cassettes of both developed donor plasmids were transposed into the p6.9-null bacmid following the Bac-to-Bac protocol (Invitrogen). Screening of transposition-positive constructs into the polh locus was done by the triplex PCR-based assay as described above for the vp80 constructs. The analysis was performed as for the vp80 constructs Results Silencing of AcMNPV vp80 does not Affect Baculovirus Very Late Gene Expression We explored the effect of transfecting Sf9 cells with different dsRNAs during infection with AcMNPV-GFP. To trigger dsRNA-induced silencing of selected baculoviral genes (vp1054, vp39, vp80, dbp and odv-ec27), we generated gene-specific dsRNAs using in vitro T7 RNA polymerase-based synthesis. However, when we began these studies it was not clear what amount and time point of dsRNA transfection is the most effective to silence baculoviral genes. To determine an optimal amount of dsRNA for RNAi assay purposes in baculovirus-infected cells, we first attempted to silence reporter egfp gene with different amounts of dsRNA. These pilot assays showed that the most potent RNAi effect is achieved using 100 pg dsRNA per cell (data not shown). At the same time, it was also proved that RNAi treatment has no negative effect on the production of infectious budded virions progeny. We also tried to transfect dsRNA into the cells at two different time points, 24 h prior to infection or 1 h p.i. The results proved that transfection performed at 1 h p.i. is more efficient in silencing of genes expressed at late/very late phases of baculoviral infection in contrast to transfection carried out at 24 h prior to infection (data not shown). In addition, to ensure that knock-down was gene-specific, dsRNA corresponding to the cat gene was transfected as an RNAi negative control. Herein, we could observe a moderate inhibition of baculovirus infection propagation in comparison to untransfected insect cells. However, the same phenomenon was also observed when insect cells were treated only with transfection reagents. Therefore, we could conclude that the effect can be explained by a negative impact (cytotoxicity) of the presence of transfection reagents on cell viability.

Figure 1B:
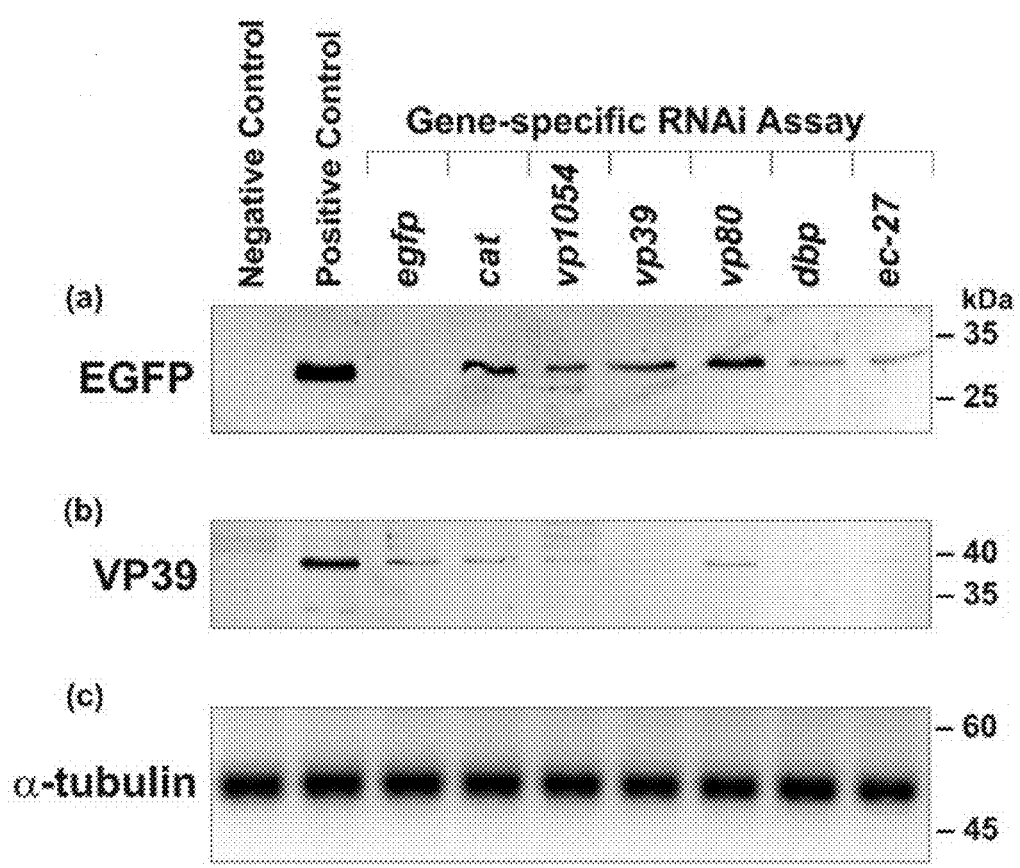

Silencing screening of baculovirus genes revealed that down-regulation of vp1054, vp39, dbp and odv/ec-27 is also associated with a reduction or inhibition of very late gene expression measured by EGFP detection (FIGS. 1A and 1B). The highest levels of this inhibition were observed in dbp- and odv/ec-27-targeted cells. The cause of this effect can be explained by the presence of bi-cistronic and overlapping mRNA transcripts, which are produced during a baculovirus replication cycle. Eventually, a cross-reaction with targets of limited sequence similarities can also be involved in the process. Only cells treated with vp80 dsRNA showed a similar level of EGFP expression as untransfected cells or particularly with cat dsRNA-treated cells. Importantly, very few EGFP-producing cells were observed in insect cells where egfp-specific dsRNA was introduced (positive RNAi control), showing that the transfection efficiency was high. Based on our RNAi screening achievements, the vp80 gene (locus) seems to be a suitable candidate for RNAi-based targeting in context of interference with baculoviral very late gene expression.

Figure 1C:
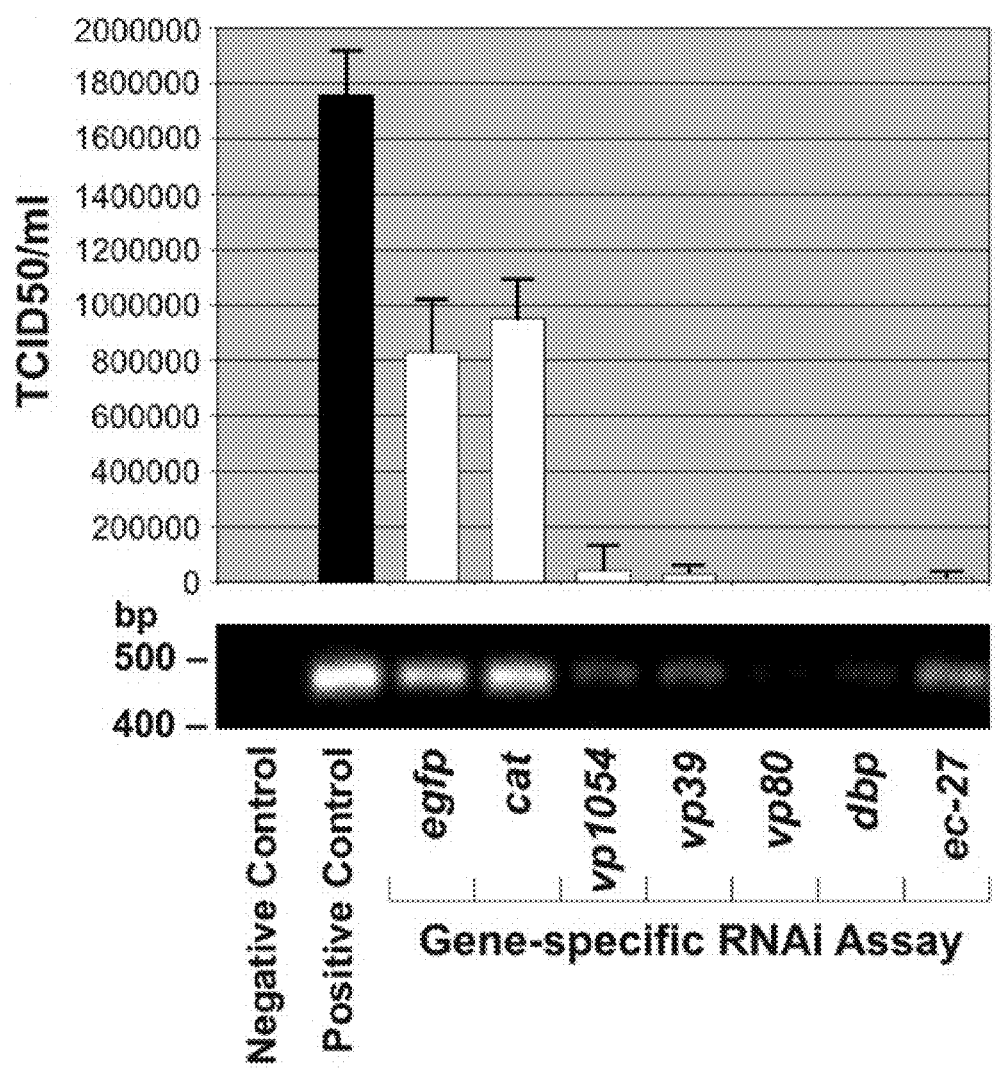
Figure 1D:
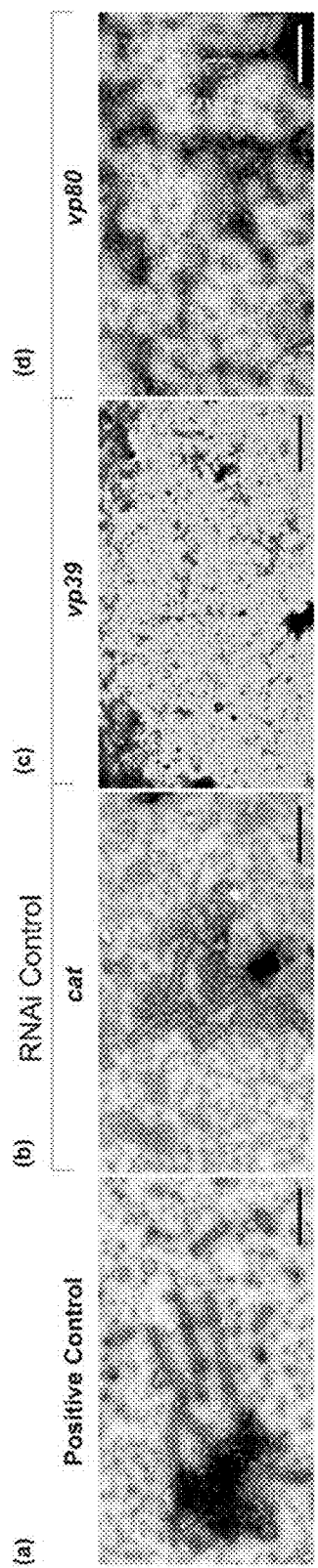

Knock-Down of vp80 Totally Prevents Production of BVs and Normally Appearing ODVs To determine the roles of selected candidate genes (vp1054, vp39, vp80, dbp and odv/ec-27) in production of budded virions progeny, cell culture medium (36 h p.i.) from dsRNA-treated cells was examined for the presence of BVs. End-point dilution-based titrations confirmed that all tested genes are essential for infectious budded virus progeny production (FIG. 1C). We were not able to detect any infectious BVs in vp80- and dbp-targeted cells. In addition, PCR-based assay indicated that defective or non-infectious viral particles are also not produced in vp80-targeted cells. It is important to point out that the results also showed a significant decrease in the production of infectious BVs in the RNAi controls (egfp- and cat-specific dsRNA-treated cells) compared to untransfected cells. The cytotoxicity of transfection reagents is again the assumed cause of this negative effect. Electron microscopy analysis of cell lysates showed that formation of ODVs and rod-like structures was totally inhibited in cells treated with dsRNA-vp39 as expected (FIG. 1D). Production of ODVs and rod-like structures was also significantly reduced in insect cells treated with dsRNA-vp80 (FIG. 1D). However, in vp80-targeted cells we could mostly find nucleocapsids of aberrant phenotypes (pointed shape). On the other hand, introduction of dsRNA-cat into insect cells did not cause any changes in the production of ODVs.

The AcMNPV vp80 Gene is Essential for Viral Replication

An AcMNPV deletion virus was constructed as detailed in FIG. 2. Repair constructs were designed such that the wild-type vp80 ORF or N- and C-terminally FLAG-tagged vp80 genes along with its native or polyhedrin promoter regions were inserted into the polyhedrin locus along with the egfp gene under the p10 promoter (FIG. 3A). To investigate the function of the vp80 gene, Sf9 cells were transfected with either the knock-out or repair bacmid constructs and monitored for EGFP expression by fluorescence microscopy. When Ac-vp80 null was introduced into Sf9 cells, no viral propagation was observed in cell culture at 72 h to 120 h p.t. We could observe only a "single-cell infection" phenotype similar to the phenotype of Ac-gp64null bacmid (FIG. 3B). The results indicate that Ac-vp80null is able to reach the very late phase of infection as confirmed by p10 promoter-driven EGFP expression. From 72 h to 120 hours p.t., widespread EGFP expression could be seen in insect cell monolayers that were transfected with the three repair (vp80 driven from its native promoter, vp80 driven from polyhedrin promoter and N-terminally FLAG-tagged vp80 driven from its native promoter) constructs indicating that these bacmids were able to produce levels of infectious budded virions sufficient to initiate secondary infection at a similar level as the wild-type bacmid (FIG. 3B). In contrast, in insect cells transfected with C-terminally FLAG-tagged vp80 repair constructs, by 72 h p.t. EGFP expression was only observed in isolated cells that were initially transfected indicating that this bacmid construct is defective in viral replication (FIG. 3B). However, by 96 h p.t. formation of tiny plaques was observed and by 120 h p.t. very few plaques of normal size were developed. The results show that the C-terminally flagged mutant is strongly delayed in producing budded virus and showed that an unmodified C-terminus is very important for the function of VP80. At 5 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with repair constructs showed numerous EGFP expressing cells (FIG. 3C). Nevertheless, cells incubated with supernatant from C-terminally FLAG-tagged constructs showed a significant reduction in the number of EGFP-positive cells. On the other hand, in insect cells incubated with supernatant from the transfection with the vp80 knockout, no EGFP expression was detected at any time-point analyzed up to 72 h (FIG. 3C).

Moreover, to characterize the exact effect of deletion of the vp80 gene on AcMNPV infection, the viral propagation in transfected Sf9 cells was compared between Ac-wt, Ac-Δvp80, Ac-Δvp80-vp80Rep, Ac-Δvp80-polh-vp80Rep, Ac-Δvp80-FLAG-vp80Rep and Ac-Δvp80-FLAGRep. Cell culture supernatants of all the above bacmid constructs were analysed at indicated time points for BV production (FIG. 4). As expected, the repaired Ac-Δvp80-vp80Rep, Ac-Δvp80-polh-vp80Rep, Ac-Δvp80-FLAG-vp80Rep viruses showed kinetics of viral replication consistent with wild-type virus (Ac-wt) propagation. Budded virion production by the C-terminally flagged Ac-Δvp80- vp80-FLAGRep virus was reduced to approximately 0.06% compared to the Ac-wt virus or the other repaired viruses.

These results indicate that the vp80 gene is essential for infectious BV production. It has clearly been proven that the whole sequence of vp80 ORF can completely be deleted from the bacmid backbone and adequately rescued by introduction of the vp80 ORF into a heterologous site (polyhedrin locus) of the genome. We also showed that vp80 gene expression can be driven by the heterologous polyhedrin promoter sequence with no negative effect on viral replication in cell culture. Additionally, we observed that the N-terminus in contrast to the C-terminus of VP80 is permissive to gene modifications (epitope tag-labeling). We noted that the kinetics of the C-terminally FLAG-tagged VP80 virus was significantly delayed when compared with all other rescue or wild-type viruses, indicating the functional importance of the VP80 C-terminus.

VP80 is Required for Production of Both BV and ODV

The results described above indicated that the Ac-vp80null mutant is completely defective in production of infectious budded virus. However, there was also a possibility that the mutant can still produce non-infectious budded particles. To investigate the ability, Sf9 cells were transfected with either the knock-out, repair or wild-type bacmid constructs and 7 days p.t. cell culture mediums were ultracentrifuged to pellet budded viruses. The formed pellets were either analyzed by negative staining electron microscopy or by Western blot- and PCR-based detection to confirm the presence of the budded viruses. No intact budded virus, virus-like particles, nor its structures (such as major capsid protein VP39 and viral genome sequence) were revealed in the pellet from the cells transfected with the Ac-vp80null mutant (FIGS. 5A and 5B). On the other hand, all analyzed repair constructs produced normally-appearing budded virus as compared with budded virus-derived from the wild-type virus (FIG. 5A). Nevertheless, it was very difficult to find representative budded virions in the pellet derived from C-terminally FLAG-tagged vp80 gene repair construct-transfected cells.

Figure 6A:
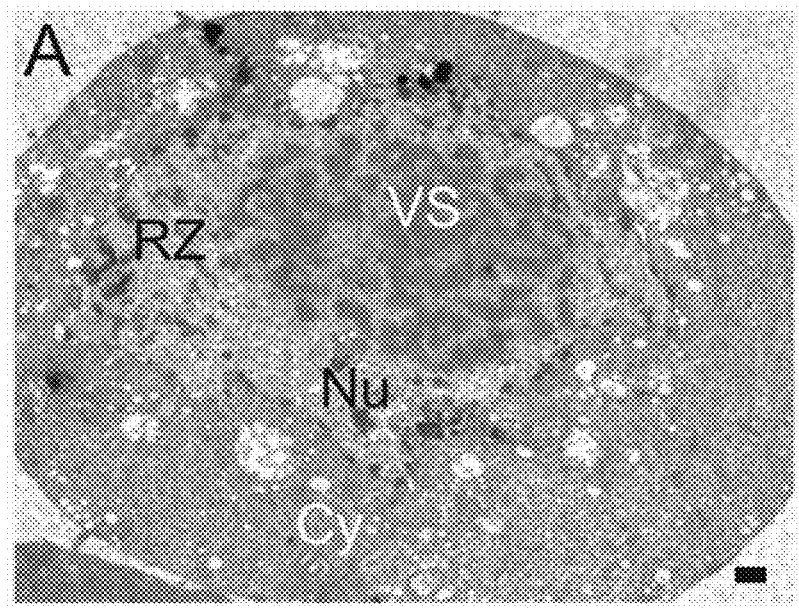
Figure 6B:
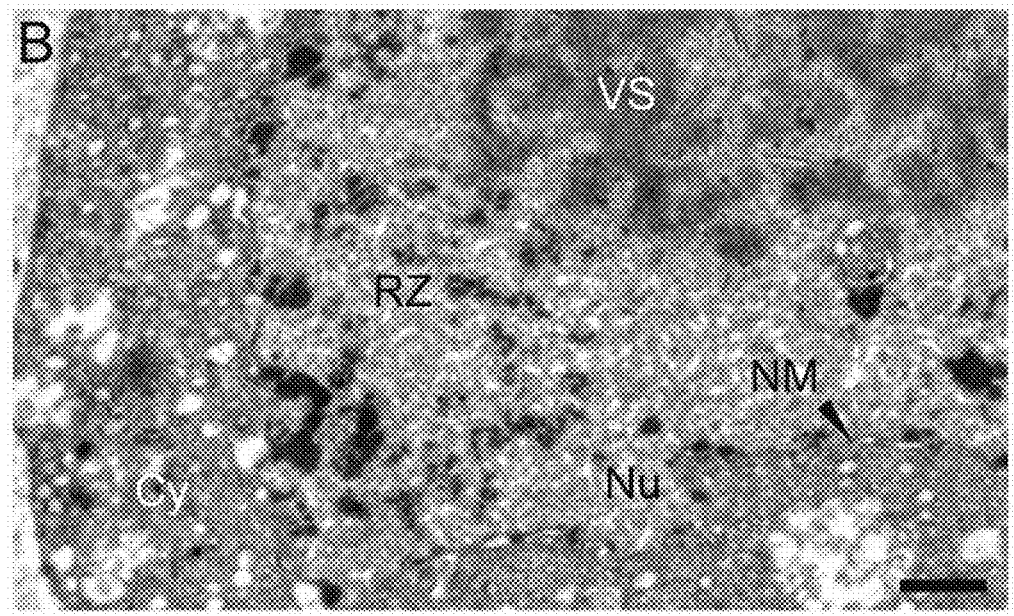
Figure 6C:
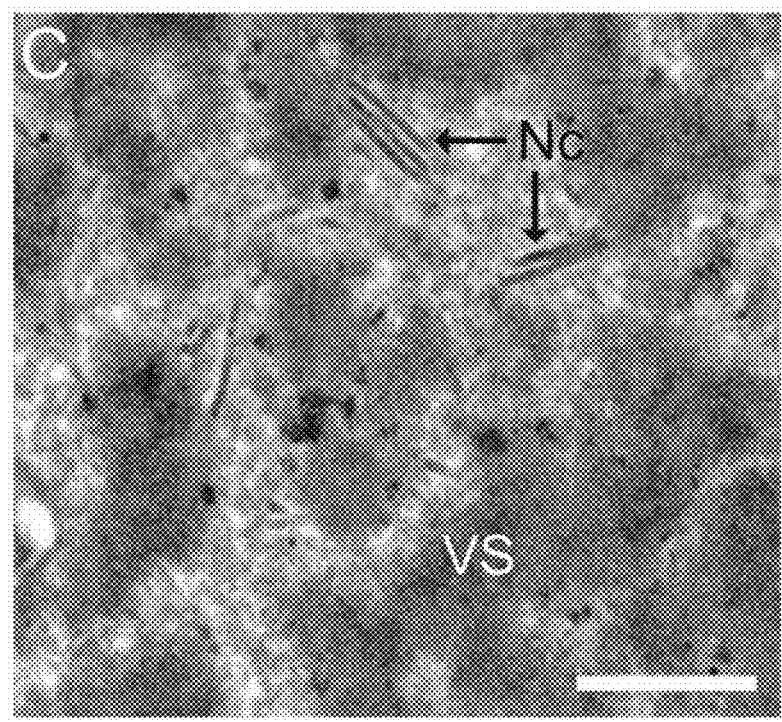
Figure 6D:
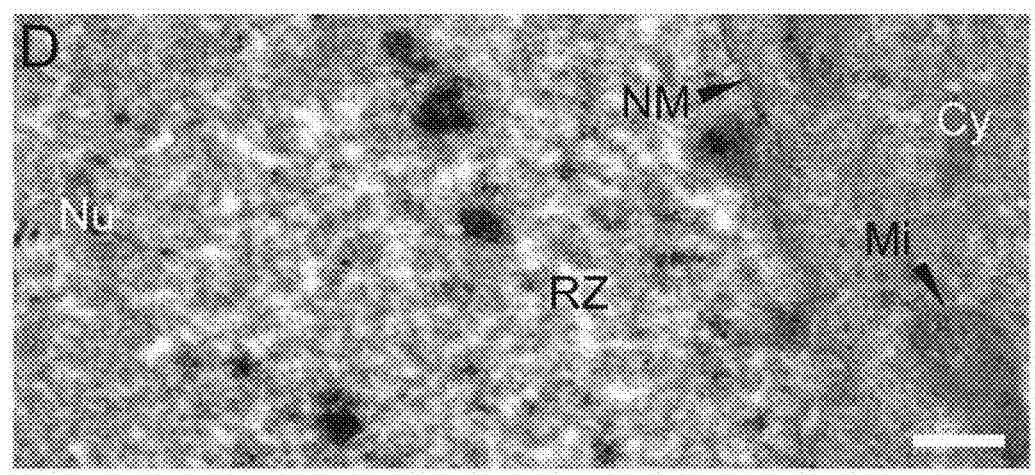
Figure 6E:
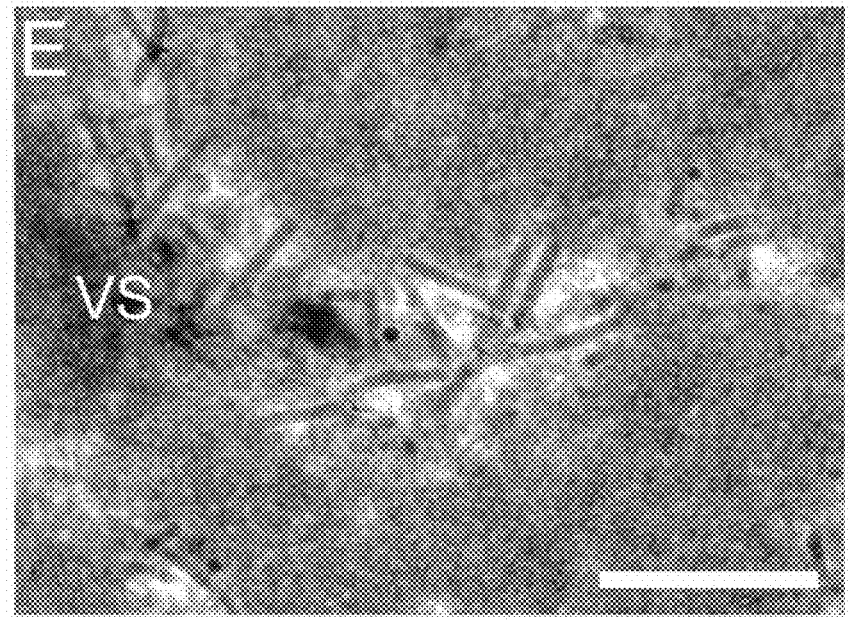
Figure 6F:
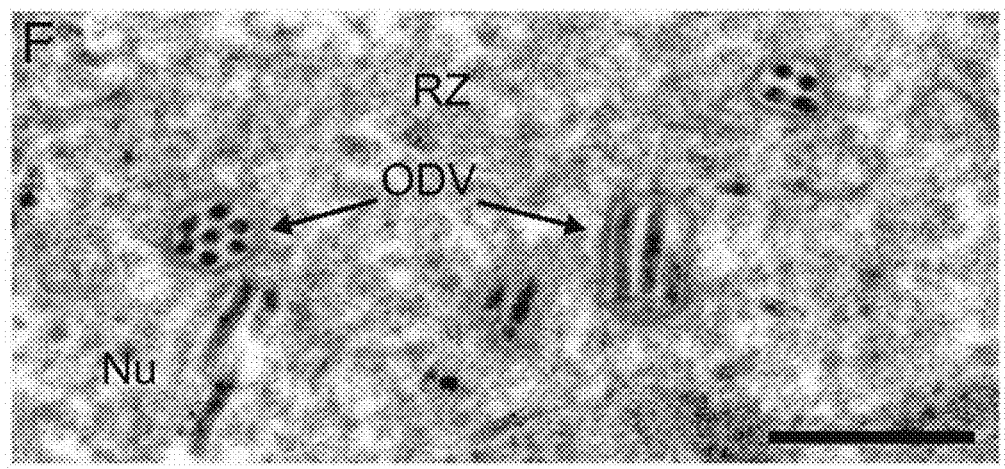
Figure 6G:
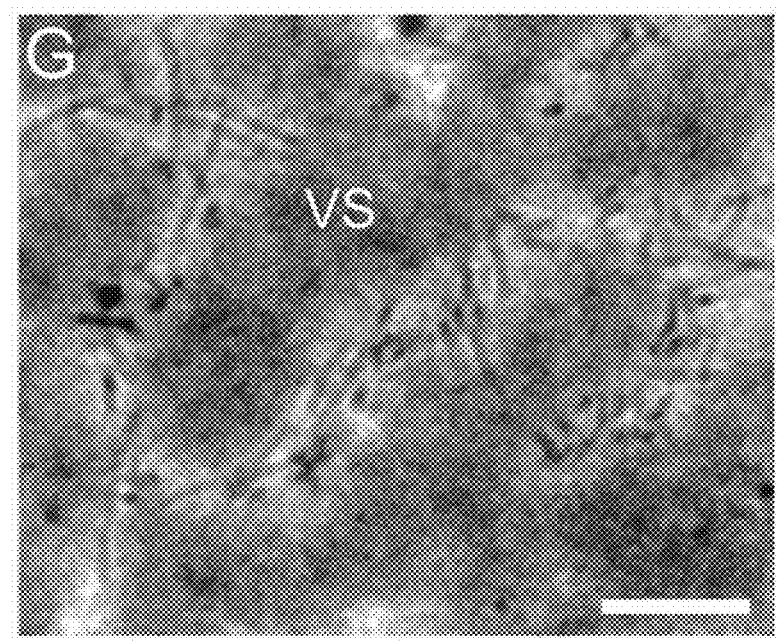
Figure 6H:
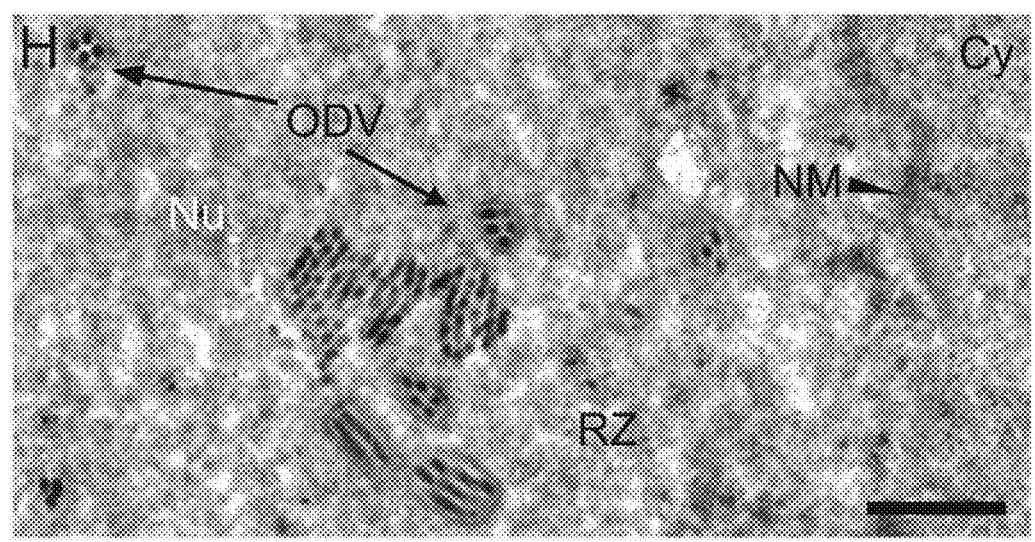

To further characterize deletion of the vp80 gene on baculovirus life cycle, electron microscopy was performed with ultra-thin sections generated from bacmid-transfected cells. The Ac-vp80null-transfected cells developed the typical phenotype of baculovirus-infected cells with an enlarged nucleus, a fragmented host chromatin, an electron-dense virogenic stroma, etc. (FIG. 6A). The absence of VP80 did not prevent formation of normally-appearing nucleocapsids inside the virogenic stroma (FIG. 6C). The formed nucleocapsids were phenotypically undistinguishable from those produced by either the Ac-vp80null repair or Ac-wt bacmids. However, an abundance of assembled nucleocapsids was rather less as compared with cells transfected with the Ac-vp80null repair or Ac-wt bacmids (FIGS. 6E and 6G). In addition, no occlusion-derived virions nor bundles of nucleocapsids prior to an envelopment could be observed in the peristromal compartment of a nucleoplasm (so called the ring zone) of Ac-vp80null bacmid-transfected cells (FIGS. 6B and 6D). It seems that VP80 plays a role during maturation of nucleocapsids and/or their release/transport from the virogenic stroma. Eventually, VP80 can somehow contribute to an efficient nucleocapsid assembly which could be explained by the small number of nucleocapsids present in the virogenic stroma of Ac-vp80null transfected cells. When the vp80 gene was re-introduced back into the bacmid mutant, a lot of nucleocapsids and occlusion-derived virions could be seen in the ring zones of transfected cells (FIG. 6F). An abundance and morphology of occlusion-derived virions produced in Ac-Δvp80-vp80 repair bacmid-transfected cells were similar to those produced by wild-type bacmid (FIGS. 6F and 6H).

VP80 Function can be Complemented by the Trans-Acting vp80 Gene

To prove that VP80 function can be complemented by the trans-acting vp80 ORF, a complementation assay was performed with a transgenic cell line, Sf9-vp80, that was stably transformed with the vp80 gene expressed under control of an early baculovirus *Orgyia pseudotsugata* ie-2 promoter. In the assay, both Sf9 and Sf9-vp80 cells were transfected with the Ac-vp80null bacmid mutant (FIG. 7). Virus infection spread was monitored by EGFP-specific fluorescence at 72 h and 96 h p.t. In Sf9-vp80 cells we could observe viral plaques demonstrating the virus spread. On the other hand, in Sf9 cells only "single-cell infection" phenotype could be seen as previously described above. After six days, the cell culture supernatants were harvested and used as an inoculum to infect fresh groups of Sf9 cells. After 5 days, EGFP-positive cells were monitored by fluorescence microscopy. Only "single-cell infection" phenotype was observed in Sf9 cells receiving the supernatant from Sf9-vp80 cells. As assumed, no EGFP signal was detected in Sf9 cells receiving the supernatant from Sf9 cells. These results show that the Ac-vp80null can be rescued by VP80-expressing cells (Sf9-vp80) and demonstrate that the observed complementation is due to VP80 protein expressed from the host cell line and not from acquisition of the vp80 gene from the cell line. In other words, the results match requirements asked to produce biopharmaceuticals (EGFP protein in our model assay) without contaminating baculovirus virions.

Generation and Characterization of vp39-Null Bacmid

To study the functionality of the AcMNPV vp39 gene during virus infection, a vp39-null AcMNPV bacmid was constructed by partial deletion of the vp39 gene. The deletion construct was selected by its resistance to chloramphenicol indicating that site-specific deletion of the vp39 gene had occurred. In the resulting vp39-null AcMNPV bacmid, the internal part of vp39 gene was correctly replaced by the cat gene. Subsequently, the cat was eliminated by Cre/LoxP recombination (FIG. 8A). The vp39 sequence was removed from nucleotides 75894 to 76391 according to the AcMNPV clone C6 genome sequence (SEQ ID NO:1). The structure of the vp39 deletion constructs was confirmed by PCR using primers 75834 and 76420 (FIG. 8B). A 647-bp DNA fragment was amplified when wild-type AcMNPV bacmid was used as a template, whereas a 1113-bp DNA fragment could be amplified on AcMNPV vp39-null(+cat) template (FIG. 8B). When the final construct AcMNPV-vp80null(–cat) with eliminated cat cassette was used in PCR analysis, only a short 183-bp DNA fragment could be detected (FIG. 8B). The results were confirmed by DNA sequencing.

Functional Mapping of vp39 ORF Indicates a Presumable Functional Relationship Between vp39 and cg-30 ORFs The repair constructs were designed in such a way that the wild-type vp39 ORF under control of the polyhedrin promoter sequence was inserted into the polyhedrin locus along with the egfp gene controlled by the p10 promoter (FIG. 9A). To investigate the function of the vp39 gene, Sf9 cells were transfected with either the knock-out or repair bacmid constructs and monitored for EGFP expression by fluorescence microscopy. When Ac-vp39 null was introduced into Sf9 cells, no viral propagation was observed from 72 h to 168 h p.t. We could observe only a "single-cell infection" phenotype similar to the phenotype of the Ac-gp64null bacmid (FIG. 9B).

These results indicate that the Ac-vp39null construct is able to reach the very late phase of infection as shown by the p10 promoter-driven EGFP expression. Unexpectedly, no viral propagation could be seen in insect cell monolayers that were transfected with the vp39 repair (vp39 driven from polyhedrin, Ac-Δvp39-polh-vp39Rep) constructs (FIG. 3B). For this reason, we decided to prepare three extra repair bacmids carrying both vp39 and lef-4 ORFs under control of their native promoters. When the insect cells were transfected with these repair constructs again viral replication did not occur (FIG. 9B) and a "single-cell infection" phenotype was observed from 72 h to 168 h p.t. Interestingly, in insect cell monolayers that were transfected with the repair constructs carrying both vp39 (or FLAG-tagged vp39) and cg-30 we could observe tiny clusters of EGFP-positive cells (3-5 cells) (FIG. 9B). However, we did not see a full-value viral replication as that of the wild-type vector (Ac-wt), At 7 days p.t., cell culture supernatants were collected and added to freshly plated Sf9 cells, which were then incubated for 3 days to detect infection by virus generated from cells transfected with all bacmids mentioned here (FIG. 9C). As expected, Sf9 cells incubated with the supernatant from Ac-wt transfections showed numerous EGFP expressing cells. On the other hand, cells incubated with supernatants from Ac-Δvp39-polh-vp39Rep and Ac-Δvp39-vp39-lef-4Rep constructs did not show any EGFP-positive cells. However, in insect cells incubated with supernatants from Ac-Δvp39-vp39-cg30Rep and Ac-Δvp39-FLAG-vp39-Rep, a number of EGFP-expressing cells were detected (FIG. 9C). These results indicated that a possible functional relationship between the vp39 and cg-30 ORFs is required for baculovirus replication.

Since the vp39 ORF sequence overlaps with the promoter sequences of the two flanking ORFs (lef-4 and cg-30), we could not delete the whole vp39 ORF in our vp39null bacmid construct. It may therefore also be that C- and/or N-truncated mutant(s) of vp39 may be expressed which may interfere as a competitive inhibitor with the normal VP39 protein.

Construction and Analysis of vp1054-Null Bacmid

To study the functionality of the AcMNPV vp1054 gene during virus infection, a vp1054-null AcMNPV bacmid was constructed by partially deleting the vp1054 gene from AcMNPV bacmid (bMON14272) by homologous recombination in E. coli. The deletion construct was selected by its resistance to chloramphenicol that indicated that site-specific deletion of the vp1054 gene had occurred. In the resulting vp1054-null AcMNPV bacmid, the 955-bp 3"-end part of the vp1054 gene was correctly replaced by the cat gene. Subsequently, the antibiotic resistance cassette (cat) was eliminated from bacmid backbone using Cre/LoxP recombination system (FIG. 10A). The deleted sequence was removed from the nucleotide coordinates 45365 to 46319 according to the AcMNPV clone C6 genome sequence (SEQ ID NO:1). The structure of all the deletion constructs was confirmed by PCR (FIG. 10B). When the vp1054 gene is present, as in the parental wild-type AcMNPV bacmid, a 775-bp PCR product can be amplified using primers 45510 and 46235, whereas a 596-bp PCR fragment amplified with cat-F and cat-R primers is produced only when the cat gene was introduced into the bacmid sequence in case of AcMNPV vp1054null(+cat) construct (FIG. 10B). Correct recombination process was also confirmed by PCR mapping of vp1054 locus using primers 45122 and 46441. A 1320-bp DNA fragment was amplified when wild-type AcMNPV bacmid was used as a template, whereas a 1353-bp DNA fragment could be amplified on AcMNPV vp1054-null(+cat) template (FIG. 10B). When final construct AcMNPV-vp1054null(−cat) with eliminated cat cassette was used in PCR analysis, only a 423-bp DNA fragment could be detected (FIG. 10B). Positive clones were successfully verified by DNA sequencing.

AcMNPV vp1054 Gene is Essential for Viral Replication

The repair construct was designed such that the AcMNPV vp1054 ORF with its native promoter region was inserted into the polyhedrin locus along with the egfp gene under the control of the p10 promoter (FIG. 11A). Since the vp1054 promoter and ORF sequences are overlapping with lef-10 ORF, the repair construct is also capable to express LEF-10. To investigate the function of the vp1054 gene, Sf9 cells were transfected with either the vp1054 knock-out or repair bacmid construct and monitored for EGFP expression by fluorescence microscopy. When Ac-vp1054 null construct was introduced into Sf9 cells, no viral propagation was observed in cell culture at 72 h to 120 h p.t. We could observe only a "single-cell infection" phenotype similar to the phenotype of Ac-gp64null bacmid (FIG. 11B). The results indicate that Ac-vp1054null is able to reach the very late phase of infection as confirmed by p10 promoter-driven EGFP expression. In other words, the results suggest that the expression of late expression factor 10, LEF-10, was not affected in vp1054-null bacmid mutant. From 72 h to 120 hours p.t., widespread EGFP expression could be seen in insect cell monolayers that were transfected with the repair constructs (Ac-Δvp1054-vp1054). The results are indicating that the repair bacmid is able to produce levels of infectious budded virions sufficient to initiate secondary infection at a similar level as the wild-type bacmid (FIG. 11B). At 6 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with the repair constructs showed numerous EGFP expressing cells (FIG. 11C). On the other hand, in insect cells incubated with supernatant from the transfection with the Ac-vp1054null knockout, no EGFP expression was detected at any time-point analyzed up to 72 h (FIG. 11C).

These results indicate that the vp1054 gene is essential for infectious BV production. It has clearly been proven that the 955-bp 3"-end sequence part of the vp1054 ORF can completely be deleted from the bacmid backbone and adequately rescued by introduction of the AcMNPV vp1054 ORF into a heterologous site (polyhedrin locus) of the genome. In addition, the results proved that deletion of the vp1054 gene does not affect very late gene expression, as demonstrated by EGFP-positive cells in cells transfected with Ac-vp1054null bacmid mutant (FIG. 11B).

Generation and Characterization of p6.9-Null Bacmid

Figure 12B:
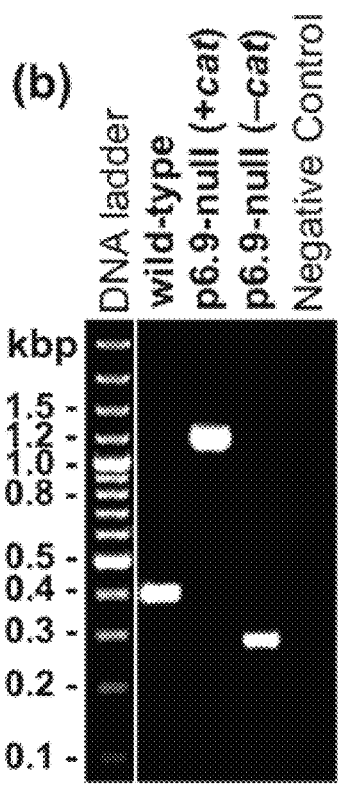

To study the functionality of the AcMNPV p6.9 gene during virus infection, a vp80-null AcMNPV bacmid was constructed by deleting the p6.9 gene from AcMNPV bacmid (bMON14272) by homologous recombination in E. coli. The deletion construct was selected by its resistance to chloramphenicol that indicated that site-specific deletion of the p6.9 gene had occurred. In the resulting p6.9-null AcMNPV bacmid, the p6.9 gene was correctly replaced by the cat gene. Subsequently, the antibiotic resistance cassette (cat) was eliminated from bacmid backbone using Cre/LoxP recombination system (FIG. 12A). The deleted sequence was removed from the translational start codon (ATG→Met) to the stop codon (TAT→Tyr), nucleotide coordinates 86716 to 86879 according to the AcMNPV clone C6 genome sequence (SEQ ID NO:1). The stop codon of the p6.9 orf was not removed since its sequence is overlapping with the stop codon of flanked lef-5 orf. The structure of all the deletion constructs was confirmed by PCR (FIG. 12 B). When the p6.9 gene is present, as in the parental wild-type AcMNPV bacmid, a 596-bp PCR fragment could be only amplified with cat-F and cat-R primers when cat gene was introduced into bacmid sequence in case of AcMNPV p6.9null(+cat) construct (FIG. 12B). Correct recombination process was also confirmed by PCR mapping of p6.9 locus using primers 86596 and 86995. A 400-bp DNA fragment was amplified when wild-type AcMNPV bacmid was used as a template, whereas a 1220-bp DNA fragment could be amplified on AcMNPV vp80-null(+cat) template (FIG. 12B). When final construct AcMNPV-vp80null(−cat) with eliminated cat cassette was used in PCR analysis, only a short 290-bp DNA fragment could be detected (FIG. 12B). Positive clones were successfully verified by DNA sequencing.

AcMNPV p6.9 Gene is Essential for Viral Replication

Figure 13D:
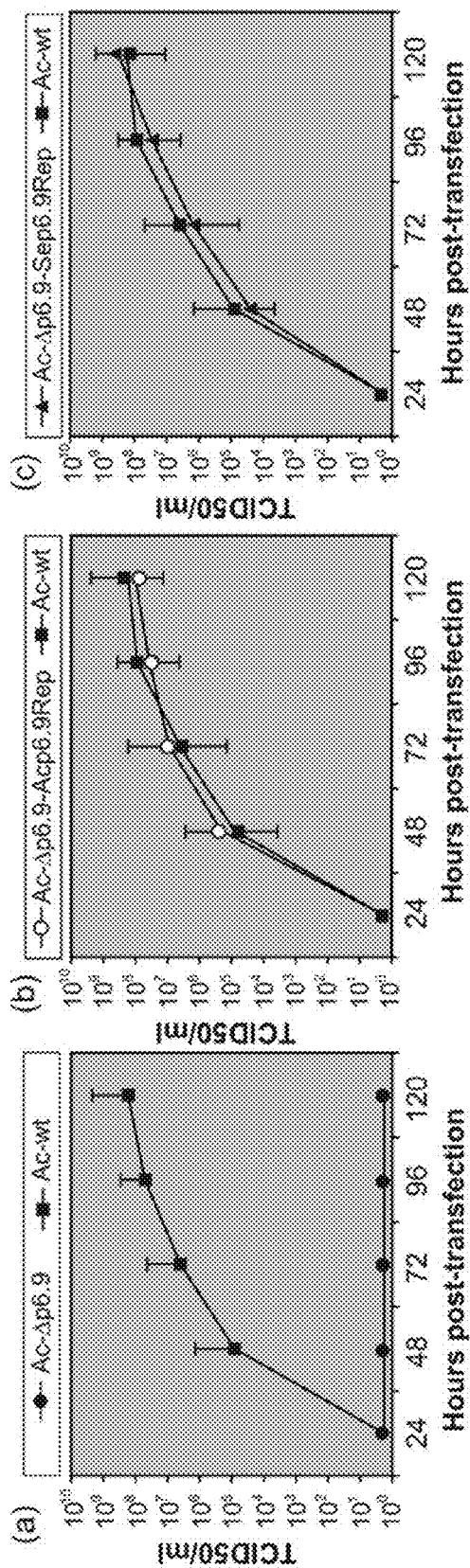

The repair constructs were designed such that the wild-type AcMNPV or SeMNPV p6.9 ORFs with AcMNPV p6.9 promoter region were inserted into the polyhedrin locus along with the egfp gene under the p10 promoter (FIG. 13A). To investigate the function of the p6.9 gene, Sf9 cells were transfected with either the p6.9 knock-out or repair bacmid constructs and monitored for EGFP expression by fluorescence microscopy. When Ac-p6.9 null was introduced into Sf9 cells, no viral propagation was observed in cell culture at 72 h to 120 h p.t. We could observe only a "single-cell infection" phenotype similar to the phenotype of Ac-gp64null bacmid (FIG. 13B). The results indicate that Ac-p6.9null is able to reach the very late phase of infection as confirmed by p10 promoter-driven EGFP expression. From 72 h to 120 hours p.t., widespread EGFP expression could be seen in insect cell monolayers that were transfected with the two repair constructs (Ac-Δp6.9-Acp6.9 and Ac-Δp6.9-Sep6.9). The results are indicating that these two repair bacmids are able to produce levels of infectious budded virions sufficient to initiate secondary infection at a similar level as the wild-type bacmid (FIG. 13B). At 6 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with the repair constructs showed numerous EGFP expressing cells (FIG. 13C). On the other hand, in insect cells incubated with supernatant from the transfection with the Ac-p6.9null knockout, no EGFP expression was detected at any time-point analyzed up to 72 h (FIG. 3C). Moreover, to characterize the exact effect of deletion of the p6.9 gene on AcMNPV infection, the viral propagation in transfected Sf9 cells was compared between Ac-wt, Ac-Δp6.9, Ac-Δp6.9-Acp6.9Rep, and Ac-Δp6.9-Sep6.9Rep). Cell culture supernatants of all the above bacmid constructs were analysed at indicated time points for BV production (FIG. 13D). As expected, the repaired Ac-Δp6.9-Acp6.9Rep and Ac-Δp6.9-Sep6.9Rep viruses showed kinetics of viral replication consistent with wild-type virus (Ac-wt) propagation.

These results indicate that the p6.9 gene is essential for infectious BV production. It has clearly been proven that the whole sequence of p6.9 ORF can completely be deleted from the bacmid backbone and adequately rescued by introduction of the AcMNPV vp80 ORF into a heterologous site (polyhedrin locus) of the genome. We also showed that p6.9 gene can be complemented efficiently by the SeMNPV-derived p6.9 ORF (M. Westenberg). In addition, the results proved that deletion of the p6.9 gene does not affect very late gene expression, as demonstrated by EGFP-positive cells in cells transfected with Ac-p6.9null bacmid mutant (FIG. 15B).

Example II

The inventors have amended the best mode of the present invention in the following example.

Materials and Methods

Generation of an Antibiotic Resistance Gene-Free AcMNPV vp80-Null Bacmid

To determine whether the VP80 protein has an essential role in the context of viral progeny production, we constructed an AcMNPV bacmid (derived from bMON14272 (from Invitrogen)) with a deletion of the vp80 ORF by homologous recombination in E. coli. To accomplish this, a cat gene flanked by mutant LoxP sites (Suzuki et al., 2005) was amplified using PCR primers vp80-KO-F and vp80-KO-R (see Table 1) from a plasmid comprising a cat gene flanked by mutant LoxP sites. The resulting PCR fragment, which contained the cat gene flanked by mutant LoxP sites and AcMNPV ~50-bp homology sequences to the 5' or 3' proximal region of the vp80 ORF, was treated with DpnI and gel-purified to eliminate the template plasmid. The PCR product was then transformed into DH101 E. coli cells containing bMON14272 (Invitrogen) and the Lambda RED recombinase-producing plasmid pKD46 (Datsenko & Wanner, 2000), which had been prepared in the following manner. Transformed DH10β-bMON14272/pKD46 E. coli cells were grown in 50-ml LB (2.0% peptone, 0.5% yeast extract, 85.5 mM NaCl, [pH 7.0]) cultures with kanamycin (50 µg/ml), ampicillin (100 µg/ml) and L-arabinose (1.5 mg/ml) at 30° C. to an $OD_{600}$ of ≈0.6 and then made electrocompetent by a standard procedure. The electroporated cells were incubated at 37° C. for 3 h in 3 ml LB medium and plated on LB-agar containing chloramphenicol at a concentration of 6.5 µg/ml. After 48-h incubation at 37° C., the chloramphenicol-resistant colonies were streaked to fresh LB-agar medium with 34 µg/ml chloramphenicol. The plates were incubated at 37° C. overnight, and colonies resistant to chloramphenicol were selected for further confirmation of the relevant genotype by PCR. Primers 90292 and 90889 were used to confirm the absence of the vp80 ORF, and primers cat-F and cat-R were employed to verify the presence of cat cassette into bacmid (detailed sequences in Table 1).

To eliminate the introduced antibiotic resistance gene (cat) from the bacmid backbone, a Cre/LoxP recombinase system was employed. A Cre recombinase-carrying plasmid pCRE obtained from Jeanine Louwerse (LUMC Leiden, The Netherlands) was introduced into DH10b-bMON14272-vp80null E. coli cells, and CRE expression was subsequently induced by the addition of isopropyl thiogalactoside (IPTG). Briefly, the electroporated cells were incubated at 37° C. for 3 h in 3 ml of LB medium (2.0% peptone, 0.5% yeast extract, 85.5 mM NaCl, [pH 7.0]) and plated on LB-agar medium containing 50 µg/ml kanamycin, 100 µg/ml ampicillin and 2 mM IPTG. After 24-h incubation, colonies resistant to kanamycin and ampicillin were selected for further verification of the desired genotype by PCR. In PCR-based analysis, primers 89507 and 91713 (Table 1) were used to verify elimination of cat gene from bacmid backbone. Positive clones were also confirmed by DNA-sequencing.

To recover transposition competence, the helper transposase-encoding plasmid pMON7124 (Invitrogen) was re-introduced into DH10β-bMON14272-vp80null *E. coli* cells. Finally, the egfp reporter gene was introduced into the vp80-null bacmid to facilitate observation of its behaviour in insect cells. Briefly, the egfp reporter gene was amplified using PCR oligonucleotides gfp-NheI-F and gfp-SphI-R (Table 1) from plasmid pEGFP-N3 (Clontech). The PCR product was cloned into plasmid pJet1.2/Blunt using Clone-JET™ PCR Cloning Kit (Fermentas) according to manufacturer's protocol. Subsequently, the egfp ORF was excised from error-free pJet1.2-egfp with NheI and SphI and subcloned into NheI/SphI-digested pFastBacDUAL (Invitrogen), to generate plasmid pFB-egfp. An expression cassette containing the egfp reporter gene under transcriptional control of the very late p10 promoter was transposed from pFB-egfp into polyhedrin locus of vp80-null bacmid as described in the Bac-to-Bac manual (Invitrogen). In the resulting genome, the complete vp80 ORF has been removed (see FIG. 2). This corresponds to the deletion of 2074 bp from nucleotide positions 89564 to 91637 in the AcMNPV clone C6 genome provided in SEQ ID NO: 1.

Construction of Repaired vp80-Null Bacmids

To prepare vp80 repair donor vectors, we modified plasmid pFB-egfp (noted above) by removing the polyhedrin promoter and replacing it with a fragment containing the vp80 promoter region and the vp80 ORF. First, a 2300-bp fragment containing both the vp80 promoter and ORF sequence was amplified using primers pvp80-StuI-F and vp80-XbaI-R (Table 1) from bacmid bMON14272 template, and cloned into vector pJet1.2/Blunt (Fermentas) to form pJet1.2-pvp80-vp80. After DNA sequence verification, the vp80 cassette was excised from pJet1.2-pvp80-vp80 by StuI/XbaI double digestion, and then subcloned into Bst1107I/XbaI-digested and gel-purified pFB-egfp to generate donor plasmid pFB-egfp-pvp80-vp80. Parallelly, a donor plasmid pFB-egfp-polh-vp80, where vp80 ORF is driven by the very late polyhedrin promoter (polh) was constructed. To this aim, a 2105-bp fragment carrying the vp80 ORF was amplified using primers vp80-SacI-F and vp80-XbaI-R (Table 1) and cloned into pJet1.2/Blunt, to generate pJet1.2-vp80. In the final step, the vp80 ORF was cut out (SacI/XbaI) from pJet1.2-vp80, and subcloned into SacI/XbaI-digested pFB-egfp, to create pFB-egfp-polH-vp80.

To overcome a problem associated with the unavailability of anti-VP80 antibody, FLAG tag decoration (N- and C-terminus fusion) of VP80 was performed to facilitate immunodetection. The N-terminally fused FLAG-vp80 sequence was generated by a double-step PCR strategy, a so-called fusion PCR. First, a 259-bp fragment containing the vp80 promoter and the FLAG tag was PCR amplified using primers pvp80-StuI-F and vp80-FLAG-R1 from the bMON14272 bacmid template. After gel-purification and DNA quantification, the 259-bp fragment was used as forward primer in a second step PCR amplification with the reverse primer vp80-XbaI-R on the bMON14272 bacmid template. The final PCR product (2324 bp) was cloned into vector pJet1.2/Blunt (Fermentas) to form pJet1.2-pvp80-FLAG-vp80. After DNA sequence verification, the FLAG-vp80 cassette was excised from pJet1.2-pvp80-FLAG-vp80 by StuI/XbaI double digestion, and then subcloned into Bst1107I/XbaI-digested and gel-purified pFB-egfp to generate donor plasmid pFB-egfp-pvp80-FLAG-vp80. The C-terminally fused vp80-FLAG cassette was amplified using pvp80-StuI-F and vp80-FLAG-R from the bMON14272 bacmid template. The 2324-bp fragment was cloned into pJet1.2/Blunt, and subsequently transferred into pFB-egfp in a similar way as previous constructs.

The inserts of all developed donor plasmids were transposed into the vp80-null bacmid following the Bac-to-Bac protocol (Invitrogen). Screening of transposition-positive constructs into the polh locus was done by a triplex PCR-based assay employing M13 forward and reverse primers and a gentamicin resistance gene-specific primer GenR (Table 1).

Transfection-Infection Assay

Bacmid DNAs were prepared from 1.5-ml overnight bacterial cultures of 2 to 3 independent colonies carrying the bacmid with the inserted heterologous gene according to the Bac-to-Bac manual (Invitrogen) and were analyzed in parallel. For transfections, 1 μg of each bacmid DNA preparation was used to transfect $1 \times 10^6$ Sf9 cells in a 6-well plate by the Cellfectin™-based transfection protocol as described in the Bac-to-Bac (Invitrogen) manual. From 72 h to 120 h post transfection (p.t.), viral propagation was checked by fluorescence microscopy. At 120 h p.t., the cell culture medium was centrifuged for 5 min at 2000×g to remove cell debris, and this clarified supernatant was used to infect $1.5 \times 10^6$ Sf9 cells in 6-well plates. After 72 h p.i., the spread of virus infection was again monitored by fluorescence microscopy. In all experiments, a wild-type bMON14272 bacmid carrying the egfp reporter gene under control of the p10 promoter was used as positive control. A bMON14272-gp64null bacmid also carrying the egfp reporter gene under control p10 promoter served as negative control, since it has lost the ability of cell-to-cell movement of the infection (Lung et al., 2002).

Time-Course Characterization of Viral Propagation in Cell Culture

Time course analyses were performed to compare budded virus production of the AcMNPV-vp80null virus and the various repair constructs in comparison to the wild type AcMNPV bacmid (Ac-wt) all containing egfp. Briefly, the Sf9 cells were seeded in 6-well tissue culture plates ($1 \times 10^6$ cells/well in 1 ml Sf900-II culture medium without serum at 28° C.). After two hours, the culture medium was removed, and the cells were transfected with 5 μg bacmid DNA, under standard conditions as recommended in Bac-to-Bac manual (Invitrogen). Cell culture supernatants were harvested at 24, 48, 72, 96 and 120 h p.t., and analysed for the production of infectious budded virus by an end-point dilution assay to determine the tissue culture infective dose 50 ($TCID_{50}$). Infection was determined by monitoring egfp expression (from the p10 promoter). The average values of infectious titers derived from three independent transfections were calculated and plotted into graphs.

Transmission Electron Microscopy

Insect Sf9 cells were seeded in a 25T flask ($3.5 \times 10^6$ cells/flask), and transfected with 20 μg either the Ac-Δvp80, rescue Ac-Δvp80-vp80 or Ac-wt bacmid construct. After 48 h p.t., the cells were harvested and prepared for transmission electron microscopy as described previously (van Lent et al., 1990). Samples were examined and photographed with a Philips CM12 electron microscope.

Budded Virus Production Assay

Insect Sf9 cells were seeded in two 25T flasks ($3.5 \times 10^6$ cells/flask), and transfected with 20 μg either Ac-Δvp80, Ac-Δvp80-vp80, Ac-Δvp80-pH-vp80, Ac-Δvp80-FLAG-vp80, Ac-Δvp80-vp80-FLAG, or Ac-wt bacmid construct. Five days p.t., the BV-enriched cell culture supernatants were harvested, and ultracentrifuged through a cushion of 10% sucrose solution (25,000 rpm for 1.5 hour, Beckman SW32). Pelleted budded virions were resuspended in sterile demi-water, and prepared for either negative staining electron microscopy, SDS-polyacrylamide electrophoresis, or PCR-based detection (as mentioned above).

Purification of ODVs and Rod-Shaped Structures from Infected Cells

The presence of ODVs and rod-like structures in infected/transfected insect cells was analyzed by electron microscopy (EM). For this purpose, insect cells were harvested 48 h p.i., lysed and the cell lysates were ultracentrifuged through a 40% sucrose cushion in TE (1 mM Tris-HCl pH 7.4, 0.1 mM EDTA) buffer (45,000 rpm for 1 hour, Beckman SW55). Pellets were resuspended in sterile demi-water and analyzed by negative staining EM as described previously (van Lent et al., 1990).

Purification and Fractionation of BV and ODV Virions

To produce BVs, $3.0 \times 10^7$ Sf9 cells were infected with Ac-Δvp80-Flag•vp80 or control Ac-wt virus at an MOI=1. Six days p.i., 72 ml of BV-enriched medium was collected and centrifuged at 1,500×g for 10 min. The supernatant was then ultracentrifuged at 80,000×g (Beckman SW28 rotor) for 60 min at 4° C. The BV pellet was resuspended in 350 µl 0.1×TE buffer, and loaded onto a linear sucrose gradient (25 to 56% (w/v)), and ultracentrifuged at 80,000×g (Beckman SW55 rotor) for 90 min at 4° C. The formed BV band was collected and diluted in 12 ml 0.1×TE. The BV preparation was concentrated at 80,000×g for 60 min at 4° C. The final virus pellet was resuspended in 150 µl of 0.1×TE.

To produce ODVs, $6.0 \times 10^7$ Sf9 cells were co-infected with Ac-Δvp80-Flag•vp80 (MOI=25) and AcMNPV (MOI=5) viruses (strain E2, Smith & Summers, 1979). Five days p.i., the infected cells were harvested, and ODVs were purified from viral occlusion bodies as described previously (Braunagel et al., 1994). The final ODV pellet was resuspended in 0.5 ml of 0.1×TE (10 mM Tris, 1 mM EDTA, pH=7.5).

The purified BV and ODV virions were fractionated into envelope and nucleocapsid fractions as described previously (Braunagel et al., 1994). Final fractions were processed for SDS-PAGE and immunoblotted against either mouse monoclonal anti-Flag antibody (Stratagene), rabbit polyclonal anti-VP39 antiserum (kindly provided by Lorena Passarelli, Kansas State University, USA), rabbit polyclonal anti-GP64 antiserum (kindly provided by Hualin Wang and Feifei Yin, Wuhan Institute of Virology, China (Yin et al., 2008)), or rabbit polyclonal antiserum against per os infectivity factor 1 (PIF-1) (kindly provided by Ke Peng, Wageningen University, The Netherlands (Peng et al., 2010)).

Development of Transgenic Sf9-Derived Cell Line Expressing vp80

To develop a cell line, which produces the VP80 protein, a 2105-bp fragment carrying the vp80 ORF was amplified using primers vp80-SacI-F and vp80-XbaI-R (Table 1) and cloned into pJet1.2/Blunt, to generate pJet1.2-vp80. In the next step, the vp80 ORF was cut out (SacI/XbaI) from pJet1.2-vp80, and subcloned into SacI/XbaI-digested pIZ (Invitrogen), to create pIZ-vp80. The resulting plasmid vector pIZ-vp80 was linearized with Eco57I, and gel-purified. Sf9 cells were seeded in a six-well plate ($1 \times 10^6$ cells/well), and transfected with 10 µg of the linearized vector. After 24 hours post-transfection, cells were selected by cell culture medium containing Zeocin™ (300 µg/ml) for 2 to 3 weeks, until no control Sf9 cells survived under the same conditions. Cells were then propagated as an uncloned cell line.

Recombinant Protein Expression with the vp80Null Virus

To measure the capacity to express recombinant protein with the Ac-Δvp80 (trans-complemented) virus seed, $3.0 \times 10^7$ non-transformed Sf9 cells were infected (independent triplicate assay) with Ac-wt, Ac-Δvp80-Flag•vp80 (both produced in non-transformed cell line) or Ac-Δvp80 virus (produced in the Sf9-vp80 cell line) at a MOI=10. All of these virus seeds are expressing egfp as a model heterologous gene from the baculovirus very late p10 promoter. At 48 h and 72 h p.i. cells and culture medium were harvested and used for Western blotting, enzyme-linked immunosorbent assay (ELISA) or BV titration (see above). For Western blotting the same antibodies as mentioned above were used to detect the Flag-tag, EGFP, and GP64, as well as a monoclonal mouse anti-actin antibody (ImmunO).

For relative quantification, Maxisorp 96-well plates (Nunc) were coated overnight at 4° C. with 100 ng of rabbit polyclonal anti-GFP antibody (Molecular Probes) in a volume of 100 µl per well, which was followed by standard ELISA procedures as previously described (Fric et al., 2008). The percentage of EGFP production was calculated (independent triplicate assay) according to the formula: % EGFP expression=(test absorbance$_{nh}$–background absorbance)/(Ac-wt EGFP$_{72h}$–background absorbance)×100%, where nh represents the time point p.i. The statistical significance of the observed differences between the control Ac-wt and the experimental Ac-Δvp80-Flag•vp80 and Ac-Δvp80 genotypes was analyzed with the Student's t-test.

Results

The AcMNPV vp80 Gene is Essential for Viral Replication

An AcMNPV deletion virus was constructed as detailed in FIG. 2. Repair constructs were designed such that the wild-type vp80 ORF or N- and C-terminally FLAG-tagged vp80 genes along with its native or polyhedrin promoter regions were inserted into the polyhedrin locus along with the egfp gene under the p10 promoter (FIG. 3A). To investigate the function of the vp80 gene, Sf9 cells were transfected with either the knock-out or repair bacmid constructs and monitored for EGFP expression by fluorescence microscopy. When Ac-vp80 null was introduced into Sf9 cells, no viral propagation was observed in cell culture at 72 h to 120 h p.t. We could observe only a "single-cell infection" phenotype similar to the phenotype of Ac-gp64null bacmid (FIG. 3B). The results indicate that Ac-vp80null is able to reach the very late phase of infection as confirmed by p10 promoter-driven EGFP expression. From 72 h to 120 hours p.t., widespread EGFP expression could be seen in insect cell monolayers that were transfected with the three repair (vp80 driven from its native promoter, vp80 driven from polyhedrin promoter and N-terminally FLAG-tagged vp80 driven from its native promoter) constructs indicating that these bacmids were able to produce levels of infectious budded virions sufficient to initiate secondary infection at a similar level as the wild-type bacmid (FIG. 3B). In contrast, in insect cells transfected with C-terminally FLAG-tagged vp80 repair constructs, by 72 h p.t. EGFP expression was only observed in isolated cells that were initially transfected indicating that this bacmid construct is defective in viral replication (FIG. 3B). However, by 96 h p.t. formation of tiny plaques was observed and by 120 h p.t. very few plaques of normal size were developed. The results show that the C-terminally flagged mutant is strongly delayed in producing budded virus and showed that an unmodified C-terminus is very important for the function of VP80. At 5 days p.t., cell culture supernatants were removed and added to freshly plated Sf9 cells and then incubated for 3 days to detect infection by virus generated from cells transfected with these bacmids. As expected, Sf9 cells incubated with supernatants from the transfections with repair constructs showed numerous EGFP expressing cells (FIG. 3C). Nevertheless, cells incubated with supernatants from C-terminally FLAG-tagged constructs showed a significant reduction in the number of EGFP-positive cells. On the other hand, in insect cells incubated with supernatants from the transfection with the vp80 knockout, no EGFP expression was detected at any time-point analyzed up to 72 h (FIG. 3C).

Moreover, to characterize the exact effect of deletion of the vp80 gene on AcMNPV infection, the viral propagation in transfected Sf9 cells was compared between Ac-wt, Ac-Δvp80, Ac-Δvp80-vp80Rep, Ac-Δvp80-polh-vp80Rep, Ac-Δvp80-FLAG-vp80Rep and Ac-Δvp80-vp80-FLAGRep. Cell culture supernatants of all the above bacmid constructs were analysed at indicated time points for BV production (FIG. 4). As expected, the repaired Ac-Δvp80-vp80Rep, Ac-Δvp80-polh-vp80Rep, and Ac-Δvp80-FLAG-vp80Rep viruses showed kinetics of viral replication consistent with wild-type virus (Ac-wt) propagation. Budded virion production by the C-terminally flagged Ac-Δvp80-vp80-FLAGRep virus was reduced to approximately 0.06% compared to the Ac-wt virus or the other repaired viruses.

These results indicate that the vp80 gene is essential for infectious BV production. It has clearly been proven that the whole sequence of vp80 ORF can completely be deleted from the bacmid backbone and adequately rescued by introduction of the vp80 ORF into a heterologous site (polyhedrin locus) of the genome. We also showed that vp80 gene expression can be driven by the heterologous polyhedrin promoter sequence with no negative effect on viral replication in cell culture. Additionally, we observed that the N-terminus in contrast to the C-terminus of VP80 is permissive to gene modifications (epitope tag-labeling). We noted that the kinetics of the C-terminally FLAG-tagged VP80 virus were significantly delayed when compared with all other rescue or wild-type viruses, indicating the functional importance of the VP80 C-terminus.

VP80 is Required for Production of Both BV and ODV

The results described above indicated that the Ac-vp80null mutant is completely defective in production of infectious budded virus. However, there was also a possibility that the mutant can still produce non-infectious budded particles. To investigate the ability, Sf9 cells were transfected with either the knock-out, repair or wild-type bacmid constructs and 7 days p.t. cell culture mediums were ultracentrifuged to pellet budded viruses. The formed pellets were either analyzed by negative staining electron microscopy or by Western blot- and PCR-based detection to confirm the presence of the budded viruses. No intact budded virus, virus-like particles, nor its structures (such as major capsid protein VP39 and viral genome sequence) were revealed in the pellet from the cells transfected with the Ac-vp80null mutant (FIGS. 5A and 5B). On the other hand, all analyzed repair constructs produced normally-appearing budded virus as compared with budded virus-derived from the wild-type virus (FIG. 5A). Nevertheless, it was very difficult to find representative budded virions in the pellet derived from C-terminally FLAG-tagged vp80 gene repair construct-transfected cells.

To further characterize deletion of the vp80 gene on baculovirus life cycle, electron microscopy was performed with ultra-thin sections generated from bacmid-transfected cells. The Ac-vp80null-transfected cells developed typical phenotypes of baculovirus-infected cells with an enlarged nucleus, a fragmented host chromatin, an electron-dense virogenic stroma, etc. (FIG. 6A). The absence of VP80 did not prevent formation of normally-appearing nucleocapsids inside the virogenic stroma (FIG. 6C). The formed nucleocapsids were phenotypically undistinguishable from those produced by either the Ac-vp80null repair or Ac-wt bacmids. However, an abundance of assembled nucleocapsids was rather less as compared with cells transfected with the Ac-vp80null repair or Ac-wt bacmids (FIGS. 6E and 6G). In addition, no occlusion-derived virions nor bundles of nucleocapsids prior to an envelopment could be observed in the peristromal compartment of a nucleoplasm (so called the ring zone) of Ac-vp80null bacmid-transfected cells (FIGS. 6B and 6D). It seems that VP80 plays a role during maturation of nucleocapsids and/or their release/transport from the virogenic stroma. Eventually, VP80 can somehow contribute to an efficient nucleocapsid assembly which could be explained by the small number of nucleocapsids present in the virogenic stroma of Ac-vp80null transfected cells. When the vp80 gene was re-introduced back into the bacmid mutant, a lot of nucleocapsids and occlusion-derived virions could be seen in the ring zones of transfected cells (FIG. 6F). An abundance and morphology of occlusion-derived virions produced in Ac-Δvp80-vp80 repair bacmid-transfected cells were similar to those produced by wild-type bacmid (FIGS. 6F and 6H).

VP80 is Associated with Nucleocapsids of Both BV and ODV

To investigate the association of VP80 with BV preparations, BVs were collected at 48 h p.i. and nucleocapsid and envelope fractions were separated. The Flag•VP80 protein was only detected in the nucleocapsid fraction as a double-band of molecular masses ranging between 80-kDa and 95-kDa that were observed in infected Sf9 cells (FIG. 14A, upper panel). Correct separation into nucleocapsid and envelope fractions was confirmed with antibodies against VP39 (nucleocapsid only) and GP64 (envelope only) (FIG. 14A, lower panels).

To examine whether VP80 is also associated with ODVs, Sf9 cells were co-infected with the Ac-Δvp80-Flag•vp80 and occlusion body (OB)-producing wt AcMNPV viruses to provide the POLH protein. Western blot analysis showed that VP80 associates with the nucleocapsid fraction of ODVs and in this case migrates as a single band of ~80 kDa, corresponding to the 80-kDa form produced in the very late phase of infection (FIG. 14B, upper panel). Proper fractionation into nucleocapsid and envelope fractions was controlled with antiserum against PIF-1, an ODV envelope protein (FIG. 14B, lower panel).

The Function of VP80 can be Rescued by Genetic Trans-Complementation

To verify whether a vp80 deletion in the viral genome can be complemented by a vp80 ORF offered in trans under control of a constitutive promoter, a transgenic cell line expressing Flag-tagged vp80 was constructed. In these cells VP80 was mainly produced as a protein of approximately 95-kDa as was shown by Western blot analysis with anti-Flag antibody (FIG. 15A). Two minor bands, one of ~80-kDa and a second of ~65-kDa were also observed.

In trans-complementation assays, Sf9-vp80 cells were transfected with the Ac-Δvp80 bacmid, and the spread of virus infection was monitored by EGFP-specific fluorescence at 96 h and 120 h p.t. (FIG. 15Ba-c). Viral plaques were seen in the transfected Sf9-vp80 cells demonstrating that the virus was transmitted from cell to cell. Nevertheless, we noted that the number and size of the developed plaques was significantly smaller than observed in Sf9 cells transfected with the Ac-wt bacmid (FIG. 15d). As a control, non-transgenic Sf9 cells showed only single-cell infections when transfected with the Ac-Δvp80 bacmid (FIG. 15Bc).

When the culture medium of the Ac-Δvp80 transfected Sf9-vp80 cells was used to infect freshly seeded non-transgenic Sf9 cells a "single-cell infection" phenotype was observed (FIG. 15Bb, right panel). Hence, the BV particles resulting from trans-complementation were able to enter cells but were defective in producing new BV. This also shows that the Ac-Δvp80 did not revert to Ac-wt in the Sf9-vp80 cells, by picking up the transgene from the host cells. As predicted, no EGFP signal was detected in Sf9 cells receiving the supernatant from Ac-Δvp80-transfected, non-transgenic Sf9 cells (FIG. 15Bc, right panel). The numbers of infectious BVs released from the Sf9-vp80 cells trans-fected with the Ac-Δvp80 bacmid were compared with those produced in Sf9 cells transfected with Ac-wt at 6 days p.i. This experiment showed that the current trans-complementation system is approximately 25 fold less effective in BV production than the classical Sf9-based production system (FIG. 15C).

Trans-Complemented, Replication-Deficient Ac-vp80null Virus is Competent to Express High Levels of Recombinant Protein To assess the effect of the vp80 gene deletion on the level of recombinant protein expression, a bench-scale comparative production assay has been performed. Herein, the Sf9 cells were in parallel infected with three types of baculovirus seeds at an MOI=10, namely (i) Ac-wt, (ii) Ac-Δvp80-Flag•vp80 (both produced in Sf9 cells), and (iii) Ac-Δvp80 (produced in Sf9-vp80 cells) all encoding EGFP. Western blotting profiles showed that the EGFP protein was expressed at identical levels for all three tested baculovirus genotypes as was the GP64 glycoprotein which served here for control purposes (FIG. 16A, upper panel). The relative amount of EGFP was quantified by ELISA at 48 and 72 h p.i. in infected cell lysates (FIG. 16B) and did not reveal any statistically significant difference in EGFP levels between the three tested baculovirus genotypes. The results thus demonstrate that the trans-complemented Ac-Δvp80 virus seed, although defective in viral replication, is as capable to produce recombinant protein as conventional baculovirus expression vectors as long as the initial multiplicity of infection is high enough to infect all cells.

Also during the production culture, revertant virus genotypes carrying the vp80 gene were not detected, as no de novo expressed Flag•VP80 protein (FIG. 16A) was detected in immunoblots. Theoretically, a certain quantity of Flag•VP80 protein associated with the trans-complemented virus seed is entering the insect cells, but this was no longer detected at very late times post-infection and is probably degraded by either lysosome- or proteasome-mediated activity. In the same experiment, no BV release was recorded in cell culture supernatants originated from Sf9 cells inoculated with the Ac-Δvp80 virus seed (FIG. 16C), demonstrating that neither revertant virus generation nor wild-type virus contamination had occurred.

Summary

In this study we focused on the improvement of conventional baculovirus-based expression tools with the goal to eliminate contaminating baculovirus progeny from manufactured recombinant protein(s). This effort is strongly driven by pharmaceutical perspectives, since recombinant baculovirus-expressed therapeutics are being more and more used in human and veterinary medicine. Hence, we aimed to identify baculovirus gene(s) whose targeting results in a deficiency of baculovirus virion production, but does not or only mildly affects very late gene expression. In this way high level expression of heterologous genes will be safeguarded.

A summarizing overview of the new technology with the vp80 gene as example is presented in FIG. 16. Using bacmid-based engineering the inventors constructed an AcMNPV genome lacking the vp80 gene (FIG. 16B). Functional genomics and electron microscopy analyses revealed that vp80 deficiency prevents production of both BVs and ODVs. In parallel, Sf9 cells were engineered to produce VP80 to trans-complement the Ac-Δvp80 knock-out bacmid (FIG. 14A,C). Finally, we proved that trans-complemented, replication-deficient baculovirus seed is capable of producing an amount of recombinant protein similar to that produced by conventional baculovirus vectors (FIG. 14D).

TABLE 1

List of PCR primers in order of appearance in the text.

| SEQ ID # | Primer name | Sequence | Orientation |
|---|---|---|---|
| 2 | vp39-F | 5'-gcttctaatacgactcactatagggtcgtatccgctaagcgttct-3' | Forward |
| 3 | vp39-R | 5'-gcttctaatacgactcactatagggacgcaacgcgttatacacag-3' | Reverse |
| 4 | 45510 | 5'-gcttctaatacgactcactatagggacagcgtgtacgagtgcat-'3 | Forward |
| 5 | 46235 | 5'-gcttctaatacgactcactatagggatctcgagcgtgtagctggt-3' | Reverse |
| 6 | 90292 | 5'-gcttctaatacgactcactatagggtaccgccgaacattacacc-3' | Forward |
| 7 | 90889 | 5'-gcttctaatacgactcactatagggtctattggcacgtttgct-3' | Reverse |
| 8 | ec-27-F | 5'-gcttctaatacgactcactatagggaaagcagacactcggcagat-3' | Forward |
| 9 | ec-27-R | 5'-gcttctaatacgactcactatagggttgagtggcttcaacctcag-3' | Reverse |
| 10 | dbp-F | 5'-gcttctaatacgactcactatagggcgctcgctagttttgttct-3' | Forward |
| 11 | dbp-R | 5'-gcttctaatacgactcactatagggaaagatcggaaggtggtga-3' | Reverse |
| 12 | gfp-F | 5'-gcttctaatacgactcactatagggctgaccctgaagttcatctg-3' | Forward |
| 13 | gfp-R | 5'-gcttctaatacgactcactatagggaactccagcaggaccatgt-3' | Reverse |
| 14 | cat-F | 5'-gcttctaatacgactcactatagggacggcatgatgaacctgaat-3' | Forward |

TABLE 1-continued

List of PCR primers in order of appearance in the text.

| SEQ ID # | Primer name | Sequence | Orientation |
| --- | --- | --- | --- |
| 15 | cat-R | 5'-gcttctaatacgactcactatagggatcccaatggcatcgtaaag-3' | Reverse |
| 16 | vp80-ko-F | 5'-ctgtattgtaatctgtaagcgcacatggtgcattcgatataaccttataatgtgtgctggaatgccct-3' | Forward |
| 17 | vp80-ko-R | 5'-aaatgtactgaatataaataaaaattaaaaatattttataattttttatttaccgttcgtatagcatacat-3' | Reverse |
| 18 | 89507 | 5'-agcggtcgtaaatgttaaacc-3' | Forward |
| 19 | 91713 | 5'-tgtataaacaatatgttaatatgtg-3' | Reverse |
| 20 | gfp-NheI-F | 5'-ccaaaccgctagcaacatggtgagcaagggcgag-3' | Forward |
| 21 | gfp-SphI | 5'-aggaaagggcatgcttaacgcgtaccggtcttgtacagctcgtccatgc-3' | Reverse |
| 22 | pvp80-StuI-F | 5'-ggaacaaaggcctgagctcaaagtaagacctttactgtcc-3' | Forward |
| 23 | vp80-XbaI-R | 5'-ccttctatctagattatataacattgtagtttgcg-3' | Reverse |
| 24 | vp80-SacI-F | 5'-ttatcttgagctcaatatgaacgattccaattctc-3' | Forward |
| 25 | vp80-FLAG-R1 | 5'-caacagagaattggaatcgttcttatcgtcgtcatccttgtaatc-catattataaggttatatcgaatg-3' | Reverse |
| 26 | vp80-FLAG-R | 5'-ccttctatctagattacttatcgtcgtcatccttgtaatctataacat-tgtagtttgcgttc-3' | Reverse |
| 27 | M13-F | 5'-cccagtcacgacgttgtaaaacg-3' | Forward |
| 28 | M13-R | 5'-agcggataacaatttcacacagg-3' | Reverse |
| 29 | GenR | 5'-agccacctactcccaacatc-3' | Reverse |
| 30 | vp39-ko-F | 5'-cttcttatcgggttgtacaac-3' | Forward |
| 31 | vp39-ko-R | 5'-gcgtatcatgacgatggatg-3' | Reverse |
| 32 | vp39-SacI-F | 5'-aaggttctctagattagacggctattcctccac-3' | Forward |
| 33 | vp39-XbaI-R | 5'-ttatcttgagctcaatatggcgctagtgcccg-3' | Reverse |
| 34 | vp39-StuI-F | 5'-ggaacaaaggcctgagctcttagacggctattcctccac-3' | Forward |
| 35 | lef-4-XbaI-R | 5'-ccttctatctagattaatttggcacgattcggtc-3' | Reverse |
| 36 | cg-30-XbaI-F | 5'-aaggttctctagattaatctacatttattgtaacatttg-3' | Forward |
| 37 | vp39-FLAG-SacI-R | 5'-ttatcttgagctcaatatggattacaaggatgacgacgataaggc-gctagtgcccgtgggt-3' | Reverse |
| 38 | vp1054-ko-F | 5'-gtactgaaagataatttattttttgatagataataattacattattttaa-acgtgttcgaccaagaaaccgat-3' | Forward |
| 39 | vp1054-ko-R1 | 5'-agggcgaattccagcacactttattacgtggacgcgttactttgc-3' | Reverse |
| 40 | vp1054-ko-R2 | 5'-gataagaatgcttgtttaacaaataggtcagctgttaaatact-ggcgatgtaccgttcgtatagcatacat-3' | Reverse |
| 41 | vp1054-Rep-F | 5'-ggttgtttaggcctgagctcctttggtacgtgttagagtgt-3' | Forward |
| 42 | vp1054-Rep-R | 5'-tcctttcctctagattacacgttgtgtgcgtgcaga-3' | Reverse |
| 43 | p6.9-ko-F | 5'-gcttcgttcattcgctactgtcggctgtgtggaatgtctggttgtt-aagtgtgctggaattcgccct-3' | Forward |
| 44 | p6.9-ko-R | 5'-aatattaataaggtaaaaattacagctacataaattacacaattta-aactaccgttcgtatagcatacat-3' | Reverse |
| 45 | Ac-p6.9-F | 5'-tttgaattcatggttgcccgaagctccaagac-3' | Forward |
| 46 | Ac-p6.9-R | 5'-tttgcggccgcttaatagtagcgtgttctgtaac-3' | Reverse |
| 47 | Se-p6.9-F | 5'-tttgaattcatgtatcgtcgtcgttcatc-3' | Forward |
| 48 | Se-p6.9-R | 5'-tttgcggccgcttaatagtggcgacgtctgtatc-3' | Reverse |

TABLE 1-continued

List of PCR primers in order of appearance in the text.

| SEQ ID # | Primer name | Sequence | Orientation |
|---|---|---|---|
| 49 | 86596 | 5'-gggcttagtttaaaatcttgca-3' | Forward |
| 50 | 86995 | 5'-aattcaaacgaccaagacgag-3' | Reverse |
| 51 | 45122 | 5'-gcaatcatgacgaacgtatgg-3' | Forward |
| 52 | 46441 | 5'-cgataatttttccaagcgctac-3' | Reverse |
| 53 | pp6.9-F | 5'-ggtcgacgtaccaaattccgttttgcgacg-3' | Forward |
| 54 | pp6.9-R | 5'-ggtcgacggatccgtttaaattgtgtaatttatg-3' | Reverse |
| 55 | 75834 | 5'-cttcttatcgggttgtacaac-3' | Forward |
| 56 | 76420 | 5'-gcgtatcatgacgatggatg-3' | Reverse |

REFERENCES

Abe, T., Takahashi, H., Hamazaki, H., Miyano-Kurosaki, N., Matsuura, Y. & Takaku, H. (2003). Baculovirus induces an innate immune response and confers protection from lethal influenza virus infection in mice. *Journal of Immunology* 171, 1133-1139.

Aslanidi, G., Lamb, K. & Zolotukhin, S. (2009). An inducible system for highly efficient production of recombinant adeno-associated virus (rAAV) vectors in insect Sf9 cells. *Proceedings of the National Academy of Sciences USA* 106, 5059-5064.

Boyce, F. M. & Bucher, N. L. R. (1996). Baculovirus-mediated gene transfer into mammalian cells. *Proceedings of the National Academy USA* 93, 2348-2352.

Braunagel, S. C. & Summers, M. D. *Autographa californica* nuclear polyhedrosis virus, PDV, and ECV viral envelopes and nucleocapsids: Structural proteins, antigens, lipid and fatty acid profiles. Virology 202, 315 (1994).

Bright, R. A., Carter, D. M., Crevar, C. J., Toapanta, F. R., Steckbeck, J. D., Cole, K. S., Kumar, N. M., Pushko, P., Smith, G., Tumpey, T. M. & Ross, T. M. (2008). Cross-clade protective immune responses to influenza viruses with H5N1 HA and NA elicited by an influenza virus-like particle. *PLoS ONE* 3.

Carbonell, L. F., Klowden, M. J. & Miller, L. K. (1985). Baculovirus-mediated expression of bacterial genes in dipteran and mammalian cells. *Journal of Virology* 56, 153-160.

Carbonell L. F., Hodge M. R., Tomalski, M. D., Miller, L. K. (1988). Synthesis of a gene coding for an insect-specific scorpion neurotoxin and attempts to express it using baculovirus vectors. *Gene* 73, 409-18.

Charlton, C. A. & Volkman, L. E. (1991). Sequential rearrangement and nuclear polymerization of actin in baculovirus-infected *Spodoptera frugiperda* cells. *Journal of Virology* 65, 1219-27.

Charlton, C. A. & Volkman, L. E. (1993). Penetration of *Autographa californica* nuclear polyhedrosis virus nucleocapsids into IPLB Sf 21 cells induces actin cable formation. *Virology* 197, 245-54.

Cohen, D. P. A., Marek, M., Davies, B. G., Vlak, J. M. & van Oers, M. M. (2009). Encyclopedia of *Autographa californica* nucleopolyhedrovirus genes. *Virologica Sinica* 24, 359.

Condreay, J. P.& Kost, T. A. (2007). Baculovirus expression vectors for insect and mammalian cells. *Curr Drug Targets* 8, 1126-31.

Cox, M. M. J. & Hollister, J. (2009). FluBlok, A next generation influenza vaccine manufactured in insect cells. *Biologicals* 37, 182-189.

Dai, X., Willis, L. G., Palli, S. R. & Theilmann, D. A. (2005). Tight transcriptional regulation of foreign genes in insect cells using an ecdysone receptor-based inducible system. *Protein Expression and Purification* 42, 236-245.

Datsenko, K. A. & Wanner, B. L. (2000). One-step inactivation of chromosomal genes in *Escherichia coli* K-12 using PCR products. *Proceedings of the National Academy of Sciences USA* 97, 6640-6645.

Fric, J., Marek, M., Hrusková, V., Holán, V. & Forstová J. (2008). Cellular and humoral immune responses to chimeric EGFP-pseudocapsids derived from the mouse polyomavirus after their intranasal administration. *Vaccine* 26, 3242.

Friesen. P. D. & Miller, L. K. (1986). The regulation of baculovirus gene expression in: "The Molecular Biology of Baculoviruses" (W. Doerfler and P. Boehm, eds.) Springer-Verlag, Berlin, pp. 31-49.

Funk, C. J. & Consigli, R. A. (1993). Phosphate cycling on the basic protein of *Plodia interpunctella* granulosis virus. *Virology* 193, 396-402.

Gheysen, D., Jacobs, E., De Foresta, F., Thiriart, C., Francotte, M., Thines, D. & De Wilde, M. (1989). Assembly and release of HIV-1 precursor pr55(gag) virus-like particles from recombinant baculovirus-infected insect cells. *Cell* 59, 103-112.

Gronowski, A. M., Hilbert, D. M., Sheehan, K. C. F., Garotta, G. & Schreiber, R. D. (1999). Baculovirus stimulates antiviral effects in mammalian cells. *Journal of Virology* 73, 9944-9951.

Harper, D. M., Franco, E. L., Wheeler, C. M., Moscicki, A.-B., Romanowski, B., Roteli-Martins, C. M., Jenkins, D., Schuind, A., Costa Clemens, S. A. & Dubin, G. (2006). Sustained efficacy up to 4.5 years of a bivalent L1 virus-like particle vaccine against human papillomavirus types 16 and 18: follow-up from a randomised control trial. *The Lancet* 367, 1247-1255.

Hill-Perkins, M. S., &, Possee, R. D. (1990). A baculovirus expression vector derived from the basic protein promoter of *Autographa californica* nuclear polyhedrosis virus. *Journal of General Virology* 71: 971-976.

Hofmann, C., Sandig, V., Jennings, G., Rudolph, M., Schlag, P. & Strauss, M. (1995). Efficient gene transfer into human hepatocytes by baculovirus vectors. *Proceedings of the National Academy of Sciences USA* 92, 10099-10103.

Jeong, S. H., Qiao, M., Nascimbeni, M., Hu, Z., Rehermann, B., Murthy, K. & Liang, T. J. (2004). Immunization with hepatitis C virus-like particles induces humoral and cellular immune responses in nonhuman primates. *Journal of Virology* 78, 6995-7003.

Jing Chen, S., Er Hui, Z., Lun Guang, Y., Hong Ling, Z. & Peng Fei, J. (2009). A high efficient method of constructing recombinant *Bombyx mori* (silkworm) multiple nucleopolyhedrovirus based on zero-background Tn7-mediated transposition in *Escherichia coli*. *Biotechnology Progress* 25, 524-529.

Kaikkonen, M. U., Viholainen, J. I., Narvanen, A., Yla-Herttuala, S. & Airenne, K. J. (2008). Targeting and purification of metabolically biotinylated baculovirus. *Human Gene Therapy* 19, 589-600.

Kanginakudru, S. S., Royer C., Edupalli S. V., Jalabert A., Mauchamp B., Chandrashekaraiah, Prasad S. V., Chavancy G., Couble P., Nagaraju J. (2007). Targeting ie-1 gene by RNAi induces baculoviral resistance in lepidopteran cell lines and in transgenic silkworms. *Insect molecular biology* 16, 635-644.

Kato, T., Kajikawa, M., Maenaka, K. & Park, E. Y. (2010). Silkworm expression system as a platform technology in life science. *Applied Microbiology and Biotechnology* 85, 459-470.

Kelly, D. C., Brown, D. A., Ayres, M. D., Allen, C. J. & Walker, I. O. (1983). Properties of the major nucleocapsid protein of *Heliothis zea* singly enveloped nuclear polyhedrosis virus. *Journal of General Virology* 64, 399-408.

Kitajima, M. & Takaku, H. (2008). Induction of antitumor acquired immunity by baculovirus *Autographa californica* multiple nuclear polyhedrosis virus infection in mice. *Clinical and Vaccine Immunology* 15, 376-378.

Kost, T. A., Condreay, J. P. & Jarvis, D. L. (2005). Baculovirus as versatile vectors for protein expression in insect and mammalian cells. *Nature Biotechnology* 23, 567-575.

Lackner, A., Genta, K., Koppensteiner, H., Herbacek, I., Holzmann, K., Spiegl-Kreinecker, S., Berger, W. & Grusch, M. (2008). A bicistronic baculovirus vector for transient and stable protein expression in mammalian cells. *Analytical Biochemistry* 380, 146-148.

Lebacq-Verheyden A M, Kasprzyk P G, Raum M G, Van Wyke Coelingh K, Lebacq J A, Battey J F. (1988) Post-translational processing of endogenous and of baculovirus-expressed human gastrin-releasing peptide precursor. *Molecular and Cell Biology* 8, 3129-35.

Lesch, H. P., Turpeinen, S., Niskanen, E. A., Mähönen, A. J., Airenne, K. J. & Ylä-Herttuala, S. (2008). Generation of lentivirus vectors using recombinant baculoviruses. *Gene Therapy* 15, 1280-1286.

Li, X., Pang, A., Lauzon, H. A. M., Sohi, S. S. & Arif, B. M. (1997). The gene encoding the capsid protein P82 of the *Choristoneura fumiferana* multicapsid nucleopolyhedrovirus: Sequencing, transcription and characterization by immunoblot analysis. *Journal of General Virology* 78, 2665-2673.

Liu, X., Li, K., Song, J., Liang, C., Wang, X. & Chen, X. (2006a). Efficient and stable gene expression in rabbit intervertebral disc cells transduced with a recombinant baculovirus vector. *Spine* 31, 732-735.

Liu, Y. K., Chu, C. C. & Wu, T. Y. (2006b). Baculovirus ETL promoter acts as a shuttle promoter between insect cells and mammalian cells. *Acta Pharmacologica Sinica* 27, 321-327.

Lopez, M. G., Alfonso, V., Carrillo, E. & Taboga, 0. (2009). Trans-complementation of polyhedrin by a stably transformed Sf9 insect cell line allows occ-baculovirus occlusion and larval per os infectivity. Journal of Biotechnology 145, 199-205.

Lu, A. & Carstens, E. B. (1992). Nucleotide sequence and transcriptional analysis of the p80 gene of *Autographa californica* nuclear polyhedrosis virus: a homologue of the *Orgyia pseudotsugata* nuclear polyhedrosis virus capsid-associated gene. *Virology* 190, 201-209.

Luckow, V. A. & Summers, M. D. (1988). Trends in the development of baculovirus expression vectors. Bio/Technology 6, 47-55.

Luckow, V. A., Lee, S. C., Barry, G. F. & Olins, P. O. (1993). Efficient generation of infectious recombinant baculoviruses by site-specific transposon-mediated insertion of foreign genes into a baculovirus genome propagated in *Escherichia coli*. *Journal of Virology* 67, 4566-79.

Ludwig, C. & Wagner, R. (2007). Virus-like particles-universal molecular toolboxes. *Current Opinion in Biotechnology* 18, 537-545.

Lung, O., Westenberg, M., Vlak, J. M., Zuidema, D. & Blissard, G. W. (2002). Pseudotyping *Autographa californica* multicapsid nucleopolyhedrovirus (AcMNPV): F proteins from group II NPVs are functionally analogous to AcMNPV GP64. *Journal of Virology*. 76, 5729-5736.

Maeda, S., Kawai, T., Obinata, M., Fujiwara, H., Horiuchi, T., Saeki, Y., Sato, Y. & Furusawa M. (1985). Production of human alpha-interferon in silkworm using a baculovirus vector. *Nature* 315, 592-4.

Maranga, L., Rueda, P., Antonis, A. F., Vela, C., Langeveld, J. P., Casal, J. I, & Carrondo, M. J. (2002). Large scale production and downstream processing of a recombinant porcine parvovirus vaccine. *Applied Microbiology Biotechnology* 59, 45-50.

Martin, B. M., Tsuji, S., LaMarca, M. E., Maysak, K., Eliason, W., Ginns, E. I. (1988). Glycosylation and processing of high levels of active human glucocerebrosidase in invertebrate cells using a baculovirus expression vector. *DNA* 7, 99-106.

McKenna, K. A., Hong, H., van Nunen & Granados, R. R. (1989). Establishment of new *Trichoplusia ni* cell lines in serum-free medium for baculovirus and recombinant protein production. *Journal of Invertebrate Pathology* 71, 82-90.

Mellado, M. C., Peixoto, C., Cruz, P. E., Carrondo, M. J. & Alves, P. M. (2008) Purification of recombinant rotavirus VP7 glycoprotein for the study of in vitro rotavirus-like particles assembly. *Journal of Chromatography B Analyicalt Technology Biomedical Life Science*. 874, 89-94.

Miller, D. W., Safer, P. & Miller, L. K. (1986). in *Genetic Engineering: Principles and Methods* Vol. 8 (eds Setlow, J. & Hollaender, A.) Plenum Publishing, New York, pp. 277-298.

Miller, L. K. (1988). Baculoviruses as gene expression vectors. Annual Review *Microbiology*. 42, 177-99.

Miyajima, A, Schreurs, J., Otsu, K., Kondo, A., Arai, K. & Maeda, S. (1987). Use of the silkworm, *Bombyx mori*, and an insect baculovirus vector for high-level expression and secretion of biologically active mouse interleukin-3. *Gene* 58, 273-81.

Mortola, E. & Roy, P. (2004). Efficient assembly and release of SARS coronavirus-like particles by a heterologous expression system. *FEBS Letters* 576, 174-178.

Muller, R., Pearson, M. N., Russell, R. L. Q. & Rohrmann, G. F. (1990). A capsid-associated protein of the multicapsid nuclear polyhedrosis virus of *Orgyia pseudot-* sugata: Genetic location, sequence, transcriptional mapping, and immunocytochemical characterization. *Virology* 176, 133-144.

Murges, D., Kremer, A. & Knebel-Morsdorf, D. (1997). Baculovirus transactivator IE1 is functional in mammalian cells. *Journal of General Virology* 78, 1507-1510.

Noad, R. & Roy, P. (2003). Virus-like particles as immunogens. *Trends in Microbiology* 11, 438-444.

Olszewski, J. & Miller, L. K. (1997). Identification and characterization of a baculovirus structural protein, VP1054, required for nucleocapsid formation. *Journal of Virology* 71, 5040-50.

Peng, K., van Oers, M. M., Hu, Z. H., van Lent, J. W. M., Vlak, J. M. (2010). Baculovirus per os infectivity factors form a complex on the surface of occlusion derived virus. *Journal of Virology* (in press).

Pijlman, G. P., Roode, E. C., Fan, X., Roberts, L. O., Belsham, G. J., Vlak, J. M. & van Oers, M. M. (2006). Stabilized baculovirus vector expressing a heterologous gene and GP64 from a single bicistronic transcript. *Journal of Biotechnology* 123, 13-21.

Ramadan, N., Flockhart, I., Booker, M., Perrimon, N. & Mathey-Prevot, B. (2007). Design and implementation of high-throughput RNAi screens in cultured *Drosophila* cells. *Nature Protocols* 2, 2245-2264.

Ramqvist, T., Andreasson, K. & Dalianis, T. (2007). Vaccination, immune and gene therapy based on virus-like particles against viral infections and cancer. *Expert Opinion on Biological Therapy* 7, 997-1007.

Salem, T. Z. & Maruniak, J. E. (2007). A universal transgene silencing approach in baculovirus-insect cell system. *Journal of Virological Methods* 145, 1-8.

Sambrook, J., Fritsch, E. F. & Maniatis, T. (1989). Molecular Cloning. A Laboratory Manual, Cold Spring Harbor, N.Y.

Slack, J. & Arif, B. M. (2006). The baculoviruses occlusion-derived virus: virion structure and function. *Advances in virus research* 69, 99-165.

Smith, G. E, Ju, G., Ericson, B. L, Moschera, J., Lahm, H. W, Chizzonite, R. & Summers, M. D. (1985). Modification and secretion of human interleukin 2 produced in insect cells by a baculovirus expression vector. *Proceedings National Academy of Sciences USA* 82, 8404-8.

Smith, R. H, Levy, J. R. & Kotin, R. M. (2009). A simplified baculovirus-AAV expression vector system coupled with one-step affinity purification yields high-titer rAAV stocks from insect cells. *Molecular Therapy* 17, 1888-1896.

Smith, G. E. & Summers, M. D. (1979). Restriction maps of five *Autographa californica* MNPV variants, *Trichoplusia ni* MNPV, and *Galleria mellonella* MNPV DNAs with endonucleases SmaI, KpnI, BamHI, SacI, XhoI, and EcoRI. *Journal of Virology* 30, 828-838.

Suzuki, N., Nonaka, H., Tsuge, Y., Okayama, S., Inui, M. & Yukawa, H. (2005). Multiple large segment deletion method for *Corynebacterium glutamicum*. *Applied Microbiology and Biotechnology* 69, 151-161.

Tang, X.-D., Xu, Y.-P., Yu, L.-I., Lang, G.-J., Tian, C.-H., Zhao, J.-F. & Zhang, C.-X. (2008). Characterization of a *Bombyx mori* nucleopolyhedrovirus with Bmvp80 disruption. *Virus Research* 138, 81-88.

Tellez, M. (2005). Process optimization protocol for tangential flow filtration of insect cells and baculovirus. Presented at WilBio Conference on Baculovirus & Insect Cell Culture—Process Development and Production Issues, Savannah/Georgia, 21-24 Feb. 2005.

Thiem, S. M. & Miller, L. K. (1989a). A baculovirus gene with a novel transcription pattern encodes a polypeptide with a zinc finger and a leucine zipper. *Journal of Virology* 63, 4489-4497.

Thiem, S. M. & Miller, L. K. (1989b). A baculovirus gene with a novel transcription pattern encodes a polypeptide with a zinc finger and a leucine zipper. *Journal of Virology* 63, 4489-97.

Thiem, S. M. & Miller, L. K. (1989c). Identification, sequence, and transcriptional mapping of the major capsid protein gene of the baculovirus *Autographa californica* nuclear polyhedrosis virus. *Journal of Virology* 63, 2008-2018.

Tjia, S. T., Meyer zu Altenschildesche, G. & Doerfler, W. (1983). *Autographa californica* nuclear polyhedrosis virus (AcNPV) DNA does not persist in mass cultures of mammalian cells. *Virology* 125, 107-117.

Urabe, M., Ding, C. & Kotin, R. M. (2002). Insect cells as a factory to produce adeno-associated virus type 2 vectors. *Human Gene Therapy* 13, 1935-1943.

van Lent, J. W. M., Groenen, J. T. M., Klinge-Roode, E. C., Rohrmann, G. F., Zuidema, D. & Vlak, J. M. (1990). Localization of the 34 kDa polyhedron envelope protein in *Spodoptera frugiperda* cells infected with *Autographa california* nuclear polyhedrosis virus. *Archives of Virology* 111, 103-114.

van Oers, M. M. (2006). Vaccines for Viral and Parasitic Diseases Produced with Baculovirus Vectors. In *Advances in Virus Research* 68. 193-253.

Vlak J. M., Klinkenberg, F. A, Zaal, K. J., Usmany, M., Klinge-Roode, E. C., Geervliet, J. B, Roosien. J, & van Lent, J. W. (1988). Functional studies on the p10 gene of *Autographa californica* nuclear polyhedrosis virus using a recombinant expressing a p10-beta-galactosidase fusion gene. *Journal of General Virology* 69, 765-76.

Wang, M. Y, Kuo, Y. Y., Lee, M. S, Doong, S. R, Ho, J. Y, Lee, L. H. (2000). Self-assembly of the infectious bursal disease virus capsid protein, rVP2, expressed in insect cells and purification of immunogenic chimeric rVP2H particles by immobilized metal-ion affinity chromatography. *Biotechnology and Bioeneneering* 67, 104-11.

Wu, W., Liang, H., Kan, J., Liu, C., Yuan, M., Liang, C., Yang, K. & Pang, Y. (2008). *Autographa californica* multiple nucleopolyhedrovirus 38K is a novel nucleocapsid protein that interacts with VP1054, VP39, VP80, and itself. *Journal of Virology* 82, 12356-12364.

Yin, F., M. Wang, Y. Tan, F. Deng, J. M. Vlak, Z. Hu, and H. Wang. 2008. A functional F analogue of AcMNPV GP64 from the *Agrotis segetum* granulovirus. *Journal of Virology* 82, 8922-8926.

The invention claimed is:

1. A method for the production of a biopharmaceutical product, comprising:
   (a) infecting a biopharmaceutical-producing insect cell with at least one baculovirus, said at least one baculovirus comprising a genome coding for said biopharmaceutical product, and
   (b) maintaining the biopharmaceutical-producing insect cell under conditions such that the biopharmaceutical product is produced,
   wherein the genome of said at least one baculovirus is mutated to eliminate functional vp1054 gene product or wherein said biopharmaceutical-producing insect cell comprises an expression control system inactivating vp1054 gene expression.

2. The method according to claim 1, wherein the vp1054 gene is mutated by nucleotide substitution, insertion or deletion.

3. The method according to claim 1, wherein the expression control system is under control of an inducible promoter.

4. The method according to claim 1, wherein the at least one baculovirus is AcMNPV or BmNPV.

5. The method according to claim 1, wherein the biopharmaceutical product is a recombinant protein, a recombinant virus or a virus-like particle.

6. The method according to claim 5, wherein the biopharmaceutical product is a recombinant AAV.

7. The method according to claim 1, wherein the biopharmaceutical product is encoded by at least one gene introduced in the recombinant baculovirus genome under the control of the polyhedrin or p10 promoter.

8. The method according to claim 1, wherein the genome of said at least one baculovirus is further mutated to eliminate functional vp80 gene product or wherein said biopharmaceutical-producing insect cell further comprises an expression control system inactivating vp80 gene.

* * * * *

UNITED STATES PATENT AND TRADEMARK OFFICE
CERTIFICATE OF CORRECTION

PATENT NO. : 9,862,934 B2
APPLICATION NO. : 14/670459
DATED : January 9, 2018
INVENTOR(S) : Otto-Wilhelm Merten, Martin Marek and Monique Van Oers Page 1 of 1

It is certified that error appears in the above-identified patent and that said Letters Patent is hereby corrected as shown below:

In the Specification

Column 16,
Line 22, "3"-end" should read --3'-end--.
Line 35, "3"-end" should read --3'-end--.

Column 19,
Lines 20-21, "5"-gcttctaatacgactcactataggg-3"." should read --5'-gcttctaatacgactcactataggg-3'.--.

Column 24,
Line 64, "3"-end" should read --3'-end--.

Column 25,
Line 23, "3"-end" should read --3'-end--.
Line 29, "5"-end" should read --5'-end--.
Line 35, "3"-end" should read --3'-end--.
Line 37, "5"-end" should read --5'-end--.

Column 31,
Line 48, "3"-end" should read --3'-end--.

Column 32,
Line 44, "3"-end" should read --3'-end--.

Column 34,
Line 26, "DH101" should read --DH10β--.

Signed and Sealed this
Eighteenth Day of September, 2018

Andrei Iancu
*Director of the United States Patent and Trademark Office*